(12) United States Patent
Van Peij et al.

(10) Patent No.: US 9,657,309 B2
(45) Date of Patent: *May 23, 2017

(54) RECOMBINATION SYSTEM

(71) Applicant: DSM IP ASSETS B.V., Heerlen (NL)

(72) Inventors: Noel Nicolaas Maria Elisabeth Van Peij, Echt (NL); Martina Beishuizen, Echt (NL); Yvonne Johannes Odilia Arendsen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/384,186

(22) PCT Filed: Mar. 12, 2013

(86) PCT No.: PCT/EP2013/055048
§ 371 (c)(1),
(2) Date: Sep. 10, 2014

(87) PCT Pub. No.: WO2013/135729
PCT Pub. Date: Sep. 19, 2013

(65) Prior Publication Data
US 2015/0050739 A1   Feb. 19, 2015

(30) Foreign Application Priority Data

Mar. 12, 2012   (EP) .................................. 12159098

(51) Int. Cl.
| | | |
|---|---|---|
| *C12N 1/14* | (2006.01) | |
| *C12N 15/80* | (2006.01) | |
| *C12N 15/81* | (2006.01) | |
| *C12N 15/85* | (2006.01) | |
| *C12N 15/82* | (2006.01) | |
| *C12N 15/90* | (2006.01) | |
| *C12N 1/15* | (2006.01) | |
| *C12N 15/09* | (2006.01) | |

(52) U.S. Cl.
CPC ............ *C12N 15/85* (2013.01); *C12N 15/80* (2013.01); *C12N 15/81* (2013.01); *C12N 15/82* (2013.01); *C12N 15/902* (2013.01)

(58) Field of Classification Search
None
See application file for complete search history.

(56) References Cited

U.S. PATENT DOCUMENTS

| | | |
|---|---|---|
| 2003/0199037 A1 | 10/2003 | Harris et al. |
| 2003/0233675 A1 | 12/2003 | Cao et al. |
| 2008/0085535 A1 | 4/2008 | Breuner et al. |

FOREIGN PATENT DOCUMENTS

| | | |
|---|---|---|
| JP | 2005-176602 A | 7/2005 |
| WO | 2012/123429 A1 | 9/2012 |

OTHER PUBLICATIONS

Kolb et al., "Insertion of a foreign gene into the β-casein locus by Cre-mediated site-specific recombination" 227 Gene 21-31 (1999).*
Barascu et al., "Homologous Recombination in Mammals" 23 Topics in Current Genetics 91-120 (2013).*
Capecchi, "Gene targeting in mice: functional analysis of the mammalian genome for the twenty-first century" 6 Nature Reviews | Genetics 507-512 (2005).*
Hartmann et al., "Validation of a SElf-Excising Marker in the Human Pathogen Aspergillus fumigatus by Employing the β-Rec/six Site-Specific Recombinase System" 76(18) Applied and Environmental Microbiology 6313-6317 (2010).*
Cheng et al., "Controlling gene expression in yeast by inducible site-specific recombination" 28(24) Nucleic Acids Research e108, 1-6 (2000).*
Fairhead et al., "New Vectors for Combinatorial Deletions in Yeast Chromosomes and for Gap-repair Cloning using 'Split-marker' Recombination" 12 Yeast 1439-1457 (1996).*
Hirrlinger et al., "Split-Cre Complementation Indicates Coincident Activity of Different Genes In Vivo" 4(1) PLoS One e4286 1-10 (2009).*
Forment et al., "Consecutive gene deletions in Aspergillus nidulans: application of the Cre/loxP system" 50 Current Genetics 217-224 (2006).*
International Search Report from corresponding PCT/EP2013/055048, mailed Jun. 14, 2013.
Kolb, "Selection-Marker-Free Modification of the Murine [beta]-Casein Gene Using a 1 ox2722 Site", Analytical Biochemistry, vol. 290, No. 2, Mar. 1, 2001 (Mar. 1, 2001), pp. 260-271, XP055033798.
Cherepanov et al., "Gene disruption in *Escherichia coli*: Tc<R> and Km<R>cassettes with the option of Flp-catalyzed excision of the antibiotic-resistance determinant", Gene. Elsevier. Amsterdam. NL, vol. 1, 158, No. 1, Jan. 1, 1995 (Jan. 1, 1995). pp. 9-14, XP004206666.
You et al., "Gene-specific disruption in the filamentous fungus *Cercospora nicotianae* using a split-marker approach", Archives of Microbiology. Springer, Berlin, DE, vol. 191, No. 7, Jun. 9, 2009, (Jun. 9, 2009), pp. 615-622. XP019701743.
Uemura et al., "Chromosomal Manipulation by Site-Specific Recombinases and Fluorescent Protein-Based Vectors", PLoS One, vol. 5, No. 3, Mar. 24, 2010 (Mar. 24, 2010), p. E9846. XP055033795.
Metzger et al., Conditional Site-Specific Recombination in Mammaliancells Using a Ligand-Dependent Chimeric Cre Recombinase, Proceedings of the National Academy of Sciences. National Academy of Sciences, US, vol. 92, No. 15, Jul. 18, 1995 (Jul. 18, 1995), pp. 6991-6995, XP000615550.
Fu et al., "Split marker transformation increases homologous integration frequency in Cryptococcus neoformans." Fungal Genetics and Biology (2006) 43(3) 200-212. XP024918894.
Bode et al., "The Transgeneticist's Toolbox: Novel Methods for the Targeted Modification of Eukaryotic Genomes" Biol. Chem. 381 (2000) 801-813. XP002282829.

(Continued)

*Primary Examiner* — Nancy J Leith
(74) *Attorney, Agent, or Firm* — McBee Moore Woodward & Vanik IP, LLC

(57) ABSTRACT

The present invention relates to a method for carrying out recombination at a target locus.

16 Claims, 13 Drawing Sheets

(56) References Cited

OTHER PUBLICATIONS

Sauer, "Functional Expression of the cre-lox Site-Specific Recombination System in the Yeast *Saccharomyces cerevisiae*." Molecular and Cellular Biology, 1987, vol. 7, pp. 2087-2096.
Waters et al., "Talaromyces emersonii Thermostable Enzyme Systems and Their Applications in Wheat Baking Systems." Journal of Agricultural and Food Chemistry, 2010, vol. 58, pp. 7415-7422.
Fairhead et al., "New Vectors for Combinatorial Deletions in Yeast Chromosomes and for Gap-repair Cloning using 'Split-marker' Recombination." Yeast, 1996, vol. 12, pp. 1439-1457.
International Search Report received in corresponding PCT/EP2013/055051, mailed Jul. 4, 2013.
Houbraken et al., A new genus comprising thermotolerant and thermophilicandspecies, Antonie Van Leeuwenhoek. Kluwer Academic Publishers. DO, vol. 101, No. 2, Oct. 2, 2011 (Oct. 2, 2011), pp. 403-421, XP03500386.
Heinzelman et al: "Efficient screening of fungal cellobiohydrolase class I enzymes for thermostabilizing sequence blocks by SCHEMA structure-guided recombination", protein Engineering, Design & Selection, Sep. 16, 2010 (Sep. 16, 2010), pp. 871-880, XP055045668.
Database, UniProt, Mar. 3, 2009 (Mar. 3, 2009), "SubName: Full=DNA repair protein Rad50;" XP002699061, retrieved from EBI accession No. Un i Prot:B8LXJ 1, Database accession No. B8LXJ1.
Database UniProt [Online], Mar. 3, 2009 (Mar. 3, 2009), "SubName: Full=DSB repair complex subunit Ku70, putative;", XP002699062, retrieved from EBI accession No. UniProt:B8MR17, Database accession No. B8MR17.
Database UniProt [Online], May 31, 2011 (May 31, 2011), "SubName: Full=Meiotic recombination protein dmc1;", XP002699063, retrieved from EBI accession No. UniProt:F2THH5, Database accession No. F2THH5.
International Search Report dated Apr. 26, 2013, issued in PCT/EP2013/055047.
Jain et al., "Development of a transformation system for the thermophilic fungus *Talaromyces* sp. CL240 based on the use of phleomycin resistamce as a dominant selectable marker." Mol Gen Genet (1992) 234: 489-493.
Murray et al., "Isolation of the glucose oxidase gene from Talaromyces flavus and characterisation of its role in the biocontrol of Verticillium dahliae." Curr Genet (1997) 32: 367-375.
Cheng, Tzu-Hao et al., "Controlling gene expression in yeast by inducible site-specific recombination", Nucleic Acids Research, 2000, pp. 1-6, vol. 28, No. 24.
Fairhead, Cecile et al., "New Vectors for Combinatorial Deletions in Yeast Chromosomes and for Gap-repair Cloning using 'Split-marker' Recombination", Nov. 1996, Yeast, pp. 1439-1457, vol. 12.
Forment, Josep V. et al., "Consecutive gene deletions in Aspergillus nidulans: application of the Cre/loxP system", Curr Genet, 2006, pp. 217-224, vol. 50.
Hirrlinger, Johannes et al., "Split-Cre Complementation Indicates Coincident Activity of Different Genese In Vivo" PLoS One, Jan. 2009, pp. 1-10, vol. 4, No. 1.

* cited by examiner

17% marker loss

79% marker loss

CBS393.64        deltaReKu80-2

Fig. 23 Step 1, transformation of the PCR fragments results in integration of all fragments in the ADE1 locus. Step 2, induction with Galactose induces Cre expression. KanMX marker and Cre are looped out leaving only the lox72 sequence in the genome.

even though the invention is exemplified using filamentous fungi, it is generally applicable for use in any cellular system. The use of counterselectable markers of prior art methods would complicate the invention as it is likely that counterselection could be achieved before the removal of the markers was completed.

RECOMBINATION SYSTEM

CROSS REFERENCE TO RELATED APPLICATIONS

This application is a §371 National Stage Application of PCT/EP2013/055048, filed Mar. 12, 2013, which claims priority to EP 12159098.8, filed Mar. 12, 2012.

BACKGROUND

Field of the Invention

The present invention relates to a method for carrying out recombination at a target locus. The method also relates to cell prepared according to a method of the invention which is carried out in vivo.

Description of Related Art

Different cell types may be used for different industrial purposes. For example: mammalian cell lines are used for antibody production; fungal cells are preferred organisms for production of polypeptides and secondary metabolites; bacterial cells are preferred for small metabolite and antibiotic production; and plant cells are preferred for taste and flavor compounds.

Recombinant techniques are widely employed for optimization of the productivity of such cells and/or the processes in which they are used. This can involve a multitude of options, including, but not limited to over expression of a gene of interest, deletion or inactivation of competing pathways, changing compartmentalization of enzymes, increasing protein or metabolite secretion, increasing organelle content and the like.

In the case of filamentous fungi, the limited availability of selectable markers complicates the construction of new cell lines. Typically, target sequences are altered in vitro to create mutant alleles with inserted antibiotic resistance markers. However, regulatory authorities in most countries object to the use of antibiotic resistance markers in view of the potential risks of spreading resistance genes to the biosphere from large-scale use of production strains carrying such genes. In addition, there is a limited number of selectable markers suitable for use in filamentous fungi.

Accordingly, selectable marker genes may need to be removed so that production strains may be used commercially and/or so that the same marker gene may be recycled for use in sequential strain modification.

SUMMARY

The invention concerns a method for carrying out recombination at a target locus, or target loci, for example within a target genome. The recombination method of the invention results in alteration of the target locus, for example the insertion of nucleic acid sequence at the target locus. The method may be carried out such that insertion of new sequence at the target locus is accompanied by removal of existing sequence from the target locus. That is to say, the method may be used to substitute a sequence at the target locus with an alternative sequence. The method may conveniently be carried out in vivo in a host cell.

Typically, when carried out in vivo, the method of the invention is not carried out on a human or animal cell. That is to say, the method of the invention is not typically carried out in the form of a method of treatment. The method of the invention may be carried out in an ex vivo or in vitro format. The terms ex vivo or in vitro should be understood to encompass methods carried out on microorganisms (both on whole living cells or on non-cellular material), but to exclude methods carried out on humans or animals.

The method is typically carried out such that at least part of the sequence inserted at the target locus is subsequently removed. If the method is carried out such that substitution of a sequence occurs at the target locus, followed by removal of the inserted sequence, the result may be deletion of sequence from the target locus.

Accordingly, the method of the invention may be carried out to achieve alteration of, the sequence of, the target locus. Such alteration may be, for example addition of new sequence, replacement of existing sequence and/or deletion/removal of existing sequence.

Typically, the invention is carried out in vivo in a host cell. The host cell may, preferably, be one which produces a compound of interest. The host cell may be capable of producing the compound of interest prior to application of the method of the invention. In this case, the method of the invention may be used to modify the target locus so that production of the compound of interest by the host cell is altered, for example production may be increased. Alternatively, the host cell may be one which produces the compound of interest as a result of application of the method of the invention.

According to the invention, there is thus provided a method for carrying out recombination at a target locus, which method comprises:

providing two or more nucleic acids which, when taken together, comprise: (a) sequences capable of homologous recombination with sequences flanking the target locus; (b) two or more site-specific recombination sites; (c) a sequence encoding a recombinase which recognizes the site-specific recombination sites; and (d) a sequence encoding a marker, wherein the two or more nucleic acids are capable of homologous recombination with each other so as to give rise to a single nucleic acid, and wherein at least two of the two or more nucleic acids each comprise a sequence encoding a non-functional portion of a marker gene; and recombining the said two or more nucleic acids with each other and with the sequences flanking the target locus so that a contiguous nucleic acid sequence encoding a functional marker and/or essential gene and the sequence encoding the recombinase are inserted at the target locus, said marker-encoding and/or recombinase-encoding sequence being flanked by at least two site-specific recombination sites and the said site-specific recombination sites being flanked by the sequences capable of homologous recombination with sequences flanking the target locus.

Thus, the at least two of the two or more nucleic acids each comprising a sequence encoding a non-functional portion of a marker gene, each comprise a partial sequence, which after recombination encodes a functional marker (and wherein the parts by itself do not encode for a functional marker.

The invention also relates to a cell produced by a process according to the invention which is carried out in vivo.

The method of the invention is advantageous in comparison with current methods in that it allows the continuous use of non-counterselectable markers in strain transformations. This is advantageous, in particular in filamentous fungi, where a limited number of counterselectable markers are known and recycling of markers for repetitive use is of utmost importance. In addition, This system allows the use of vectors which do not comprise a full knock-out cassette in a single polynucleotide. This avoids cloning problems and a more stable nucleotide fragment (a site-specific recombinase cannot work on its recombination sites in yeast or *E. coli* for example since they are not both present).

Also, the method of the invention is carried out using nucleic acid fragment which can be generated via amplification using automated methods. This leads to a more flexible system with higher throughputs since fragment amplification (for example by PCR) is much easier to automate then restriction digestion.

Using the method of the invention, extremely efficient strain construction may be achieved (near 100% efficiency) and the method may be used to generate multiple knock-outs more quickly than using existing techniques since multiple markers may be introduced and/or removed in one step.

Using the method of the invention, strain construction and modifications may be traceable more easily characterized since a site-specific recombination site may remain at the target locus or loci.

BRIEF DESCRIPTION OF THE DRAWINGS

FIG. 10 shows the phenotypic and PCR analysis of marker-free *R. emersonii* transformants. Transformant A-A4, containing multiple *R. emersonii* Cbhl copies and the pDEL_Pdx-A2 plasmid carrying loxP flanked ble expression cassette, was transformed with milliQ water (control) or the pEBA513 construct for transient expression of cre-recombinase.

BRIEF DESCRIPTION OF SEQUENCE LISTING

Figure 1:
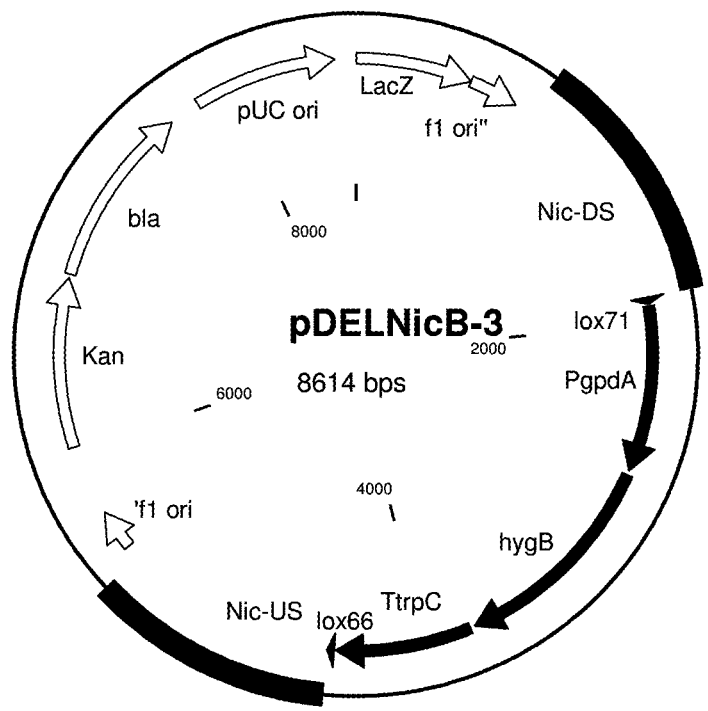
FIG. 1 sets out a schematic diagram of plasmid pDEL-NicB-3, which is the basis for a replacement cassette to inactivate the nicB gene in *A. niger*. The replacement cassette comprises the nicB flanking regions, the hygB marker cassette, mutant loxP sites and *E. coli* DNA. More details for pDELNicB-3 can be found in the Examples section (vide infra).

SEQ ID No: 1 sets out the mutant lox P site, lox66.
SEQ ID No: 2 sets out the mutant lox P site, lox71.
SEQ ID NO: 3 sets out the double-mutant lox72 site.
SEQ ID NO: 4 sets out a first non-functional hygB marker fragment (PgpdA-HygB sequence missing the last 27 bases of the coding sequence at the 3' end of hygB).
SEQ ID NO: 5 sets out a second non-functional hygB fragment (HygB-TtrpC sequence missing the first 44 bases of the coding sequence at the 5' end of hygB).
SEQ ID NO: 6 sets out the cre recombinase cassette containing the A. nidulans xylanase A promoter, a cre recombinase and xylanase A terminator, to allow xylose-inducible expression of the cre recombinase.

SEQ ID NO: 7 sets out the DNA sequence of the Ble-forward PCR primer;

SEQ ID NO: 8 sets out the DNA sequence of the Ble-reverse PCR primer;

SEQ ID NO: 9 sets out the DNA sequence of the EBA205-forward PCR primer;

SEQ ID NO: 10 sets out the DNA sequence of the EBA205-reverse PCR primer;

SEQ ID NO: 11 sets out the DNA sequence of the pGBTOPEBA4-forward PCR primer;

SEQ ID NO: 12 sets out the DNA sequence of the pGBTOPEBA4-reverse PCR primer;

SEQ ID NO: 13 sets out the DNA sequence of the pGBTOPEBA8-forward PCR;

SEQ ID NO: 14 sets out the DNA sequence of the pGBTOPEBA8-reverse PCR;

SEQ ID NO: 15 sets out the DNA sequence of the Pdx-forward PCR primer;

SEQ ID NO: 16 sets out the DNA sequence of the Pdx-reverse PCR primer;

SEQ ID NO: 17 sets out the DNA sequence of the Hyg-forward PCR primer;

SEQ ID NO: 18 sets out the DNA sequence of the Hyg-reverse PCR primer;

SEQ ID NO: 19 sets out the nucleic acid sequence of the ReKu70 genomic region including flanking sequence.

SEQ ID NO: 20 sets out the nucleic acid sequence of the ReKu70 cDNA.

SEQ ID NO: 21 sets out the amino acid sequence of the ReKu70 polypeptide.

SEQ ID NO: 22 sets out the nucleic acid sequence of the ReKu80 genomic region including flanking sequence.

SEQ ID NO: 23 sets out the nucleic acid sequence of the ReKu80 cDNA.

SEQ ID NO: 24 sets out the amino acid sequence of the ReKu80 polypeptide.

SEQ ID NO: 25 sets out the nucleic acid sequence of the ReRad50 genomic region including flanking sequence.

SEQ ID NO: 26 sets out the nucleic acid sequence of the ReRad50 cDNA.

SEQ ID NO: 27 sets out the amino acid sequence of the ReRad50 polypeptide.

SEQ ID NO: 28 sets out the nucleic acid sequence of the ReRad51 genomic region including flanking sequence.

SEQ ID NO: 29 sets out the nucleic acid sequence of the ReRad51 cDNA.

SEQ ID NO: 30 sets out the amino acid sequence of the ReRad51 polypeptide.

SEQ ID NO: 31 sets out the nucleic acid sequence of the ReRad52 genomic region including flanking sequence.

SEQ ID NO: 32 sets out the nucleic acid sequence of the ReRad52 cDNA.

SEQ ID NO: 33 sets out the amino acid sequence of the ReRad52 polypeptide.

SEQ ID NO: 34 sets out the nucleic acid sequence of the ReRad54a genomic region including flanking sequence.

SEQ ID NO: 35 sets out the nucleic acid sequence of the ReRad54a cDNA.

SEQ ID NO: 36 sets out the amino acid sequence of the ReRad54a polypeptide.

SEQ ID NO: 37 sets out the nucleic acid sequence of the ReRad54b genomic region including flanking sequence.

SEQ ID NO: 38 sets out the nucleic acid sequence of the ReRad54b cDNA.

SEQ ID NO: 39 sets out the amino acid sequence of the ReRad54b polypeptide.

SEQ ID NO: 40 sets out the nucleic acid sequence of the ReRad55 genomic region including flanking sequence.

SEQ ID NO: 41 sets out the nucleic acid sequence of the ReRad55 cDNA.

SEQ ID NO: 42 sets out the amino acid sequence of the ReRad55 polypeptide.

SEQ ID NO: 43 sets out the nucleic acid sequence of the ReRad57 genomic region including flanking sequence.

SEQ ID NO: 44 sets out the nucleic acid sequence of the ReRad57 cDNA.

SEQ ID NO: 45 sets out the amino acid sequence of the ReRad57 polypeptide.

SEQ ID NO: 46 sets out the nucleic acid sequence of the ReCDC2 genomic region including flanking sequence.

SEQ ID NO: 47 sets out the nucleic acid sequence of the ReCDC2 cDNA.

SEQ ID NO: 48 sets out the amino acid sequence of the ReCDC2 polypeptide.

SEQ ID NO: 49 sets out the nucleic acid sequence of the ReLIG4 genomic region including flanking sequence.

SEQ ID NO: 50 sets out the nucleic acid sequence of the ReLIG4 cDNA.

SEQ ID NO: 51 sets out the amino acid sequence of the ReLIG4 polypeptide.

SEQ ID NO: 52 sets out the nucleic acid sequence of the ReMRE11 genomic region including flanking sequence.

SEQ ID NO: 53 sets out the nucleic acid sequence of the ReMRE11 cDNA.

SEQ ID NO: 54 sets out the amino acid sequence of the ReMRE11 polypeptide.

SEQ ID NO 55: sets out the DNA sequence of the Ku80-forward PCR primer;

SEQ ID NO 56: sets out the DNA sequence of the Ku80-reverse PCR primer.

SEQ ID NO: 57 sets out the nucleic acid sequence the *Rasamsonia emersonii* pepA genomic region+flanks.

SEQ ID NO: 58 sets out sets out the nucleic acid sequence of the *Rasamsonia emersonii* pepA cDNA.

SEQ ID NO: 59 sets out sets out the amino acid sequence of the *Rasamsonia emersonii* pepA polypeptide.

SEQ ID NO: 60 sets out a first non-functional ble marker fragment (PgpdA-ble sequence missing the last 104 bases of the coding sequence at the 3' end of ble).

SEQ ID NO: 61 sets out a second non-functional ble fragment (ble-TtrpC sequence missing the first 12 bases of the coding sequence at the 5' end of ble). SEQ ID NO: 62 sets out the sequence of basic construct 1

SEQ ID NO: 63 sets out the Sequence of basic construct 2

SEQ ID NO: 64 sets out the sequence of forward primer Left ADE1 KO flank

SEQ ID NO: 65 sets out the sequence of the reverse primer left ADE1 KO flank

SEQ ID NO: 66 sets out the sequence of the forward primer basic construct 1 with 50 bp ADE1 KO flank SEQ ID NO: 67 sets out the sequence of the reverse primer basic construct 1

SEQ ID NO: 68 sets out the sequence of the forward primer basic construct 2 creating overlap towards basic construct 1

SEQ ID NO: 69 sets out the sequence of the reverse primer basic construct 2 with 50 bp ADE1 KO flank SEQ ID NO: 70 sets out the sequence of the forward primer for amplification of right ADE1 KO flank SEQ ID NO: 71 sets out the sequence of the reverse primer for amplification of right ADE1 KO flank SEQ ID NO: 72 sets out the sequence of the PCR fragment 1 left flank ADE1

SEQ ID NO: 73 sets out the sequence of the PCR fragment 2 Basic construct 1 with ADE1 KO flanks SEQ ID NO: 74 sets out the sequence of the PCR fragment 3 Basic construct 2 with ADE1 KO flanks SEQ ID NO: 75 sets out the sequence of the PCR fragment left flank ADE1

DETAILED DESCRIPTION OF A PREFERRED EMBODIMENT

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The method according to the invention is one for carrying out recombination at a target locus. Recombination refers to a process in which a molecule of nucleic acid is broken and then joined to a different one. The recombination process of the invention typically involves the artificial and deliberate recombination of disparate nucleic acid molecules, which may be from the same or different organism, so as to create recombinant nucleic acids.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

The method of the invention relies on a combination of homologous recombination and site-specific recombination.

"Homologous recombination" refers to a reaction between nucleotide sequences having corresponding sites containing a similar nucleotide sequence (i.e., homologous sequences) through which the molecules can interact (recombine) to form a new, recombinant nucleic acid sequence. The sites of similar nucleotide sequence are each referred to herein as a "homologous sequence". Generally, the frequency of homologous recombination increases as the length of the homology sequence increases. Thus, while homologous recombination can occur between two nucleic acid sequences that are less than identical, the recombination frequency (or efficiency) declines as the divergence between the two sequences increases. Recombination may be accomplished using one homology sequence on each of two molecules to be combined, thereby generating a "single-crossover" recombination product. Alternatively, two homology sequences may be placed on each of two molecules to be recombined. Recombination between two homology sequences on the donor with two homology sequences on the target generates a "double-crossover" recombination product.

If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule.

"Site-specific recombination", also known as conservative site-specific recombination, is a type of recombination in which nucleic acid strand exchange takes place between segments possessing only a limited degree of sequence homology. Site-specific recombinase enzymes perform rearrangements of nucleic acid segments by recognizing and binding to short DNA sequences (sites), at which they cleave the DNA backbone, exchange the two DNA helices involved and rejoin the DNA strands. In some site-specific recombination systems having just a recombinase enzyme together with the recombination sites is enough to perform all these reactions, in some other systems a number of accessory proteins and accessory sites may also needed.

The method may be use to carry out recombination at a target locus resulting in modification of that target locus. Accordingly, the invention may be used to add, delete or otherwise change a target locus. The target locus may be a coding or a non-coding sequence. The method of the invention may be used so that such coding or non-coding sequence may be disrupted and/or partially or fully deleted and/or replaced. Thus, the method of the invention may be used to replace sequence at target locus, for example with a marker-encoding sequence.

Typically, the invention is carried out in vivo in a host cell (such as a cell of a microorganism). The host cell may, preferably, be one which produces a compound of interest. The host cell may be capable of producing the compound of interest prior to application of the method of the invention. In this case, the method of the invention may be used to modify the target locus so that production of the compound of interest by the host cell is altered, for example production may be increased. Alternatively, the host cell may be one which produces the compound of interest as a result of application of the method of the invention.

Accordingly, the invention may be used, for example, in the optimization of the productivity of a host cell and/or the processes in which they are used. Alternatively, the invention may be used, for example, to introduce novel nucleic acids such that the host cell is rendered capable of producing a new compound of interest. The invention may be used sequentially, such that a plurality of novel nucleic acid sequences is introduced into the host cell, resulting in the introduction of an entirely new pathway or metabolic pathway.

A target locus may be any nucleic sequence which is to be modified. Typically, the target locus may be a sequence within a genome (the complete genetic material of an organism), for example a locus on a chromosome. Such a chromosome could be a linear or a circular chromosome. However, the target locus could be extrachromosomal for example a locus on a plasmid, a minichromosome or artificial chromosome. The target locus may be located on a plasmid, a phage, or any other nucleic acid sequence which is able to replicate or be replicated in vitro or in a host cell The method of the invention may be carried out in vitro, ex vivo or in vivo.

The method of the invention comprises:
providing two or more nucleic acids which, when taken together, comprise: (a) sequences capable of homologous recombination with sequences flanking the target locus; (b) two or more site-specific recombination sites; (c) a sequence encoding a recombinase which recognizes the site-specific recombination sites; and (d) a sequence encoding a marker,
wherein the two or more nucleic acids are capable of homologous recombination with each other so as to give rise to a single nucleic acid, and wherein at least two of the two or more nucleic acids each comprise a sequence encoding a non-functional portion of the marker; and recombining the said two or more nucleic acids with each other and with the sequences flanking the target locus so that a contiguous nucleic acid sequence encoding a functional marker and the sequence encoding the recombinase are inserted at the target locus, said marker-encoding and/or recombinase-encoding sequence being flanked by at least two site-specific recombination sites and the said site-specific recombination sites being flanked by the sequences capable of homologous recombination with sequences flanking the target locus.

In the invention, at least two of the two or more nucleic acids each comprise a sequence encoding a non-functional portion of a marker. That is to say, the marker-encoding sequence is split across at least two of the two or more nucleic acids. Accordingly, the method may be referred to as a split-marker approach.

Out-recombination of the nucleic acid sequence between the site-specific recombination sites, for example of the marker, may be carried out in vivo.

In the method of the invention, the in vivo recombination may be carried out in any suitable host cell, for example carried out in a prokaryotic or a eukaryotic cell.

In the method of the invention, recombination of the nucleic acids with each other and with the target locus is carried out in vivo.

In the method of the invention, two or more nucleic acids are provided. Taken together, the two or more nucleic acids provide: (a) sequences capable of homologous recombination with sequences flanking the target locus; (b) two or more site-specific recombination sites; (c) a sequence encoding a recombinase which recognizes the site-specific recombination sites; and (d) a sequence encoding a marker It is not intended that each of the two or more nucleic acids comprises the sequences set out in (a), (b), (c) and (d). Rather, the sequences set out in (a), (b), (c) and (d) must be comprised by the two or more nucleic acids when those nucleic acids are taken together as a group. Thus, one nucleic acid may comprise one or more of the sequences set out in (a), (b), (c) (d) and a second nucleic acid may comprise the other sequences set out in (a), (b), (c) and (d). Typically, each of the two or more nucleic acids will comprise at least one of the sequences set out in (a), (b), (c) and (d). However, additional nucleic acids may be provided which do not comprise at least one of the sequences set out in (a), (b), (c) or (d).

Figure 6:
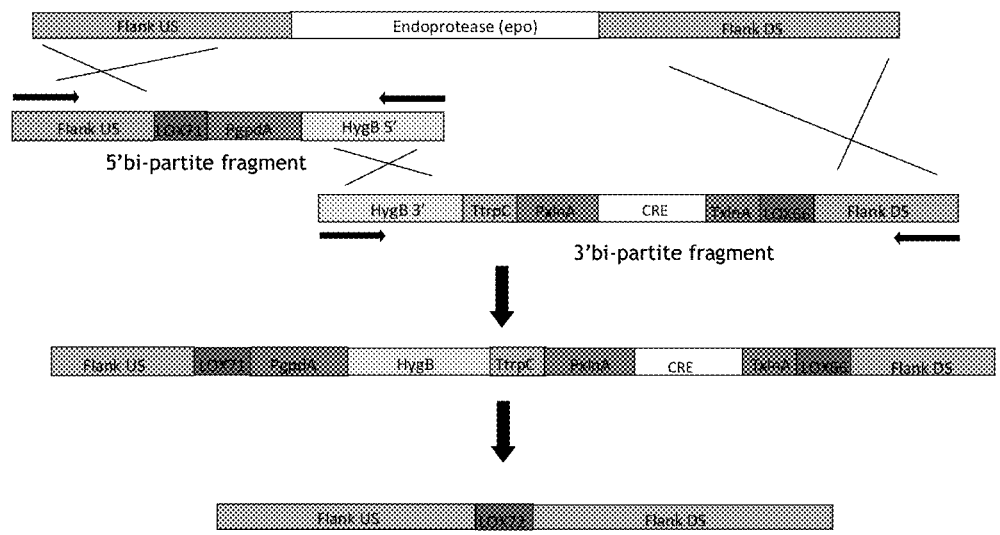
FIG. 6 sets out sets out a schematic representation for fragment generation and use of these fragments in transformation and recombination in *A. niger* as also shown in FIG. 5. The respective bipartite fragments in this specific example differ since they comprise a Cre recombinase cassette in addition. The last panel shows resulting layout of the genomic locus after a Cre induced recombination event.

One format for the method is set out in FIG. 6 in which two nucleic acids are used, but the skilled person will readily be able to conceive of further formats. The number of nucleic acids used in the method may be two, three, four, five, six or more.

Typically, the marker-encoding sequence will be split over two nucleic acid sequences (each of these two nucleic acid sequences encoding a non-functional portion of the marker, but when recombined the two will encode a functional marker). However, the marker-encoding sequence could be split of three, four or more nucleic acid sequences.

When the marker-encoding sequence is split over two nucleic acid sequences, each of those two sequences may typically also comprise a site-specific recombination site. This approach is shown is FIG. 6. Alternatively, the site-specific recombination sites may be provided on additional nucleic acid sequences capable of recombining with the nuclei acid sequences comprising the marker-encoding sequence.

In the method of the invention, the two or more nucleic acids are capable of homologous recombination with each other so as to give rise to a single nucleic acid. The nucleic acids are incorporated as a single contiguous sequence at a target locus due to the presence of the sequences capable of homologous recombination with sequences flanking the target locus. In addition, at least two of the two or more nucleic acids each comprise a sequence encoding a non-functional portion of the marker.

Accordingly, in the method of the invention, the two or more nucleic acids are recombined with each other and with sequences flanking the target locus. In this way, a contiguous nucleic acid sequence encoding a functional marker may be inserted at the target locus together with a recombinase-encoding sequence and at least two site-specific recombination sites. This functional marker-encoding sequence is typically inserted at the target locus such that it is flanked by at least two site-specific recombination sites. When the recombinase is expressed, the sequence situated between the site-specific recombination sites may be out-recombined. If the marker-encoding and/or recombinase-encoding sequence is located between the site-specific recombination sites, it/they will be out-recombined. However, if the marker-encoding and/or recombinase-encoding sequence sequence lies outside the site-specific recombination sites, it will be retained at the target locus.

When recombination has taken place, the site-specific recombination sites, marker and recombinase sequence will be flanked by the sequences capable of homologous recombination with sequences flanking the target locus.

It also be possible to carry out the method of the invention by adding the recombinase separately, using for example a plasmid (comprising a sequence encoding the recombinase), or by use of direct addition of a recombinase protein.

The method of the invention may be carried out so that more than one, for example two, three, four, five or more target loci are targeted simultaneously. In such a method, the two or more nucleic acids, when taken together, comprise sequences capable of homologous recombination with sequences flanking two or more target loci. In this way, recombination of the said two or more nucleic acids with each other and with the sequences flanking the target loci results in the insertion of at least two site-specific recombination sites at each target loci. The two or more nucleic acids provided are such that a nucleic acid sequence encoding a functional recombinase is inserted in at least one target locus, optionally located between at least two site-specific recombination sites. It is not necessary for other target loci to comprise a function recombinase-encoding sequence, but each target loci will comprise at least two site-specific recombination sites (which may be targeted by the recombinase). At least two nucleic acids are provided, each comprising sequence encoding a non-functional marker. Thus, one or more functional marker-encoding sequences may be inserted at one or more of the target loci. The method of the invention may though be carried out such that a sequence encoding a functional marker is inserted at all or some of the target loci.

Again, at each target locus, the said site-specific recombination sites and any marker-encoding and recombinase-encoding sequence will be flanked by the sequences capable of homologous recombination with sequences flanking the target locus.

In the method of the invention, the two or more nucleic acids are capable of homologous recombination with each other so as to give rise to a single nucleic acid. The nucleic acids are incorporated as a single contiguous sequence at a target locus due to the presence of the sequences capable of homologous recombination with sequences flanking the target locus.

In more detail, the two or more nucleic acids provided in the invention, when taken together, comprise sequences capable of homologous recombination two or more homologous recombination sites directed against the target locus. Where the method targets a single target locus typically, the two or more nucleic acids will provide two such sequences. These sequences are provided such that a contiguous nucleic acid sequence comprising the at least two or more nucleic acids (when recombined with each other) is inserted at the target locus via recombination with substantially homologous sequences which flank the target sequence.

It will be obvious to the skilled person that, in order to achieve homologous recombination via a double cross-over event, these flanking sequences need to be present at both sides/ends of the contiguous sequence resulting from recombination of the two or more nucleic acids and need to be substantially homologous to sequences at both sides of the target loci. Thus, the sequences capable of homologous recombination are typically provided such that they are located at the "5'" and "3'" ends of the nucleic acid sequence resulting from recombination of the two or more nucleic acids.

Moreover, the at least two nucleic acids provided according to the invention are capable of undergoing recombination with each other. Thus, the ends of the nucleic acids are conveniently designed such that this may take place and that the nucleic acids will be assembled in the desired orientation and order. Accordingly the sequence of the ends of a provided nucleic acid will be substantially homologous to the sequences of the ends of the nucleic acids with which it is intended to be recombined.

With the term "substantially homologous" as used in this invention is meant that a first nucleic acid sequence has a degree of identity with a second nucleic acid sequence with which it is to be recombined of at least about 70%, at least about 80%, preferably at least about 90%, at least 95%, at least 98%, at least 99%, most preferably 100% over a region of not more than about 3 kb, preferably not more than about 2 kb, more preferably not more than about 1 kb, even more preferably not more than about 0.5 kb, even more preferably not more than about 0.2 kb, even more preferably not more than about 0.1 kb, such not more than about 0.05 kb, for example not more than about 0.03 kb. In filamentous fungi, the optimal size may be from about 500 bp to about 2.5 kb. The degree of required identity may thereby depend on the length of the substantially homologous sequence. The shorter the homologous sequence, the higher the percentage homology may be.

In the invention, the two or more nucleic acids, taken together, comprise two or more site-specific recombination sites. These site-specific recombination sites are recognised by a recombinase which is encoded by the two or more nucleic acids, taken together.

The site-specific recombination sites and recombinase are selected such that the recombinase may target the site-specific recombination sites leading to out-recombination of sequence locate between the recombination sites.

The terms "recombinase" or "site-specific recombinase" or the like refers to enzymes or recombinases that recognize and bind to a short nucleic acid site or "site-specific recombinase site", i.e., a recombinase recognition site, and catalyze the recombination of nucleic acid in relation to these sites. These enzymes include recombinases, transposases and integrases.

The "site-specific recombinase site" or the like refers to short nucleic acid sites or sequences, i.e., recombinase recognition sites, which are recognized by a sequence- or site-specific recombinase and which become the crossover regions during a site-specific recombination event. Examples of sequence-specific recombinase target sites include, but are not limited to, lox sites, att sites, dif sites and frt sites.

The term "lox site" as used herein refers to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as lox66, lox71, loxP511, loxP514, lox486, lox4117, loxC2, loxP2, loxP3 and lox P23.

The term "frt site" as used herein refers to a nucleotide sequence at which the product of the FLP gene of the yeast 2 micron plasmid, FLP recombinase, can catalyze site-specific recombination.

The site-specific recombination sites may be such that out-recombination following recombinase expression gives rise to a single mutant site-specific recombination site at the target locus which is not recognized by the recombinase. In particular, the lox sites may be lox66 and lox 71 (Albert, H., Dale, E. C., Lee, E., & Ow, D. W. (1995). Site-specific integration of DNA into wild-type and mutant lox sites placed in the plant genome. *Plant Journal*, 7(4), 649-659). In a specific embodiment, the lox66 and lox71 site-specific recombination sites may be such that out-recombination following recombinase expression gives rise to a lox72 mutant site-specific recombination site at the target locus which is not recognized by the recombinase.

In addition to the recombinase, site-specific recombination site and sequences capable of homologous recombination with sequences flanking the target locus, the method of the invention is carried out, wherein the two or more nucleic acids, taken together, comprise a marker-encoding sequence such that recombination of the two or more nucleic acids results in the said marker gene-encoding sequence being inserted at the target locus or loci. Such a marker-encoding sequence may be located between the at least two of the sequences capable of homologous recombination with sequences flanking the target locus or loci.

Critically, the two or more nucleic acids are provided so that at least two of the nucleic acids each comprise a sequence encoding a non-functional part of the marker-encoding sequence. When the two or more nucleic acids are recombined, this gives rise to a contiguous sequence encoding a functional marker. Accordingly, the method of the invention is referred to as a "split-marker" approach.

Non-functional in the context of this invention refers a sequence which does not encode a product capable of acting as a functional selection marker.

Typically, the method may be carried out so that a marker-encoding sequence is located between two or more site-specific recombination sites. In this way, the marker gene may be out-recombined on expression of the recombinase. Accordingly the method can be used for dominant markers and counter selectable markers.

In this way, the method may be carried out in a repeated fashion with more than one cycle of homologous recombination with sequences flanking the target locus followed by out-recombination following recombinase expression using the same marker. This approach may be further combined with the use of mutant site-specific recombination sites which cannot be targeted by the recombinase once the marker has out-recombined.

One advantage of the invention is that it allows multiple recombination events to be carried out simultaneously, sequentially or separately.

Accordingly the method may be carried out in a repeated fashion with more than one cycle of recombination using the same marker. Accordingly the method is especially applicable if a limited set of markers is available. This approach may be further combined with the use of mutant site-specific recombination sites which cannot be targeted by the recombinase once the marker has out-recombined. This allows multiple sites to be targeted and the amount of sites targeted is not limited by the availability of different markers since the marker is eliminated via activation of the recombinase.

In a method of the invention, the two or more nucleic acids, taken together, may comprise two or more different marker-encoding sequences such that recombination of the two or more nucleic acids results in two or more different marker gene-encoding sequence being inserted at a target locus or loci. This method may be carried out where sequences capable of homologous recombination with sequences flanking two or more target loci are provided. It is further possible, that one marker may be used to target at least two target loci and a different marker used to target a one or more further target loci.

In a method of the invention, one of the marker-encoding sequences will be split. In another preferred embodiment of the invention, two or more or even all of the marker-encoding sequences will typically be split. That is to say, for each marker the two or more nucleic acids are provided so that at least two of the nucleic acids each comprise a sequence encoding a non-functional part of the marker-encoding sequence. When the two or more nucleic acids are recombined, this gives rise to a contiguous sequence encoding a functional marker. A method of the invention may include at least one split marker. Typically, all marker-encoding sequences used are provided in a split format.

The method may be carried out such that one or more identical or non-identical markers, each marker being flanked by lox sites, are recombined into a cell. The method of the invention may then be used to provide a further recombination event and at the same time remove all of such markers.

In the method of the invention, the target locus may comprise a coding sequence which is disrupted and/or partially or fully deleted. Typically, the method adds new sequence at the target locus; this new sequence will typically replace, delete and/or modify a sequence at the target locus.

As set out above, the replacement sequence may for instance confer a selectable phenotype when the recombination is carried out in vivo in a host cell. In that case, the replacement sequence comprises a selection marker. Preferentially, such a method is carried out so that the marker may be out-recombined on expression of the recombinase.

The replacement sequence may also be a modified version of the target sequence, for instance to provide for altered regulation of a sequence of interest or expression of a modified gene product with altered properties as compared to the original gene product.

The replacement sequence may also constitute additional copies of a sequence of interest being present in the genome of the host cell, to obtain amplification of that sequence of interest.

The replacement sequence may be a sequence homologous or heterologous to the host cell. It may be obtainable from any suitable source or may be prepared by custom synthesis.

The target sequence may be any sequence of interest. For instance, the target sequence may be a sequence of which the function is to be investigated by inactivating or modifying the sequence. The target sequence may also be a sequence of which inactivation, modification or over expression is desirable to confer on the host cell with a desired phenotype. Typically, the method of the invention will result in some nucleic acid sequence being removed at the target locus. However, the method of the invention may be used to insert sequence at the target locus without any sequence being lost from the target locus.

In the context of this disclosure, the terms "nucleic acid", "nucleic acid sequence", "polynucleotide", "polynucleotide sequence", "nucleic acid fragment", "isolated nucleic acid fragment" may be used interchangeably herein.

These terms encompass nucleotide sequences and the like. A nucleic acid may be a polymer of DNA or RNA that may be single- or double-stranded, that optionally contains synthetic, non-natural or altered nucleotide bases.

A nucleic acid in the form of a polymer of DNA may be comprised of one or more segments of cDNA, genomic DNA, synthetic DNA, or mixtures thereof.

The term "isolated nucleic acid" and the like refers to a nucleic acid that is substantially free from other nucleic acid sequences, such as and not limited to other chromosomal and extrachromosomal DNA and/or RNA. Isolated nucleic acids may be purified from a host cell in which they naturally occur.

Conventional nucleic acid purification methods known to skilled artisans may be used to obtain isolated nucleic acids. The term also embraces recombinant nucleic acids and chemically synthesized nucleic acids. Typically, each of the two or more nucleic acids suitable for use in the invention may be generated by any amplification process known in the art (e.g., PCR, RT-PCR and the like). The terms "amplify", "amplification", "amplification reaction", or "amplifying" as used herein refer to any in vitro process for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is typically different than a one-time, single primer extension step.

The two or more nucleic acids are typically introduced into a host cell so that the recombination events may take place. The two or more nucleic acids can be introduced into a host cell using various techniques which are well-known to those skilled in the art. Non-limiting examples of methods used to introduce heterologous nucleic acids into various organisms include; transformation, transfection, transduction, electroporation, ultrasound-mediated transformation, particle bombardment and the like. In some instances the addition of carrier molecules can increase the uptake of DNA in cells typically though to be difficult to transform by conventional methods. Conventional methods of transformation are readily available to the skilled person.

The procedures used to generate the two or more nucleic acids and to then introduce them into a host cell are well known to one skilled in the art (see, e.g. Sambrook & Russell, *Molecular Cloning: A Laboratory Manual*, 3rd Ed., CSHL Press, Cold Spring Harbor, N.Y., 2001; and Ausubel et al., *Current Protocols in Molecular Biology*, Wiley Inter-Science, NY, 1995).

Furthermore, standard molecular biology techniques such as DNA isolation, gel electrophoresis, enzymatic restriction modifications of nucleic acids, Southern analyses, transformation of cells, etc., are known to the skilled person and are for example described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego.

A nucleic acid suitable for use in the method of the invention may be amplified using cDNA, mRNA or alternatively, genomic DNA, as a template and appropriate oligonucleotide primers according to standard PCR amplification techniques. The nucleic acid so amplified can be cloned into an appropriate vector if desirable and/or characterized by nucleic acid sequence analysis.

The method of the invention may be carried out such that the two or more nucleic acids are recombined as a single nucleic acid which is then recombined with the target locus.

The method of the invention may be carried out where recombination of the said two or more nucleic acids with each other and with the target locus takes place simultaneously.

In a method of the invention two of the at least two nucleic acids may each comprise a part of the marker-encoding sequence such that together they comprise the entire marker-encoding sequence.

The method of the invention may be carried out so that the recombinase directed against the site-specific recombination sites is expressed such that the sequence located between the two site-specific recombination sites is out-recombined.

The expression of the marker and recombinase will typically be under the control of control sequences including a promoter which enable expression of the recombinase within the host cell. That is to say, the marker- and recombinase-encoding sequences will typically be in operable linkage with a promoter sequence.

The term "operable linkage" or "operably linked" or the like are defined herein as a configuration in which a control sequence is appropriately placed at a position relative to the coding sequence of the DNA sequence such that the control sequence directs the production of an mRNA or a polypeptide.

The term "control sequences" is defined herein to include all components, which are necessary or advantageous for the production of mRNA or a polypeptide, either in vitro or in a host cell. Each control sequence may be native or foreign to the nucleic acid sequence encoding the polypeptide. Such control sequences include, but are not limited to, a leader, Shine-Delgarno sequence, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and a transcriptional stop signal as well as translational start and stop signals. Control sequences may be optimized to their specific purpose. Preferred optimized control sequences used in the present invention are those described in WO2006/077258.

The term "promoter" is defined herein as a DNA sequence that binds RNA polymerase and directs the polymerase to the correct downstream transcriptional start site of a nucleic acid sequence encoding a biological compound to initiate transcription. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors.

Accordingly, a marker may be split by providing a promoter on a first nucleic acid and the coding sequence on a second nucleic acid such that the promoter and coding sequence are brought into operable linkage on recombination, i.e. recombination will give rise to a functional marker-encoding sequence.

The promoter may be any appropriate promoter sequence suitable for a eukaryotic or prokaryotic host cell, which shows transcriptional activity, including mutant, truncated, and hybrid promoters, and may be obtained from polynucleotides encoding extra-cellular or intracellular polypeptides either homologous (native) or heterologous (foreign) to the cell. The promoter may be a constitutive or inducible promoter. Expression of the recombinase by an inducible promoter will allow out-recombination of the sequence located between the site-specific recombination sites to be controlled, for example including the recombinase encoding sequence.

The promoter may be a constitutive or inducible promoter.

Examples of inducible promoters that can be used are a starch-, cellulose-, hemicellulose (such as xylan- and/or xylose-inducible), copper-, oleic acid-inducible promoters. The promoter may be selected from the group, which includes but is not limited to promoters obtained from the polynucleotides encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof. Other examples of promoters are the promoters described in WO2006/092396 and WO2005/100573, which are herein incorporated by reference. An even other example of the use of promoters is described in WO2008/098933. Other examples of inducible (heterologous) promoters are the alcohol inducible promoter alcA, the tet system using the tetracycline-responsive promoter, the estrogen-responsive promoter (Pachlinger et al. (2005), Appl & Environmental Microbiol 672-678).

The control sequences may also include suitable transcription terminator (terminator) sequence, a sequence recognized by a filamentous fungal cell to terminate transcription. The terminator sequence is operably linked to the 3'-terminus of the nucleic acid sequence encoding the polypeptide. Any terminator, which is functional in the cell, may be used in the present invention.

The control sequence may also be a suitable leader sequence (leaders), a non-translated region of an mRNA which is important for translation by the filamentous fungal cell. The leader sequence is operably linked to the 5'-terminus of the nucleic acid sequence encoding the polypeptide. Any leader sequence, which is functional in the cell, may be used in the present invention.

Depending on the host, suitable leaders may be obtained from the polynucleotides encoding *A. oryzae* TAKA amylase and *A. nidulans* triose phosphate isomerase and *A. niger* GlaA and phytase.

Other control sequences may be isolated from the *Penicillium* IPNS gene, or pcbC gene, the beta tubulin gene. All the control sequences cited in WO 01/21779 are herewith incorporated by reference.

The control sequence may also be a polyadenylation sequence, a sequence which is operably linked to the 3'-terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention.

As set out herein, in a method of the invention, the two or more nucleic acids, taken together, may comprise a sequence encoding a marker so that recombination of the two or more nucleic acids results in the said marker-encoding sequence being located between the homologous recombination sites.

Recombination of the two or more nucleic acids may result in the said marker-encoding sequence being located between the site-specific recombination sites such that the marker may be out-recombined on expression of the recombinase.

Any suitable marker may be used and such markers are well-known to determine whether a nucleic acid is included in a cell. Typically, a marker, such as a selectable marker, permits easy selection of transformed cells. A selectable marker is a gene the product of which provides for biocide or viral resistance, resistance to heavy metals, prototrophy to auxotrophs, and the like.

Examples of marker genes include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotic resistance markers (e.g., β-lactamase), β-galactosidase, fluorescent or other coloured markers, such as green fluorescent protein (GFP), yellow fluorescent protein (YFP), red fluorescent protein (RFP) and cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments as described in 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; (13) nucleic acid segments that encode conditional replication functions, e.g., replication in certain hosts or host cell strains or under certain environmental conditions (e.g., temperature, nutritional conditions, and the like); and/or nucleic acid segments that encode an essential gene.

A selectable marker for use in a filamentous fungal cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), NAT or NTC (Nourseothricin) and trpC (anthranilate synthase), as well as equivalents from other species. Preferred for use in an *Aspergillus*, and *Penicillium* cell are the amdS (see for example EP 635574 B1, EP0758020A2, EP1799821A2, WO 97/06261A2) and pyrG genes of *A. nidulans* or *A. oryzae* and the bar gene of *Streptomyces hygroscopicus* and hyg and pheo. More preferably an amdS gene is used, even more preferably an amdS gene from *A. nidulans* or *A. niger*. A most preferred selectable marker gene is the *A. nidulans* amdS coding sequence fused to the *A. nidulans* gpdA promoter (see EP 635574 B1). Other preferred AmdS markers are those described in WO2006/040358. AmdS genes from other filamentous fungi may also be used (WO 97/06261).

In the method of the invention, the in vivo recombination may be carried out in any suitable host cell, for example carried out in a prokaryotic or a eukaryotic cell. A suitable eukaryotic host cell may be a mammalian, insect, plant, fungal or algal cell. A host cell may be a microorganism or microbial host cell, for example a prokaryotic or eukaryotic host cell. Typically, the method of the invention will not be carried out in vivo in a human or animal.

Typically, a host cell used in the method according to the invention may be one suitable for the production of a compound of interest and the selection of the host cell may be made according to such use. For example, if the compound of interest produced in a host cell according to the invention is to be used in food applications, a host cell may be selected from a food-grade organism such as *Saccharomyces cerevisiae*. Specific uses include, but are not limited to, food, (animal) feed, pharmaceutical, agricultural such as crop-protection, and/or personal care applications.

The method of the invention may be used to confer on a host cell the ability to produce the compound of interest and/or to modify the way in which an existing compound of interest is produced, for example to increase the production of such a compound of interest.

A microbial host cell suitable for use in the method according to the invention may be a prokaryotic cell. Preferably, the prokaryotic host cell is a bacterial cell. The term "bacterial cell" includes both Gram-negative and Gram-positive microorganisms. Suitable bacteria may be selected from e.g. *Escherichia, Anabaena, Caulobactert, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. Preferably, the bacterial cell is selected from the group consisting of *B. subtilis, B. amyloliquefaciens, B. licheniformis, B. puntis, B. megaterium, B. halodurans, B. pumilus, G. oxydans, Caulobactert crescentus* CB 15, *Methylobacterium extorquens, Rhodobacter sphaeroides, Pseudomonas zeaxanthinifaciens, Paracoccus denitrificans, E. coli, C. glutamicum, Staphylococcus carnosus, Streptomyces lividans, Sinorhizobium melioti* and *Rhizobium radiobacter.*

A host cell suitable for use in the invention may be a eukaryotic host cell. Such a eukaryotic cell may be a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, for example a yeast cell, such as *Candida, Hansenula, Kluyveromyces, Pichia, Saccharomyces, Schizosaccharomyces,* or *Yarrowia* strain. More preferably from *Kluyveromyces lactis, S. cerevisiae, Hansenula polymorpha, Yarrowia lipolytica* and *Pichia pastoris*. Most preferably, the eukaryotic cell is a filamentous fungal cell.

Filamentous fungi include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Geosmithia, Humicola, Magnaporthe, Mucor, Myceliophthora, Neocallimastix, Neurospora, Paecilomyces, Penicillium, Piromyces, Phanerochaete, Pleurotus, Rasamsonia, Schizophyllum, Talaromyces, Thermoascus, Thermomyces, Thielavia, Tolypocladium,* and *Trichoderma.*

Preferred filamentous fungal cells belong to a species of an *Acremonium, Aspergillus, Chrysosporium, Myceliophthora, Penicillium, Rasamsonia, Talaromyces, Thielavia, Fusarium* or *Trichoderma* genus, and most preferably a species of *Aspergillus niger, Acremonium alabamense, Aspergillus awamori, Aspergillus foetidus, Aspergillus sojae, Aspergillus fumigatus, Talaromyces emersonii, Talaromyces thermophilus, Thermomyces lanuginosus, Thermoascus thermophilus, Thermoascus aurantiacus, Thermoascus crustaceus, Rasamsonia emersonii, Rasamsonia byssochlamyoides, Rasamsonia argillacea, Rasamsonia brevistipitata, Rasamsonia cylindrospora, Aspergillus oryzae, Chrysosporium lucknowense, Fusarium oxysporum, Myceliophthora thermophila, Trichoderma reesei, Thielavia terrestris* or *Penicillium chrysogenum.* A more preferred host cell belongs to the genus *Aspergillus,* more preferably the host cell belongs to the species *Aspergillus niger.* When the host cell according to the invention is an *Aspergillus niger* host cell, the host cell preferably is CBS 513.88, CBS124.903 or a derivative thereof. A more preferred host cell belongs to the genus *Penicillium,* more preferably the host cell belongs to the species *Penicillium chrysogenum.* When the host cell according to the invention is a *Penicillium chrysogenum* host cell, the host cell preferably is Wisconsin 54-1255 or a derivative thereof. A more preferred host cell belongs to the genus *Rasamsonia* also known as *Talaromyces,* more preferably the host cell belongs to the species *Talaromyces emersonii* also known as *Rasamsonia emersonii.*

In the method of the invention, the in vivo recombination is carried out in a *Rasamsonia* cell. Accordingly, a cell for use in the invention belongs to the genus *Rasamsonia* also known as *Talaromyces,* more preferably the host cell belongs to the species *Talaromyces emersonii* also known as *Rasamsonia emersonii.* When the host cell according to the invention is a *Talaromyces emersonii* also known as *Rasamsonia emersonii* host cell, the host cell preferably is TEC-142S a single isolate of TEC-142 (CBS 124.902) or a derivative thereof.

It may be desirable to use a thermophilic or thermotolerant fungal cell which case *Humicola, Rhizomucor, Myceliophthora, Rasamsonia, Talaromyces, Thermomyces, Thermoascus* or *Thielavia* cells are preferred.

Preferred thermophilic or thermotolerant fungi are *Humicola grisea* var. *thermoidea, Humicola lanuginosa, Myceliophthora thermophila, Papulaspora thermophilia, Rasamsonia byssochlamydoides, Rasamsonia emersonii, Rasamsonia argillacea, Rasamsonia eburnean, Rasamsonia brevistipitata, Rasamsonia cylindrospora, Rhizomucor pusillus, Rhizomucor miehei, Talaromyces bacillisporus, Talaromyces leycettanus, Talaromyces thermophilus, Thermomyces lenuginosus, Thermoascus crustaceus, Thermoascus thermophilus Thermoascus aurantiacus* and *Thielavia terrestris*

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), Agricultural Research Service Patent Culture Collection, Northern Regional Research Center (NRRL), and All-Russian Collection of Microorganisms of Russian Academy of Sciences, (abbreviation in Russian—VKM, abbreviation in English—RCM), Moscow, Russia. Useful strains in the context of the present invention may be *Aspergillus niger* CBS 513.88, CBS124.903, *Aspergillus oryzae* ATCC 20423, IFO 4177, ATCC 1011, CBS205.89, ATCC 9576, ATCC14488-14491, ATCC 11601, ATCC12892, *P. chrysogenum* CBS 455.95, *P. chrysogenum* Wisconsin 54-1255 (ATCC28089), *Penicillium citrinum* ATCC 38065, *Penicillium chrysogenum* P2, *Thielavia terrestris* NRRL8126, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Myceliophthora thermophila* C1, Garg 27K, VKM-F 3500 D, *Chrysosporium lucknowense* C1, Garg 27K, VKM-F 3500 D, ATCC44006 and derivatives thereof.

Eukaryotic cells have at least two separate pathways (one via homologous recombination (HR) and one via non-homologous recombination (NHR)) through which nucleic acids (in particular DNA) can be integrated into the host genome. The yeast *Saccharomyces cerevisiae* is an organism with a preference for homologous recombination (HR). The ratio of non-homologous to homologous recombination (NHR/HR) of this organism may vary from about 0.07 to 0.007.

WO 02/052026 discloses mutants of *S. cerevisiae* having an improved targeting efficiency of DNA sequences into its genome. Such mutant strains are deficient in a gene involved in NHR (KU70).

Contrary to *S. cerevisiae,* most higher eukaryotes such as filamentous fungal cells up to mammalian cells have a preference for NHR. Among filamentous fungi, the NHR/HR ratio ranges between 1 and more than 100. In such organisms, targeted integration frequency is rather low.

Thus, to improve the efficiency of polynucletide assembly at the target locus, it is preferred that the efficiency of homologous recombination (HR) is enhanced in the host cell in the method according to the invention.

Accordingly, preferably in the method according to the invention, the host cell is, preferably inducibly, increased in its efficiency of homologous recombination (HR). Since the NHR and HR pathways are interlinked, the efficiency of HR can be increased by modulation of either one or both pathways. Increase of expression of HR components will increase the efficiency of HR and decrease the ratio of NHR/HR. Decrease of expression of NHR components will also decrease the ratio of NHR/HR The increase in efficiency of HR in the host cell of the vector-host system according to the invention is preferably depicted as a decrease in ratio of NHR/HR and is preferably calculated relative to a parent host cell wherein the HR and/or NHR pathways are not modulated. The efficiency of both HR and NHR can be measured by various methods available to the person skilled in the art. A preferred method comprises determining the efficiency of targeted integration and ectopic integration of a single vector construct in both parent and modulated host cell. The ratio of NHR/HR can then be calculated for both cell types. Subsequently, the decrease in NHR/HR ration can be calculated. In WO2005/095624, this method is extensively described.

Host cells having a decreased NHR/HR ratio as compared to a parent cell may be obtained by modifying the parent eukaryotic cell by increasing the efficiency of the HR pathway and/or by decreasing the efficiency of the NHR pathway. Preferably, the NHR/HR ratio thereby is decreased at least twice, preferably at least 4 times, more preferably at least 10 times. Preferably, the NHR/HR ratio is decreased in the host cell of the vector-host system according to the invention as compared to a parent host cell by at least 5%, more preferably at least 10%, even more preferably at least 20%, even more preferably at least 30%, even more preferably at least 40%, even more preferably at least 50%, even more preferably at least 60%, even more preferably at least 70%, even more preferably at least 80%, even more preferably at least 90% and most preferably by at least 100%.

According to one embodiment, the ratio of NHR/HR is decreased by increasing the expression level of an HR component. HR components are well-known to the person skilled in the art. HR components are herein defined as all genes and elements being involved in the control of the targeted integration of polynucleotides into the genome of a host, said polynucleotides having a certain homology with a certain pre-determined site of the genome of a host wherein the integration is targeted.

The ratio of NHR/HR may be decreased by decreasing the expression level of an NHR component. NHR components are herein defined as all genes and elements being involved in the control of the integration of polynucleotides into the genome of a host, irrespective of the degree of homology of said polynucleotides with the genome sequence of the host. NHR components are well-known to the person skilled in the art. Preferred NHR components are a component selected from the group consisting of the homolog or ortholog for the host cell of the vector-host system according to the invention of the yeast genes involved in the NHR pathway: KU70, KU80, RAD50, MRE11, XRS2, LIG4, LIF1, NEJ1 and SIR4 (van den Bosch et al., 2002, Biol. Chem. 383: 873-892 and Allen et al., 2003, Mol. Cancer Res. 1:913-920). Most preferred are one of KU70, KU80, and LIG4 and both KU70 and KU80. The decrease in expression level of the NHR component can be achieved using the methods well known to those skilled in the art.

Since it is possible that decreasing the expression of components involved in NHR may result in adverse phenotypic effects, it is preferred that in the host cell of the vector-host system according to the invention, the increase in efficiency in homologous recombination is inducible. This can be achieved by methods known to the person skilled in the art, for example by either using an inducible process for an NHR component (e.g. by placing the NHR component behind an inducible promoter) or by using a transient disruption of the NHR component, or by placing the gene encoding the NHR component back into the genome.

Preferably, when the host cell used in the methods according to the invention is a filamentous fungal host cell, the host cell which has been modified in its genome such that it results in a deficiency in the production of at least one non-ribosomal peptide synthase, preferably a non-ribosomal peptide synthase according to the invention, more preferably a non-ribosomal peptide synthase npsE (see International patent application no. WO2012/001169) additionally comprises one or more modifications in its genome in a polynucleotide encoding a product selected from the group of glucoamylase (glaA), acid stable alpha-amylase (amyA), neutral alpha-amylase (amyBI and amyBII), oxalic acid hydrolase (oahA), a toxin, preferably ochratoxin and/or fumonisin, and protease transcriptional regulator prtT such that the host cell is deficient in at least one product encoded by the polynucleotide comprising the modification.

Therefore the fungal host cell additionally comprises modifications in its genome such that it is deficient in at least one of glucoamylase (glaA), acid stable alpha-amylase (amyA), neutral alpha-amylase (amyBI and amyBII), oxalic acid hydrolase (oahA), a toxin, such as ochratoxin and fumonisin, preferably ochratoxin and/or fumonisin, more preferably ochratoxin A and/or fumonisin B2, and protease transcriptional regulator prtT. Preferably, the host cell additionally comprises one or more modifications in its genome in a polynucleotide encoding the major extracellular aspartic protease PepA such that the host cell is deficient in the major aspartic protease PepA. For example the host cell according to the invention may further comprise a disruption of the pepA gene encoding the major extracellular aspartic protease PepA. Preferably the host cell according to the invention additionally comprises one or more modifications in its genome in a polynucleotide encoding the hdfA gene such that the host cell is deficient in hdfA. For example the host cell according to the invention may further comprise a disruption of the hdfA gene or other genes involved in the process of NHEJ (as also described in WO06/040312).

Preferably the host cell additionally may comprise at least two substantially homologous DNA domains suitable for integration of one or more copies of a polynucleotide encoding a compound of interest wherein at least one of the at least two substantially homologous DNA domains is adapted to have enhanced integration preference for the polynucleotide encoding a compound of interest compared to the substantially homologous DNA domain it originates from, and wherein the substantially homologous DNA domain where the adapted substantially homologous DNA domain originates from has a gene conversion frequency that is at least 10% higher than one of the other of the at least two substantially homologous DNA domains. These cells have been described in WO2011/009700. Strains containing two or more copies of these substantially homologous DNA domains are also referred hereafter as strain containing two or more amplicons. Examples of host cells comprising such amplicons are e.g. described in van Dijck et al, 2003, Regulatory Toxicology and Pharmacology 28; 27-35: *On the safety of a new generation of DSM Aspergillus niger enzyme production strains*. In van Dijck et al, an *Aspergillus niger* strain is described that comprises 7 amplified glucoamylase gene loci, i.e. 7 amplicons. In this context preferred host cells which may contain two or more amplicons belong to a species of a *Acremonium, Agaricus, Aspergillus, Aureobasidium, Chrysosporium, Coprinus, Cryptococcus, Filibasidium, Fusarium, Geosmithia, Humicola, Magnaporthe, Mucor, Myceliophthora, Neocallimastix, Neurospora, Paecilomyces, Penicillium, Piromyces, Phanerochaete, Pleurotus, Rasamsonia, Schizophyllum, Talaromyces, Thermoascus, Thermomyces, Thielavia, Tolypocladium,* and *Trichoderma.*

Preferred host cells within this context are filamentous fungus host cells, preferably *A. niger* host cells, comprising two or more amplicons, preferably two or more ΔglaA amplicons (preferably comprising 3, 4, 5, 6, 7 ΔglaA amplicons) wherein the amplicon which has the highest frequency of gene conversion, has been adapted to have enhanced integration preference for the polynucleotide encoding a compound of interest compared to the amplicon it originates from. Adaptation of the amplicon can be performed according to any one of the methods described in WO2011/009700 (which is here fully incorporated by reference). An example of these host cells, described in WO2011/009700, are host cells comprising three ΔglaA amplicons being a BamHI truncated amplicon, a SalI truncated amplicon and a Bg/II truncated amplicon and wherein the BamHI amplicon has been adapted to have enhanced integration preference for a polynucleotide encoding a compound of interest compared to the BamHI amplicon it originates from. Host cells comprising two or more amplicons wherein one amplicon has been adapted to have enhanced integration preference for a polynucleotide encoding a compound of interest compared to the amplicon it originates from are hereafter referred as host cells comprising an adapted amplicon.

Preferably, the host cell according to the invention additionally comprises a modification of Sec61. A preferred SEC61 modification is a modification which results in a one-way mutant of SEC61; i.e. a mutant wherein the de novo synthesized protein can enter the ER via SEC61, but the protein cannot leave the ER via SEC61. Such modifications are extensively described in WO2005/123763. Most preferably, the SEC 61 modification is the S376W mutation in which Serine 376 is replaced by Tryptophan.

A preferred filamentous fungal host cell used in the method according to the invention, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII) and oxalic acid hydrolase (oahA). Another preferred host cell, deficient in a non-ribosomal peptide synthase, preferably a non-ribosomal peptide synthase as defined above additionally is deficient in pepA, glucoamylase (glaA), acid stable alpha-amylase (amyA), neutral alpha-amylase (amyBI and amyBII), oxalic acid hydrolase (oahA) and hdfA. Another preferred host cell, deficient in a non-ribosomal peptide synthase, preferably a non-ribosomal peptide synthase as defined above additionally is deficient in pepA, glucoamylase (glaA), acid stable alpha-amylase (amyA), neutral alpha-amylase (amyBI and amyBII), oxalic acid hydrolase (oahA), a toxin, such as ochratoxin and/or fumonisin and hdfA. Another preferred host cell, deficient in a non-ribosomal peptide synthase preferably a non-ribosomal peptide synthase as defined above, additionally is deficient in pepA, glucoamylase (glaA), acid stable alpha-amylase (amyA), neutral alpha-amylase (amyBI and amyBII), oxalic acid hydrolase (oahA), a toxin, such as ochratoxin and/or fumonisin and hdfA. Preferably, these host cells are also deficient in prtT. Therefore another preferred host cell, deficient in a non-ribosomal peptide synthase, preferably a non-ribosomal peptide synthase as defined above, additionally is deficient in pepA, glucoamylase (glaA), acid stable alpha-amylase (amyA), neutral alpha-amylase (amyBI and amyBII), oxalic acid hydrolase (oahA), a toxin, such as ochratoxin and/or fumonisin, prtT and hdfA.

Another preferred host cells, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), ochratoxin, fumonisin, prtT, hdfA and comprises a SEC 61 modification being a S376W mutation in which Serine 376 is replaced by Tryptophan.

Preferably these host cells are filamentous fungal cells, more preferably *A. niger* host cells comprising an adapted amplicon as defined above. Therefore the host cells used in the method according to the invention, deficient in a non-ribosomal peptide synthase, preferably deficient in a non-ribosomal peptide synthase according to the invention, more preferably in a non-ribosomal peptide synthase npsE (see WO2012/001169) are filamentous fungus host cells, preferably *A. niger* host cells additionally deficient in pepA, glucoamylase (glaA), acid stable alpha-amylase (amyA), neutral alpha-amylase (amyBI and amyBII) and oxalic acid hydrolase (oahA) and comprising an adapted amplicon as defined above. Another preferred filamentous fungus host cell such as an *A. niger* host cell, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA) and hdfA and comprises an adapted amplicon as defined above. Another preferred filamentous fungus host cell such as an *A. niger* host cell, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), one or more toxins, preferably ochratoxin and/or fumonisin and hdfA and comprises an adapted amplicon as defined above. Another preferred filamentous fungus host cell such as an *A. niger* host cell, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), one or more toxins, preferably ochratoxin and/or fumonisin and hdfA and comprises an adapted amplicon as defined above. Another preferred filamentous fungus host cell such as an *A. niger* host cell, deficient in a non-ribosomal peptide synthase, preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), one or more toxins, preferably ochratoxin and/or fumonisin prtT and hdfA and comprises an adapted amplicon as defined above.

Another preferred filamentous fungus host cell such as an *A. niger* host cells, deficient in a non-ribosomal peptide synthase preferably deficient in a non-ribosomal peptide synthase according to the invention, more preferably in a non-ribosomal peptide synthase npsE (see WO2012/001169) additionally is deficient in pepA, glucoamylase (glaA), acid stable alpha-amylase (amyA), neutral alpha-amylase (amyBI and amyBII), oxalic acid hydrolase (oahA), one or more toxins, preferably ochratoxin and/or fumonisin, prtT, hdfA, comprises a SEC 61 modification being a S376W mutation in which Serine 376 is replaced by Tryptophan and comprises an adapted amplicon as defined above.

These and other possible host modifications are also described in WO2012/001169, WO2011/009700, WO2007/062936, WO2006/040312 or WO2004/070022.

Typically, in the invention, the host cell will be one which produces a compound of interest. The host cell may be capable of producing the compound of interest prior to application of the method of the invention. In this case, the method of the invention may be used to modify the target locus so that production of the compound of interest by the host cell is altered, for example production may be increased. Alternatively, the host cell may be one which produces the compound of interest as a result of application of the method of the invention.

Accordingly, the host cell preferably comprises a recombinant polynucleotide construct comprising a polynucleotide encoding a compound involved in the synthesis of a compound of interest. The polynucleotide may also directly encode a compound of interest. The recombinant polynucleotide construct encoding a compound of interest or a polypeptide involved in the synthesis of a biological compound of interest may be located on an extrachromosomal vector or at a locus in the genome of the host cell.

A host cell of the invention may be capable of producing a desired compound, such as an enzyme, which optionally may be encoded by a recombinant nucleic acid introduced into the cell.

Typically, such a host cell may harbour one or more genes capable of expressing a cellulase, hemicellulase and/or pectinase. The one or more nucleic acid sequence capable of expressing a cellulase, hemicellulase and/or pectinase may include cellobiohydrolase, endoglucanase and/or beta-glucosidase gene. A suitable cellobiohydrolyse is cellobiohydrolase I and/or cellobiohydrolase II.

Typically then, in the invention, the host cell will be one which produces a compound of interest. The host cell may be capable of producing the compound of interest prior to application of the method of the invention. In this case, the method of the invention may be used to modify the target locus so that production of the compound of interest by the host cell is altered, for example production may be increased. Alternatively, the host cell may be one which produces the compound of interest as a result of application of the method of the invention.

Accordingly, the host cell preferably comprises a recombinant polynucleotide construct comprising a polynucleotide encoding a compound involved in the synthesis of a compound of interest. The polynucleotide may also directly encode a compound of interest. The recombinant polynucleotide construct encoding a compound of interest or a polypeptide involved in the synthesis of a biological compound of interest may be located on an extrachromosomal vector or at a locus in the genome of the host cell.

The compound of interest may a primary metabolite, secondary metabolite, a biopolymer such as a peptide or polypeptide or it may include biomass comprising the host cell itself. The compound may be encoded by a single polynucleotide or a series of polynucleotides composing a biosynthetic or metabolic pathway or may be the direct product of a single polynucleotide or may be products of a series of polynucleotides. The biological compound may be native to the host cell or heterologous. The biological compound may be modified according WO2010/102982.

The term "heterologous biological compound" is defined herein as a biological compound which is not native to the cell; or a native biological compound in which structural modifications have been made to alter the native biological compound.

The term "metabolite" encompasses both primary and secondary metabolites; the metabolite may be any metabolite. Preferred metabolites are citric acid, gluconic acid and succinic acid, antibiotics, bioactive drugs, biofuels and building blocks of biomaterials.

The metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

The primary metabolite may be, but is not limited to, an amino acid, carboxylic acid, fatty acid, nucleoside, nucleotide, sugar, triglyceride, or vitamin.

The term "biopolymer" is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide.

The biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. Polypeptides further include naturally occurring allelic and engineered variations of the above-mentioned polypeptides and hybrid polypeptides. The polypeptides may be a modified polypeptide according WO2010/102982.

The polynucleotide of interest according to the invention may encode an enzyme involved in the synthesis of a primary or secondary metabolite, such as organic acids, carotenoids, antibiotics, anti-cancer drug, pigments isoprenoids, alcohols, fatty acids and vitamins. Such metabolite may be considered as a biological compound according to the present invention.

The compound of interest may be an organic compound selected from glucaric acid, gluconic acid, glutaric acid, adipic acid, succinic acid, tartaric acid, oxalic acid, acetic acid, lactic acid, formic acid, malic acid, maleic acid, malonic acid, citric acid, fumaric acid, itaconic acid, levulinic acid, xylonic acid, aconitic acid, ascorbic acid, kojic acid, coumeric acid, an amino acid, a poly unsaturated fatty acid, ethanol, 1,3-propane-diol, ethylene, glycerol, xylitol, carotene, astaxanthin, lycopene and lutein.

Alternatively, the compound of interest may be a β-lactam antibiotic such as Penicillin G or Penicillin V and fermentative derivatives thereof, a cephalosporin, cyclosporin or lovastatin. The secondary metabolite may be an antibiotic, antifeedant, attractant, bacteriocide, fungicide, hormone, insecticide, or rodenticide. Preferred antibiotics are cephalosporins and beta-lactams.

The biopolymer may be a polysaccharide. The polysaccharide may be any polysaccharide, including, but not limited to, a mucopolysaccharide (e.g., heparin and hyaluronic acid) and nitrogen-containing polysaccharide (eg., chitin). In a more preferred option, the polysaccharide is hyaluronic acid.

The compound of interest may be a peptide selected from an oligopeptide, a polypeptide, a (pharmaceutical or industrial) protein and an enzyme. In such processes the peptide is preferably secreted from the host cell, more preferably secreted into the culture medium such that the peptide may easily be recovered by separation of the host cellular biomass and culture medium comprising the peptide, e.g. by centrifugation or (ultra)filtration.

The polypeptide may be any polypeptide having a biological activity of interest. The term "polypeptide" is not meant herein to refer to a specific length of the encoded product and, therefore, encompasses peptides, oligopeptides, and proteins. Polypeptides further include naturally occurring allelic and engineered variations of the above-mentioned polypeptides and hybrid polypeptides. The polypeptides may be a modified polypeptide according WO2010/102982. The polypeptide may be native or may be heterologous to the host cell. The polypeptide may be a collagen or gelatin, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase, non-ribosomal synthetase or polyketide synthetase. The polypeptide may be an enzyme secreted extracellularly Examples of proteins or (poly)peptides with industrial applications that may be produced in the methods of the invention include enzymes such as e.g. lipases (e.g. used in the detergent industry), proteases (used inter alia in the detergent industry, in brewing and the like, such as carboxypeptidases, endo-proteases, metallo-proteases, serine-proteases), carbohydrases and cell wall degrading enzymes (such as, amylases, glucosidases, cellulases (such as endo-glucanases, β-glucanases, cellobiohydrolases, GH61 enzymes or β-glucosidases), GH61-enzymes, hemicellulases or pectinolytic enzymes, beta-1,3/4- and beta-1,6-glucanases, rhamnoga-lacturonases, mannanases, xylanases, pullulanases, galactanases, esterases and the like, used in fruit processing, wine making and the like or in feed), phytases, phospholipases, asparaginases, glycosidases (such as amylases, beta.-glucosidases, arabinofuranosidases, rhamnosidases, apiosidases and the like), dairy enzymes and products (e.g. chymosin, casein), oxidoreductases such as oxidases, transferases, or isomerases or polypeptides (e.g. poly-lysine and the like, cyanophycin and its derivatives).

Mammalian, and preferably human, polypeptides with therapeutic, cosmetic or diagnostic applications include, but are not limited to, collagen and gelatin, insulin, serum albumin (HSA), lactoferrin and immunoglobulins, including fragments thereof. The polypeptide may be an antibody or a part thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase.

According to the present invention, a polypeptide can also be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter (s) and terminator. The hybrid polypeptides may comprise a combination of partial or complete polypeptide sequences obtained from at least two different polypeptides wherein one or more may be heterologous to the host cell.

The compound of interest may also be the product of a selectable marker. A selectable marker is a product of a polynucleotide of interest which product provides for biocide or viral resistance, resistance to heavy metals, prototrophy to auxotrophs, and the like. Selectable markers include, but are not limited to, amdS (acetamidase), argB (ornithinecarbamoyltransferase), bar (phosphinothricinacetyltransferase), hygB (hygromycin phosphotransferase), niaD (n itratereductase), pyrG (orotidine-5'-phosphate decarboxylase), sC (sulfate adenyltransferase), trpC (anthranilate synthase), ble (phleomycin resistance protein), as well as equivalents thereof.

When the compound of interest is a biopolymer as defined earlier herein, the host cell may already be capable to produce the biopolymer. The host cell may also be provided with a recombinant homologous or heterologous polynucleotide construct that encodes a polypeptide involved in the production of the biological compound of interest. The person skilled in the art knows how to modify a microbial host cell such that it is capable of production of the compound involved in the production of the biological compound of interest.

The term "recombinant polynucleotide" herein refers to a nucleic acid molecule, either single- or double-stranded, which has been introduced into a *Rasamsonia* cell, for example a nucleic acid which is present in the cell in a form or at a locus in which it would not normally be present (in relation to a corresponding cell not comprising the recombinant polynucleotide).

The term "recombinant polynucleotide construct" is herein referred to as a nucleic acid molecule, either single- or double-stranded, which is isolated from a naturally occurring gene or which has been modified to contain segments of nucleic acid which are combined and juxtaposed in a manner which would not otherwise exist in nature. The term recombinant polynucleotide construct is synonymous with the term "expression cassette" when the nucleic acid construct contains all the control sequences required for expression of a coding sequence, wherein said control sequences are operably linked to said coding sequence. Suitable control sequences are described herein.

A host cell of the invention may comprise one or more recombinant polynucleotides or recombinant polyncleotide constructs in order that a compound of interest may be produced.

In order to facilitate expression, the polynucleotide encoding the polypeptide involved in the production of the compound of interest may be a synthetic polynucleotide. The synthetic polynucleotides may be optimized in codon use, preferably according to the methods described in WO2006/077258 or WO2008/000632. WO2008/000632 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence (CDS).

Furthermore, standard molecular cloning techniques such as DNA isolation, gel electrophoresis, enzymatic restriction modifications of nucleic acids, Southern analyses, transformation of cells, etc., are known to the skilled person and are for example described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego.

A nucleic acid may be amplified using cDNA, mRNA or alternatively, genomic DNA, as a template and appropriate oligonucleotide primers according to standard PCR amplification techniques. The nucleic acid so amplified can be cloned into an appropriate vehicle and characterized by DNA sequence analysis.

A host cell (transformant) according to the invention may be cultured using procedures known in the art. For each combination of a promoter and a host cell, culture conditions are available which are conducive to the expression the DNA sequence encoding the polypeptide. After reaching the desired cell density or titre of the polypeptide the culture is stopped and the polypeptide is recovered using known procedures.

The fermentation medium can comprise a culture medium containing a carbon source (e.g. glucose, maltose, molasses, starch, cellulose, xylan, pectin, lignocellulytic biomass hydrolysate, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (e.g. cellulose, pectin, xylan, maltose, maltodextrin or xylogalacturonan) may be included.

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating microorganisms.

The fermentation can be performed over a period of from about 0.5 to about 30 days. It may be a batch, fed-batch, or continuous process, suitably at a temperature in the range of, for example, from about 20 to about 90° C., preferably 20-55° C. more preferably 40-50° C. and/or at a pH, for example, from about 2 to about 8, preferably from about 3 to about 5. The appropriate conditions are usually selected based on the choice of the expression host and the polypeptide to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

A nucleic acid may be amplified using cDNA, mRNA or alternatively, genomic DNA, as a template and appropriate oligonucleotide primers according to standard PCR amplification techniques. The nucleic acid so amplified can be cloned into an appropriate vehicle and characterized by DNA sequence analysis.

For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983). An overview of sequence comparison In D. Sankoff and J. B. Kruskal, (ed.), Time warps, string edits and macromolecules: the theory and practice of sequence comparison, pp. 1-44, Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: *The European Molecular Biology Open Software Suite* (2000) Rice, P. Longden, I. and Bleasby, A. Trends in Genetics 16, (6) pp. 276-277, eboss.bioinformatics.nl). For protein sequences, EBLOSUM62 is used for the substitution matrix. For nucleotide sequences, EDNAFULL is used. Other matrices can be specified. For purpose of the invention, the parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The protein sequences mentioned herein can further be used as a "query sequence" to perform a search against sequence databases, for example to identify other family members or related sequences. Such searches can be performed using the BLAST programs. Software for performing BLAST analyses is publicly available through the National Center for Biotechnology Information (www.ncbi.nlm.nih.gov). BLASTP is used for amino acid sequences and BLASTN for nucleotide sequences. In the BLAST program, the default settings may be used:
  Cost to open gap: default=5 for nucleotides/11 for proteins
  Cost to extend gap: default=2 for nucleotides/1 for proteins
  Penalty for nucleotide mismatch: default=−3
  Reward for nucleotide match: default=1
  Expect value: default=10
  Wordsize: default=11 for nucleotides/28 for megablast/3 for proteins The nucleic acid sequences as mentioned herein can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, word-length=12 to obtain nucleotide sequences homologous to the nucleic acid molecules of the invention.

The sequence information as provided herein should not be so narrowly construed as to require inclusion of erroneously identified bases. The specific sequences disclosed herein can be readily used to isolate the complete gene from filamentous fungi, in particular *A. niger* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a nucleic acid sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Strains

WT 1: This *Aspergillus niger* strain is used as a wild-type strain. This strain is deposited at the CBS Institute under the deposit number CBS 513.88.

GBA302: The strain *Aspergillus niger* GBA 302 (ΔglaA, ΔpepA, ΔhdfA) is used herein as recipient strain in transformations. Construction of GBA 302 is described in WO2011009700.

The *Rasamsonia emersonii* (*R. emersonii*) strains used herein are derived from ATCC16479, which is used as wild-type strain. ATCC16479 was formerly also known as *Talaromyces emersonii* and *Penicillium geosmithia emersonii*. Upon the use of the name *Rasamsonia emersonii* also *Talaromyces emersonii* is meant. Other strain designations of *R. emersonii* ATCC16479 are CBS393.64, IFO31232 and IMI116815.

*Rasamsonia* (*Talaromyces*) *emersonii* strain TEC-142 is deposited at CENTRAAL BUREAU VOOR SCHIMMELCULTURES, Uppsalalaan 8, P.O. Box 85167, NL-3508 AD Utrecht, The Netherlands on 1 Jul. 2009 having the Accession Number CBS 124902. TEC-142S is a single isolate of TEC-142.

Molecular Biology Techniques

In these strains, using molecular biology techniques known to the skilled person (see: Sambrook & Russell, *Molecular Cloning: A Laboratory Manual,* 3rd Ed., CSHL Press, Cold Spring Harbor, N.Y., 2001), several genes were over expressed and others were down regulated as described below. Examples of the general design of expression vectors for gene over expression and disruption vectors for down-regulation, transformation, use of markers and selective media can be found in for example WO199846772, WO199932617, WO2001121779, WO2005095624, EP 635574B and WO2005100573.

Media and Solutions

Potato Dextrose Agar, PDA, (Fluka, Cat. No. 70139)

| Potato extract | 4 g/l |
|---|---|
| Dextrose | 20 g/l |
| Bacto agar | 15 g/l |
| pH | 5.4 |
| Water | Adjust to one liter |
| Sterilize | 20 min at 120° C. |

Minimal Medium Agar Plates 8.8 g glucose, 6.6 g agarose, $H_2O$ to 400 ml. Autoclave 20 minutes at 115° C. and cool to 55° C. Add Solution I, mix and pour plates.

Solution I 11 ml stock A, 11 ml stock B, 0.44 ml stock trace elements (1000×), 4.4 ml Penicillin/Streptomycin Solution, 13.2 ml $H_2O$.

Stock A 120 g $NaNO_3$, 10.4 g KCl, 30.4 g $KH_2PO_4$, 22.5 ml 4M KOH, $H_2O$ to 500 ml. Autoclave 20 minutes at 120° C.

Stock B (40×)

10.4 g $MgSO_4.7H_2O$, $H_2O$ to 500 ml. Autoclave 20 minutes at 120° C.

Stock Trace Elements (1000×)

2.2 g $ZnSO_4.7H_2O$, 1.1 g $H_3BO_3$, 0.5 g $FeSO_4.7H_2O$, 0.17 g $CoCl_2.6H_2O$, 0.16 g $CuSO_4.5H_2O$, 0.5 g $MnCl_2.4H_2O$, 0.15 g $Na_2MoO_4.2H_2O$, 5.0 g EDTA.

Dissolve EDTA and ZnSO4.7H2O in 75 ml of milliQ water and set the pH to 6.0 with NaOH 1M. Whilst maintaining the pH at 6.0 dissolve the components one by one. When ready set the pH to 4.0 with HCl 1 M, and adjust the volume to 100 ml with milliQ water. Autoclave 20 minutes at 120° C.

Rasamsonia Agar Medium

| Salt fraction no. 3 | 15 g |
|---|---|
| Cellulose (3%) | 30 g |
| BACTO ™ peptone | 7.5 g |
| Grain flour | 15 g |
| $KH_2PO_4$ | 5 g |
| CaCl2•2aq | 1 g |
| Bacto agar | 20 g |
| pH | 6.0 |
| Water | Adjust to one liter |
| Sterilize | 20 min at 120° C. |

Salt Fraction Composition

The "salt fraction no. 3" was fitting the disclosure of WO98/37179, Table 1. Deviations from the composition of this table were CaCl2.2 aq 1.0 g/l, KCl 1.8 g/L, citric acid 1 aq 0.45 g/L (chelating agent).

Shake Flask Media for Rasamsonia

Rasamsonia Medium 1

| Glucose | 20 g/L |
|---|---|
| Yeast extract (Difco) | 20 g/L |
| Clerol FBA3107 (AF) | 4 drops/L |
| pH | 6.0 |
| Sterilize | 20 min at 120° C. |

Rasamsonia Medium 2

| Salt fraction no. 3 | 15 g |
|---|---|
| Cellulose | 20 g |
| BACTO ™ peptone | 4 g |
| Grain flour | 7.5 g |
| $KH_2PO_4$ | 10 g |
| $CaCl_2$•2H2O | 0.5 g |
| Clerol FBA3107 (AF) | 0.4 ml |
| pH | 5 |
| Water | Adjust to one liter |
| Sterilize | 20 min at 120° C. |

Spore Batch Preparation for Rasamsonia

Strains were grown from stocks on Rasamsonia agar medium in 10 cm diameter Petri dishes for 5-7 days at 40° C. For MTP fermentations, strains were grown in 96-well plates containing Rasamsonia agar medium. Strain stocks were stored at −80° C. in 10% glycerol.

Chromosomal DNA Isolation

Strains were grown in YGG medium (per liter: 8 g KCl, 16 g glucose.H20, 20 ml of 10% yeast extract, 10 ml of 100× pen/strep, 6.66 g YNB+amino acids, 1.5 g citric acid, and 6 g $K_2HPO_4$) for 16 hours at 42° C., 250 rpm, and chromosomal DNA was isolated using the DNEASY® plant mini kit (Qiagen, Hilden, Germany).

MTP Fermentation of Rasamsonia 96 wells microtiter plates (MTP) with sporulated Rasamsonia strains were used to harvest spores for MTP fermentations. To do this, 200 µl of Rasamsonia medium 1 was added to each well and after resuspending the mixture, 100 µl of spore suspension was incubated in humidity shakers (Infors) for 44° C. at 550 rpm, and 80% humidity for 16 hours. Subsequently, 50 µl of pre-culture was used to inoculate 250 µl of Rasamsonia medium 2 in MTP plates. The 96-well plates were incubated in humidity shakers (Infors) for 44° C. at 550 rpm, and 80% humidity for 6 days. Plates were centrifuged and supernatants were harvested.

Protein Analysis

Protein samples were separated under reducing conditions on NuPAGE® 4-12% Bis-Tris gel (Invitrogen, Breda, The Netherlands) and stained as indicated. Gels were stained with either INSTANTBLUE™ (Expedeon, Cambridge, United Kingdom), SIMPLYBLUE™ safestain (Invitrogen, Breda, The Netherlands) or SYPRO® Ruby (Invitrogen, Breda, The Netherlands)) according to manufacturer's instructions.

For Western blotting, proteins were transferred to nitrocellulose. The nitrocellulose filter was blocked with TBST (Tris buffered saline containing 0.1% TWEEN® 40) containing 3% skim-milk and incubated for 16 hours with anti-FLAG M2 antibody (Sigma, Zwijndrecht, The Netherlands). Blots were washed twice with TBST for 10 minutes and stained with Horseradish-peroxidase conjugated rabbit-anti-mouse antibody (DAKO, Glostrup, Denmark) for 1 hour. After washing the blots five times with TBST for 10 minutes, proteins were visualized using SUPERSIGNAL® (Pierce, Rockford, U.S.A).

Enzyme Activity Measurements

Proline Specific Endoprotease Activity

The proteolytic activity of the proline specific endoprotease is spectrophoto-metrically measured at 410 nm in time using CBZ-Gly(cine)-Pro(line)-pNA at 37° C. in a citrate/disodium phosphate buffer at pH 5. 1 U proline specific endoprotease is defined as the amount of enzyme which converts 1 µmol (micromol) CBZ-Gly(cine)-Pro(line)-pNA per min at pH 5 and 37° C. at the conditions described above.

Cellulase Assay: Wheat Straw Assay (WSU Assay).

Preparation of Pre-Treated, Washed Wheat Straw Substrate

Dilute-acid pre-treated wheat straw which was washed with water until the solution with wheat straw was pH 6.5 or higher and the mass was homogenised using an ultra-turrax, lyophilized and grinded prior to analysis. To obtain pre-treated wheat straw a dilute acid pre-treatment as described in Linde, M. et al, Biomass and Bioenergy 32 (2008), 326-332 and equipment as described in Schell, D. J., Applied Biochemistry and Biotechnology (2003), vol. 105-108, pp 69-85, may be used.

Measurement of Cellulase Activity in WSU/Ml

With 1 WSU is meant 0.119 mg/ml glucose released from 2.1 w/v % washed pre-treated wheat straw by 200 µl of enzyme mix in 20 hours at 65° C. at pH 4.50.

The glucose release is not a linear function of the quantity of enzyme in the composition. In other words, twice the amount of enzyme does not automatically result in twice the amount of glucose in equal time. Therefore, it is preferred to choose the dilution of the composition to be tested for WSU activity such that a WSU does not exceed 40.

400 µl of supernatants harvested from shake flask experiments were diluted 4.5-fold. Diluted sample was used to perform two measurements in which 200 µl of diluted sample was analysed. In the first measurement, 200 µl diluted sample was transferred to a vial containing 700 µL water containing 3% (w/v) dry matter of the pretreated washed wheat straw substrate and 100 µl of 250 mM citrate buffer, the final pH was adjusted to pH 4.5. In the second measurement, the blank sample, 200 μl of diluted sample was transferred to a vial that contained 700 μl of water instead of pretreated washed wheat straw substrate, and 100 μl of 250 mM citrate buffer, the final pH was adjusted to pH 4.5. The assay samples were incubated for 20 hours at 65° C. After incubation of the assay samples, 100 μl of internal standard solution (20 g/L maleic acid, 40 g/L EDTA in D2O) was added. The amount of glucose released, was based on the signal at 5.20 ppm, relative to Dimethyl-sila-pentane-sulfonate determined by means of 1D 1H NMR operating at a proton frequency of 500 MHz, using a pulse program with water suppression, at a temperature of 27° C. The WSU number was calculated from the data by subtracting by the amount of glucose that was detected in the blank sample from the amount of glucose that was measured in the sample incubated with wheat straw.

Example 1

Construction and Description of *Aspergillus* Deletion Vectors

Three genes, which are candidates for disruption were identified in the genome sequence of *A. niger* CBS513.88. All nucleotide sequences for *A. niger* genes and their genomic context can be derived for example from NCBI (www.ncbi.nlm.nih.gov/) or EMBL (www.ebi.ac.uk/embl). The nicB gene is encoded by ORF An11g10910, the PdxA gene by An03g04280, whereas the epo gene is encoded by An08g04490.

Gene replacement vectors were designed according to known principles and constructed according to routine cloning procedures as also described in EP635574B and WO 98/46772. In essence, these vectors comprise approximately 1-2 kb flanking regions of the respective ORF sequences, to target for homologous recombination at the predestined genomic loci. They may contain for example the *A. nidulans* bi-directional amdS selection marker, the hygromycin B marker or the phleomycin selection marker for transformation. The method applied for gene replacements in all examples herein uses linear DNA, which integrates into the genome at the homologous locus of the flanking sequences by a double cross-over, thus substituting the gene to be deleted by a marker gene (such as the amdS gene). Loss of the amdS marker for example can be selected for by plating on fluoro-acetamide media.

Based on genomic sequences, gene replacement vectors for nicB and PdxA and epo were designed as follows: In essence, the nicB deletion vector pDELNicB-3 comprises approximately a 1000 bp 5' upstream flanking region (Nic-US) and a 1000 bp 3' downstream flanking region (Nic-DS) of the nicB ORF to allow targeting for homologous recombination at the predestined genomic nicB locus. In addition, pDELNicB-3 contains the hygromycinB selection marker cassette (from pAN7-1, NCBI gi: 475166) and mutant loxP sites (lox66 and lox71, SEQ ID Nos: 1 and 2 respectively) were placed around the HygB marker as indicated (for general layout of pDELNicB-3 see FIG. 1).

Figure 2:
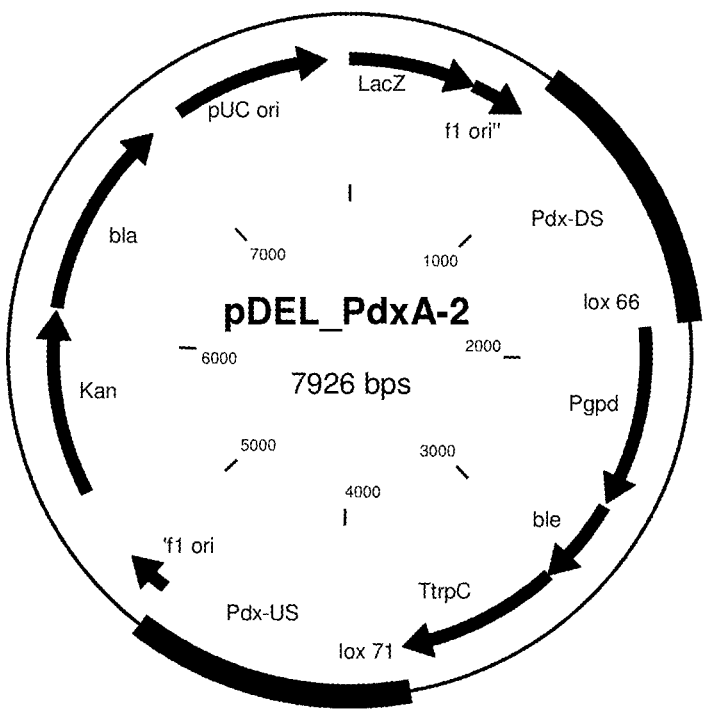
FIG. 2 sets out a schematic diagram of plasmid pDEL_PdxA-2, which is the basis for a replacement cassette to inactivate the pdxA gene in *A. niger*. The replacement cassette comprises the pdxA flanking regions, the ble marker cassette, mutant loxP sites and *E. coli* DNA. More details for pDEL_PdxA-2 can be found in the Examples section (vide infra).

The pDEL_PdxA-2 vector for pdxA deletion was constructed like-wise with 5' flanking regions (Pdx-US) and 3' flanking region (Pdx_DS) of similar length for the PdxA ORF. In contrast to pDEL_NicB-3, the pDEL_PdxA-2 vector comprises the phleomycin selection marker (phleomycin marker as in pAN8-1, NCBI gi: 475899) with mutant LoxP sites (lox66 and lox71, SEQ ID No: 1 and 2, respectively) positioned around the marker cassette. (for general layout of pDEL_PdxA-2 see FIG. 2). For reference, the double mutant lox72 site is shown in SEQ ID NO: 3.

Figure 3:
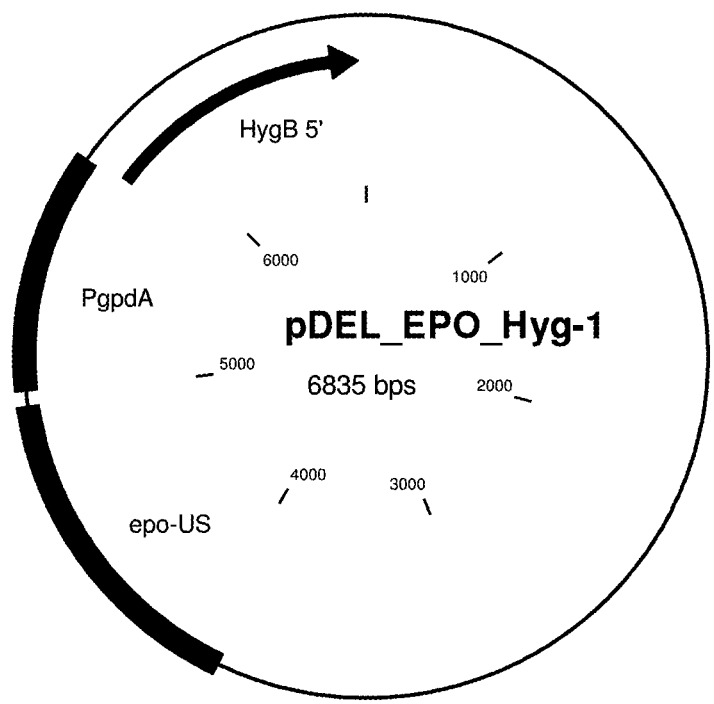
FIG. 3 sets out a schematic diagram of plasmid pDEL_EPO_Hyg-1, which comprises part of a replacement cassette to inactivate the epo gene in *A. niger*. The replacement cassette comprises an epo flanking region, part of a hygB marker cassette, a mutant loxP site and *E. coli* DNA. More details for pDEL_EPO_Hyg-1 can be found in the Examples section (vide infra).
Figure 4:
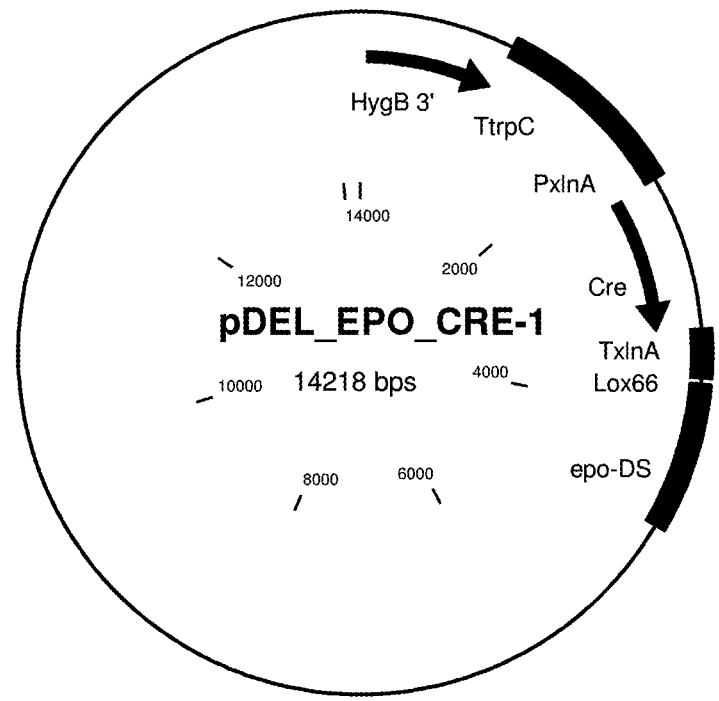
FIG. 4 sets out a schematic diagram of plasmid pDEL_EPO_CRE-1, which comprises part of a replacement cassette to inactivate the epo gene in *A. niger*. The replacement cassette comprises an epo flanking region, part of a hygB marker cassette, a mutant loxP site, a cre recombinase expression cassette and *E. coli* DNA. More details for pDEL_EPO_CRE-1 can be found in the Examples section (vide infra).

Vectors for deletion of the epo gene were designed in a slightly different way comprising the construction and use of two different vectors. The insert fragments of both vectors together can be applied in the so-called "bipartite gene-targeting" method (Nielsen et al., 2006, 43: 54-64). This method is using two non-functional DNA fragments of a selection marker which are overlapping (see also WO2008113847 for further details of the bipartite method) together with gene-targeting sequences. Upon correct homologous recombination the selection marker becomes functional by integration at a homologous target locus. As also detailed in WO 2008113847, two different deletion vectors pDEL_EPO_Hyg-1 and pDEL_EPO_CRE-1 were designed and constructed to be able to provide the two overlapping DNA molecules for bipartite gene-targeting. The first vector pDEL_EPO_Hyg-1 (General layout as in FIG. 3) comprises a first non-functional hygB marker fragment (PgpdA-HygB sequence missing the last 27 bases of the coding sequence at the 3' end of hygB, SEQ ID NO: 4) and at one side of the hygB cassette a Lox71 sequence site and the 5'-upstream gene flanking region of the epo ORF (EPO-US). The second pDEL_EPO_CRE-1 vector (General layout as in FIG. 4) comprises a non-functional hygB fragment (HygB-TtrpC sequence missing the first 44 bases of the coding sequence at the 5' end of hygB, SEQ ID NO: 5) and at one side of the hygB cassette, a cre recombinase cassette, a Lox66 sequence site and the 3'-downstream gene flanking region of the epo ORF (EPO-DS). The cre recombinase cassette contains the *A. nidulans* xylanase A promoter, a cre recombinase and xylanase A terminator, to allow xylose-inducible expression of the cre recombinase (SEQ ID NO: 6). Upon homologous recombination, the first and second non-functional fragments become functional producing a functional hygB cassette. Both epo upstream and downstream gene flanking regions target for homologous recombination of the bipartite fragments at the predestined epo genomic locus.

In the following examples we will show that the cre-lox system as used herein is a very efficient system for gene disruption and marker removal after a single transformation. In addition, when using strains deficient in NHEJ, the bipartite gene-targeting approach combined with the cre-lox system results in a highly efficient system for making marker-free strains with defined modifications.

Example 2

Figure 5:
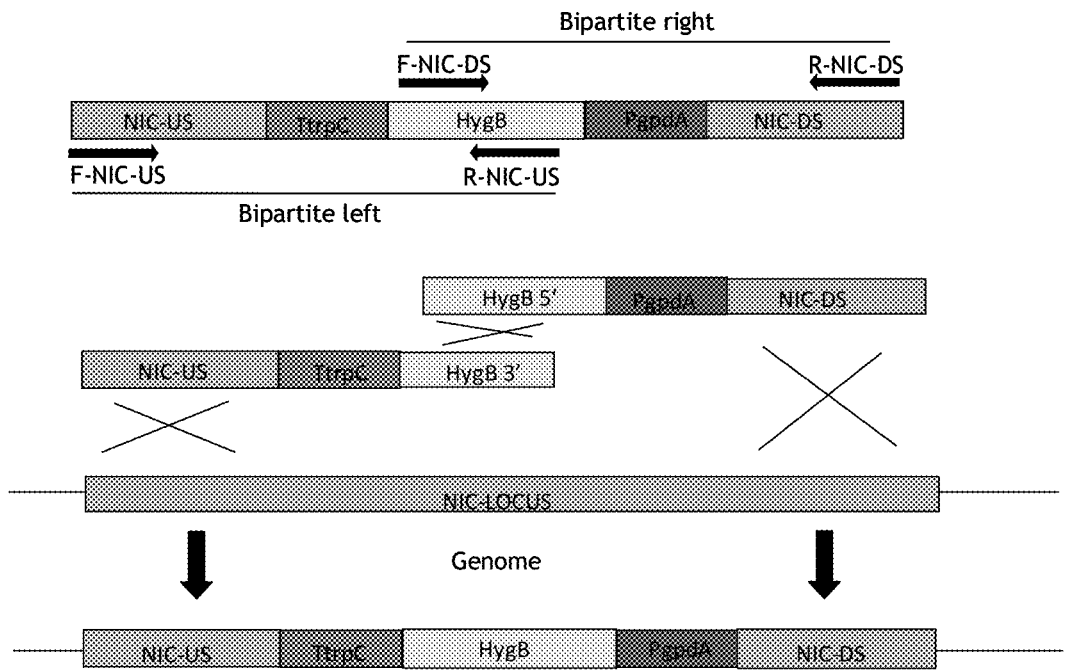
FIG. 5 sets out a schematic representation for fragment generation and use of these fragments in transformation and recombination in *A. niger*. In the top part is demonstrated the generation of the "bipartite left" and "bipartite right" fragments as amplified by PCR. In the lower panels, *A. niger* transformation through homologous recombination of the bipartite left and right fragments within the genome is shown.

Efficient Gene Deletion Using Multiple Overlapping DNA Fragments without a Functional Marker (Bipartite Gene-Targeting Approach) and a Small Overlapping Sequence In this experiment the effect of the overlap sequence size of the non-functional marker fragments on the transformation efficiency and targeting frequency through double homologous recombination was investigated. PCR fragments, encompassing the variable hygB marker length, flanked by NicB flanking regions of 1 kb (see FIG. 5), were generated using the pDELNicB-3 plasmid as template in sufficient quantities. Protoplasts of strain GBA302 (ΔglaA, ΔpepA, ΔhdfA) were transformed with 2 μg of each PCR fragment. Transformants were selected based on hygromycin B resistance, colony purified according to standard procedures as described in EP635574B and subsequently analyzed after purification. The targeting frequency was determined using diagnostic PCR using a primer within the hygB cassette and a primer within the genomic flanking region but outside the nucleotide region for targeting (see FIG. 5). The data shown in Table 1 clearly demonstrate that with good transformation efficiencies targeting frequencies of the integrative cassettes were high and efficient for the different sizes of overlapping marker sequences. Therefore, we conclude that smaller overlapping sequences than the size of roughly 1 kb mentioned in Example 1 herein and Example 4 of WO 2008113847, have no negative effect on targeting frequencies. In this manner, generation of fragments either by PCR or DNA synthesis is simplified and therefore construction of disruption mutants is more efficient.

TABLE 1

Transformation efficiency and targeting frequencies of nicB deletion cassettes using variable length of the overlapping marker sequences

| Length of overlap (bp) | Nr. of transformants | Targeting (%) |
|---|---|---|
| 960 | 236 | 100 |
| 750 | 240 | 95 |
| 640 | 88 | 85 |
| 380 | 252 | 100 |

Example 3

Simultaneous Gene Deletion Using Multiple Overlapping DNA Fragments without a Functional Marker with loxP Sites and Marker Removal after a Single Transformation Step Use of a mutant which is deficient in a gene encoding a component involved in NHEJ, such as inactivation of at least one of the hdf genes results in a significant increase of the targeting efficiency of integration vectors through (double) homologous recombination (as earlier described in WO2005095624 and WO2008113847 for example).

In addition, increase of the targeting efficiency for homologous recombination can be obtained as described in WO2008113847. This bipartite gene-targeting method comprises providing two sets of DNA molecules of which the first set comprises DNA molecules each comprising a first non-functional fragment of the replacement sequence of interest flanked at its 5'-side by a DNA sequence substantially homologous to a sequence of the chromosomal DNA flanking the target sequence and the second set comprises DNA molecules each comprising a second non-functional fragment of the DNA replacement sequence of interest overlapping with the first non-functional fragment and flanked at its 3'-side by a DNA sequence substantially homologous to a sequence of the chromosomal DNA flanking the target sequence, wherein the first and second non-functional fragments become functional upon recombination.

Gene replacement vectors pDEL_EPO_Hyg-1 and pDEL_EPO_CRE-1 (layouts as described in Example 1) both comprise approximately a 1 kb flanking region for homologous recombination at the epo ORF. In addition, they both contain a (non functional) hygB selection marker and a loxP site (lox71 or lox66). The pDEL_EPO_CRE-1 construct also contains the bacteriophage P1 Cre gene under control of the *A. nidulans* xylanase A promoter to allow inducible Cre expression upon xylose induction.

The two linear bipartite gene-targeting fragments for epo disruption were generated by PCR in sufficient quantities using the pDEL_EPO_Hyg-1 and pDEL_EPO_CRE-1 plasmids as template. The overlap of the two nucleotide fragments at the non-functional hygB gene was around 1 kb in this case. For each fragment, 2 µg of DNA was used to transform *Aspergillus niger* GBA302. Transformants were selected based on hygromycin B resistance, colony purified according to standard procedures as described in EP635574B and subsequently analyzed after purification. From Example 2, it was learned that the majority of the transformants obtained with a flanking sequence of 1 kb and an overlap of 1 kb should result in a high frequency of targeted integration at the homologous epo locus, thus substituting the target locus by the functional hygB gene as depicted in FIG. 6.

For inducing the cre-recombinase under control of the xylanase promoter, minimal medium agar plates containing 1% xylose and 1% glucose (xylanase inducing medium) were used. Transformants were transferred from PDA plates to xylanase induction medium. Subsequently, the plates were incubated for 5 days at 30° C. When Cre recombinase is induced by xylose, deletion of the DNA cassette in between the two specific loxP sites can occur by excision. Resulting colonies after growth on xylanase inducing medium were tested for their hygromycin B resistance. Spores from the transformants were transferred to PDA plates with and without hygromycin B (60 µg/ml) using toothpicks. The plates were incubated for 48 hours at 30° C.

Figure 7:
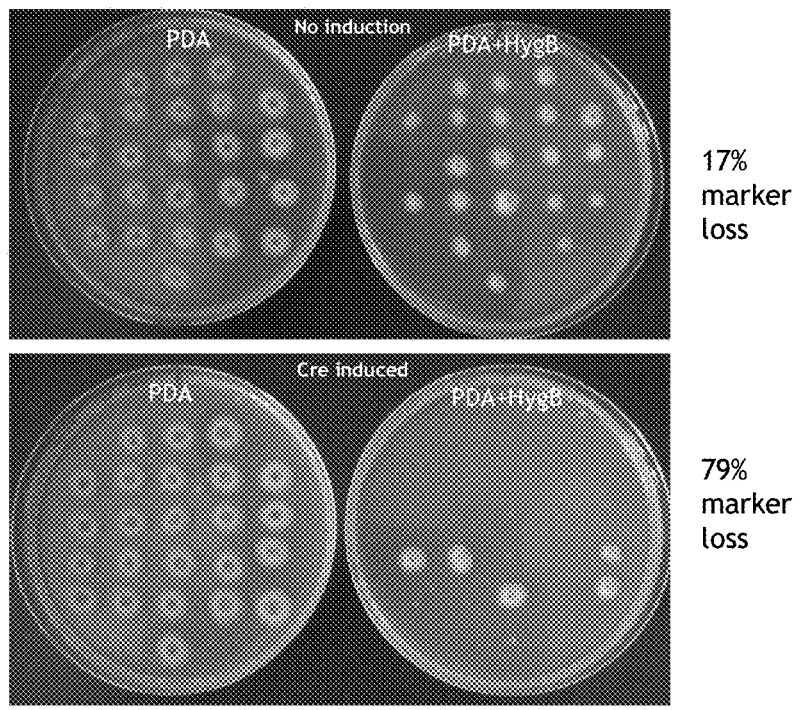
FIG. 7 sets out Cre induced loss of loxP flanked hygB selection marker. The upper plates are Cre non-induced transformants. Lower plates are Cre induced by plating on xylose as carbon source. The percentages show the percentage of marker removal in *A. niger* colonies after Cre induction.

Of 24 initial hygromycin B resistant colonies after growth on PDA starch, 4 transformants lost their hygromycin B resistance spontaneously (see also FIG. 7 for strain testing). Of 24 initial hygromycin B resistant colonies after growth on xylose, 19 transformants lost their hygromycin B resistance. Loss of hygromycin B resistance likely is coupled to loss of the hygB marker cassette through cre recombinase activity. Indeed marker removal was confirmed by PCR analysis of the epo locus.

This Example shows that in a strain deficient in NHEJ, use of bipartite gene-targeting and combination with an inducible recombination system according the invention allows for a very efficient strain construction/disruption in building marker-free strains without the need of a second transformation or counter-selection procedures in strain construction.

Example 4

Simultaneous Multiple Gene Deletions Using Multiple Overlapping DNA Fragments without Functional Markers and Multiple Marker Removal after a Single Transformation Step In this Example we describe a method to significantly shorten strain construction procedures by combining the use of multiple bipartite fragments in combination with cre-lox in a NHEJ deficient host strain to obtain multiple gene deletions. To facilitate multiple marker removal in a single transformation step, it is essential that at least one construct contains the Cre gene with the inducible xylanaseA promoter.

Two times two linear bipartite gene-targeting fragments for pdxA and epo disruption, respectively, were generated by PCR in sufficient quantities using the pDEL_Pdx-2 and pDEL_EPO_Hyg-1 & pDEL_EPO_CRE-1 plasmids as template. The overlap of the two nucleotide fragments at the non-functional phleomycin ble gene was around 350 bp and for the hygB gene it was around 1 kb. For each of the four fragments, 2 µg of DNA was used to transform *Aspergillus niger* GBA302. Double deletion transformants were selected on a medium containing both hygromycin B and phleomycin. Colony purified strains were tested for correct phenotype and diagnosed by PCR for gene replacement of PdxA and epo. Upon induction of CRE by switching to a xylose containing growth medium, both selection markers were removed. Marker removal was confirmed by PCR analysis of the NicB and PdxA loci.

This Example shows that in a strain deficient in NHEJ, use of multiple bipartite gene-targeting and combination with an inducible recombination system according the invention allows for a very efficient strain construction/disruption in building marker-free strains with two modifications without the need of a second or third transformation step or counter-selection procedures in strain construction.

Example 5

Transformation of *Rasamsonia emersonii* Resulting in Selection Marker-Free Transformants Capable of Producing a Desired Enzyme which is Encoded by a Gene Introduced in the Transformant This Example describes the construction of a marker-free *R. emersonii* transformant containing one or more additional copies of CbhI. The marker is removed by transient expression of cre-recombinase in *R. emersonii* transformants.

Figure 8:
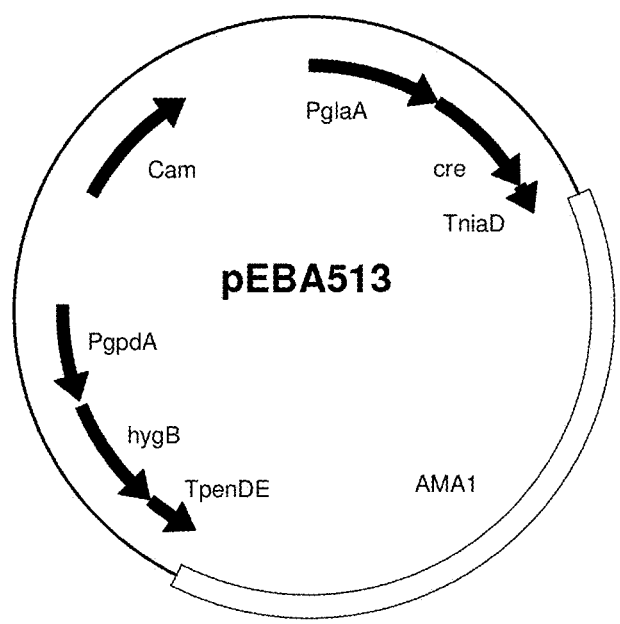
FIG. 8 depicts a map of pEBA513 for transient expression of cre recombinase in fungi. pEBA513 is a pAMPF21 derived vector containing the AMA1 region and the CAT chloramphenicol resistance gene. Depicted are the cre recombinase gene (cre) expression cassette, containing the *A. niger* glaA promoter (Pgla), cre recombinase coding region, and niaD terminator. In addition, the hygromycin resistance cassette consisting of the *A. nidulans* gpdA promoter (PgpdA), hygB coding region and the *P. chrysogenum* penDE terminator is indicated.

Cloning of Transient Expression Plasmid pEBA513 Encoding Cre Recombinase pEBA513 was constructed by DNA2.0 (Menlo Park, USA) and contains the following components: expression cassette consisting of the *A. niger* glaA promoter, ORF encoding cre-recombinase (AAY56380) and *A. nidulans* niaD terminator; expression cassette consisting of the *A. nidulans* gpdA promoter, ORF encoding hygromycin B resistance protein and *P. chrysogenum* penDE terminator (Genbank: M31454.1, nucleotides 1750-2219); pAMPF21 derived vector containing the AMA1 region and the CAT chloramphenicol resistance gene. FIG. 8 represents a map of pEBA513.

Transformation of *R. emersonii* with pDEL PdxA-2 and CbhI Expression Construct pGBTOP205

In order to obtain a *R. emersonii* strain overexpressing CbhI, *R. emersonii* was transformed to obtain a multicopy CbhI strain. Plasmid pGBTOPEBA205, described in WO2011\054899, encoding *R. emersonii* CbhI driven by the *A. niger* glucoamylase promoter was used in the transformation. *R. emersonii* transformation was performed according to the protocol described in WO2011\054899. *R. emersonii* was co-transformed with 1 µg of pDEL_pPdxA-2 (for cloning details and description see Example 1 and FIG. 2) and 9 µg of pGBTOPEBA205 and co-transformants were identified using PCR analysis. The presence of pDEL_PdxA-2 plasmid was determined using primer Ble-For (SEQ ID NO: 7) and Ble-Rev (SEQ ID NO: 8) and of pGBTOPEBA205 with primer EBA205-For (SEQ ID NO: 9 and EBA205-Rev (SEQ ID NO: 10). Primers directed against pGBTOPEBA4 (SEQ ID NO: 11 and 12) and pGBTOPEBA8 (SEQ ID NO: 13 and 14) were used as a control.

```
Ble-For (SEQ ID NO: 7):
5'-AGTTGACCAGTGCCGTTCC-3';
and
```

```
Ble-Rev (SEQ ID NO: 8):
5'-CACGAAGTGCACGCAGTTG-3'.

EBA205-For (SEQ ID NO: 9):
5'-CTTCTGCTGAGCAGCTCTGCC-3';
and

EBA205-Rev (SEQ ID NO: 10):
5'-GTTCAGACCGCAAGGAAGGTTG-3'.

EBA4-For (SEQ ID NO: 11):
5'-CGAGAACCTGGCCTACTCTCC-3'

EBA4-Rev (SEQ ID NO: 12):
5'-CAGAGTTGTAGTCGGTGTCACG-3'

EBA8-For (SEQ ID NO: 13):
5'-GAAGGGTATCAAGAAGCGTGCC-3'

EBA8-Rev (SEQ ID NO: 14):
5'-GCCGAAGTTGTGAGGGTCAATG-3'
```

PCR conditions for the reactions: 50 µl reaction mix with 5 µl of template DNA, 20 pmol of each primer, 0.2 mM of dNTPs, 1× PHUSION® HF buffer and 1 U of PHUSION® DNA-Polymerase, according to PHUSION® High-Fidelity DNA Polymerase Manual (Finnzymes, Espoo, Finland), 30 s denaturation at 98° C., amplification in 30 cycles (10 s 98° C., 10 s 55° C., 15 s 72° C.), and a final incubation of 10 min at 72° C.

Figure 9:
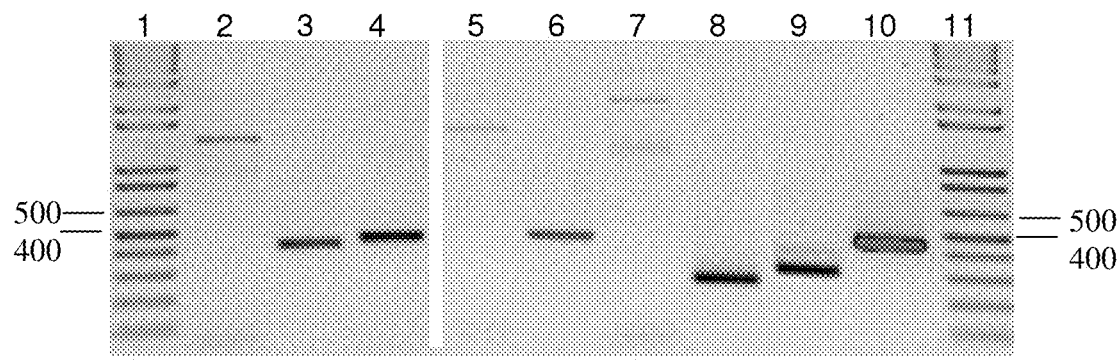
FIG. 9 shows the detection of pGBTOPEBA-205 expression plasmid in the *R. emersonii* genome by PCR. Genomic DNA was isolated and analysed by PCR from transformant A-A4 (lanes 2-4) and the empty strain (lanes 5-7). Plasmid DNA was used as control template for the PCR reactions: pGBTOPEBA-4 (lane 8), pGBTOPEBA-8 (lane 9) and pGBTOPEBA-205 (lane 10). In the PCR reactions primers were added directed against pGBTOPEBA-4 (lanes 2, 5, and 8, expected fragment: 256 bp), pGBTOPEBA-8 (lanes 3, 6, and 9, expected fragment: 306 bp), and pGBTOPEBA-205 (lanes, 4, 7, and 10, expected fragment: 452 bp). Lanes 1 and 11 contain a molecular weight marker.

Transformant A-A4 is a co-transformant that contains one or more copies of pGBTOPEBA205. In lane 4, the expected 452 bp PCR product of pGBTOPEBA-205 bp was observed in the transformant (FIG. 9, lane 4), which is detected in the control PCR in which pGBTOPEBA205 was used as a template (lane 10), but not in the empty strain (lane 7). In the EBA4 and EBA8 PCR reactions, no specific bands were observed in the transformants, but the expected PCR products of 256 bp and 306 bp, respectively, were generated when plasmid DNA was used as template (lanes 8 and 9).

In conclusion, a *R. emersonii* transformants was generated carrying multiple copies of *R. emersonii* CbhI.

Cellulase Activity Assay

Transformant A-A4 and control strains were fermented in MTP and supernatants and were analysed for cellulase activity in a WSU cellulase activity assay. A 1.25-fold increase in cellulase activity was observed in supernatants of transformant A-A4 compared to the empty strain, indicating that the obtained transformant with multiple *R. emersonii* CbhI copies is improved in cellulase activity.

Transformation of Phleomycin Resistant *R. emersonii* Transformants with AMA Plasmid pEBA513 Carrying the Cre Recombinase Gene and Selection of Phleomycin-Sensitive Transformants.

Figure 10A:
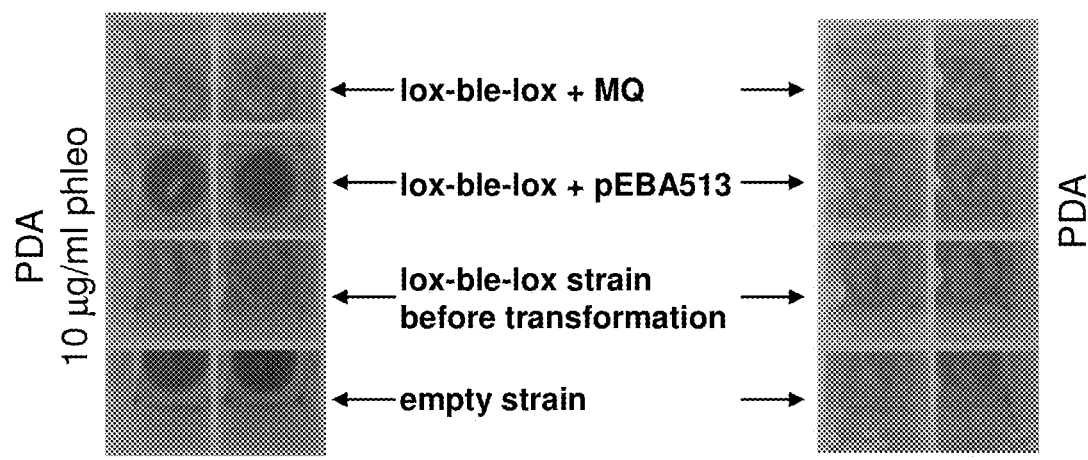
(FIG. 10A): Pictures of MTP plates of transformants and the empty strain grown on PDA medium with 10 μg/ml phleomycin (left panel) and PDA without selection (right panel). Row A shows two milliQ control transformants of A-A4 that contain the pDEL_Pdx-A2 with the loxP flanked ble expression cassette (lox-ble-lox). Growth of two pEBA513 transformed A-A4 transformants (lox-ble-lox+pEBA513) are shown in row B. The parental transformant A-A4 (lox-ble-lox, before transformation), was grown in row C. Finally, growth of the empty strain is shown in row D.

Cre recombinase was transiently expressed in *R. emersonii* transformant A-A4 to remove the loxP-flanked phleomycin resistance gene by recombination over the lox66 and lox71 site. The transformant was transformed with milliQ water (control) or with 10 µg of pEBA513 carrying a Cre recombinase and hygromycin expression cassette. pEBA513 transformed protoplasts were plated in overlay on regeneration medium containing 50 µg/ml of hygromycin B. Hygromycin-resistant transformants were grown on PDA containing 50 µg/ml of hygromycin B to allow expression of the cre recombinase. Removal of the ble marker was tested phenotypically by growing the transformants on media with and without 10 µg/ml of phleomycin. The majority (>90%) of the transformants after transformation with pEBA513 (with the cre recombinase) were phleomycin sensitive, indicating that cre recombinase works very efficiently in *R. emersonii* and that transformants lost the (ble) marker upon introduction and expression of the recombinase. In FIG. 10A, examples of different transformants and empty strains on PDA with 10 µg/ml phleomycin and PDA are shown.

A subset of transformants was also analysed by PCR. Transformants were grown in YGG medium for 16 hours at 44 degrees, 250 rpm, and chromosomal DNA was isolated using the DNeasy plant mini kit (Qiagen, Hilden, Germany). Both parental strains containing the loxP-flanked ble gene and transformants in which cre recombinase was overexpressed were analysed by PCR using pdx primers directed against the flanks just outside the loxP sites:

```
Pdx-For (SEQ ID NO: 15):
5'-TTGAGCTGTTGCTCCGGTAG-3';
and

Pdx-Rev (SEQ ID NO: 16):
5'-CTCCGTAGTCATCGTCAATGG-3'
```

In addition, the presence of pEBA513 was determined by PCR using primers directed against the HygB selection marker of the plasmid:

```
Hyg-For (SEQ ID NO: 17):
5'-GCGTCGGTTTCCACTATC-3'

Hyg-Rev (SEQ ID NO: 18):
5'-GAGGTCGCCAACATCTTC-3'
```

Figure 10B:
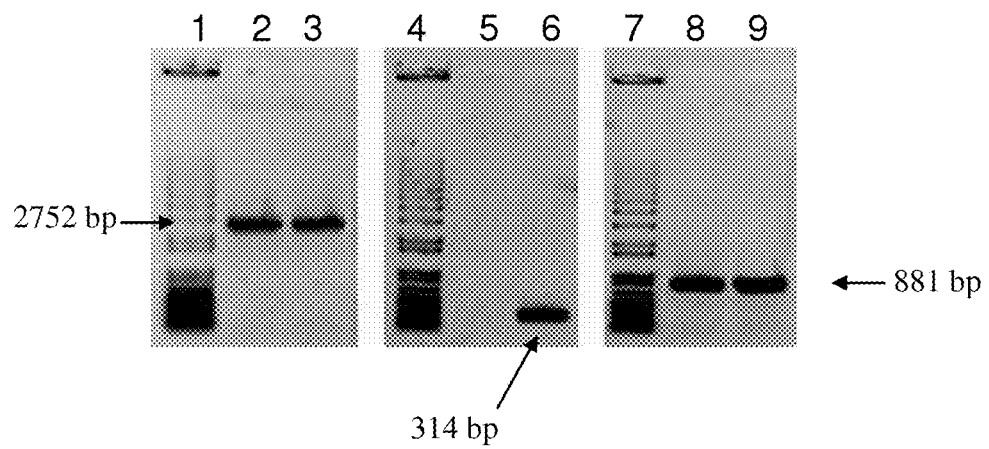
(FIG. 10B): PCR analysis of transformants before and after marker removal by cre-recombinase and of the cre-recombinase construct. Lanes 2 and 3 show PCR fragments obtained by PCR analysis of two milliQ control A-A4 transformants using primers directed against the pdx flanks of the ble expression construct. The 2752 bp PCR band is the expected amplified PCR fragment if the transformant still contains the ble selection marker. Lanes 5 and 6 show PCR analysis of two A-A4 transformants that were transformed with pEBA513 using primers directed against the hygB gene of the pEBA513 cre recombinase expression plasmid (314 bp fragment). Lanes 8 and 9 show PCR fragments of two A-A4 transformants that were transformed with pEBA513 using primers directed against the pdx flanks of the ble expression construct. The 881 bp PCR fragment is indicative for the deletion of the ble expression cassette from the *R. emersonii* transformant. Lanes 1, 4 and 7 contain a molecular weight marker.

PCR conditions for the reactions were as described above. The result of the agarose gel is presented in FIG. 10B. A specific PCR band of 2752 bp is observed in transformants containing the loxP-flanked ble expression cassette (lanes 2 and 3). In contrast, in transformants in which the ble recombinase is removed by cre recombinase a PCR fragment of 881 bp was amplified (lanes 8 and 9), indicating that the ble gene was removed by the cre recombinase. Thus, we successfully removed the loxP-flanked ble selection marker from *R. emersonii* transformants using the cre-lox system.

The presence of the pEBA513 AMA-Cre plasmid was determined by a HygB PCR. Interestingly, in one of the two transformant no HygB fragment was detectable. As the transformant were grown under conditions without hygB selection, the transformant probably already lost the episomal cre expression plasmid and linked to that the hygB marker.

Removal of the pEBA513 Plasmid to Obtain a Marker-Free Transformants.

After removing the ble selection marker, strains were identified that spontaneously lost the pEBA513 plasmid. We already observed that part of the transformants already lost the AMA plasmid while selecting for phleomycin-sensitive clones on PDA plates with and without phleomycin. In order to check spontaneous loss of the episomal AMA plasmid pEBA513 after growing the transformants without hygromycin selection, spores were transferred to plates with and without hygromycin B. After one round of growth without selection already 50-75% of the transformants were hygromycin B sensitive, which was confirmed by hygB PCRs as described above.

After marker removal, the transformant still contained multiple *R. emersonii* Cbhl copies and also the cellulase activity was still 1.25-fold improved compared to the empty strain.

In conclusion, we successfully generated marker-free *R. emersonii* transformants by using two dominant markers: a loxP-flanked ble marker that was used for co-transformation with a gene of interest, and a hygromycin marker that was used to transiently transform *R. emersonii* transformants with an AMA plasmid carrying the cre recombinase gene. Transient transformation of *R. emersonii* with cre recombinase was sufficient to remove the loxP-flanked ble marker.

Example 6

Identification of *Rasamsonia emersonii* Genes Involved in Non-Homologous End-Joining and Construction of the Deletion Vectors Genomic DNA of *Rasamsonia emersonii* strain CBS393.64 was sequenced and analyzed. The genes with translated proteins annotated as homologues to known genes involved in non-homologous end-joining are listed in Table 2:

TABLE 2

Genes involved in non-homologous end-joining in *Rasamsonia emersonii* and their homologues in *A. niger*, *P. chrysogenum* and *S. cerevisiae*

| R. emersonii | S. cerevisiae | Genomic sequence | cDNA | protein |
| --- | --- | --- | --- | --- |
| ReKu70 | Ku70 | SEQ ID NO: 19 | SEQ ID NO: 20 | SEQ ID NO: 21 |
| ReKu80 | Ku80 | SEQ ID NO: 22 | SEQ ID NO: 23 | SEQ ID NO: 24 |
| ReRad50 | Rad50 | SEQ ID NO: 25 | SEQ ID NO: 26 | SEQ ID NO: 27 |
| ReRad51 | Rad51 | SEQ ID NO: 28 | SEQ ID NO: 29 | SEQ ID NO: 30 |
| ReRad52 | Rad52 | SEQ ID NO: 31 | SEQ ID NO: 32 | SEQ ID NO: 33 |
| ReRad54 | Rad54 | SEQ ID NO: 34 | SEQ ID NO: 35 | SEQ ID NO: 36 |
| ReRad54 | Rad54 | SEQ ID NO: 37 | SEQ ID NO: 38 | SEQ ID NO: 39 |
| ReRad55 | Rad55 | SEQ ID NO: 40 | SEQ ID NO: 41 | SEQ ID NO: 42 |
| ReRad57 | Rad57 | SEQ ID NO: 43 | SEQ ID NO: 44 | SEQ ID NO: 45 |
| ReCDC2 | CDC2 | SEQ ID NO: 46 | SEQ ID NO: 47 | SEQ ID NO: 48 |
| ReLIG4 | LIG4 | SEQ ID NO: 49 | SEQ ID NO: 50 | SEQ ID NO: 51 |
| ReMRE11 | MRE11 | SEQ ID NO: 52 | SEQ ID NO: 53 | SEQ ID NO: 54 |

Sequences of the *R. emersonii* genes involved in non-homologous end-joining, comprising the genomic sequences of the open reading frames (ORF) (with introns) and approximately 1500 bp of the 5' and 3' flanking regions, cDNA and protein sequences.

Figure 11:
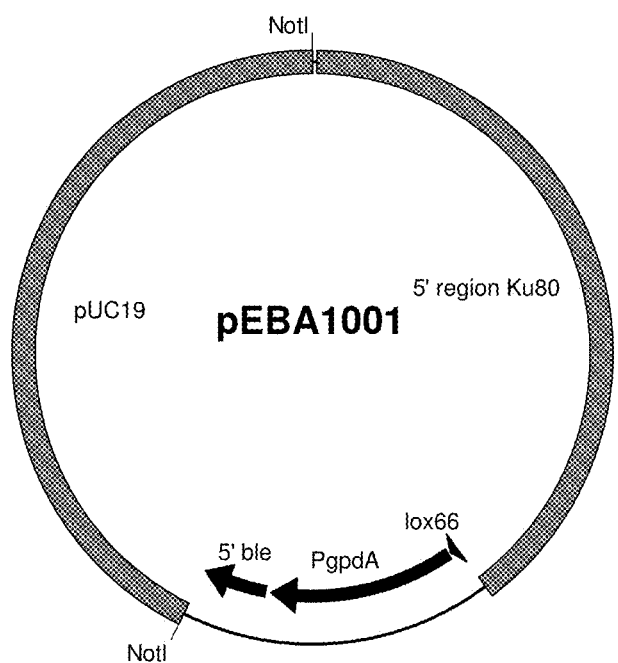
FIG. 11 depicts the pEBA1001 vector. Part of the vector fragment was used in bipartite gene-targeting method in combination with the pEBA1002 vector with the goal to delete the ReKu80 ORF in Rasamsonia emersonii. The vector comprises a 2500 bp 5' upstream flanking region, a lox66 site, the 5' part of the ble coding sequence driven by the A. nidulans gpdA promoter and the backbone of pUC19 (Invitrogen, Breda, The Netherlands). The E. coli DNA was removed by digestion with restriction enzyme NotI, prior to transformation of the R. emersonii strains.
Figure 12:
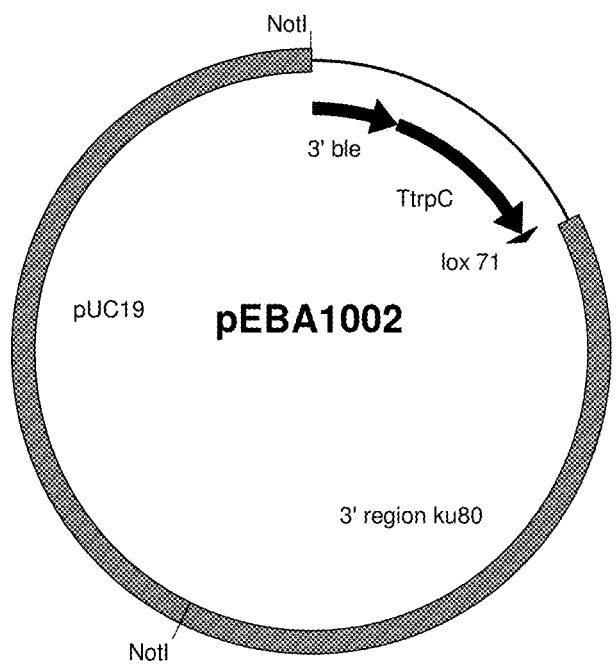
FIG. 12 depicts the pEBA1002 vector. Part of the vector fragment was used in bipartite gene-targeting method in combination with the pEBA1001 vector with the goal to delete the ReKu80 ORF in Rasamsonia emersonii. The vector comprises the 3' part of the ble coding region, the A. nidulans trpC terminator, a lox71 site, a 2500 bp 3' downstream flanking region of the ReKu80 ORF, and the backbone of pUC19 (Invitrogen, Breda, The Netherlands). The E. coli DNA was removed by digestion with restriction enzyme NotI, prior to transformation of the R. emersonii strains.

Two replacement vectors for ReKu80, pEBA1001 and pEBA1002, were constructed according to routine cloning procedures (see FIGS. 11 and 12). The insert fragments of both vectors together can be applied in the so-called "bipartite gene-targeting" method (Nielsen et al., 2006, 43: 54-64). This method is using two non-functional DNA fragments of a selection marker which are overlapping (see also WO2008113847 for further details of the bipartite method) together with gene-targeting sequences. Upon correct homologous recombination the selection marker becomes functional by integration at a homologous target locus. The deletion vectors pEBA1001 and pEBA1002 were designed as described in WO 2008113847, to be able to provide the two overlapping DNA molecules for bipartite gene-targeting.

The pEBA1001 vector comprises a 2500 bp 5' flanking region of the ReKu80 ORF for targeting in the ReKu80 locus, a lox66 site, and the non-functional 5' part of the ble coding region driven by the *A. nidulans* gpdA promoter (PgpdA-ble sequence missing the last 104 bases of the coding sequence at the 3' end of ble, SEQ ID NO: 60) (FIG. 11). The pEBA1002 vector comprises the non-functional 3' part of the ble coding region and the *A. nidulans* trpC terminator (ble-TtrpC sequence missing the first 12 bases of the coding sequence at the 5' end of ble, SEQ ID NO: 61), the *A. nidulans* trpC terminator, a lox71 site, and a 2500 bp 3' flanking region of the ReKu80 ORF for targeting in the ReKu80 locus (FIG. 12).

Example 7

Inactivation of the ReKu80 Gene in *Rasamsonia emersonii*

Figure 13:
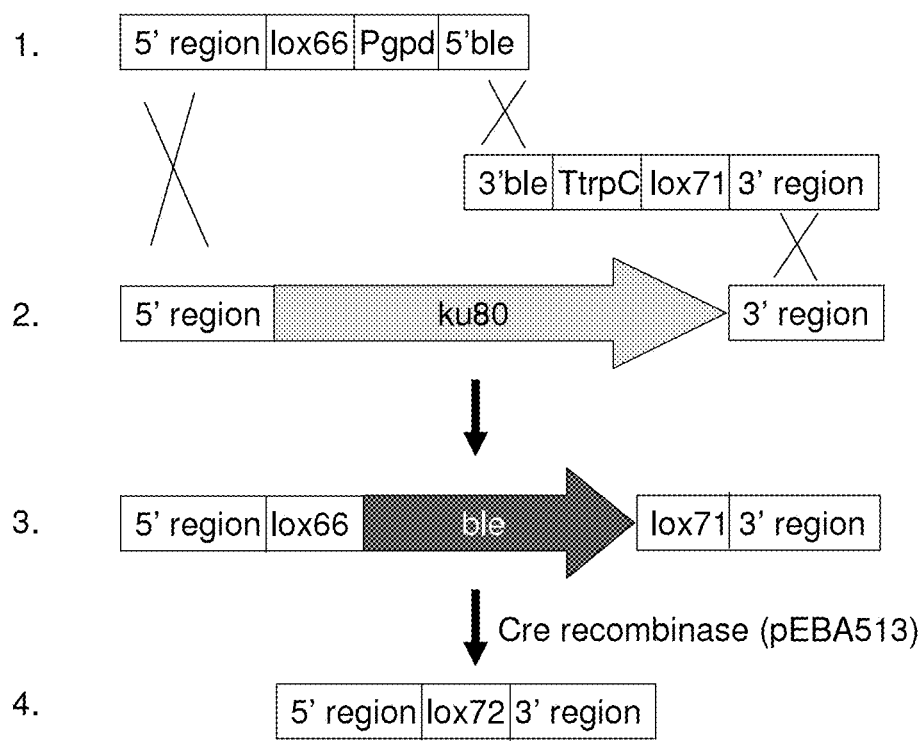
FIG. 13 depicts the strategy used to delete the ReKu80 gene of R. emersonii. The vectors for deletion of ReKu80 comprise the overlapping non-functional ble selection marker fragments (split marker) flanked by loxP sites and 5' and 3' homologous regions of the ReKu80 gene for targeting (1). The constructs integrate through triple homologous recombination (X) at the genomic ReKu80 locus and at the overlapping homologous non-functional ble selection marker fragment (2) and replaces the genomic ReKu80 gene copy (3). Subsequently, the selection marker is removed by transient expression of cre recombinase leading to recombination between the lox66 and lox71 sites resulting in the deletion of the ble gene with a remainder double-mutant lox72 site left within the genome (4). Using this overall strategy, the ReKu80 ORF is removed from the genome.

Linear DNA of the deletion constructs pEBA1001 and pEBA1002 were isolated and used to transform *Rasamsonia emersonii* strain TEC-142S using method as described earlier in WO2011\054899. These linear DNAs can integrate into the genome at the ReKu80 locus, thus substituting the ReKu80 gene by the ble gene as depicted in FIG. 13. Transformants were selected on phleomycin media and colony purified and tested according to procedures as described in WO2011\054899. Growing colonies were diagnosed by PCR for integration at the ReKu80 locus using a primer in the gpdA promoter of the deletion cassette and a primer directed against the genomic sequence directly upstream of the 5' targeting region. From a pool of approximately 250 transformants, 4 strains showed a removal of the genomic ReKu80 gene.

Subsequently, 3 candidate ReKu80 knock out strains were transformed with pEBA513 to remove the ble selection marker by transient expression of the cre recombinase. pEBA513 transformants were plated in overlay on regeneration medium containing 50 μg/ml of hygromycin B. Hygromycin-resistant transformants were grown on PDA containing 50 μg/ml of hygromycin B to allow expression of the cre recombinase. Single colonies were plated on nonselective *Rasamsonia* agar medium to obtain purified spore batches. Removal of the ble marker was tested phenotypically by growing the transformants on media with and without 10 μg/ml of phleomycin. The majority (>90%) of the transformants after transformation with pEBA513 (with the cre recombinase) were phleomycin sensitive, indicating removal of the pEBA1001 and pEBA1002-based ble marker. Removal of the pEBA513 construct in ble-negative strains was subsequently diagnosed phenotypically by growing the transformants on media with and without 50 μg/ml of hygromycin. Approximately 50% of the transformants lost hygromycin resistance due to spontaneously loss of the pEBA513 plasmid.

Figure 14:
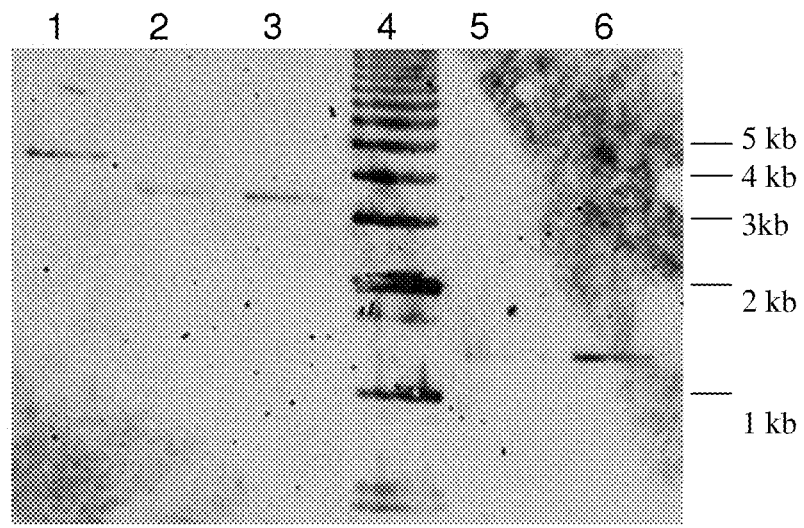
FIG. 14 shows the Southern blot analysis of ReKu80 knock out strains. Genomic DNA was isolated from strains and digested with restriction enzyme HindIII. The Southern blot was hybridized using a probe directed against the 3' region of the ReKu80 gene. Lane 1: wild-type strain; lanes 2 and 3: two phleomycin resistant strains showing fragment size for correct ReKu80 knock out integration; lane 4: labeled molecular weight marker; lanes 5 and 6: two phleomycin sensitive strains with fragment size for correct ReKu80 knock out integration.

Candidate marker-free knock-out strains were tested by Southern analysis for deletion of the ReKu80 gene. Chromosomal DNA was isolated and digested with restriction enzyme HindIII. Southern blots were hybridized with a probe directed against the 3' region of the ReKu80 gene (FIG. 14). The following primers were used to generate the probe:

```
SEQ ID NO: Ku80-For:
                                    (SEQ ID NO: 55)
AGGGTATATGTGGTCTAGTAACGC

SEQ ID NO: Ku80-Rev:
                                    (SEQ ID NO: 56)
TCACAAGTCCATCACGGAACCGGG
```

The expected fragment sizes in wild-type strains, phleomycin resistant ReKu80 knock-out strains and in the phleomycin sensitive strains, were, respectively, 4132 bp, 3197 bp and 1246 bp. The wild-type control strain showed the expected 4132 bp fragment (FIG. 14, lane 1). The 2 candidate phleomycin resistant ReKu80 knock out strains indeed showed the expected 3197 bp fragment (lanes 2 and 3). Removal of the ble gene by cre recombinase resulted in a size reduction of the fragment; a 1246 bp band was detectable on the Southern blot (lanes 5 and 6). In conclusion, we confirmed by Southern blotting that we obtained 2 independent marker-free ReKu80 deletion strains.

Strain deltaReKu80-2 was selected as a representative strain with the ReKu80 gene inactivated.

Example 8

Cloning of RePepA Deletion Vectors

Genomic DNA of *Rasamsonia emersonii* strain CBS393.64 was sequenced and analyzed. The gene with translated protein annotated as protease pepA was identified. Sequences of *Rasamsonia emersonii* pepA (RePepA), comprising the genomic sequence of the ORF and approximately 2500 bp of the 5' and 3' flanking regions, cDNA and protein sequence, are shown in sequence listings 57, 58 and 59 respectively.

Figure 15:
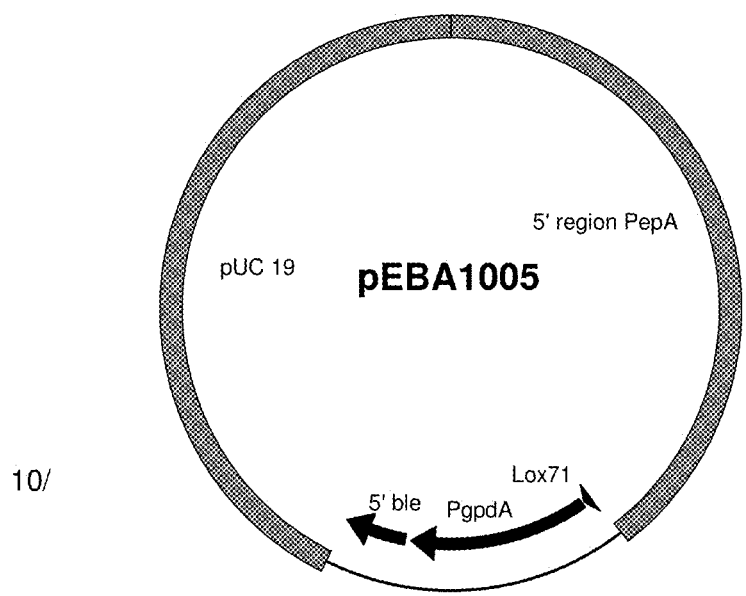
FIG. 15 depicts the pEBA1005 vector that was used in bipartite gene-targeting method in combination with the pEBA1006 vector with the goal to delete the RePepA ORF in Rasamsonia emersonii. The vector comprises a 2500 bp 5' flanking region, a lox66 site, the 5' part of the ble coding region driven by the A. nidulans gpdA promoter and the backbone of pUC19 (Invitrogen, Breda, The Netherlands).
Figure 16:
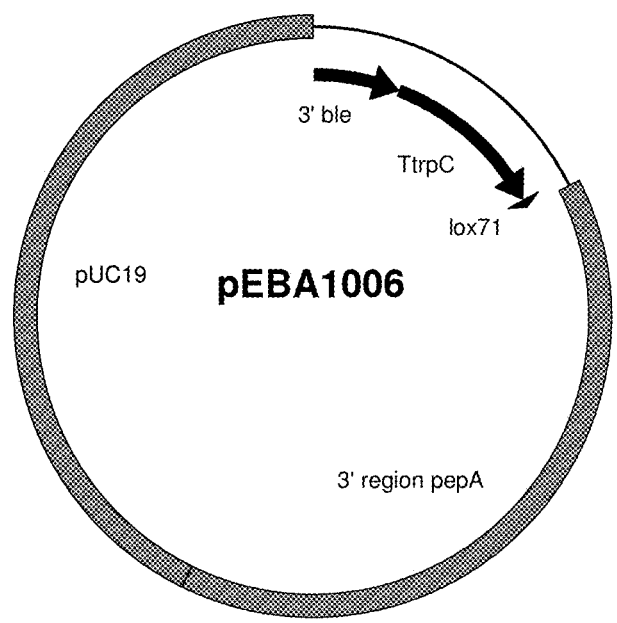
FIG. 16 depicts the pEBA1006 vector that was used in bipartite gene-targeting method in combination with the pEBA1005 vector with the goal to delete the RePepA ORF in Rasamsonia emersonii. The vector comprises the 3' part of the ble coding region, the A. nidulans trpC terminator, a lox71 site, a 2500 bp 3' flanking region of the ReKu80 ORF, and the backbone of pUC19 (Invitrogen, Breda, The Netherlands).
Figure 17:
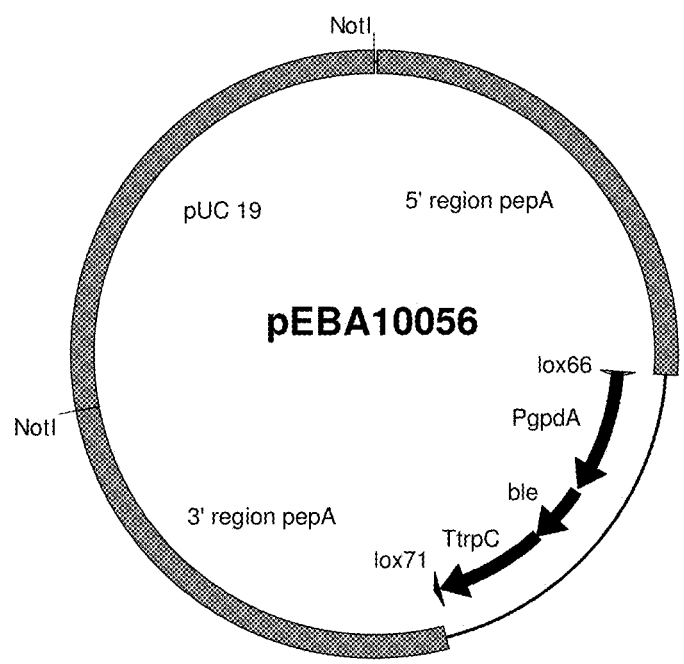
FIG. 17 depicts the pEBA10056 vector that was used to delete the RePepA ORF in Rasamsonia emersonii. The vector comprises a 2500 bp 5' flanking region, a lox66 site, the ble expression cassette consisting of the A. nidulans gpdA promoter, ble coding region and A. nidulans trpC terminator, a lox71 site, a 2500 bp 3' flanking region of the ReKu80 ORF, and the backbone of pUC19 (Invitrogen, Breda, The Netherlands).

Gene replacement vectors for RePepA were designed using the bipartite gene-targeting method and constructed according to routine cloning procedures (see FIGS. 15 and 16). The pEBA1005 construct comprises a 2500 bp 5' flanking region of the RePepA ORF for targeting in the RePepA locus, a lox66 site, and the 5' part of the ble coding region driven by the *A. nidulans* gpdA promoter (PgpdA-ble sequence missing the last 104 bases of the coding sequence at the 3' end of ble, SEQ ID NO: 60). (FIG. 15). The pEBA1006 construct comprises the 3' part of the ble coding region (ble-TtrpC sequence missing the first 12 bases of the coding sequence at the 5' end of ble, SEQ ID NO: 61), the *A. nidulans* trpC terminator, a lox71 site, and a 2500 bp 3' flanking region of the RePepA ORF for targeting in the RePepA locus (FIG. 16). In addition, pEBA10056 was constructed carrying a complete RePepA deletion cassette (FIG. 17). The pEBA10056 construct comprises a 2500 bp 5' flanking region of the RePepA ORF for targeting in the RePepA locus, a lox66 site, the ble expression cassette containing the *A. nidulans* gpdA promoter, ble coding region and the *A. nidulans* trpC terminator, a lox71 site, and a 2500 bp 3' flanking region of the RePepA ORF for targeting in the RePepA locus.

In addition to pEBA1005 and pEBA1006 containing 1500 bp RePepA flanks, constructs were generated consisting of 500, 1000 and 1500 bp RePepA flanks to test the optimal flank length. pEBA1005 and pEBA1006 are representative for those constructs that only differ in flank length.

Example 9

Improved Targeting for Homologous Recombination Events at the RePepA Locus

The targeting efficiency in the ReKu80 knock out strain vs a wild-type strain was assessed by transformation of TEC-142S and the deltaReKu80-2 strain with deletion vectors designed for the inactivation of the RePepA gene encoding the major extracellular acid aspartyl protease from the genome. The RePepA deletion vectors were amplified by PCR and the PCR product was used to transform protoplasts of TEC-142S and the deltaReKu80-2 strain. Transformant selection was performed as described in Example 7.

Figure 18:
FIG. 18 shows a picture of PDA plates supplemented with 1% Casein sodium salt with TEC-142S and the deltaReKu80-2 strains transformed with RePepA deletion constructs containing 2.5 kb flanks.

The targeting frequency was assessed by activity-based plate assays indicative of the inactivation of RePepA. The plate assays were performed by propagating transformants on PDA plates supplemented with 1% Casein sodium salt. In total 20 transformants of each transformation were analysed for halo formation. Most transformants of CBS393.64 still showed halo formation after transformation with 2.5 kb RePepA deletion constructs, whereas no halo formation was observed in transformants of deltaReKu80-2 (FIG. 18). In Table 3, the targeting frequency, as judged by halo formation on casein plates is shown.

TABLE 3

Targeting frequencies of RePepA deletion vectors with different flanking lengths in the deltaReKu80-2 strain as compared with strain CBS393.64. Deletion vectors using the bipartite gene-targeting method are indicated with "(bipartite)"

| Flanking length | Targeting (%) | |
|---|---|---|
| | TEC-142S | deltaReKu80-2 |
| 2.5 kb | <5 | 90 |
| 2.5 kb (bipartite) | 10 | 100 |
| 1.5 kb (bipartite) | 5 | 100 |
| 1 kb (bipartite) | <5 | 85 |
| 0.5 kb (bipartite) | <5 | n.d.* |

*not determined because of low amount of transformants

The targeting efficiency was significantly improved in de deltaReKu80-2 strain compared to the CBS393.64 strain. In the wild-type strain highest targeting efficiencies (10%) were observed when using 2.5 flanks using the bipartite gene-targeting method. Deletion of RePepA using a plasmid carrying the complete deletion cassette was successful in 90% of the transformants of the deltaReKu80-2 strain. When using the bipartite gene-targeting method, in the deltaReKu80-2 strain 1.5 kb flanks are already sufficient to obtain 100% targeting and 1 kb flanks to obtain correct transformants with high efficiency.

These findings indicate that strains with improved efficiency for homologous recombination after inactivation of at least one of the genes involved in non homologous end joining in Rasamsonia emersonii results in a significant increase of the targeting efficiency of vectors for integration through double homologous recombination. In this example this has been illustrated for disruption of ReKU80.

Example 10

Figure 19:
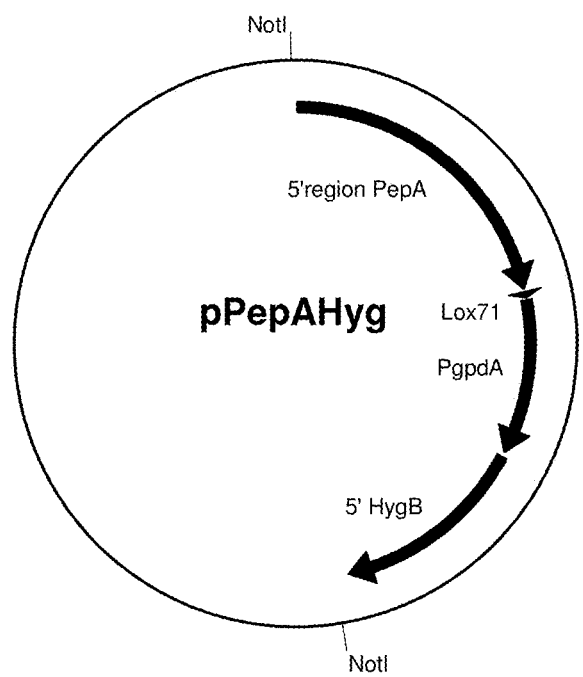
FIG. 19 sets out a schematic diagram of plasmid pPepAHyg, which comprises part of a replacement cassette to inactivate the RePepA gene in R. emersonii. The replacement cassette comprises a 1500 nuleotice RePepA 5' flanking region, part of a hygB marker cassette, a mutant loxP site and E. coli DNA. More details for pPepAHyg can be found in the Examples section (vide infra).
Figure 20:
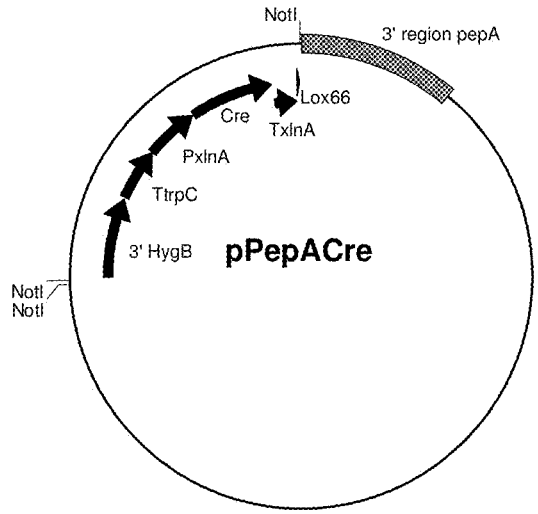
FIG. 20 sets out a schematic diagram of plasmid pPepA-Cre, which comprises part of a replacement cassette to inactivate the RePepA gene in R. emersonii. The replacement cassette comprises a RePepA 3' flanking region, part of a hygB marker cassette, a mutant loxP site, a cre recombinase expression cassette and E. coli DNA. More details for pPepACre can be found in the Examples section (vide infra).

Construction of Rasamsonia Deletion Vector for Simultaneous Gene Deletion Using Multiple Overlapping DNA Fragments without a Functional Marker with loxP Sites and Marker Removal after a Single Transformation Step Gene replacement vectors for RePepA were designed using the bipartite-targeting method as described in Example 3, with one exception: RePepA flanking regions of approximately 1500 base-pairs were used for homologous recombination at the RePepA ORF. The first vector pPepAHyg (General layout as in FIG. 19) comprises a first non-functional hygB marker fragment (PgpdA-HygB sequence missing the last 27 bases of the coding sequence at the 3' end of hygB, SEQ ID NO: 4) and at one side of the hygB cassette a Lox71 sequence site and the 5'-upstream gene flanking region of the RePepA ORF (5' region pepA). The second pPepACre vector (General layout as in FIG. 20) comprises a non-functional hygB fragment (HygB-TtrpC) sequence missing the first 44 bases of the coding sequence at the 5' end of hygB, SEQ ID NO: 5) and at one side of the hygB cassette, a cre recombinase cassette, a Lox66 sequence site and the 3'-downstream gene flanking region of the RePepA ORF (3' region RePepA). The cre recombinase cassette contains the A. nidulans xylanase A promoter, a cre recombinase and xylanase A terminator, to allow xylose-inducible expression of the cre recombinase (SEQ ID NO: 6). Upon homologous recombination, the first and second non-functional fragments become functional producing a functional hygB cassette. Both RePepA upstream and downstream gene flanking regions target for homologous recombination of the bipartite fragments at the predestined RePepA genomic locus.

In the following example we will show that the cre-lox system as used herein is a very efficient system for gene disruption and marker removal after a single transformation. In addition, when using strains deficient in NHEJ, the bipartite gene-targeting approach combined with the cre-lox system results in a highly efficient system for making marker-free strains with defined modifications.

Example 11

Efficient Gene Deletion Using Multiple Overlapping DNA Fragments without a Functional Marker (Bipartite Gene-Targeting Approach) and a Small Overlapping Sequence Use of a mutant which is deficient in a gene encoding a component involved in NHEJ, such as inactivation of at least one of the Ku genes results in a significant increase of the targeting efficiency of integration vectors through (double) homologous recombination (see Example 9).

In addition, increase of the targeting efficiency for homologous recombination can be obtained as described in Example 9. This bipartite gene-targeting method comprises providing two sets of DNA molecules of which the first set comprises DNA molecules each comprising a first non-functional fragment of the replacement sequence of interest flanked at its 5'-side by a DNA sequence substantially homologous to a sequence of the chromosomal DNA flanking the target sequence and the second set comprises DNA molecules each comprising a second non-functional fragment of the DNA replacement sequence of interest overlapping with the first non-functional fragment and flanked at its 3'-side by a DNA sequence substantially homologous to a sequence of the chromosomal DNA flanking the target sequence, wherein the first and second non-functional fragments become functional upon recombination.

Gene replacement vectors pPepAHyg and pPepACre (layouts as described in Example 10) both comprise approximately a 1.5 kb flanking region for homologous recombination at the RePepA ORF. In addition, they both contain a (non functional) hygB selection marker and a loxP site (lox71 or lox66). The pPepACre construct also contains the bacteriophage P1 Cre gene under control of the *A. nidulans* xylanase A promoter to allow inducible Cre expression upon xylose induction.

Figure 21:
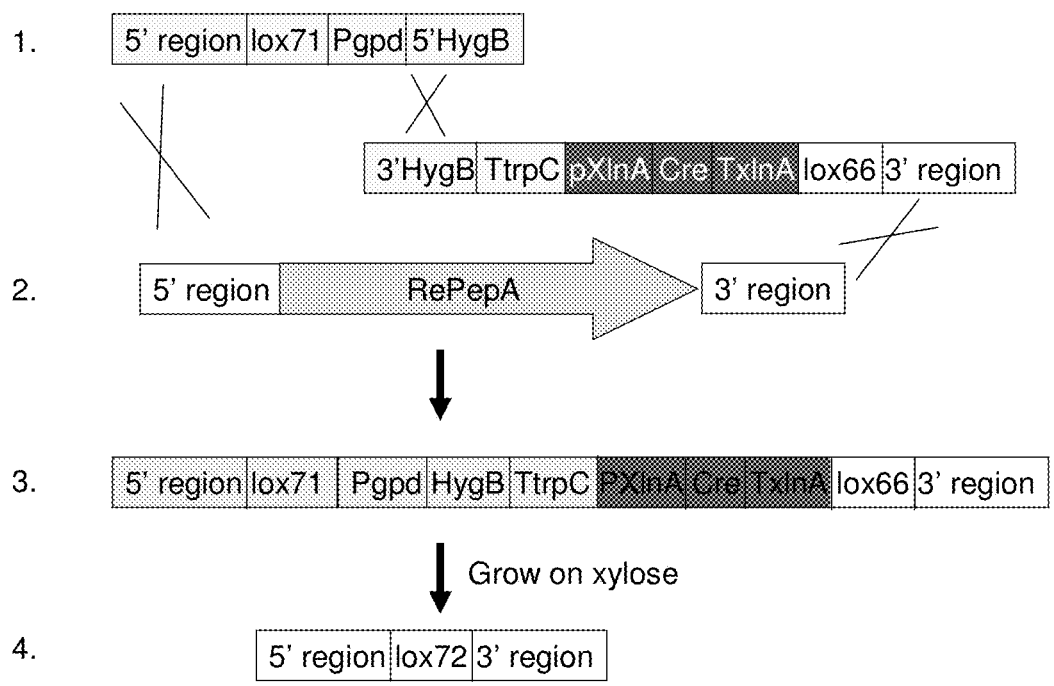
FIG. 21 sets out a schematic representation for fragment use in transformation and recombination in R. emersonii. The vectors for deletion of RePepA comprise the overlapping non-functional hygB selection marker fragments (split marker) flanked by loxP sites and 5' and 3' homologous regions of the RePepA gene for targeting (1). The constructs integrate through triple homologous recombination (X) at the genomic RePepA locus and at the overlapping homologous non-functional hygB selection marker fragment (2) and replaces the genomic RePepA gene copy (3). Subsequently, the selection marker is removed by growing transformants on xylose to induce cre recombinase expression leading to recombination between the lox66 and lox71 sites resulting in the deletion of the hygB and Cre expression cassettes with a remainder double-mutant lox72 site left within the genome (4).

The two linear bipartite gene-targeting fragments for RePepA disruption were generated by PCR in sufficient quantities using the pPepAHyg and pPepACre plasmids as template. The overlap of the two nucleotide fragments at the non-functional hygB gene was around 1 kb in this case. These linear DNAs can integrate into the genome at the RePepA locus, thus substituting the RePepA gene by the hygB gene as depicted in FIG. 21.

For each fragment, 2 μg of DNA was used to transform *R. emersonii* strain deltaReKu80-2. Transformants were selected based on hygromycin B resistance, colony purified according to standard procedures as described in Example 5 and subsequently analyzed after purification.

Figure 22:
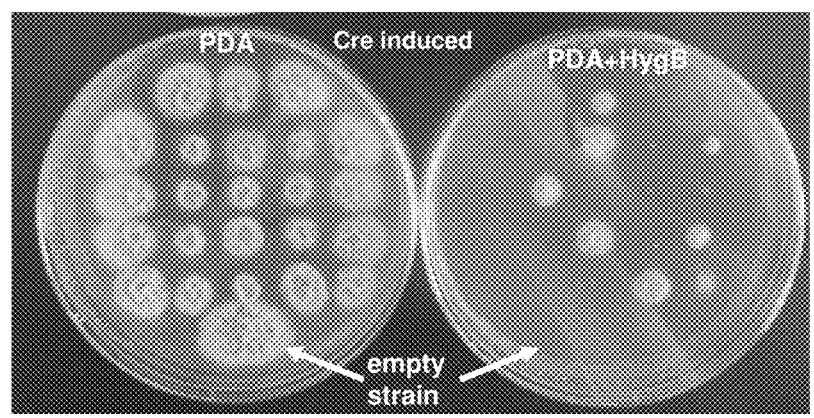
FIG. 22 sets out Cre induced loss of loxP flanked hygB selection marker in Rasamsonia emersonii. Transformants carrying the loxP flanked hygB selection marker and cre recombinase expression cassette integrated into the RePepA locus were plated on xylose as carbon source to induce cre recombinase. After cre induction colonies were transferred to PDA without selection (left) and PDA with hygromycinB selection (right). An empty strain was included as a control for selection.

For inducing the cre-recombinase under control of the xylanase promoter, minimal medium agar plates containing 1% xylose and 1% glucose (xylanase induction medium) and 0.2% yeast extract were used. Transformants were transferred from PDA plates to xylanase induction medium with yeast extract. Subsequently, the plates were incubated for 5 days at 42° C. Resulting colonies after growth on xylose were plated on non-selective *Rasamsonia* agar medium to obtain purified spore batches. When Cre recombinase is induced by xylose, deletion of the DNA cassette in between the two specific loxP sites can occur by excision. Removal of the hygB marker was tested phenotypically by growing the transformants on media with and without 50 μg/ml of hygromycin B. Approximately, 65% of the cre-induced transformants were not able to grow on hygromycin B (FIG. 22). Loss of hygromycin B resistance likely is coupled to loss of the hygB marker cassette through cre recombinase activity. Indeed marker removal was confirmed by PCR analysis of the RePepA locus.

This Example shows that in a strain deficient in NHEJ, use of bipartite gene-targeting and combination with an inducible recombination system according the invention allows for a very efficient strain construction/disruption in building marker-free strains without the need of a second transformation or counter-selection procedures in strain construction.

Example 12

Knocking Out the ADE1 Gene in *S. cerevisiae* Using a Bipartite Marker and Cre-Recombinase with Inducible Promoter all Flanked Between Lox71 and Lox66

Figure 23:
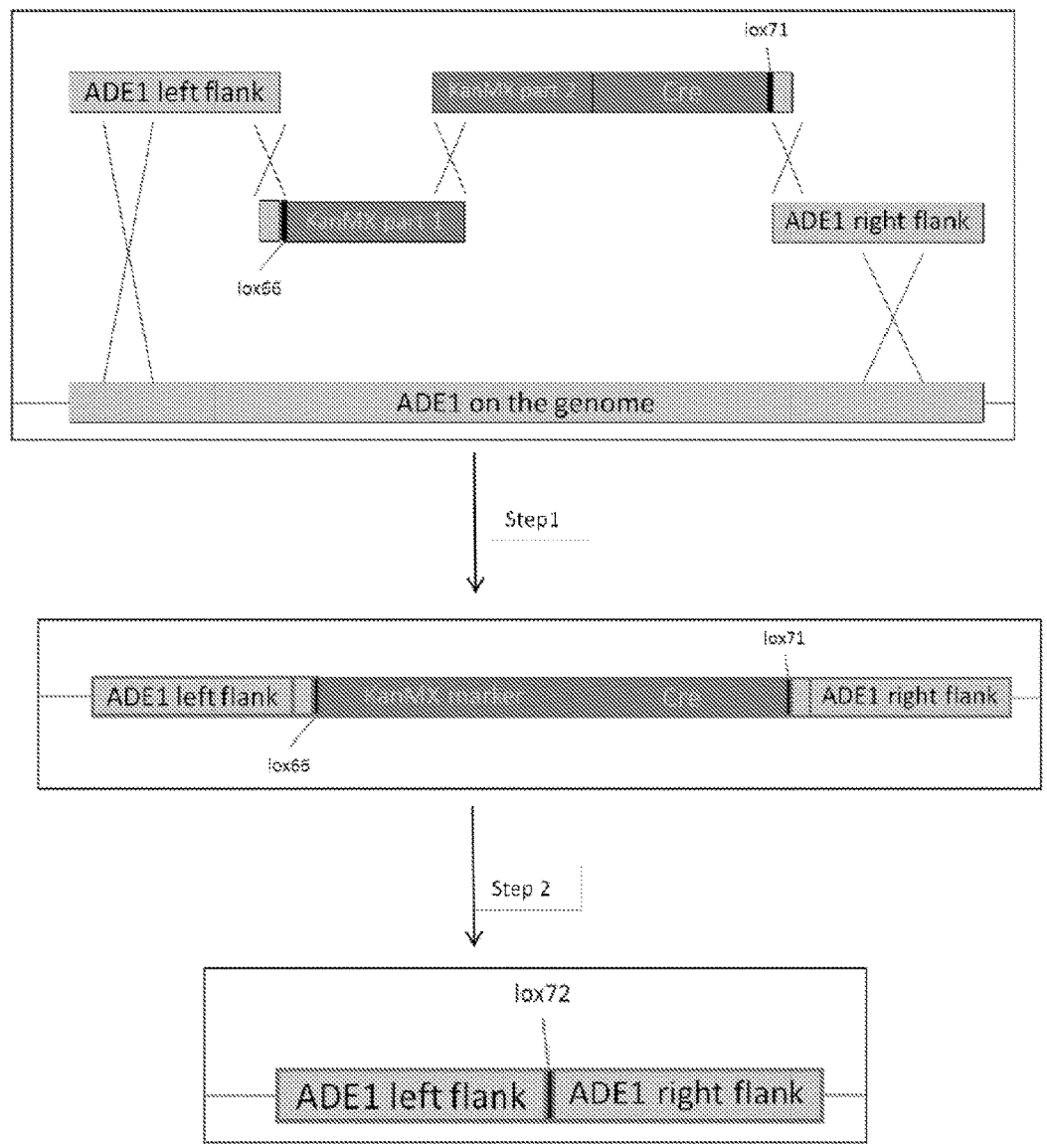
FIG. 23 sets out a schematic procedure for knocking-out the ADE1 gene in S. cerevisiae using a bipartite marker and cre-recombinase with inducible promoter all flanked between lox71 and lox66

This procedure is set out schematically in FIG. 23. Use two basic constructs in this cloning procedure. The basic constructs can be ordered at DNA2.0 or any other commercial company providing synthetic DNA sequences. Basic construct 1 contains the lox71 site followed by a non-functional part of the KanMX marker cassette (SEQ ID NO: 62). The sequence can be cloned in a standard *E. coli* cloning vector used by the synthetic DNA provider. The second basic construct contains a non-functional part of the KanMX marker cassette with overlapping sequences of 50 bp towards the non-functional part of KanMX of the first construct. When both non-functional KanMX marker fragments recombine via in vivo homologous recombination a full functional KanMX marker cassette will be formed. The second construct also contains the cre-recombinase with the galactose inducible GAL promoter and lox66. The sequence of basic construct 2 is provided as SEQ ID NO: 63 in the sequence list. Perform the following steps to knock out the ADE1 gene in *S. cerevisiae*.

Chromosomal DNA Isolation with YeaStar Genomic DNA Kit™ (ZYMO Research)

Inoculate the *S. cerevisiae* CEN.PK113-7D (MATa MAL2-8c SUC2) yeast strain in 1 ml YephD (2% glucose) in a 24 well plate and incubate ON at 30° C., 550 rpm and 80% humidity in a shaker. Measure the OD660 with a biochrom Ultrospec 2000 spectrophotometer to obtain the right amount of cells (1-5×10$^7$ cells) as described in the manual of the kit. Proceed with the isolation as described in Protocol II in the manual of the YeaStar Genomic DNA Kit™. After isolation, measure the concentration with a NANODROP™ ND-1000 (Thermo Scientific), concentrations are usually low, in the order of 10 ng/μl, but suitable enough for PCR purposes.

PCR Amplify and Purify Fragments for Transformation to *S. Cerevisiae*

First PCR amplify the fragments necessary for the transformation to *S. cerevisiae*. PCR fragment 1 (SEQ ID NO: 72) is a genomic integration flank upstream of the ADE1 sequence that needs to be deleted. It is amplified using the forward primer with SEQ ID NO: 64 and the reverse primer with sequence SEQ ID NO: 65.

PCR fragment 2 (SEQ ID NO: 73) is the sequence of basic construct 1 with 50 bp overlapping homologous sequences towards PCR fragment 1. It is amplified using the primers with sequence SEQ ID NO: 66 and SEQ ID NO: 67. It contains lox66 and a non-functional part of the KanMX marker cassette.

PCR fragment 3 (SEQ ID NO: 74) is the sequence of basic construct 2 containing the overlapping sequence towards the non-functional KanMX marker cassette in PCR fragment 2. It also contains the Cre recombinase expression cassette and the lox71 site. The 3' end sequence of PCR fragment 3 contains a 50 bp overlapping sequence towards PCR fragment 4. PCR fragment 3 is amplified using the primers with sequence SEQ ID NO: 68 and sequence SEQ ID NO: 69.

PCR fragment 4 (SEQ ID NO: 75) is the genomic integration flank downstream of ADE1 sequence to delete. PCR fragment 4 is amplified using the primers with sequence SEQ ID NO: 70 and sequence SEQ ID NO: 71.

Amplify the DNA fragments with Phusion polymerase (Finnzymes) according to the manual. Use basic construct 1 and 2 for PCR reaction 2 and 3 respectively as template. Use CEN.PK113-7D genomic DNA (isolated as described previously) as template for the amplification of the 5' and 3' ADE1 deletion flanks. Check the size of the PCR fragments with standard agarose electrophoresis techniques. Purify the PCR amplified DNA fragments with the NucleoMag® 96 PCR magnetic beads kit of Macherey-Nagel, according to the manual and measure the DNA concentrations with the Trinean DropSense® 96 of GC biotech.

Transformation of the PCR Fragments to *S. cerevisiae*

Perform transformation of *S. cerevisiae* according to Gietz and Woods (2002; Transformation of the yeast by the LiAc/SS carrier DNNPEG method. Methods in Enzymology 350: 87-96). Transform CEN.PK113-7D (MATa MAL2-8c SUC2) with 1 µg of each of the amplified and purified PCR fragments (PCR fragments 1-4). Plate transformation mixtures on YEPhD-agar (BBL PHYTONE™ peptone 20.0 g/l, Yeast Extract 10.0 g/l, Sodium Chloride 5.0 g/l, Agar 15.0 g/l and 2% glucose) containing G418 (400 µg/ml). After 3 to 5 days of incubation at 30° C., colonies will appear on the plates, whereas the negative control (i.e., no addition of DNA in the transformation experiment) will result in blank plates. The correct KO of the ADE1 gene will give a red or pink collared phenotype of the colonies.

Efficient Out-Recombination of the Marker Cassette and Cre Recombinase

Pick six red colonies from the transformation plates and transfer with an inoculation loop to 2 ml YEP medium (Peptone 10.0 g/l, Yeast Extract 10.0 g/l, Sodium Chloride 5.0 g/l) with 20 g/l galactose and 0.5 g/l glucose in a 12 ml greiner tube. After ON incubation at 30° C. plate the cultures on YEP-agar with 2% galactose in the appropriate dilution to obtain single colonies on the plate and incubate for 2-4 days at 30° C. Pick and restreak some colonies each on an individual fresh YEPhD-agar plate and restreak the same colony on an individual YEPhD-agar plate containing G418 (400 µg/ml). The *S. cerevisiae* transformants will grow on the YEPhD-agar plate without the G418 and most of them will not grow on the YEPhD-agar plate containing G418, indicating loss of the KanMX marker cassette and cre-recombinase gene by recombination of the lox66 and lox71 sites induced by the cre-recombinase. Continue with the colonies that lost the marker and Cre cassette.

This is a method that enables the knockout of a gene and removal of the marker in *S. cerevisiae* with a fast and efficient one step procedure using a split marker and cre recombinase gene both between lox66 and lox71 sites.

Example 13

Automated and High Throughput Gene Deletion Using Multiple Overlapping DNA Fragments without a Functional Marker (Bipartite Gene-Targeting Approach) and a Small Overlapping Sequence Based on the approach used for the epo gene in the Example 1, where two different gene replacement vectors were used, two gene replacement vectors were designed for a large set of target genes. In essence, these vectors comprise approximately 0.9-1.2 kb flanking regions of the respective ORF sequences, to target for homologous recombination at the predestined genomic loci. They contain the hygromycin B marker but also may contain for example the *A. nidulans* bi-directional amdS selection marker or the phleomycin selection marker for transformation.

Based on genomic sequences, gene replacement vectors for 96 selected genes were designed as follows:

A first vector pDEL_UP_Hyg-1 (General layout as in FIG. 3) comprises a first non-functional hygB marker fragment (PgpdA-HygB sequence missing the last 27 bases of the coding sequence at the 3' end of hygB, SEQ ID NO: 4) and at one side of the hygB cassette a Lox71 sequence site and the 900-1200 bp 5'-upstream gene flanking region of the target ORF (-US). This upstream gene flanking region can be made synthetically or made by PCR using fragment-specific oligonucleotides for PCR amplification.

A second pDEL_Down_CRE-1 vector (General layout as in FIG. 4) comprises a non-functional hygB fragment (HygB-TtrpC sequence missing the first 44 bases of the coding sequence at the 5' end of hygB, SEQ ID NO: 5) and at one side of the hygB cassette, a cre recombinase cassette, a Lox66 sequence site and the 3'-downstream gene flanking region of the targete ORF (-DS). The cre recombinase cassette is described in Example 1 above. For each specific target gene/genomic area a specific set of gene replacement vectors is made: one pDEL_UP_Hyg-1 type for the upstream fragment, one pDEL_Down_CRE-1 type or the downstream fragment. These vectors can be made through various methods as for example, gene synthesis, Gibson cloning (Gibson D G, Young L, Chuang R Y, Venter J C, Hutchison C A 3rd, Smith H O. (2009). "Enzymatic assembly of DNA molecules up to several hundred kilobases". *Nature Methods* 6 (5): 343-345; Gibson D G. (2011). "Enzymatic assembly of overlapping DNA fragments". *Methods in Enzymology* 498: 349-361), cloning through restriction digestion, ligation and *E. coli* transformation, in vivo recombination in yeast, preferably a method which can be automated and performed in MTP.

The method applied for gene replacements in this example uses linear DNA fragments, preferably made by PCR in an MTP plate, using the two different types of gene replacement vectors pDEL_UP_Hyg-1 and pDEL_Down_CRE-1 as template for each specific gene. As also detailed in WO 2008113847, these two different fragments were designed and constructed to be able to provide the two overlapping DNA molecules for bipartite gene-targeting. Therefore, linear DNA fragments are made by PCR using the respective gene-specific plasmid as template in sufficient quantities. Preferably, the PCR fragments are mixed by using pipetting robots and made in an MTP plate. Protoplasts of strain GBA302 (ΔglaA, ΔpepA, ΔhdfA) are transformed with 2 µg of each PCR fragment.

Preferably, the transformation is done according the method of (WO 2008/000715) and performed in MTP. Transformants are selected based on hygromycin B resistance, preferably in regeneration plates with hygB. In addition to previously described large scale agar plates, preferably this plate can be an MTP plate with agar medium. A second selection step is done to colony purify the strains, which can be done according to standard procedures as described (EP635574B) or by replating on PDA medium with 60 µg/ml hygB in MTP format.

For inducing the cre-recombinase under control of the xylanase promoter, minimal medium agar plates containing 1% xylose and 1% glucose (xylanase inducing medium) were used. Transformants were transferred from PDA plates to xylanase induction medium, preferrably in MTP plate. Subsequently, the plates were incubated for 6 days at 30° C. Subsequently, spores were transferred to a new agar MTP plate plates containing 1% xylose and 1% glucose. Resulting colonies after re-growth on xylanase inducing medium were tested for their hygromycin B resistance, by testing growth on plates with and without hygromycin B (60 µg/ml) as described above.

Most colonies analyzed after purification and growth on xylanase inducing medium have lost their hygromycin B resistance. Individual transformants can be tested for their respective gene disruptions. Targeting frequency obtained through this method is similar to that of the transformations using a single type of fragment such as for nicB or epo as described above. In addition, overall success percentage obtained after fragment cloning, PCR amplification, transformation of fragment and colony purification for the 96 genes is over 90%.

In this example we show that the cre-lox system as used herein is a very efficient system for gene disruption and marker removal after a single transformation. In addition, when using strains deficient in NHEJ, the bipartite gene-targeting approach combined with the cre-lox system results in a highly efficient system for making marker-free strains with defined modifications, which very well can be automated and efficiently used for high throughput gene and genome-wide gene disruption programs, thereby generating marker-free strains which can be used in subsequent transformations.

The invention claimed is:

1. A method for carrying out recombination at a target locus to delete an existing sequence at the target locus, which method comprises:
providing two or more nucleic acids which, when taken together, comprise: (a) sequences capable of homologous recombination with sequences flanking the target locus; (b) two or more site-specific recombination sites; (c) a sequence encoding a recombinase which recognizes the site-specific recombination sites; and (d) a sequence encoding a marker,
wherein the two or more nucleic acids are capable of homologous recombination with each other so as to give rise to a single nucleic acid, and
wherein at least two of the two or more nucleic acids each comprise a sequence encoding a non-functional portion of the marker; and
recombining the said two or more nucleic acids with each other and with the sequences flanking the target locus so that a contiguous nucleic acid sequence encoding a functional marker, the sequence encoding the recombinase and at least two site-specific recombination sites are inserted at the target locus, said marker-encoding and/or recombinase-encoding sequence being flanked by at least two site-specific recombination sites and the said site-specific recombination sites being flanked by the sequences capable of homologous recombination with sequences flanking the target locus, wherein recombination of the nucleic acids with each other and with sequences flanking the target locus is carried out in vivo in a fungal cell,
the method further comprising expressing the recombinase so that the sequence located between the site-specific recombination sites is out-recombined, wherein out-recombination of the nucleic acid sequence between site-specific recombination sites is carried out in vivo, and
wherein the site-specific recombination sites are lox sites and the recombinase is Cre; wherein the site-specific recombination sites are FRT sites and the recombinase is Flp; wherein the recombination sites are Vlox sites and the recombinase is VCre; or wherein the recombination sites are Slox and the recombinase is SCre.

2. A method according to claim 1, wherein the two or more nucleic acids, when taken together, comprise sequences capable of homologous recombination with sequences flanking two or more target loci, so that recombining the said two or more nucleic acids with each other and with the sequences flanking the target loci results in the insertion of at least two site-specific recombination sites at each target locus, wherein recombining the two or more nucleic acids results in:
a contiguous sequence encoding a functional marker is present at each target locus;
a sequence encoding a functional recombinase is present in at least one target locus;
said marker-encoding and/or recombinase-encoding sequence located between at least two site-specific recombination sites; and
the said site-specific recombination sites are flanked by the sequences capable of homologous recombination with sequences flanking the target locus.

3. A method according to claim 1, wherein two of the at least two nucleic acids each comprise a sequence encoding a non-functional portion of the recombinase such that together they comprise nucleic acid sequence encoding a functional recombinase.

4. A method according to claim 1, wherein the marker or markers is/are out-recombined.

5. A method according to claim 1, wherein expression of the recombinase is controlled by an inducible promoter.

6. A method according to claim 2, wherein the two or more nucleic acids, taken together, comprise sequences encoding at least two different markers, wherein, for each marker, at least two of the two or more nucleic acids each comprise a sequence encoding a non-functional portion of the marker, such that recombination of the two or more nucleic acids results in a different marker gene-encoding sequence being inserted at each target locus.

7. A method according to claim 6, wherein recombination of the two or more nucleic acids results in the said marker-encoding sequences being inserted at each target locus so that they are located between site-specific recombination sites and may be out-recombined from the target loci on expression of the recombinase.

8. A method according to claim 1, wherein the fungal cell is a yeast cell.

9. A method according to claim 1, wherein the fungal cell is a filamentous fungal cell.

10. A method according to claim 1, wherein the method is carried out in a cell which is variant of a parent host cell, the parent host cell having a preference for non-homologous recombination, wherein a ratio of non-homologous recombination/homologous recombination is decreased in the variant as compared to said ratio in said parent host cell measured under the same conditions.

11. A method according to claim 1, wherein the site-specific recombination sites are such that out-recombination following recombinase expression gives rise to a single mutant site-specific recombination site at the target locus which is not recognized by the recombinase.

12. A method according to claim 1, wherein the target locus comprises a coding sequence which is disrupted and/or partially or fully deleted.

13. A method according to claim 1, wherein the method is carried out two or more times in parallel.

14. A method according to claim 13, wherein each parallel reaction is carried out in a volume of about 250 µl or less.

15. A method according to claim 8, wherein the fungal cell is a yeast cell selected from the group consisting of *S. cerevisiae, Yarrowia lypolytica*, and *K. lactis*.

16. A method according to claim 9, wherein the filamentous fungal cell is from a species of a genus selected from the group consisting of *Aspergillus, Penicillium, Talaromyces*, and *Trichoderma*.

* * * * *

SEQUENCE LISTING

```
<160> NUMBER OF SEQ ID NOS: 75

<210> SEQ ID NO 1
<211> LENGTH: 34
<212> TYPE: DNA
<213> ORGANISM: Artificial Sequence
<220> FEATURE:
<223> OTHER INFORMATION: mutant loxP site, lox66

<400> SEQUENCE: 1
ataacttcgt atagcataca ttatacgaac ggta                               34

<210> SEQ ID NO 2
<211> LENGTH: 34
<212> TYPE: DNA
<213> ORGANISM: Artificial Sequence
<220> FEATURE:
<223> OTHER INFORMATION: mutant loxP site, lox71

<400> SEQUENCE: 2
taccgttcgt atagcataca ttatacgaag ttat                               34

<210> SEQ ID NO 3
<211> LENGTH: 34
<212> TYPE: DNA
<213> ORGANISM: Artificial Sequence
<220> FEATURE:
<223> OTHER INFORMATION: double-mutant loxP site, lox72 site

<400> SEQUENCE: 3
taccgttcgt ataatgtatg ctatacgaac ggta                               34

<210> SEQ ID NO 4
<211> LENGTH: 1790
<212> TYPE: DNA
<213> ORGANISM: Artificial Sequence
<220> FEATURE:
<223> OTHER INFORMATION: non-functional hygB marker fragment (PgpdA-HygB
      sequence missing the last 27 bases of the coding sequence at the 3
      end of hygB)

<400> SEQUENCE: 4
cagacagctc tggcggctct gaggtgcagt ggatgattat taatccggga ccggccgccc     60
ctccgccccg aagtggaaag gctggtgtgc ccctcgttga ccaagaatct attgcatcat    120
cggagaatat ggagcttcat cgaatcaccg gcagtaagcg aaggagaatg tgaagccagg    180
ggtgtatagc cgtcggcgaa atagcatgcc attaacctag gtacagaagt ccaattgctt    240
ccgatctggt aaaagattca cgagatagta ccttctccga agtaggtaga gcgagtaccc    300
ggcgcgtaag ctccctaatt ggcccatccg gcatctgtag ggcgtccaaa tatcgtgcct    360
ctcctgcttt gcccggtgta tgaaaccgga aaggccgctc aggagctggc cagcggcgca    420
gaccgggaac acaagctggc agtcgaccca tccggtgctc tgcactcgac ctgctgaggt    480
ccctcagtcc ctggtaggca gctttgcccc gtctgtccgc ccggtgtgtc ggcggggttg    540
acaaggtcgt tgcgtcagtc caacatttgt tgccatattt tcctgctctc cccaccagct    600
gctcttttct tttctctttc ttttcccatc ttcagtatat tcatcttccc atccaagaac    660
ctttatttcc cctaagtaag tactttgcta catccatact ccatccttcc catcccttat    720
```

```
tcctttgaac ctttcagttc gagctttccc acttcatcgc agcttgacta acagctaccc    780
cgcttgagca gacatcacca tgcctgaact caccgcgacg tctgtcgaga agtttctgat    840
cgaaaagttc gacagcgtct ccgacctgat gcagctctcg gagggcgaag aatctcgtgc    900
tttcagcttc gatgtaggag ggcgtggata tgtcctgcgg gtaaatagct gcgccgatgg    960
tttctacaaa gatcgttatg tttatcggca ctttgcatcg gccgcgctcc cgattccgga   1020
agtgcttgac attggggaat tcagcgagag cctgacctat tgcatctccc gccgtgcaca   1080
gggtgtcacg ttgcaagacc tgcctgaaac cgaactgccc gctgttctgc agccggtcgc   1140
ggaggccatg gatgcgatcg ctgcggccga tcttagccag acgagcgggt tcggcccatt   1200
cggaccgcaa ggaatcggtc aatacactac atggcgtgat tcatatgcgc gattgctga    1260 tccccatgtg tatcactggc aaactgtgat ggacgcacac cgtcagtgcgt ccgtcgcgca   1320 ggctctcgat gagctgatgc tttgggccga ggactgcccc gaagtccggc acctcgtgca   1380
cgcggatttc ggctccaaca atgtcctgac ggacaatggc cgcataacag cggtcattga   1440
ctggagcgag gcgatgttcg gggattccca atacgaggtc gccaacatct tcttctggag   1500
gccgtggttg gcttgtatgg agcagcagac gcgctacttc gagcggaggc atccggagct   1560
tgcaggatcg ccgcggctcc gggcgtatat gctccgcatt ggtcttgacc aactctatca   1620
gagcttggtt gacggcaatt tcgatgatgc agcttgggcg cagggtcgat gcgacgcaat   1680
cgtccgatcc ggagccggga ctgtcgggcg tacacaaatc gcccgcagaa gcgcggccgt   1740
ctggaccgat ggctgtgtag aagtactcgc cgatagtgga aaccgacgcc              1790
```

<210> SEQ ID NO 5
<211> LENGTH: 1682
<212> TYPE: DNA
<213> ORGANISM: Artificial Sequence
<220> FEATURE:
<223> OTHER INFORMATION: non-functional hygB fragment (HygB-TtrpC sequence missing the first 44 bases of the coding sequence at the 5' end of hygB)

<400> SEQUENCE: 5

```
aaagttcgac agcgtctccg acctgatgca gctctcggag ggcgaagaat ctcgtgcttt     60
cagcttcgat gtaggagggc gtggatatgt cctgcgggta aatagctgcg ccgatggttt    120
ctacaaagat cgttatgttt atcggcactt tgcatcggcc gcgctcccga ttccggaagt    180
gcttgacatt ggggaattca gcgagagcct gacctattgc atctcccgcc gtgcacaggg    240
tgtcacgttg caagacctgc ctgaaaccga actgcccgct gttctgcagc cggtcgcgga    300
ggccatggat gcgatcgctg cggccgatct tagccagacg agcgggttcg gcccattcgg    360
accgcaagga atcggtcaat acactacatg gcgtgatttc atatgcgcga ttgctgatcc    420
ccatgtgtat cactggcaaa ctgtgatgga cgcacaccgt cagtgcgtcc gtcgcgcaggc    480 tctcgatgag ctgatgcttt gggccgagga ctgccccgaa gtccggcacc tcgtgcacgc    540
ggatttcggc tccaacaatg tcctgacgga caatggccgc ataacagcgg tcattgactg    600
gagcgaggcg atgttcgggg attcccaata cgaggtcgcc aacatcttct ctggaggcc    660 gtggttggct tgtatggagc agcagacgcg ctacttcgag cggaggcatc cggagcttgc    720
aggatcgccg cggctccggg cgtatatgct ccgcattggt cttgaccaac tctatcagag    780
cttggttgac ggcaatttcg atgatgcagc ttgggcgcag ggtcgatgcg acgcaatcgt    840
ccgatccgga gccgggactg tcgggcgtac acaaatcgcc cgcagaagcg cggccgtctg    900
```

```
gaccgatggc tgtgtagaag tactcgccga tagtggaaac cgacgcccca gcactcgtcc    960
gagggcaaag gaatagagta gatgccgacc gcgggatcca cttaacgtta ctgaaatcat   1020
caaacagctt gacgaatctg gatataagat cgttggtgtc gatgtcagct ccggagttga   1080
gacaaatggt gttcaggatc tcgataagat acgttcattt gtccaagcag caaagagtgc   1140
cttctagtga tttaatagct ccatgtcaac aagaataaaa cgcgttttcg ggtttacctc   1200
ttccagatac agctcatctg caatgcatta atgcattgac tgcaacctag taacgccttt   1260
caggctccgg cgaagagaag aatagcttag cagagctatt tcatttttcg ggagacgaga   1320
tcaagcagat caacggtcgt caagagacct acgagactga ggaatccgct cttggctcca   1380
cgcgactata tatttgtctc taattgtact ttgacatgct cctcttcttt actctgatag   1440
cttgactatg aaaattccgt caccagcccg gggttcgcaa agataattgc atgtttcttc   1500
cttgaactct caagcctaca ggacacacat tcatcgtagg tataaacctc gaaatcattc   1560
ctactaagat ggtatacaat agtaaccatg catggttgcc tagtgaatgc tccgtaacac   1620
ccaatacgcc ggtcctggaa gtgcgttgat cattattccc cgaaaatgta gtacccagta   1680
ag                                                                 1682
```

<210> SEQ ID NO 6
<211> LENGTH: 2009
<212> TYPE: DNA
<213> ORGANISM: Artificial Sequence
<220> FEATURE:
<223> OTHER INFORMATION: cre recombinase cassette containing the A. nidulans xylanase A promoter, a cre recombinase and xylanase A terminator, to allow xylose-inducible expression of the cre recombinase

<400> SEQUENCE: 6

```
tcctggaagt gcgttgatca ttattccccg aaaatgtagt acccagtaag tggtctagcg     60
gtggctatgg taggacatct atgcctaagc tggagttctc attgaacgtg taccggccga    120
ttgccctaaa ctctgattga gagccggaaa cctcatctac ctgatgctca ggggccatcc    180
aatagcttcc gatagcatta cagacagatg gactcgtctt ggcccacggg tctagaacag    240
tcgccggaac tgcctctatt tgaaacggag ctgaaccatg atacttaagc gtgccaagcg    300
gcgccgtttc ccactggaac aaggagcaat agaattctgc agagattctt cattcaggct    360
attcagcaat tcggtttgtg gagcggatcg gggtccactg ggtttagtct ggggtttttc    420
tttgcccgca tgggctctag cacatgcaca gcttgcagtt gctgctacgc tatctgggaa    480
aacgaatggc tattcaggag tttataacca aagagccgg  aaacaggctg attgccctct    540
cacggggaga cgttgtactt ctgatccaga ggctattaac cggacactac ctataaagga    600
ggtagcattc ctttctgtcc ggctcccaga ttccaacaac ccaactgaca ggatcagcac    660
aatgcaggaa ttccaccatg tccaatttac tgaccgtaca ccaaaatttg cctgcattac    720
cggtcgatgc aacgagtgat gaggttcgca agaacctgat ggacatgttc agggatcgcc    780
aggcgttttc tgagcatacc tggaaaatgc ttctgtccgt ttgccggtcg tgggcggcat    840
ggtgcaagtt gaataaccgg aaatggtttc ccgcagaacc tgaagatgtt cgcgattatc    900
ttctatatct tcaggcgcgc ggtctggcag taaaaactat ccagcaacat ttgggccagc    960
taaacatgct tcatcgtcgg tccgggctgc cacgaccaag tgacagcaat gctgtttcac   1020
tggttatgcg gcggatccga aaagaaaacg ttgatgccgg tgaacgtgca aaacaggctc   1080
tagcgttcga acgcactgat ttcgaccagg ttcgttcact catggaaaat agcgatcgct   1140
```

-continued

```
gccaggatat acgtaatctg gcatttctgg ggattgctta taacaccctg ttacgtatag   1200
ccgaaattgc caggatcagg gttaaagata tctcacgtac tgacggtggg agaatgttaa   1260
tccatattgg cagaacgaaa acgctggtta gcaccgcagg tgtagagaag gcacttagcc   1320
tgggggtaac taaactggtc gagcgatgga tttccgtctc tggtgtagct gatgatccga   1380
ataactacct gttttgccgg gtcagaaaaa atggtgttgc cgcgccatct gccaccagcc   1440
agctatcaac tcgcgccctg aagggatttt tgaagcaac  tcatcgattg atttacggcg   1500
ctaaggatga ctctggtcag agatacctgg cctggtctgg acacagtgcc cgtgtcggag   1560
ccgcgcgaga tatggcccgc gctggagttt caataccgga gatcatgcaa gctggtggct   1620
ggaccaatgt aaatattgtc atgaactata tccgtaacct ggatagtgaa acaggggcaa   1680
tggtgcgcct gctggaagat ggcgattaga gttctgtagc gaagtcagga cctttgtccg   1740
cgcttccttg atcctgcacg gggctgccgt catctctggt ttctgatatg gtattcagct   1800
atactgtcac tcgaagtcct ataactctct tactagcaat atgcttagcc aagaactata   1860
tcaggagagt tttactaaac aggatctctc aataacatgg agtagcctgg caattataaa   1920
tctagtatta aatctagtac taactcgata gatatagggc ttttctggcg aatgcctgta   1980
tggtagctgg aactcgcact gctgcagga                                    2009
```

```
<210> SEQ ID NO 7
<211> LENGTH: 19
<212> TYPE: DNA
<213> ORGANISM: Artificial Sequence
<220> FEATURE:
<223> OTHER INFORMATION: Ble-For primer

<400> SEQUENCE: 7
agttgaccag tgccgttcc                                                19

<210> SEQ ID NO 8
<211> LENGTH: 19
<212> TYPE: DNA
<213> ORGANISM: Artificial Sequence
<220> FEATURE:
<223> OTHER INFORMATION: Ble-Rev primer

<400> SEQUENCE: 8
cacgaagtgc acgcagttg                                                19

<210> SEQ ID NO 9
<211> LENGTH: 21
<212> TYPE: DNA
<213> ORGANISM: Artificial Sequence
<220> FEATURE:
<223> OTHER INFORMATION: EBA205-For primer

<400> SEQUENCE: 9
cttctgctga gcagctctgc c                                             21

<210> SEQ ID NO 10
<211> LENGTH: 22
<212> TYPE: DNA
<213> ORGANISM: Artificial Sequence
<220> FEATURE:
<223> OTHER INFORMATION: EBA205-Rev primer

<400> SEQUENCE: 10
gttcagaccg caaggaaggt tg                                            22
```

```
<210> SEQ ID NO 11
<211> LENGTH: 21
<212> TYPE: DNA
<213> ORGANISM: Artificial Sequence
<220> FEATURE:
<223> OTHER INFORMATION: EBA4-For primer

<400> SEQUENCE: 11
cgagaacctg gcctactctc c                                              21

<210> SEQ ID NO 12
<211> LENGTH: 22
<212> TYPE: DNA
<213> ORGANISM: Artificial Sequence
<220> FEATURE:
<223> OTHER INFORMATION: EBA4-Rev primer

<400> SEQUENCE: 12
cagagttgta gtcggtgtca cg                                             22

<210> SEQ ID NO 13
<211> LENGTH: 22
<212> TYPE: DNA
<213> ORGANISM: Artificial Sequence
<220> FEATURE:
<223> OTHER INFORMATION: EBA8-For primer

<400> SEQUENCE: 13
gaagggtatc aagaagcgtg cc                                             22

<210> SEQ ID NO 14
<211> LENGTH: 22
<212> TYPE: DNA
<213> ORGANISM: Artificial Sequence
<220> FEATURE:
<223> OTHER INFORMATION: EBA8-Rev primer

<400> SEQUENCE: 14
gccgaagttg tgagggtcaa tg                                             22

<210> SEQ ID NO 15
<211> LENGTH: 20
<212> TYPE: DNA
<213> ORGANISM: Artificial Sequence
<220> FEATURE:
<223> OTHER INFORMATION: Pdx-For primer

<400> SEQUENCE: 15
ttgagctgtt gctccggtag                                                20

<210> SEQ ID NO 16
<211> LENGTH: 21
<212> TYPE: DNA
<213> ORGANISM: Artificial Sequence
<220> FEATURE:
<223> OTHER INFORMATION: Pdx-Rev primer

<400> SEQUENCE: 16
ctccgtagtc atcgtcaatg g                                              21

<210> SEQ ID NO 17
<211> LENGTH: 18
<212> TYPE: DNA
<213> ORGANISM: Artificial Sequence
<220> FEATURE:
<223> OTHER INFORMATION: Hyg-For primer
```

```
<400> SEQUENCE: 17
gcgtcggttt ccactatc                                                   18

<210> SEQ ID NO 18
<211> LENGTH: 18
<212> TYPE: DNA
<213> ORGANISM: Artificial Sequence
<220> FEATURE:
<223> OTHER INFORMATION: Hyg-Rev primer

<400> SEQUENCE: 18
gaggtcgcca acatcttc                                                   18

<210> SEQ ID NO 19
<211> LENGTH: 4198
<212> TYPE: DNA
<213> ORGANISM: Rasamsonia emersonii

<400> SEQUENCE: 19
cgagttcgta gagcgtctcg atgtggtcgc tggtaaaagc aatggggacg aggattatgt      60
ccgtctgccc ccgtttgacg tactcttgca ccgtatcgtt cgtctgagct cccagccagg     120
cggatggtcc cacctgggac tgccagcaga gccggtaggg gttggaaaac ccgagacgct     180
gcatgacggc gtgcaccgtc gcagcaacct cggccggata cgggtcgcct ggggtcttgt     240
cagcgcccat cagccatggg atagaaagcg cgcagcaact gacctcgatt gacaacgctc     300
atgggcaagc tgtgggcgga gaacagcagc acgactgaat tcctccgctc ttcggggtac     360
gtcgccagct ggtcctcgat gttcttcgca aacgcctcga ccaggcccgg atgcgtcggc     420
caccggtcga tcacgctcca ctggatcgtg ccctcctcgt cttcgttggc gcgccggccc     480
tcgaggcggt tcctccattt ccacagctca ttgagagagc tccccgtcgt ggaacaggag     540
tattgaggat actgcgtgaa tgcaaccgcg cgaccgcccc ggcctctgcc aaacccgtcc     600
tccagcagtt tcgcgtacat ctcctccgtc agcggtgctg cgtatctgaa cgcgacgtat     660
ggcttatgcg gcgccgtctc gggggaaatc tcatccaaaa tcttgcacat ctccgcgcat     720
tggtattccg accacttgcg aatcggggac ccgcctccga tgtctgcgta ttgttttttgg    780 atcattgggg ttcggcggcg agcgatgaga gggccaaggt atttctgaag acgtccaagc     840
ggtatcaagt cgccatcggc ctagaaatgg aacagaaccg gtcagctgta gactctagca     900
gggagaagag gcagcaccta caaataatcg gctcaagaag tcctcaacat cgtcggtcgt     960
tgacgggccg cccatgttga gaaagaccat ggccgtcggg cctttggagc ccttcgccgg    1020
cgacaccgac gtcgccaggc cagacctctg attccaattg catgctagaa gactccgcgc    1080
cgcgggtctg atgttggcac atggatagct tgagcttatg cgcccgggta ttaagaaggg    1140
attgcgcagc gccatggtgg ctggcacttg cagacgacct cagtcgctgc tatataagag    1200
gaaagagacc aagattggaa tggagatgtg aataaaaaaa tatagataga tatcttggca    1260
agaccccgaa ttgactggaa cggttcggat ggcacagctc cggctgcatt gggaaaaccc    1320
ggggaagccc accaatcaga ccgaaggcgg aagtcatcaa tggccgggcg tcacgtgacc    1380
atcgtgtctc cccgcgtcgg catcgcgtca ccgacacgag caggcagcag tgcatctaca    1440
cttttctaaa gctgattttc tgaagttgaa ctcagctcag gagatgatat agtgtccaaa    1500
atggctgatc cacacgactc gcgagaggac gaggccgtcg aggaagaaga ggagatcgac    1560
gagacggtat ggctgcacca gagatagcca gtagccgctg ctgacgatcg atcagggata    1620
taaatcagtg aacgatgccg ttctcttcgc gatcgaagtc agcgaatcca tgctggcgcc    1680
```

```
ccggcccagc gctgatctga agaaagccgg gccagagtcg cccgcgagag ccgccatcaa    1740
atgtgcatac cacctgatgc agcagcgcat catctccaac ccgaaggaca tgatgggcgt    1800
gttgttttt gggactgagg cgtcgaagtt ctatgatgag gacgagaaca gccggggcga    1860
cctctcctac cctcactgct acctgttcac tgacctggac gtccccgccg ctgaggatgt    1920
gaagaaactt cgggcgctgg cggaggacga cgaggagacg aaccagatat tggtgccgtc    1980
gaaggagcgg gtgtcgatgg cgaacgtgct gttctgcgca aaccagatct tcacgtccaa    2040
ggcatccaat ttcctgtcga gacggctctt tgttgtaacg gacaacgata atccgcatgg    2100
cgacgaccgg tccttgcggt ctgctgccac tgttcgagcg aaggatctgt acgaccttgg    2160
agtcatcatc gagctgttcc ccatatccag accagatcac gagttcgaca ggaccaagtt    2220
ttatgatgtg ggttcttcca cttctttcct tcctcgtgct caatctctac ttacactgtg    2280
gaggatatta tttataaaac ctctcccacc gatccggaag ctccttccgc tgatccggcc    2340
agcacgcaaa ccccgtcagt tgggggcgac gggattactt tgctcaagtc tcttttgtct    2400
tctatcagct ccaagtctgt gccccggcga gcgctgttct ccaatatacc actggagatc    2460
ggcccgggtt tcaagatttc cgtgaaggga tatcttattt tcaagcgtca ggaaccggcg    2520
agaagctgct atatctggct aggaggggag aaacccgaga tcgccaaagg cgtaaccacg    2580
cagatagcgg atgataccgc gcggacggtg gagaaatggg agatacgaaa agcatacaag    2640
ttcggcggcg aacaaatctc gtttactccg gaggagcaac aggcattgcg gaatttcggc    2700
gatcctgtga tccagattat cggattcaaa ccgatctcag ccctcccgtt ctgggcttcg    2760
atcaaacatc ccaccttcat ttacccgtcc gaagaggatt atgttgggtc gacacgggta    2820
ttctccgccc tgtatcagaa gctcctcaag gaccagaaga tggcgcttgt ctggttcatc    2880
gcgcgacgga acgcaagtcc ggtgctggct gcgatgctcc caggcgctga gaagctggac    2940
gagaatggag tgcaaaggat cccaccgggg atgtggcttt tgcctctgcc atttgcggac    3000
gatatccgac agaacccgga gacgaacctg gtggtggcgc cggagccgtt gatcgaccag    3060
atgaggacgg tgatccagca gctgcagctg cccaaggcgc agtacgatcc tctcaagtac    3120
cccaacccgt cgctgcagtg gcattatcgg attctgcagg cgctcgcgtt ggacgaagac    3180
ctgccggagc aaccggagga caagacgatt ccgcggtacc ggcagatcga caagcgggcg    3240
ggagagtatg tcatctcgtg gggggaggag ctagaagcgc agtaccggaa gatgttcgag    3300
gagcagccca gacatcgac cctggctaag aggccgggca gagcagaggc agcggaaggt    3360
ccgtcaaaga gggccaaaac cgaggccgac ggcggacagg gcgtgacagc cgaagtccga    3420
agccactatg agagaggcga tctgtcgaag ctgacactgc cggtgctgaa ggaattcctt    3480
gctgcgcaga agctgtcgac agcggggaag aaggcagaac tgatcgagcg ggttgaagag    3540
tatttcgaac ggaagggcgg gtagtctagt attaactgtc aactatgtcg actcatggat    3600
gagaagaacg cagtatttga ttgagggcac tttttttga tgtcacgaca tggatatgga    3660
tatgatatcc tggtctagtc tagtcctaat tagctgttgc tattatcttg tataatagat    3720
accatatcaa acatattaga atgggaatga aagaaaaaaa aggtacatta cagtacatca    3780
gcagaacata catatataca tatacatata tgaacagagc acgacacac tccctcctct    3840
tcggacagaa aagttcagat attacatcca catcttaccg cggaggtaaa ttaaatcaag    3900
acttaattaa acaatatata ccttaggtac ctaggttgat aagctaatag atatcttgac    3960
taaaccaata gcttttattt atttatttat tcacttagtc aatatttact taatagacta    4020
```

```
gggatgtagg tataatataa tataagttaa aatttatcta gactaaatac gtattctaga    4080
taatagtcaa tgtatgtact gcatctgagt cttctgagaa tgtttctctc tctttgctag    4140
ttatattatg atctttatta acgacaatac ttctcagttg atcaagaaag aggagttt     4198

<210> SEQ ID NO 20
<211> LENGTH: 1959
<212> TYPE: DNA
<213> ORGANISM: Rasamsonia emersonii

<400> SEQUENCE: 20
atggctgatc cacacgactc gcgagaggac gaggccgtcg aggaagaaga ggagatcgac      60
gagacgggat ataaatcagt gaacgatgcc gttctcttcg cgatcgaagt cagcgaatcc     120
atgctggcgc cccggcccag cgctgatctg aagaaagccg gccagagtc gcccgcgaga     180 gccgccatca aatgtgcata ccacctgatg cagcagcgca tcatctccaa cccgaaggac     240
atgatgggcg tgttgttttt tgggactgag gcgtcgaagt tctatgatga ggacgagaac     300
agccggggcg acctctccta ccctcactgc tacctgttca ctgacctgga cgtccccgcc     360
gctgaggatg tgaagaaact tcgggcgctg gcggaggacg acgaggagac gaaccagata     420
ttggtgccgt cgaaggagcg ggtgtcgatg gcgaacgtgc tgttctgcgc aaaccagatc     480
ttcacgtcca aggcatccaa tttcctgtcg agacggctct tgttgtaac ggacaacgat     540 aatccgcatg gcgacgaccg gtccttgcgg tctgctgcca ctgttcgagc gaaggatctg     600
tacgaccttg gagtcatcat cgagctgttc cccatatcca gaccagatca cgagttcgac     660
aggaccaagt tttatgatga tattatttat aaaacctctc ccaccgatcc ggaagctcct     720
tccgctgatc cggccagcac gcaaaccccg tcagttgggg gcgacgggat tactttgctc     780
aagtctcttt tgtcttctat cagctccaag tctgtgcccc ggcgagcgct gttctccaat     840
ataccactgg agatcggccc gggtttcaag attccgtga agggatatct tattttcaag     900
cgtcaggaac cggcgagaag ctgctatatc tggctaggag gggagaaacc cgagatcgcc     960
aaaggcgtaa ccacgcagat agcggatgat accgcgcgga cggtggagaa atgggagata    1020
cgaaaagcat acaagttcgg cggcgaacaa atctcgttta ctccggagga gcaacaggca    1080
ttgcggaatt tcggcgatcc tgtgatccag attatcggat tcaaaccgat ctcagccctc    1140
ccgttctggg cttcgatcaa acatcccacc ttcatttacc cgtccgaaga ggattatgtt    1200
gggtcgacac gggtattctc cgccctgtat cagaagctcc tcaaggacca gaagatggcg    1260
cttgtctggt tcatcgcgcg acggaacgca agtccggtgc tggctgcgat gctcccaggc    1320
gctgagaagc tggacgagaa tggagtgcaa aggatcccac cggggatgtg cttttgcct    1380 ctgccatttg cggacgatat ccgacagaac ccggagacga acctggtggt ggcgccggag    1440
ccgttgatcg accagatgag gacggtgatc cagcagctgc agctgcccaa ggcgcagtac    1500
gatcctctca gtaccccaa cccgtcgctg cagtggcatt atcggattct gcaggcgctc    1560
gcgttggacg aagacctgcc ggagcaaccg gaggacaaga cgattccgcg gtaccggcag    1620
atcgacaagc gggcgggaga gtatgtcatc tcgtgggggg aggagctaga agcgcagtac    1680
cggaagatgt tcgaggagca gcccaagaca tcgaccctgg ctaagaggcc gggcagagca    1740
gaggcagcgg aaggtccgtc aaagagggcc aaaaccgagg ccgacggcgg acagggcgtg    1800
acagccgaag tccgaagcca ctatgagaga ggcgatctgt cgaagctgac actgccggtg    1860
ctgaaggaat tccttgctgc gcagaagctg tcgacagcgg gaagaaggc agaactgatc    1920 gagcggggttg aagagtattt cgaacggaag ggcgggtag                           1959
```

```
<210> SEQ ID NO 21
<211> LENGTH: 652
<212> TYPE: PRT
<213> ORGANISM: Rasamsonia emersonii

<400> SEQUENCE: 21
```

| | | | | | | | | | | | | | | | |
|---|---|---|---|---|---|---|---|---|---|---|---|---|---|---|---|
| Met | Ala | Asp | Pro | His | Asp | Ser | Arg | Glu | Asp | Glu | Ala | Val | Glu | Glu | Glu |
| 1 | | | | 5 | | | | | 10 | | | | | 15 | |
| Glu | Glu | Ile | Asp | Glu | Thr | Gly | Tyr | Lys | Ser | Val | Asn | Asp | Ala | Val | Leu |
| | | | 20 | | | | | 25 | | | | | 30 | | |
| Phe | Ala | Ile | Glu | Val | Ser | Glu | Ser | Met | Leu | Ala | Pro | Arg | Pro | Ser | Ala |
| | | | 35 | | | | | 40 | | | | | 45 | | |
| Asp | Leu | Lys | Lys | Ala | Gly | Pro | Glu | Ser | Pro | Ala | Arg | Ala | Ala | Ile | Lys |
| | 50 | | | | | 55 | | | | | 60 | | | | |
| Cys | Ala | Tyr | His | Leu | Met | Gln | Gln | Arg | Ile | Ile | Ser | Asn | Pro | Lys | Asp |
| 65 | | | | | 70 | | | | | 75 | | | | | 80 |
| Met | Met | Gly | Val | Leu | Phe | Phe | Gly | Thr | Glu | Ala | Ser | Lys | Phe | Tyr | Asp |
| | | | | 85 | | | | | 90 | | | | | 95 | |
| Glu | Asp | Glu | Asn | Ser | Arg | Gly | Asp | Leu | Ser | Tyr | Pro | His | Cys | Tyr | Leu |
| | | | 100 | | | | | 105 | | | | | 110 | | |
| Phe | Thr | Asp | Leu | Asp | Val | Pro | Ala | Ala | Glu | Asp | Val | Lys | Lys | Leu | Arg |
| | | 115 | | | | | 120 | | | | | 125 | | | |
| Ala | Leu | Ala | Glu | Asp | Asp | Glu | Glu | Thr | Asn | Gln | Ile | Leu | Val | Pro | Ser |
| | 130 | | | | | 135 | | | | | 140 | | | | |
| Lys | Glu | Arg | Val | Ser | Met | Ala | Asn | Val | Leu | Phe | Cys | Ala | Asn | Gln | Ile |
| 145 | | | | | 150 | | | | | 155 | | | | | 160 |
| Phe | Thr | Ser | Lys | Ala | Ser | Asn | Phe | Leu | Ser | Arg | Arg | Leu | Phe | Val | Val |
| | | | | 165 | | | | | 170 | | | | | 175 | |
| Thr | Asp | Asn | Asp | Asn | Pro | His | Gly | Asp | Asp | Arg | Ser | Leu | Arg | Ser | Ala |
| | | | 180 | | | | | 185 | | | | | 190 | | |
| Ala | Thr | Val | Arg | Ala | Lys | Asp | Leu | Tyr | Asp | Leu | Gly | Val | Ile | Ile | Glu |
| | | 195 | | | | | 200 | | | | | 205 | | | |
| Leu | Phe | Pro | Ile | Ser | Arg | Pro | Asp | His | Glu | Phe | Asp | Arg | Thr | Lys | Phe |
| | 210 | | | | | 215 | | | | | 220 | | | | |
| Tyr | Asp | Asp | Ile | Ile | Tyr | Lys | Thr | Ser | Pro | Thr | Asp | Pro | Glu | Ala | Pro |
| 225 | | | | | 230 | | | | | 235 | | | | | 240 |
| Ser | Ala | Asp | Pro | Ala | Ser | Thr | Gln | Thr | Pro | Ser | Val | Gly | Gly | Asp | Gly |
| | | | | 245 | | | | | 250 | | | | | 255 | |
| Ile | Thr | Leu | Leu | Lys | Ser | Leu | Leu | Ser | Ser | Ile | Ser | Ser | Lys | Ser | Val |
| | | | 260 | | | | | 265 | | | | | 270 | | |
| Pro | Arg | Arg | Ala | Leu | Phe | Ser | Asn | Ile | Pro | Leu | Glu | Ile | Gly | Pro | Gly |
| | | 275 | | | | | 280 | | | | | 285 | | | |
| Phe | Lys | Ile | Ser | Val | Lys | Gly | Tyr | Leu | Ile | Phe | Lys | Arg | Gln | Glu | Pro |
| | 290 | | | | | 295 | | | | | 300 | | | | |
| Ala | Arg | Ser | Cys | Tyr | Ile | Trp | Leu | Gly | Gly | Lys | Pro | Glu | Ile | Ala |
| 305 | | | | | 310 | | | | | 315 | | | | | 320 |
| Lys | Gly | Val | Thr | Thr | Gln | Ile | Ala | Asp | Asp | Thr | Ala | Arg | Thr | Val | Glu |
| | | | | 325 | | | | | 330 | | | | | 335 | |
| Lys | Trp | Glu | Ile | Arg | Lys | Ala | Tyr | Lys | Phe | Gly | Gly | Glu | Gln | Ile | Ser |
| | | | 340 | | | | | 345 | | | | | 350 | | |
| Phe | Thr | Pro | Glu | Glu | Gln | Gln | Ala | Leu | Arg | Asn | Phe | Gly | Asp | Pro | Val |
| | | 355 | | | | | 360 | | | | | 365 | | | |
| Ile | Gln | Ile | Ile | Gly | Phe | Lys | Pro | Ile | Ser | Ala | Leu | Pro | Phe | Trp | Ala |

```
                    370             375             380
Ser Ile Lys His Pro Thr Phe Ile Tyr Pro Ser Glu Glu Asp Tyr Val
385                 390                 395                 400

Gly Ser Thr Arg Val Phe Ser Ala Leu Tyr Gln Lys Leu Leu Lys Asp
                405                 410                 415

Gln Lys Met Ala Leu Val Trp Phe Ile Ala Arg Arg Asn Ala Ser Pro
            420                 425                 430

Val Leu Ala Ala Met Leu Pro Gly Ala Glu Lys Leu Asp Glu Asn Gly
            435                 440                 445

Val Gln Arg Ile Pro Pro Gly Met Trp Leu Leu Pro Leu Pro Phe Ala
450                 455                 460

Asp Asp Ile Arg Gln Asn Pro Glu Thr Asn Leu Val Val Ala Pro Glu
465                 470                 475                 480

Pro Leu Ile Asp Gln Met Arg Thr Val Ile Gln Gln Leu Gln Leu Pro
                485                 490                 495

Lys Ala Gln Tyr Asp Pro Leu Lys Tyr Pro Asn Pro Ser Leu Gln Trp
                500                 505                 510

His Tyr Arg Ile Leu Gln Ala Leu Ala Leu Asp Glu Asp Leu Pro Glu
            515                 520                 525

Gln Pro Glu Asp Lys Thr Ile Pro Arg Tyr Arg Gln Ile Asp Lys Arg
            530                 535                 540

Ala Gly Glu Tyr Val Ile Ser Trp Gly Glu Glu Leu Glu Ala Gln Tyr
545                 550                 555                 560

Arg Lys Met Phe Glu Glu Gln Pro Lys Thr Ser Thr Leu Ala Lys Arg
                565                 570                 575

Pro Gly Arg Ala Glu Ala Ala Glu Gly Pro Ser Lys Arg Ala Lys Thr
            580                 585                 590

Glu Ala Asp Gly Gly Gln Gly Val Thr Ala Glu Val Arg Ser His Tyr
            595                 600                 605

Glu Arg Gly Asp Leu Ser Lys Leu Thr Leu Pro Val Leu Lys Glu Phe
610                 615                 620

Leu Ala Ala Gln Lys Leu Ser Thr Ala Gly Lys Lys Ala Glu Leu Ile
625                 630                 635                 640

Glu Arg Val Glu Glu Tyr Phe Glu Arg Lys Gly Gly
                645                 650

<210> SEQ ID NO 22
<211> LENGTH: 7890
<212> TYPE: DNA
<213> ORGANISM: Rasamsonia emersonii

<400> SEQUENCE: 22
ggagcctggc tcagcatgct cacggactgc aggatgaaca cgcgtctccg aaggtgcaac      60
cggggagaag ataaccaccg tccttgaggg aagaacatct gtcatcatcg aaacagaagc     120
agtctcagtc tcggtctcgg tctcagtccc gtcatctata gtcgtcacag ttgggatcgg     180
aaacgtggcc gaccagtccc tggtcttgta ccaggtgtta ttctcgtatc gcggcggcgc     240
gatcatgtcg agcgcctcac caatccttcc gaggacatag cccatcctga acccgccctg     300
gaggcgctcg atgaagttgt tggcgggatg aacggcggtg aaagggatgg catgaagat      360 gccgaggatg ccatggcca tggagaacat gaacaggccg aagggtcca tggtgatgat       420 gattcgatcg atatcagaca gctgaatatg tattagcttt ccaaatttct tctatcatga     480
aattcgacag gaaatagaaa aagaaaggat gctggctttg attaaagaga gtagctgggt     540
```

```
cttatcacaa gagattaaaa agtgtcttaa acaaagacaa gacaagacaa gcatccgtct    600
gatgcatgag tttcgagata tatataatac aaaggatgga ttcactgaac agttcgttga    660
cttctgaaga acaaaggctg gtctctgcat gcccgagaat agtaacaaca ataaagagca    720
aatacaacgt tgtgtacagc aagcgaatga cctgccttga atgagtctgg cagatttatt    780
cccccatcta ctaccttcaa gtacctcatc agatggccag cagaaggtgc aagtgggtat    840
atcttctcat tcgaagaact tagtgtttag ttttctgagc agcaatatag ctagttgcaa    900
gttagaaaag agtataaaga accgtttccg caacaccagc taccctcaaa gaaaggaatt    960
gaacaaactg ggaactaccg attactacca agctggaggg cataggcaat gaacgccagg   1020
aattggtaaa gactgaagat aggaaggtat ggtgaatact gcatagtgca atgtagacct   1080
tcagtatcat aaggatcatc cattcattat agacgctaat ataaagtatt tctgaaaaaa   1140
aatgttggag aggagatcaa gtcttttttat tcaacggctt tcaaagacta aaagctggaa   1200
aaggcaggct atcatcatga tacctagcat agcataccat gtttgcgttt atcacttcat   1260
attcaggaca acctcctgcc caggaccacg ccataggcaa ctgtcgccag gagaccgccc   1320
aggttgacca gcgtcgagat tccatgcagc ttggcaaact tcttgttgag ctcggtcatc   1380
tccttggagt gaggaggcgg gtcataactc ttcttgccgt cgatcgattc tgccagagat   1440
catatatatc agcccgtacc tatacagtgt actcgtgcgt actcggcagc agccaaaccg   1500
gtaggtagta ggcaggtacc aaccttgctg ccacctctgc ttgataactc ccacaacctt   1560
cggggtcaga tagagcaggt tggtcagtcc cgaaacgaag acgatcgaaa gcggcagcaa   1620
caccgtcaga cgattctcct cgagaagcac ccccgcgagg ctagagggcc cagttcccag   1680
gaccgttctg gctcccgggt aggtcagcgc tgcgacaacg gggagagcgc tctgcagggt   1740
gaagtagatc gggaacaggc tattctggag cgtcgagaac tgctgacggg gaagcgtcct   1800
gaacgcgacg gttccgccaa cgaaggtcta catatataac ggaatgttgt aggagctttt   1860
gatgagttat ctatcctcct gaccaattga ccagaaacaa aactcaggat gtcaaacctg   1920
atagatctcg actcccagaa gggtgccgta gctgattgaa gtgtgatgtc agccgatcta   1980
ttagtagcag ccgtagtact ggtgacgcac cttagtatgt ggaagggggcc caggatagac   2040 atcctgctct gttgtactga tatggaaaca cctcgtgact ggaacagaac tatatgggat   2100
tatacttaga cagataccccc actgactggg aattcagagg gaagagtaag ttgtgttatg   2160
ctacgggtag gttagagaag ctgtcaagct tgggtctccc gagctaacgc tagctgcatg   2220
tggggcatgt tcttatctcc acggcccgct caaacctaga tctgcttcca acaaagcaca   2280
aatatctata cacacggcct tttccgtaag gcccacgcac cttcccgacg tcatgtgcac   2340
tcgcgtctgc cgcgcctcaa aaaggaaata tcacgcgtct gcctggaggc gctccttagt   2400
catagaaaga aacgcatcta cgccatgcag tgatttattt atctgacatt tccttcctct   2460
tcgttgcagc aggagggaca gctgacatct cttttgcaaa atggctgaca aggaggccac   2520
cgtctacgtg atcgatgtgg gaaagtccat ggggaggcgc cgccatggac ggccggtatc   2580
tgacctggaa tgggcaatgc aatatgtctg ggacaagatt acgacaaccg tatgctgaca   2640
cttgatccgg tctcctggaa attaaattcc tgcgttgaga actgacatat cttctgttag   2700
gttgccacgg ggcggaaaac ggctacaatt ggagtggtcg ggctgaggac agatggtgag   2760
attttaccgt gcccgaatca ggtaaatatg atttactgat gtatctggac agaaacatcg   2820
aacgacttgc aggatgatga cagctattcg cacatctctg tctttcagga aattggacag   2880
tatgtgcctc agctgacact gatgactagt gacttttcct cgcatatact aaataaatca   2940
```

```
ctgccagggt cctcatgcct gatctgcgaa aactgcgcga cctgatcaag cctagcaaca      3000
ctgatgaagg agatggtgag ttttgcccgt atcttcggac tcatttgatt tgatattgag      3060
acctatctac ctatagctat ctcctcccctt gtcgtcgcga tccagatgat caccacttat     3120
accaaaaagc tgaagtatcg acggaaaatc attctcgtga cgaacgggga aggatccatg      3180
agtaccgatg gtcttgatga gatcgtgaaa aagctcaagt ccgatagcat tgaattggtg      3240
gtcttgtatg tttttcactt ctctttgact tttcttgtgg ctggtatgca aaatggctaa      3300
actggtttcg ttgcaggggt gttgactttg atgatcctga atttggtgtc aaagaggagg      3360
acaagaatcc agcaaaagta ttcaatgttt ttttttttagc aggttggaag agttgctgat     3420
tcgatctgcc gcaggctgag aatgaagcgg tcctcagagg tctcgttgat tcctgcgacg      3480
gagtctacgg gacattacaa caggccatat tggagctgga cacccgcgt gtgaaggttg       3540 ttcgtggaat accctccttt agaggagagc tccgactggg gaaccctgaa gagtattcgt      3600
ctgcccttcg tatcccagtc gaaagatact accgaactta tgttgccaag ccgccgacag      3660
cgagctcctt tgtcctacga tctgacgctg cagctggtca gagggtgca gagaatgcac       3720 tgacaagcgt ccgaaacgca cggacatatc acgtcagtga tgagtccgca ccaggaggca     3780
agagagacgt ggagcgagaa gatctcgcca agggctacga gtatgggaga accgcggtgc     3840
acattagtga gtccgatgag aatatcacca aactccagac gaaccctggt ctggaaatca      3900
tcggcttcat tcagagtgac catgtatgtt tctcgtcaag ggtatctcat ctgaaccgtg      3960
attaacctag gatccagtac gaccgataca tgcacatgtc taccagcaat gtcataattg      4020
cacagaaagc aaacgaaaag gcgatccttg ctctttcatc tttcattcac gccttgttcg      4080
agttggactg ttatgctgtg gccagacttg ttaccaagga caacaagccc ccactcatcg      4140
tattactggc accatctatt gaagcagact ttgaatgtct tctagaagtc cagctccctt      4200
ttgctgaaga tgttcggtcg taccgttttcc ctcccttgga caaggtggtc actgtctctg     4260
gaaagacagt caaagagcac cgacatctcc caagtgacga attgctgaat gcgatgagca     4320
aatacgtcga cagcatggag ctcgtcgaca aggatgaaaa cgggtgagtc atcacaggga     4380
aaccgtcatg ctgctcatct caagtatact gacaactcca cagagaacca gttgacagcc     4440
tggctcccag actggaggat tcgtactctc cactgctgca caggatcgag caagctatcc      4500
ggtggcgtgc catccatcca aacgagcctc ttccgccccc ttctgagaag ttgacgcagc      4560
tgtcacgacc gccagcagat ctgcaagcgc gcgcgaagaa atacctggat cgggtcattg      4620
ccgccgccga tgtgaagaaa ggtctgtcaa cttctacgct cccccagaat gcatctgact      4680
aaaaaatgct gcacagttcc accaaaagca aaggtcgca agcggaatcg cgaagccgac       4740
aaacccctat cgggtcttga cgttgacgag ctccttcgtc gcgagaagcg cgccaagatc      4800
tcagccaaca acgccatccc cgagttcaaa cagtcgctgg tcaacgccga gaccatcgac      4860
gccgtccgtg acgcagtcag ccagatggaa agcatcatcg agaaccacat ccgaagcagc      4920
tttggagacg ccaactacga ccgcgtgatc gaggagctgg gtgtcctccg cgaggagctg      4980
atcgcctacg aagagccgga tctctacaac gacttcctgc ggaggctgaa ggacaagatc      5040
ctcaatgagg agctgggcgg agacagacga gagctgtggt ggctcgtcag gaggcaacgg      5100
gtcggtctga tagacaagaa ggcgtcggaa cgggttgaag ttactgaaca ggaagccagg      5160
gaggtaagta agcagataca ttattccttt agttccatta aacgagctgc atgatgagct      5220
gacttttgtt cactagttca tgacctcgaa ataaaatagt ccattattgc tatgtatgtc      5280
```

```
aaggcgcctg gccgtagtag tcttaacatg ctgatgctgt gaatcaaagc gccagatgaa    5340
caataataga aataatacca cttggtagct gtctccattc tcacagatag acaacgttaa    5400
agaaaagaaa aacgtaaaaa gagggtatat gtggtctagt aacgccgcaa ggaaaaaaaa    5460
actcatacgt tagtttcgaa cgcaaatctc aaaatcgagc acttcgagta aatactctgt    5520
cgtatcgttt cgcctcagga tatcttcccg agccttctct ttccgatatc gattttccgt    5580
tgtaatctag ttattattac tccagttagt aaatgcacga cgggcagtat tgtaaataat    5640
gaaatcagca gcgagagtac gaacatgtcc acatcctcat cggctttccg gagcaactcg    5700
ttctggatct ccagctcatt gttaatggcg atccccagct ccttctgtcg agcgacgatt    5760
ttcatcaact cctccacgct ccggtcctgc tcttccatcg tctgcttctg cagctggagc    5820
acgccctggt tgtcgagttc ccgcgtcttg tccgtttcct tgcccaggac tcgtccagaa    5880
cggggtttgg cgctccccac cagggcgtcc ttgtcctgca tcgaagcgac agcgttgtcg    5940
agcttgctct tcgtcaccat cgcgttgtgc agattctcca atccgtcctt ctctttcttg    6000
gcgctcgcga tgagatcctt cctccgacgg atctctccct cgcctaacct gctgccgccc    6060
catccagacg acttgtcgct caggttcttc agcccttcct caagagcgcc gatcatcgac    6120
cctgctttca ccaagctgct tttggcctgt gccgagctct cgtgttgttt ctgtggagtc    6180
gtggcctgat cacgtctcgt cagatgcagc ctcgtctcgt gtaagtgcgc cttcatctcc    6240
cggtagcaat ccagccacag gactggatcc gtgatcggtc cgccgcctgg cgcgcccggt    6300
tccgtgatgg acttgtgaag cttcgatgcg gcagagctat ccgacagggc ttgggagggg    6360
aggtttagaa aggacctcca gacgcttgtt tgacgccatc gcgggtcctc gctctcgttg    6420
atggcccgca ggtatctttc caggcctttg cgccgctctt cgcgcagagt ctcgttcgag    6480
ttcgtgttgg aaaaccagga cttcccgggc agagcgacgg gtggtgggc gccaacctgg    6540 cggactagtg cgtcatggaa cgatgcaaat tctgaatagc gtttctggac aacgaacgac    6600
cgtagaggca gccggatggt gatgttgtat agcgtatacg gactgggagc gtccgcgatg    6660
gtggctgtcg ggatggaaat ttcgacattc ggggccatga ttatagttca gacgggaaaa    6720
agaacaaaac aaagagcagg cccttgttat cgaccaggaa gcataattcc cgccgcttct    6780
cttgcggtat ctctgtcgtt gcagagttgg ttgcagagta gtggagtcgg ccggcgggtg    6840
gaaactcccg caatgacgca ggcgcccat cttcttctgc caccgccgat ctgtggctta    6900
gcttcttctt gtcaagactc gactccacca tcgcgactcc aggcagcacg aatcgcacga    6960
ttgccgaaaa actacaccgt actaggggaa ggcctaatta atctattacc ctagctaaaa    7020
atggggttgt caaacttatc atatagccgt gcgacccgcc cttggaggtc actagatcca    7080
acctgcgcac ggcctggtta cggttgatgg gagctaaaat tagaacgaaa gatatactgg    7140
cggtccgtcc ccgcgtctat ccacaatcca aaactcgtat gcagagttat ctacaggtcg    7200
atccaatcat gagtcctttg tgacatgtcg ttgaatacat ggtctcaatc gagtctgccg    7260
ttcttacatg accatcctca ccaagatcaa tgtcccgtga ttcgactgtc agccaagata    7320
cgtctcacct ggccccatct ctactgtcga caacgtctgc ctatactgta ggtgatcaga    7380
atacgcagtc ccggggagtc tactcgcgat ggggtggttc atacgtcggc tcctcgtcga    7440
cgttgtctct gggtccgtcg gagagcgtca atatagacgg gagacgaaag ttgctcttga    7500
tctatatcca tggcttcatg ggtgaagaag cgagcttcca caagttccct gctcatgtcc    7560
ataaccttgt caccattgct ctggccgagt cgcacgttgt gtattcgaag gtatatcctc    7620
gatacaaatc ccgccgagca atggacattg cacgtgatga tttcagtcga tggtgcgttt    7680
```

```
gcagactggc atatctctct ttagagatca tcctagaaag aaacgcatga tactaagtgt   7740
cgaataggct atcaccgcat gagtcggaag atacagatgt gatcctactc ggccacagcc   7800
tgggtgggat cctagccgca gaggttgcgc tgctcccatc agcccctggg agcaaggaga   7860
tcttcgagca tcgtatcctg ggactcatca                                    7890

<210> SEQ ID NO 23
<211> LENGTH: 2145
<212> TYPE: DNA
<213> ORGANISM: Rasamsonia emersonii

<400> SEQUENCE: 23
atggctgaca aggaggccac cgtctacgtg atcgatgtgg aaagtccat ggggaggcgc      60 cgccatggac ggccggtatc tgacctggaa tgggcaatgc aatatgtctg gacaagatt     120 acgacaaccg ttgccacggg gcggaaaacg gctacaattg gagtggtcgg gctgaggaca    180
gatgaaacat cgaacgactt gcaggatgat gacagctatt cgcacatctc tgtctttcag    240
gaaattggac aggtcctcat gcctgatctg cgaaaactgc gcgacctgat caagcctagc    300
aacactgatg aaggagatgc tatctcctcc cttgtcgtcg cgatccagat gatcaccact    360
tataccaaaa agctgaagta tcgacggaaa atcattctcg tgacgaacgg ggaaggatcc    420
atgagtaccg atggtcttga tgagatcgtg aaaaagctca agtccgatag cattgaattg    480
gtggtcttgg gtgttgactt tgatgatcct gaatttggtg tcaaagagga ggacaagaat    540
ccagcaaaag ctgagaatga agcggtcctc agaggtctcg ttgattcctg cgacggagtc    600
tacgggacat acaacaggc catattggag ctggacacac cgcgtgtgaa ggttgttcgt     660 ggaatacct cctttagagg agagctccga ctggggaacc ctgaagagta ttcgtctgcc     720
cttcgtatcc cagtcgaaag atactaccga acttatgttg ccaagccgcc gacagcgagc    780 tccttgtcc tacgatctga cgctgcagct ggtcaagagg gtgcagagaa tgcactgaca    840
agcgtccgaa acgcacggac atatcacgtc agtgatgagt ccgcaccagg aggcaagaga    900
gacgtggagc gagaagatct cgccaagggc tacgagtatg ggagaaccgc ggtgcacatt    960
agtgagtccg atgagaatat caccaaactc cagacgaacc ctggtctgga atcatcggc   1020 ttcattcaga gtgaccatta cgaccgatac atgcacatgt ctaccagcaa tgtcataatt   1080
gcacagaaag caaacgaaaa ggcgatcctt gctctttcat ctttcattca cgccttgttc   1140
gagttggact gttatgctgt ggccagactt gttaccaagg acaacaagcc cccactcatc   1200
gtattactgg caccatctat tgaagcagac tttgaatgtc ttctagaagt ccagctccct   1260
tttgctgaag atgttcggtc gtaccgtttc cctcccttgg acaaggtggt cactgtctct   1320
ggaaagacag tcaaagagca ccgacatctc ccaagtgacg aattgctgaa tgcgatgagc   1380
aaatacgtcg acagcatgga gctcgtcgac aaggatgaaa acggagaacc agttgacagc   1440
ctggctccca gactggagga ttcgtactct ccactgctgc acaggatcga gcaagctatc   1500
cggtggcgtg ccatccatcc aaacgagcct cttccgcccc cttctgagaa gttgacgcag   1560
ctgtcacgac cgccagcaga tctgcaagcg cgcgcgaaga aatacctgga tcgggtcatt   1620
gccgccgccg atgtgaagaa agttccacca aaagcaaaag gtcgcaagcg gaatcgcgaa   1680
gccgacaaac ccctatcggg tcttgacgtt gacgagctcc ttcgtcgcga agcgcgcc    1740 aagatctcag ccaacaacgc catccccgag ttcaaacagt cgctggtcaa cgccgagacc   1800
atcgacgccg tccgtgacgc agtcagccag atggaaagca tcatcgagaa ccacatccga   1860
```

```
agcagctttg agacgccaa ctacgaccgc gtgatcgagg agctgggtgt cctccgcgag    1920
gagctgatcg cctacgaaga gccggatctc tacaacgact tcctgcggag gctgaaggac    1980
aagatcctca atgaggagct gggcggagac agacgagagc tgtggtggct cgtcaggagg    2040
caacgggtcg gtctgataga caagaaggcg tcggaacggg ttgaagttac tgaacaggaa    2100
gccagggagt ccattattgc tatctgtctc cattctcaca gatag                    2145
```

<210> SEQ ID NO 24
<211> LENGTH: 714
<212> TYPE: PRT
<213> ORGANISM: Rasamsonia emersonii

<400> SEQUENCE: 24

```
Met Ala Asp Lys Glu Ala Thr Val Tyr Val Ile Asp Val Gly Lys Ser
1               5                   10                  15

Met Gly Arg Arg Arg His Gly Arg Pro Val Ser Asp Leu Glu Trp Ala
            20                  25                  30

Met Gln Tyr Val Trp Asp Lys Ile Thr Thr Val Ala Thr Gly Arg
        35                  40                  45

Lys Thr Ala Thr Ile Gly Val Val Gly Leu Arg Thr Asp Glu Thr Ser
50                  55                  60

Asn Asp Leu Gln Asp Asp Asp Ser Tyr Ser His Ile Ser Val Phe Gln
65                  70                  75                  80

Glu Ile Gly Gln Val Leu Met Pro Asp Leu Arg Lys Leu Arg Asp Leu
                85                  90                  95

Ile Lys Pro Ser Asn Thr Asp Glu Gly Asp Ala Ile Ser Ser Leu Val
            100                 105                 110

Val Ala Ile Gln Met Ile Thr Thr Tyr Thr Lys Lys Leu Lys Tyr Arg
        115                 120                 125

Arg Lys Ile Ile Leu Val Thr Asn Gly Glu Gly Ser Met Ser Thr Asp
130                 135                 140

Gly Leu Asp Glu Ile Val Lys Lys Leu Lys Ser Asp Ser Ile Glu Leu
145                 150                 155                 160

Val Val Leu Gly Val Asp Phe Asp Asp Pro Glu Phe Gly Val Lys Glu
                165                 170                 175

Glu Asp Lys Asn Pro Ala Lys Ala Glu Asn Glu Ala Val Leu Arg Gly
            180                 185                 190

Leu Val Asp Ser Cys Asp Gly Val Tyr Gly Thr Leu Gln Gln Ala Ile
        195                 200                 205

Leu Glu Leu Asp Thr Pro Arg Val Lys Val Val Arg Gly Ile Pro Ser
210                 215                 220

Phe Arg Gly Glu Leu Arg Leu Gly Asn Pro Glu Glu Tyr Ser Ser Ala
225                 230                 235                 240

Leu Arg Ile Pro Val Glu Arg Tyr Tyr Arg Thr Tyr Val Ala Lys Pro
                245                 250                 255

Pro Thr Ala Ser Ser Phe Val Leu Arg Ser Asp Ala Ala Gly Gln
            260                 265                 270

Glu Gly Ala Glu Asn Ala Leu Thr Ser Val Arg Asn Ala Arg Thr Tyr
        275                 280                 285

His Val Ser Asp Glu Ser Ala Pro Gly Gly Lys Arg Asp Val Glu Arg
        290                 295                 300

Glu Asp Leu Ala Lys Gly Tyr Glu Tyr Gly Arg Thr Ala Val His Ile
305                 310                 315                 320

Ser Glu Ser Asp Glu Asn Ile Thr Lys Leu Gln Thr Asn Pro Gly Leu
```

```
                        325                 330                 335
Glu Ile Ile Gly Phe Ile Gln Ser Asp His Tyr Asp Arg Tyr Met His
                340                 345                 350
Met Ser Thr Ser Asn Val Ile Ile Ala Gln Lys Ala Asn Glu Lys Ala
                355                 360                 365
Ile Leu Ala Leu Ser Ser Phe Ile His Ala Leu Phe Glu Leu Asp Cys
            370                 375                 380
Tyr Ala Val Ala Arg Leu Val Thr Lys Asp Asn Lys Pro Pro Leu Ile
385                 390                 395                 400
Val Leu Leu Ala Pro Ser Ile Glu Ala Asp Phe Glu Cys Leu Leu Glu
                405                 410                 415
Val Gln Leu Pro Phe Ala Glu Asp Val Arg Ser Tyr Arg Phe Pro Pro
                420                 425                 430
Leu Asp Lys Val Val Thr Val Ser Gly Lys Thr Val Lys Glu His Arg
                435                 440                 445
His Leu Pro Ser Asp Glu Leu Leu Asn Ala Met Ser Lys Tyr Val Asp
            450                 455                 460
Ser Met Glu Leu Val Asp Lys Asp Glu Asn Gly Glu Pro Val Asp Ser
465                 470                 475                 480
Leu Ala Pro Arg Leu Glu Asp Ser Tyr Ser Pro Leu Leu His Arg Ile
                485                 490                 495
Glu Gln Ala Ile Arg Trp Arg Ala Ile His Pro Asn Glu Pro Leu Pro
                500                 505                 510
Pro Pro Ser Glu Lys Leu Thr Gln Leu Ser Arg Pro Pro Ala Asp Leu
            515                 520                 525
Gln Ala Arg Ala Lys Lys Tyr Leu Asp Arg Val Ile Ala Ala Ala Asp
            530                 535                 540
Val Lys Lys Val Pro Pro Lys Ala Lys Gly Arg Lys Arg Asn Arg Glu
545                 550                 555                 560
Ala Asp Lys Pro Leu Ser Gly Leu Asp Val Asp Glu Leu Leu Arg Arg
                565                 570                 575
Glu Lys Arg Ala Lys Ile Ser Ala Asn Asn Ala Ile Pro Glu Phe Lys
                580                 585                 590
Gln Ser Leu Val Asn Ala Glu Thr Ile Asp Ala Val Arg Asp Ala Val
            595                 600                 605
Ser Gln Met Glu Ser Ile Ile Glu Asn His Ile Arg Ser Ser Phe Gly
            610                 615                 620
Asp Ala Asn Tyr Asp Arg Val Ile Glu Glu Leu Gly Val Leu Arg Glu
625                 630                 635                 640
Glu Leu Ile Ala Tyr Glu Glu Pro Asp Leu Tyr Asn Asp Phe Leu Arg
                645                 650                 655
Arg Leu Lys Asp Lys Ile Leu Asn Glu Leu Gly Gly Asp Arg Arg
                660                 665                 670
Glu Leu Trp Trp Leu Val Arg Arg Gln Arg Val Gly Leu Ile Asp Lys
            675                 680                 685
Lys Ala Ser Glu Arg Val Glu Val Thr Glu Gln Glu Ala Arg Glu Ser
            690                 695                 700
Ile Ile Ala Ile Cys Leu His Ser His Arg
705                 710

<210> SEQ ID NO 25
<211> LENGTH: 6954
<212> TYPE: DNA
<213> ORGANISM: Rasamsonia emersonii
```

<400> SEQUENCE: 25

```
cttaggagga gcgctattaa ctccaatacc gtggttaaat aacacggacc cggacggtaa      60
taatacggat tcgactgcgg aaggtaagtg gactatggat tcgaattctg cacgcgatgt     120
gtcatcgatc aacgtgctga tttatgacga tataggagcc gcgagtcaaa gcgggcttgt     180
cggacaagag caggaggttg gcaccgttat gagtccgcgt ccagaacatg ccactgctgt     240
aaccgttgag aatgaaacag gagagtcgca tacgtccccg ccgcctgaag aaatccccca     300
tgcgcgtggt ccaccagtgg taggtgtgga ggacatgggg ctgcagaacg ggaggggcat     360
cgagatgtct cttgcaacga atgccgcgcc agacagcgat gagtctggaa acaaacccga     420
gcaggtgaca ggggattctg gtgccaagag caataccggt ggagatgctg atgggatgg     480
ggacattgtt ctggacgatg ttacgggcaa gggagttgat caaggacagg ccggcccaga     540
atcagaagaa cggcagcaag agcaacaacg accatcggaa acggatacc ctacagatta      600
attaattgat taattgcaaa actaatctaa tctgacgggt tgtgatgacc atgacacgga     660
atttaatgac ttgaaaagca attactttc tatacaagtc tccagacatg accaattctg      720
aataatagtc aagtcgtata ttagctaatt caaacatagg ctgtattaga ctgctcaaac     780
actttatatt cagttaatgt aaactaggat atctgatttt ttcctccccg acaagttaac     840
atgcaaagtt cactccatag atcgacacta caaatatacg taattcatat gatagaaccg     900
gttcaaggaa accctcccat cttcttttg atgaatcttg aaaccctcta acagactcca      960
tgtgatagtt tattcttggg tcatggtgta gatacaaaat accaattagg taaacaagac    1020
tgagttaatc acgtgacctc gcgccaccga ccccgcgtct ctgacgcgcc aggcagcctc    1080
atctcatttc ggtaagaagc tacctgcacc gccttcaaac cggacggacg gttgagagga    1140
gagagagcac atcaaagctt tctcctactc agcgttcatt cctcagagag agctggtcaa    1200
gatgtaagtt ttctatcttc gtccctttat gagacaaaaa acaaagaaga aagtctgttg    1260
ctaactccgt taggtgtaag ttttttctgga cataacggct ttagggaatt ggaactctgg    1320
tctgatactc ttgcagcgag aatcgacaag cttccattc ttgggtgggt cttcttttc      1380
tcgattcgac gacgtggttt gttatagatc taacgagtcg atgtagtgta cgttcgttcg    1440
acaataccag gagcgagacc atccagttcc acacgccttt gaccttgatc gttggatata    1500
atgggtcggg aaagactgta cgtgggagaa ttgctctctg tcttgatatg tgcttacaca    1560
tcccagacga tcattgaatg cctcaaatat gccaccactg gcgagctacc gcccaacagc    1620
aagggcggag ccttcatcca cgatcccaag gtgcgcacct ttgacctttg gagccgacgt    1680
ttgctaaaat taggatatag ctatgtggag aaaaggaggt tcttgcccaa gtgaagctcg    1740
cgttcaagag tacgtcgggg gctaagatgg tggcgacccg gagtttgcag ctcacagtga    1800
agaagacaac gcgacagcag aaaactctgg agggccagct cttgatggtc aaggatggcg    1860
aaaggactgc gatctcttcc cgtgttgcgg agctggacca gattatgccc cagtaccttg    1920
gtgtttctaa agcgatcctc gactcggtca tattctgcca ccaggacgaa agtctctggc    1980
cgatgagtga gccttctgtt ctaaagaaaa aatttgatga gattttcgaa gccatgaaat    2040
acaccaaggc tatcgagaac atcaaagctc taaggaagaa acaaaacgaa gagcttgcaa    2100
aatacaaaat tatggagcag cacgcgaaag aggacaagga taaagccgat cgtgctgaaa    2160
agagatcgat caagcttcag gaggagatcg aggccttgcg cgaagagaca cataaactct    2220
cgcaggagat gcggcaagct gctgagttgg ccgacaaagc ttggaaggaa tcagagagct    2280
```

```
acgctcaaat tatcggtgcc ctggaaggaa agcgtattga ggctaagagc atccagacga   2340
gtatcgataa cttaaagcgg catctggttg aagtcgacga accagacgaa tggctccagt   2400
cgactttgga gcagttcgag tctaggcaga tccagctcca gaaccaggag gaagaacaga   2460
aggaaaggta tatgaatatc aaggaacaga tcgcgagagc ccggcgacag ctgggtttga   2520
agcaggccga atgcggcaag ttcgaaaatg acaaagcaca gtttgagcga caggtggaaa   2580
gaagggaaaa tatgatcaag gaaatcgcgc gtcgaaataa tatccgcggg tttgacgaca   2640
ctcttgacga aacccagatt gatgaattca tgcagaggat gcggaaactt gtcaaggatc   2700
acaaccaagc cctagagcgc accagaaagg aggggcaggc cgagctgcga gaaacgcaaa   2760
atattctcaa ccagattgca cagcgcaaat ctgcgcttca ggaaagcaag aatgttgcaa   2820
gaaggcaaat ttcagagtat gacaaagagg catcaaagta tcaaaccaga cttgacgaga   2880
tcgacgtcga tgagggaaca atcgctgttc tcgaatccaa aaaagaaagt gtcgaggctc   2940
gcttaagtaa actcaaagag actgcacgca ctgcttcttg ggacaaggaa atccaaaatg   3000
ccaatgccga gctcaagtcc ctcgaggacg agagctcccg gctgaacgca gagctcatag   3060
cgggaacaaa aaaggaccgg agatctagct cgcttggatc atctgaagaa ggagctcaaa   3120
gatcgcgagc gtcaattgga gactatgaag ggagcacatg gggataggct ggccaagctc   3180
ataagcccaa gttggcatcc tgagacttta gagcaagatt tccaaaagac tctagaggaa   3240
gaatctaggt ctctgacgct tgcagagcgt gatcgtgatg gagttggaag ggggctggaa   3300
catgtggagt tcaagctcaa gaacgtcagg aagaactga dacagcggca gaaagagctt   3360
gacgaatgcg ttaaaaggat tcgtgaggcg atcgatgatg agccttccga gtatcctgac   3420
gttgtcaaac aacgccaagc acagctagat atggctaaaa gggacgcaga ccagtatgct   3480
gggatgggtg aatatctcaa taatgtttg gaagcagcga acagagaaa ggtttgcaga   3540 acctgtgcaa ggccgttcaa gacagaagca gaattccagg cgttcaaaaa taaattggaa   3600
gcgcttgtca agaaggccac ccaagatgcc gaggatgaaa atctgcagca actcgaagag   3660
gacctggaaa atgcgcgagc agctagtact gattacgata catgggttcg cctgtctcag   3720
actgatatcc cgggccttga aaggaagaa gagcaatgtg aatctcagag ggaagggctc   3780
ttggctaaga tcgaagaaca cgacaatatt gttagtgagc ggatggacaa gagagagag   3840 gttgagtctc ttaccaaaac ggtggcgtcg attgttcgat atgacggcga aatcaagtct   3900
cttcgatctc aaatccagga tcttacttcg aaacagcaag attcagattc ttcacggact   3960
ctggaggaca ttcaagacga aattgctgcc gttggagaga agtctcgggc tgtcaagaaa   4020
accatatcga aacttactgc cgagaaggac cagtcgcgaa ctgacataaa caagctggaa   4080
ctagaattga gagacgtgca aagtagtctc gataacgcta gccaccagtt ggagaagaag   4140
tctggactcg ttgctcggat cgaagagtac aagaaattga ttgccaagca gcgggaggcc   4200
attgagaaag ccgacgaaga catcgagaag cttgctcccg aaatggcaaa agcccaagct   4260
aggcatgatg atatcagtca acgtgctgaa gctagagaga gggagctgca gcaaactcta   4320
tcgcacctgt ctgaaagcct gcatcagctg aaccttgcaa atgaggagat caagtcctac   4380
aatgaccgag gggggccaga tcaattagcc aagagcagga atgacttgag agcgattgag   4440
gaagagatca actccctcga agcagaacag gccaatatca cgcgggagat aaacaaaatc   4500
tcggctcagt tgaaggatag tgagaatacc aaacggcagt attcggacaa tcttgcctac   4560
cgccaggcat gcagagcgct agagcaagtg caggcggaaa tcgaaaagct ggaggctcaa   4620
aacgcagaga ttgaccgtaa tcgctttaag gaagaatccg agcgctggac ccggaaacac   4680
```

```
aatgctctcg cggcacagca agcaagcaag atgggcgaga tgaagtccaa ggatgatcag   4740
ctcatgcagc tcttggcgga ctggaatacc gattataaag atgcggcaca gaagtacaag   4800
gaggctcata taaaagtgga aacgacaaag gcggctgttg aagacctggg tcgatatgga   4860
agcgcgcttg acaaggccat catgaagtac cacagcctaa agatggagga gattaaccgg   4920
atcatcgaag agctgtggca aaagacgtat agaggcaccg atgtagatac catccaaatc   4980
cgctccgaca atgaaaatgc caagggaaac cggtcttata actaccgtgt tgtcatggtc   5040
aagcaaggtg ctgaaatgga catgcgtggc cgttgcagcg ctgggcaaaa ggtgcttgcc   5100
agtatcatta tccgtcttgc tcttgcagaa tgttttggcg ttaactgcgg acttattgcg   5160
cttgatgagc cgactacgaa ccttgaccgg gacaacattc ggtctctcgc tgaatcgctc   5220
cacgacatca ttaaggctcg tcagcagcag gctaatttcc agctgattgt cattactcac   5280
gacgaagaat ttctgcatca tatgcagtgc ggagacttca gtgactatta ttaccgagtg   5340
tcaaggaacg agaagcagaa atcgatcatt gagaggcagt ctatcgctga ggtgtgtctt   5400
ctgttgagaa attatatcat tgtatggact aactgacaag aataggttat gtgatattgc   5460
gtacgatttt acctgccact ctattccgtc ttccgagttt cttaggaggc cagggcggtt   5520
gtccttgata gcttctgaaa gttgttagtc gaaccttggt atttacgtta tcattgtata   5580
gatagagtgc tccactggag ttagggcgtt ccggttatct gcagctggat ataatgggaa   5640
tatagatgag aatgaaccac atcgtacagt acgttactct ggtctttaca tgtagtggca   5700
tacgtaagga aaagcacttg cgttttttt tttgaattct ttttccaaca aagaagcaga   5760
gcttcttaat gcgtgagact aaactatacg atgtatcaag gtaagggcag ccggggtttc   5820
acaacaaact acacggtaca gtgtacctca tccctacaga tcgtcctctc ctccgtcatc   5880
accatcatca tactcttctc ccacttccct atcgtcgttg tcctcctcct cctcatcatc   5940
gaccaacggc acaaaccgga agtcgacgaa gctcacgttg ctgccgaagc cgccactcgg   6000
cagcggcaca cctcccgaag aagctccatt gttgctgtca ttatttcccc cgagctcgat   6060
catgaattgc agactcagca cgccctgtat gtcgccgcga atgctgactt tgctggcgac   6120
ggccattgcg cgggcggctt tgcggattag agagaagcgg tagttttgtt tgacgcgact   6180
gcccatggat gacggtgggt tgacgaggaa ggtctccgtt actgtaggag cgagcttgga   6240
cttcttcttc gaaggctggg gtctaccgtc cccagttagg actttgtaat gggtgtgaga   6300
tagcgagctt ccactgccct cgccgtcttt ttctatcgag aactcgacgg tggactcgct   6360
gaacgggcca ccagagccag agagtgcaaa gaacggttct cgcttggctg atgcggagat   6420
cgtgaggatg tttgggttcg tcgcatctag ttcggttatg gcattgtgca gccacgctga   6480
tcgcatgatg atcttcatta ttatcgcatc gcgttcagc gggatgtcca gctcgccagc   6540
cgccgaaccg aaggaaggat cgtctgggtc gtaggtcgtg agttcgcagg tcgtcgttac   6600
gcccgcttcg gaaaggatga tgctgagagg actcccgaca tggagtagc gcaatgtgca   6660 tgaccgattg agaagtaagg ccggggttgt gaaagcgtct gaacctgtgg ggttctgttg   6720
ttgcgcactt gttgctgctg cgaacgagtt actactcgct gacgtgttgt tatcgctgat   6780
gccgaaaatc tggagtgtct ccaggagagc ggaaaggag atcaagaaat ggggatataa   6840
tacgccggcg tccgagtcat catcgttgtc gttgttgtta ttattggggc cgggaggtgg   6900
gttgaagcta taagtcgtaa agagggcctt gtctagaaac gccaatccct gcat         6954
```

<210> SEQ ID NO 26

<211> LENGTH: 3813
<212> TYPE: DNA
<213> ORGANISM: Rasamsonia emersonii

<400> SEQUENCE: 26

| | | | | | |
|---|---|---|---|---|---|
| atgggtcggg | aaagactgta | cgtgggagaa | ttgctctctg | tcttgatatg | tgcttacaca | 60 |
| tcccagacga | tcattgaatg | cctcaaatat | gccaccactg | gcgagctacc | gcccaacagc | 120 |
| aagggcggag | ccttcatcca | cgatcccaag | ctatgtggag | aaaaggaggt | tcttgcccaa | 180 |
| gtgaagctcg | cgttcaagag | tacgtcgggg | gctaagatgg | tggcgacccg | gagtttgcag | 240 |
| ctcacagtga | agaagacaac | gcgacagcag | aaaactctgg | agggccagct | cttgatggtc | 300 |
| aaggatggcg | aaaggactgc | gatctcttcc | cgtgttgcgg | agctggacca | gattatgccc | 360 |
| cagtaccttg | gtgttctaa | agcgatcctc | gactcggtca | tattctgcca | ccaggacgaa | 420 |
| agtctctggc | cgatgagtga | gccttctgtt | ctaaagaaaa | aatttgatga | gattttcgaa | 480 |
| gccatgaaat | acaccaaggc | tatcgagaac | atcaaagctc | taaggaagaa | acaaaacgaa | 540 |
| gagcttgcaa | aatacaaaat | tatggagcag | cacgcgaaaa | aggacaagga | taaagccgat | 600 |
| cgtgctgaaa | agagatcgat | caagcttcag | gaggagatcg | aggccttgcg | cgaagagaca | 660 |
| cataaactct | cgcaggagat | gcggcaagct | gctgagttgg | ccgacaaagc | ttggaaggaa | 720 |
| tcagagagct | acgctcaaat | tatccggtgcc | ctggaaggaa | agcgtattga | ggctaagagc | 780 |
| atccagacga | gtatcgataa | cttaaagcgg | catctggttg | aagtcgacga | accagacgaa | 840 |
| tggctccagt | cgactttgga | gcagttcgag | tctaggcaga | tccagctcca | gaaccaggag | 900 |
| gaagaacaga | aggaaaggta | tatgaatatc | aaggaacaga | tcgcgagagc | ccggcgacag | 960 |
| ctgggtttga | agcaggccga | atgcggcaag | ttcgaaaatg | acaaagcaca | gtttgagcga | 1020 |
| caggtggaaa | gaagggaaaa | tatgatcaag | gaaatcgcgc | gtcgaaataa | tatccgcggg | 1080 |
| tttgacgaca | ctcttgacga | aacccagatt | gatgaattca | tgcagaggat | gcggaaactt | 1140 |
| gtcaaggatc | acaaccaagc | cctagagcgc | accagaaagg | aggggcaggc | cgagctgcga | 1200 |
| gaaacgcaaa | atattctcaa | ccagattgca | cagcgcaaat | ctgcgcttca | ggaaagcaag | 1260 |
| aatgttgcaa | gaaggcaaat | ttcagagtat | gacaaagagg | catcaaagta | tcaaaccaga | 1320 |
| cttgacgaga | tcgacgtcga | tgagggaaca | atcgctgttc | tcgaatccaa | aaagaaagt | 1380 |
| gtcgaggctc | gcttaagtaa | actcaaagag | actgcacgca | ctgcttcttg | ggacaaggaa | 1440 |
| atccaaaatg | ccaatgccga | gctcaagtcc | ctcgaggacg | agagctcccg | gctgaacgca | 1500 |
| gagctcatag | cgggaacaaa | aaaggaccgg | agatctagct | cgcttggatc | atctgaagaa | 1560 |
| ggagctcaaa | gatcgcgagc | gctggccaag | ctcataagcc | caagttggca | tcctgagact | 1620 |
| ttagagcaag | atttccaaaa | gactctagag | gaagaatcta | ggtctctgac | gcttgcagag | 1680 |
| cgtgatcgtg | atggagttgg | aagggggctg | gaacatgtgg | agttcaagct | caagaacgtc | 1740 |
| aggaaagaac | tgagacagcg | gcagaaagag | cttgacgaat | gcgttaaaag | gattcgtgag | 1800 |
| gcgatcgatg | atgagccttc | cgagtatcct | gacgttgtca | acaacgcca | agcacagcta | 1860 |
| gatatggcta | aagggacgc | agaccagtat | gctgggatgg | gtgaatatct | caataaatgt | 1920 |
| ttggaagcag | cgaaacagag | aaaggtttgc | agaacctgtg | caaggccgtt | caagacagaa | 1980 |
| gcagaattcc | aggcgttcaa | aaataaattg | gaagcgcttg | tcaagaaggc | cacccaagat | 2040 |
| gccgaggatg | aaaatctgca | gcaactcgaa | gaggacctgg | aaaatgcgcg | agcagctagt | 2100 |
| actgattacg | atacatgggt | tcgcctgtct | cagactgata | tcccgggcct | tgagaaggaa | 2160 |
| gaagagcaat | gtgaatctca | gagggaaggg | ctcttggcta | agatcgaaga | acacgacaat | 2220 |

```
attgttagtg agcggatgga caagaagaga gaggttgagt ctcttaccaa aacggtggcg   2280
tcgattgttc gatatgacgg cgaaatcaag tctcttcgat ctcaaatcca ggatcttact   2340
tcgaaacagc aagattcaga ttcttcacgg actctggagg acattcaaga cgaaattgct   2400
gccgttggag agaagtctcg ggctgtcaag aaaaccatat cgaaacttac tgccgagaag   2460
gaccagtcgc gaactgacat aaacaagctg gaactagaat tgagagacgt gcaaagtagt   2520
ctcgataacg ctagccacca gttggagaag aagtctggac tcgttgctcg gatcgaagag   2580
tacaagaaat tgattgccaa gcagcgggag gccattgaga aagccgacga agacatcgag   2640
aagcttgctc ccgaaatggc aaaagcccaa gctaggcatg atgatatcag tcaacgtgct   2700
gaagctagag agagggagct gcagcaaact ctatcgcacc tgtctgaaag cctgcatcag   2760
ctgaaccttg caaatgagga gatcaagtcc tacaatgacc gagggggggcc agatcaatta   2820 gccaagagca ggaatgactt gagagcgatt gaggaagaga tcaactccct cgaagcagaa   2880
caggccaata tcacgcggga gataaacaaa atctcggctc agttgaagga tagtgagaat   2940
accaaacggc agtattcgga caatcttgcc taccgccagg catgcagagc gctagagcaa   3000
gtgcaggcgg aaatcgaaaa gctggaggct caaaacgcag agattgaccg taatcgcttt   3060
aaggaagaat ccgagcgctg gacccggaaa cacaatgctc tcgcggcaca gcaagcaagc   3120
aagatgggcg agatgaagtc caaggatgat cagctcatgc agctcttggc ggactggaat   3180
accgattata agatgcggc acagaagtac aaggaggctc atataaaagt ggaaacgaca   3240
aaggcggctg ttgaagacct gggtcgatat ggaagcgcgc ttgacaaggc catcatgaag   3300
taccacagcc taaagatgga ggagattaac cggatcatcg aagagctgtg gcaaaagacg   3360
tatagaggca ccgatgtaga taccatccaa atccgctccg acaatgaaaa tgccaaggga   3420
aaccggtctt ataactaccg tgttgtcatg gtcaagcaag gtgctgaaat ggacatgcgt   3480
ggccgttgca gcgctgggca aaaggtgctt gccagtatca ttatccgtct tgctcttgca   3540
gaatgttttg gcgttaactg cggacttatt gcgcttgatg agccgactac gaaccttgac   3600
cgggacaaca ttcggtctct cgctgaatcg ctccacgaca tcattaaggc tcgtcagcag   3660
caggctaatt tccagctgat tgtcattact cacgacgaag aatttctgca tcatatgcag   3720
tgcggagact tcagtgacta ttattaccga gtgtcaagga acgagaagca gaaatcgatc   3780
attgagaggc agtctatcgc tgaggttatg tga                                3813
```

<210> SEQ ID NO 27
<211> LENGTH: 1270
<212> TYPE: PRT
<213> ORGANISM: Rasamsonia emersonii

<400> SEQUENCE: 27

```
Met Gly Arg Glu Arg Leu Tyr Val Gly Glu Leu Leu Ser Val Leu Ile
1               5                   10                  15

Cys Ala Tyr Thr Ser Gln Thr Ile Ile Glu Cys Leu Lys Tyr Ala Thr
            20                  25                  30

Thr Gly Glu Leu Pro Pro Asn Ser Lys Gly Gly Ala Phe Ile His Asp
        35                  40                  45

Pro Lys Leu Cys Gly Glu Lys Glu Val Leu Ala Gln Val Lys Leu Ala
    50                  55                  60

Phe Lys Ser Thr Ser Gly Ala Lys Met Val Ala Thr Arg Ser Leu Gln
65                  70                  75                  80

Leu Thr Val Lys Lys Thr Thr Arg Gln Gln Lys Thr Leu Glu Gly Gln
```

-continued

```
                85                  90                  95
Leu Leu Met Val Lys Asp Gly Glu Arg Thr Ala Ile Ser Ser Arg Val
            100                 105                 110

Ala Glu Leu Asp Gln Ile Met Pro Gln Tyr Leu Gly Val Ser Lys Ala
            115                 120                 125

Ile Leu Asp Ser Val Ile Phe Cys His Gln Asp Glu Ser Leu Trp Pro
            130                 135                 140

Met Ser Glu Pro Ser Val Leu Lys Lys Phe Asp Glu Ile Phe Glu
145                 150                 155                 160

Ala Met Lys Tyr Thr Lys Ala Ile Glu Asn Ile Lys Ala Leu Arg Lys
                165                 170                 175

Lys Gln Asn Glu Glu Leu Ala Lys Tyr Lys Ile Met Glu Gln His Ala
            180                 185                 190

Lys Glu Asp Lys Asp Lys Ala Asp Arg Ala Glu Lys Arg Ser Ile Lys
            195                 200                 205

Leu Gln Glu Glu Ile Glu Ala Leu Arg Glu Glu Thr His Lys Leu Ser
            210                 215                 220

Gln Glu Met Arg Gln Ala Ala Glu Leu Ala Asp Lys Ala Trp Lys Glu
225                 230                 235                 240

Ser Glu Ser Tyr Ala Gln Ile Ile Gly Ala Leu Glu Gly Lys Arg Ile
                245                 250                 255

Glu Ala Lys Ser Ile Gln Thr Ser Ile Asp Asn Leu Lys Arg His Leu
            260                 265                 270

Val Glu Val Asp Glu Pro Asp Glu Trp Leu Gln Ser Thr Leu Glu Gln
            275                 280                 285

Phe Glu Ser Arg Gln Ile Gln Leu Gln Asn Gln Glu Glu Gln Lys
290                 295                 300

Glu Arg Tyr Met Asn Ile Lys Glu Gln Ile Ala Arg Ala Arg Gln
305                 310                 315                 320

Leu Gly Leu Lys Gln Ala Glu Cys Gly Lys Phe Glu Asn Asp Lys Ala
                325                 330                 335

Gln Phe Glu Arg Gln Val Glu Arg Arg Glu Asn Met Ile Lys Glu Ile
            340                 345                 350

Ala Arg Arg Asn Asn Ile Arg Gly Phe Asp Asp Thr Leu Asp Glu Thr
            355                 360                 365

Gln Ile Asp Glu Phe Met Gln Arg Met Arg Lys Leu Val Lys Asp His
            370                 375                 380

Asn Gln Ala Leu Glu Arg Thr Arg Lys Glu Gly Gln Ala Glu Leu Arg
385                 390                 395                 400

Glu Thr Gln Asn Ile Leu Asn Gln Ile Ala Gln Arg Lys Ser Ala Leu
            405                 410                 415

Gln Glu Ser Lys Asn Val Ala Arg Gln Ile Ser Glu Tyr Asp Lys
            420                 425                 430

Glu Ala Ser Lys Tyr Gln Thr Arg Leu Asp Glu Ile Asp Val Asp Glu
            435                 440                 445

Gly Thr Ile Ala Val Leu Glu Ser Lys Lys Glu Ser Val Glu Ala Arg
            450                 455                 460

Leu Ser Lys Leu Lys Glu Thr Ala Arg Thr Ala Ser Trp Asp Lys Glu
465                 470                 475                 480

Ile Gln Asn Ala Asn Ala Glu Leu Lys Ser Leu Glu Asp Glu Ser Ser
                485                 490                 495

Arg Leu Asn Ala Glu Leu Ile Ala Gly Thr Lys Lys Asp Arg Arg Ser
            500                 505                 510
```

```
Ser Ser Leu Gly Ser Ser Glu Glu Gly Ala Gln Arg Ser Arg Ala Leu
        515                 520                 525

Ala Lys Leu Ile Ser Pro Ser Trp His Pro Glu Thr Leu Glu Gln Asp
        530                 535                 540

Phe Gln Lys Thr Leu Glu Glu Ser Arg Ser Leu Thr Leu Ala Glu
545                 550                 555                 560

Arg Asp Arg Asp Gly Val Gly Arg Gly Leu Glu His Val Glu Phe Lys
                565                 570                 575

Leu Lys Asn Val Arg Lys Glu Leu Arg Gln Arg Gln Lys Glu Leu Asp
                580                 585                 590

Glu Cys Val Lys Arg Ile Arg Ala Ile Asp Asp Glu Pro Ser Glu
        595                 600                 605

Tyr Pro Asp Val Val Lys Gln Arg Gln Ala Gln Leu Asp Met Ala Lys
        610                 615                 620

Arg Asp Ala Asp Gln Tyr Ala Gly Met Gly Glu Tyr Leu Asn Lys Cys
625                 630                 635                 640

Leu Glu Ala Ala Lys Gln Arg Lys Val Cys Arg Thr Cys Ala Arg Pro
                645                 650                 655

Phe Lys Thr Glu Ala Glu Phe Gln Ala Phe Lys Asn Lys Leu Glu Ala
                660                 665                 670

Leu Val Lys Lys Ala Thr Gln Asp Ala Glu Asp Glu Asn Leu Gln Gln
        675                 680                 685

Leu Glu Glu Asp Leu Glu Asn Ala Arg Ala Ala Ser Thr Asp Tyr Asp
        690                 695                 700

Thr Trp Val Arg Leu Ser Gln Thr Asp Ile Pro Gly Leu Glu Lys Glu
705                 710                 715                 720

Glu Glu Gln Cys Glu Ser Gln Arg Glu Gly Leu Leu Ala Lys Ile Glu
                725                 730                 735

Glu His Asp Asn Ile Val Ser Glu Arg Met Asp Lys Lys Arg Glu Val
                740                 745                 750

Glu Ser Leu Thr Lys Thr Val Ala Ser Ile Val Arg Tyr Asp Gly Glu
        755                 760                 765

Ile Lys Ser Leu Arg Ser Gln Ile Gln Asp Leu Thr Ser Lys Gln Gln
        770                 775                 780

Asp Ser Asp Ser Ser Arg Thr Leu Glu Asp Ile Gln Asp Glu Ile Ala
785                 790                 795                 800

Ala Val Gly Glu Lys Ser Arg Ala Val Lys Lys Thr Ile Ser Lys Leu
                805                 810                 815

Thr Ala Glu Lys Asp Gln Ser Arg Thr Asp Ile Asn Lys Leu Glu Leu
                820                 825                 830

Glu Leu Arg Asp Val Gln Ser Ser Leu Asp Asn Ala Ser His Gln Leu
        835                 840                 845

Glu Lys Lys Ser Gly Leu Val Ala Arg Ile Glu Glu Tyr Lys Lys Leu
        850                 855                 860

Ile Ala Lys Gln Arg Glu Ala Ile Glu Lys Ala Asp Glu Asp Ile Glu
865                 870                 875                 880

Lys Leu Ala Pro Glu Met Ala Lys Ala Gln Ala Arg His Asp Asp Ile
                885                 890                 895

Ser Gln Arg Ala Glu Ala Arg Glu Arg Glu Leu Gln Gln Thr Leu Ser
                900                 905                 910

His Leu Ser Glu Ser Leu His Gln Leu Asn Leu Ala Asn Glu Glu Ile
        915                 920                 925
```

Lys Ser Tyr Asn Asp Arg Gly Gly Pro Asp Gln Leu Ala Lys Ser Arg
930                 935                 940

Asn Asp Leu Arg Ala Ile Glu Glu Ile Asn Ser Leu Glu Ala Glu
945                 950                 955                 960

Gln Ala Asn Ile Thr Arg Glu Ile Asn Lys Ile Ser Ala Gln Leu Lys
                965                 970                 975

Asp Ser Glu Asn Thr Lys Arg Gln Tyr Ser Asp Asn Leu Ala Tyr Arg
                980                 985                 990

Gln Ala Cys Arg Ala Leu Glu Gln Val Gln Ala Glu Ile Glu Lys Leu
                995                 1000                1005

Glu Ala Gln Asn Ala Glu Ile Asp Arg Asn Arg Phe Lys Glu Glu
    1010                1015                1020

Ser Glu Arg Trp Thr Arg Lys His Asn Ala Leu Ala Ala Gln Gln
    1025                1030                1035

Ala Ser Lys Met Gly Glu Met Lys Ser Lys Asp Asp Gln Leu Met
    1040                1045                1050

Gln Leu Leu Ala Asp Trp Asn Thr Asp Tyr Lys Asp Ala Ala Gln
    1055                1060                1065

Lys Tyr Lys Glu Ala His Ile Lys Val Glu Thr Thr Lys Ala Ala
    1070                1075                1080

Val Glu Asp Leu Gly Arg Tyr Gly Ser Ala Leu Asp Lys Ala Ile
    1085                1090                1095

Met Lys Tyr His Ser Leu Lys Met Glu Ile Asn Arg Ile Ile
    1100                1105                1110

Glu Glu Leu Trp Gln Lys Thr Tyr Arg Gly Thr Asp Val Asp Thr
    1115                1120                1125

Ile Gln Ile Arg Ser Asp Asn Glu Asn Ala Lys Gly Asn Arg Ser
    1130                1135                1140

Tyr Asn Tyr Arg Val Val Met Val Lys Gln Gly Ala Glu Met Asp
    1145                1150                1155

Met Arg Gly Arg Cys Ser Ala Gly Gln Lys Val Leu Ala Ser Ile
    1160                1165                1170

Ile Ile Arg Leu Ala Leu Ala Glu Cys Phe Gly Val Asn Cys Gly
    1175                1180                1185

Leu Ile Ala Leu Asp Glu Pro Thr Thr Asn Leu Asp Arg Asp Asn
    1190                1195                1200

Ile Arg Ser Leu Ala Glu Ser Leu His Asp Ile Ile Lys Ala Arg
    1205                1210                1215

Gln Gln Gln Ala Asn Phe Gln Leu Ile Val Ile Thr His Asp Glu
    1220                1225                1230

Glu Phe Leu His His Met Gln Cys Gly Asp Phe Ser Asp Tyr Tyr
    1235                1240                1245

Tyr Arg Val Ser Arg Asn Glu Lys Gln Lys Ser Ile Ile Glu Arg
    1250                1255                1260

Gln Ser Ile Ala Glu Val Met
    1265                1270

<210> SEQ ID NO 28
<211> LENGTH: 4322
<212> TYPE: DNA
<213> ORGANISM: Rasamsonia emersonii

<400> SEQUENCE: 28
atcttactcc tgtcaagcct gttccctttt catcttttt taatcaggcc gccgagacct    60

-continued

| | |
|---|---|
| tctactgaca aactcatcac acataaatcc cacggccctc tggttcgaac cacacaaaaa | 120 |
| gcggacaaag ctaagtcttc gctcttcaca aagagaacaa acttcaccat gaagttctgg | 180 |
| gatggttggg aggcatggga gaagatggtt tttgtatggc tatgactgct cgcaatatcc | 240 |
| aatgccattt caatttgcta accactgaga aatgagacag atccttggct gcgccatagt | 300 |
| aatcaaccac accaccacat tacaaccgtg ctgctaacaa tgttaggtta ttgtcatcgt | 360 |
| cattgccttt ggtgttctga gctatagcag gtggagactc aggaagtatg ctagagcaca | 420 |
| gtcataccag gtggccgagc gtgcgagggg cgtggatttg aacgaaatgt tgatagatga | 480 |
| cgtcccttttt ggtgcaaggg cactcgagag tggagtacgg gttgagggta tctggactcc | 540 |
| aaaccacaac acgccgtcgc caaacgtcag cccatatcta tcctgtactc cagtgggaag | 600 |
| cagaccacca gtccacctc tacgtctgcc acgtccagag cagcggcctt ggcctaccc | 660 |
| ttctctgcct caagtgaaca gctactcacc gaaacggagc tcagatgtct cacttatcaa | 720 |
| caacaataca atgcttccat agagctcttg catggggagc gagttcgcgg gaaagagatc | 780 |
| ggcctagaca gaatagttgg acggtcaact gaagacattg ccatcttacc agaaacactg | 840 |
| ttatgtttca agggaaaata cgcatggtgg attgtactgg gcattgaact gggggcgttg | 900 |
| atgagtcgag aagataaaga cttggcgtga tccagaagtc actacggagt acatgagatt | 960 |
| gatagcattg atggaacgtc aataatcatg acagttggaa ctttagctct tccaagaatc | 1020 |
| tgaaaactaa aaatcagtgt aaagccttt aaacgcgacga aaaagcattg ttttctgga | 1080 |
| ttaagtagat ttgtcataac tttctgtgta cagccgttag gtaaacagtg gttgcggaaa | 1140 |
| taatgttctt gtttccggtt tgttatcttc acgtgatgtc gcgacgtggc gacgcctcgg | 1200 |
| acgcgtccat gtcctctccc gatgaccaca attagtgacc ccaacaatca ggggcattac | 1260 |
| caagtcctag agactagagc tgaataatca tttcttcatc aatcgtctca tgcagtgatc | 1320 |
| tgtggagaat tacctggctt tgaattcctg cttttgctat tccatttgag aaccatcacg | 1380 |
| agaatcgtct ggccctgatt gcgtcgagtc tcggataacc cctcaccact cgcatattcg | 1440 |
| tccagcacac ccacctcttt gcaccattcc ccgttattga cagcggccgg accaagcgat | 1500 |
| atggctgccg acgaagaaac gcagaatgaa tatgatgaca atgggcttcc tggccctggg | 1560 |
| gcgcctactc ctatcacggc cctcgaggta aacaaaccga ctgatcagga gagattgggg | 1620 |
| aattctgggg tagtctcaaa gtgaattagt attaggaggc taacatgtcc tttgcagggt | 1680 |
| gttgctggct taacggcgag agacatcaag ctcataatcg atgcaggttt tcataccgtg | 1740 |
| gaagcggtag catacacgta cgtctctata tcaatttcct atactttttg tcgtgttcta | 1800 |
| tagatgtctt gaagggtaat tttgaatttt gtactgacag agttacctct acatagaccg | 1860 |
| aaacgggtac tggagcagat taagggtatc tcagaacaga aagccgcgaa gattttggct | 1920 |
| gagggtgagt aactcgcaga ggcaaaaagt ttgcatgcat ttccttggag acaacattga | 1980 |
| agctcattta atttttttcc cttgaattag catctaagct agttccaatg gcttcacga | 2040 |
| cggccacgga gatgcacgca cgccggagcg agctcatatg tatcaccact ggttcgaaac | 2100 |
| aactggacac cctactggca ggaggcattg agacagggtc gatcacagaa atattcggag | 2160 |
| aattcaggac tggaaagagt cagatttgtc atacacttgc tgtaacgtgc caattaccgt | 2220 |
| tcgacatggg cggaggagaa ggaaagtgtc tgtatatcga taccgagggc acgttccgac | 2280 |
| cagttaggtt gctggccgtt gctcagcggt acggattggt tggagaagag gtcctggata | 2340 |
| acgttgccta cgctcgagca tacaattcgg accatcaact gcagttgctg aatcaagcat | 2400 |
| ctcaaatgat gaccgagaca cgcttctcac ttctcattgt cgactcagcc acatctctct | 2460 |

```
atcgaacgga cttcaatggt cgcggtgaat tgtcctctcg tcaaactcat ctcgccaaat      2520
tcctccgtac cttacagcgg ttggcagatg agttcggtat tgctgtggtt atcaccaacc      2580
aagtggtctc tcaagtcgat ggaggcccca gttctatgtt caaccctgac ccgaagaaac      2640
caataggagg gaacatcatt gcacatgcga gcacaaccag gctgagcctg aagaagggtc      2700
gcggggaaac taggatttgt aagatctatg acagtccctg tctccccgaa agcgactgta      2760
tgttcgcgat cagagaggat gggattggtg accccagccc taaggatctg gagggcgagt      2820
gagacacctt tgtacctgcg ctcgtctgac atgatttcga tcacgagcaa tgcttacgaa      2880
ctgtcttttg ttgctgtgta ttctgtgtct ttccatctcg catagcagcc ggtgctggga      2940
ttgaagaagt cattgcatta gtcagttttt gttttttttt tttaattttt gctgttgata      3000
tgtgttcgct tctattcatg acgaaaaaat atatcactga ttgtacttaa gattaatgag      3060
aaatacgagg aatgctagag ataagatgtt tgtagtgaat gaatagattt aaatctgcaa      3120
ggcaaactcc gcctgtttga gcttggcgtt gcttcggtac cctgcgcgta ctccgtaagc      3180
gcgcgctaac agttttttcgg agctcccagc tgcccgccct ttgtataaca agacttcgcg      3240
caccgcaaga ccaaccaccg tgagcatggg cttctaaatg tgacacccct ctgagccgtg      3300
gattcctcca gcctcctcaa tgaccatggc caaaatttac aaggaaacta agtcgacgt      3360 ccggcccatc gcgccgaatg ccgtcgtcga catccagatt ccgacgcagg agaacgccca      3420
gcgtcgggcc cgattctcga tttcttcagt gacggcgcaa gatatcccca gtatcaagga      3480
cgaggacgat ttcgcgagac gatttctagc aacacaaggc tcactttatt tccgacgacg      3540
gaaagtctat cctcgaacgt ttctgtggag agtcgtcgat gacaacaagg tcctggagat      3600
tcaatctgcg gacttggtga ggggtggcat tgagcaccat gaagtgaatc tcatgctccg      3660
gtttgatttc caggaggcga ttctgccttc aggagtcgca ctggcagata cggaggaaca      3720
cgaggtgctg aatgtcttcg tgctcacggc ttccaggcgt cttcatactc tagctctgcg      3780
accggagttc tttcgacggg cttccgcgat cgatgaaaat atcctagact ggtgcaaagc      3840
gtgtacaccg tcgccactga ccttctcgca tcctcatcgc cttcacgcga gcagtaccac      3900
ggagctattc atctcgttgg acagtggggc gctgcttcgg ttgactagga gagctggcga      3960
cgatggtaca gtttcttctg ttactataca caaaagtgtg ggtgacgttt gctgacttct      4020
gctgggttga aaggttcaca ctggtcccaa ataactttcg atgaaagggg ctggggtgct      4080
tcgcttcgtg gtcttatgaa atggggcaca caaccgacaa tccgctataa cgggcgcagc      4140
ctcgatcaga atacaccgaa tgccattgct acgacatctg atcagaccta tgtcttcgcg      4200
gtttgtttga atcacactct aaaggtttgg aatctcgcaa cgaacaaact ggttggttcg      4260
aaggatctcc tcgaccgtca ggtacagcag caggactcag cagcgtactt tttgaacccg      4320
tc                                                                      4322
```

<210> SEQ ID NO 29
<211> LENGTH: 1035
<212> TYPE: DNA
<213> ORGANISM: Rasamsonia emersonii

<400> SEQUENCE: 29

```
atggctgccg acgaagaaac gcagaatgaa tatgatgaca tgggcttcc tggccctggg       60 gcgcctactc ctatcacggc cctcgagggt gttgctggct taacggcgag agacatcaag     120
ctcataatcg atgcaggttt tcataccgtg gaagcggtag catacacacc gaaacgggta     180
```

```
ctggagcaga ttaagggtat ctcagaacag aaagccgcga agattttggc tgaggttcca      240
atgggcttca cgacggccac ggagatgcac gcacgccgga gcgagctcat atgtatcacc      300
actggttcga acaactgga caccctactg gcaggaggca ttgagacagg gtcgatcaca      360
gaaatattcg gagaattcag gactggaaag agtcagattt gtcatacact tgctgtaacg      420
tgccaattac cgttcgacat gggcggagga gaaggaaagt gtctgtatat cgataccgag      480
ggcacgttcc gaccagttag gttgctggcc gttgctcagc ggtacggatt ggttggagaa      540
gaggtcctgg ataacgttgc ctacgctcga gcatacaatt cggaccatca actgcagttg      600
ctgaatcaag catctcaaat gatgaccgag acacgcttct cacttctcat tgtcgactca      660
gccacatctc tctatcgaac ggacttcaat ggtcgcggtg aattgtcctc tcgtcaaact      720
catctcgcca aattcctccg taccttacag cggttggcag atgagttcgg tattgctgtg      780
gttatcacca accaagtggt ctctcaagtc gatggaggcc ccagttctat gttcaaccct      840
gacccgaaga aaccaatagg agggaacatc attgcacatg cgagcacaac caggctgagc      900
ctgaagaagg gtcgcgggga aactaggatt tgtaagatct atgacagtcc ctgtctcccc      960
gaaagcgact gtatgttcgc gatcagagag gatgggattg gtgacccccag ccctaaggat     1020 ctggagggcg agtga                                                       1035
```

<210> SEQ ID NO 30
<211> LENGTH: 344
<212> TYPE: PRT
<213> ORGANISM: Rasamsonia emersonii

<400> SEQUENCE: 30

```
Met Ala Ala Asp Glu Glu Thr Gln Asn Glu Tyr Asp Asp Asn Gly Leu
1               5                   10                  15

Pro Gly Pro Gly Ala Pro Thr Pro Ile Thr Ala Leu Glu Gly Val Ala
            20                  25                  30

Gly Leu Thr Ala Arg Asp Ile Lys Leu Ile Ile Asp Ala Gly Phe His
        35                  40                  45

Thr Val Glu Ala Val Ala Tyr Thr Pro Lys Arg Val Leu Glu Gln Ile
    50                  55                  60

Lys Gly Ile Ser Glu Gln Lys Ala Ala Lys Ile Leu Ala Glu Val Pro
65                  70                  75                  80

Met Gly Phe Thr Thr Ala Thr Glu Met His Ala Arg Arg Ser Glu Leu
                85                  90                  95

Ile Cys Ile Thr Thr Gly Ser Lys Gln Leu Asp Thr Leu Leu Ala Gly
            100                 105                 110

Gly Ile Glu Thr Gly Ser Ile Thr Glu Ile Phe Gly Glu Phe Arg Thr
        115                 120                 125

Gly Lys Ser Gln Ile Cys His Thr Leu Ala Val Thr Cys Gln Leu Pro
    130                 135                 140

Phe Asp Met Gly Gly Gly Glu Gly Lys Cys Leu Tyr Ile Asp Thr Glu
145                 150                 155                 160

Gly Thr Phe Arg Pro Val Arg Leu Leu Ala Val Ala Gln Arg Tyr Gly
                165                 170                 175

Leu Val Gly Glu Glu Val Leu Asp Asn Val Ala Tyr Ala Arg Ala Tyr
            180                 185                 190

Asn Ser Asp His Gln Leu Gln Leu Leu Asn Gln Ala Ser Gln Met Met
        195                 200                 205

Thr Glu Thr Arg Phe Ser Leu Leu Ile Val Asp Ser Ala Thr Ser Leu
    210                 215                 220
```

```
Tyr Arg Thr Asp Phe Asn Gly Arg Gly Glu Leu Ser Ser Arg Gln Thr
225                 230                 235                 240

His Leu Ala Lys Phe Leu Arg Thr Leu Gln Arg Leu Ala Asp Glu Phe
            245                 250                 255

Gly Ile Ala Val Val Ile Thr Asn Gln Val Val Ser Gln Val Asp Gly
        260                 265                 270

Gly Pro Ser Ser Met Phe Asn Pro Asp Pro Lys Lys Pro Ile Gly Gly
            275                 280                 285

Asn Ile Ile Ala His Ala Ser Thr Thr Arg Leu Ser Leu Lys Lys Gly
        290                 295                 300

Arg Gly Glu Thr Arg Ile Cys Lys Ile Tyr Asp Ser Pro Cys Leu Pro
305                 310                 315                 320

Glu Ser Asp Cys Met Phe Ala Ile Arg Glu Asp Gly Ile Gly Asp Pro
                325                 330                 335

Ser Pro Lys Asp Leu Glu Gly Glu
            340

<210> SEQ ID NO 31
<211> LENGTH: 5101
<212> TYPE: DNA
<213> ORGANISM: Rasamsonia emersonii

<400> SEQUENCE: 31
tctgatatcg gttccccgct gacatgttat tcgacctgta gtgcaaggcg ctctcgaatg      60
gctcgaagcc aaccaagata aatctctcga gaaattaag  gcggccgaat cacgttcaga     120
agagacacag gagggacctc cgctcaaaga gggtgaacag cctcgaagtc tcgtttgcaa     180
cgagtgcgga aagaaattca ggagccaagc acaggctgaa ttccatgcat ccaagacaga     240
gcatgtcgat ttttcggaat caacggaaga gattgctccc ctaacggagg aggagaaaaa     300
ggcgaaactg gcagaattac gggagaaact cgcggcgaaa cgagcaatgc aatcggagca     360
aaacaagctg aaccagaaga gaaacgaggt aaatacacca agctgtcact aacgacacgc     420
ttttccactt ttacttacca ttcgctagga atccggcgg  aagagcacca aggaggctca     480
agacatcaga gaagaactac agaagaagga gctgatgagg gaggcagcca agaaacggaa     540
agagaagcaa gaagaactcg aagcgaagca gaaaatcagg gccaagatag ctgcagacaa     600
agaagagcgg agactgaaag ccgaaagaga gaaggctgag cgggcaggcc aggctccccc     660
accgcaacca gcagcacccg ctccaacgac gtctggaccg gtgacatcca aacctgcatc     720
cgcctacaca gaaactcgcc tgcggttcca gacgtccaaa ggaaacatta tgaagacctt     780
ccccgtggat acaacccttt tcgaggttgc cgccgccctc aacaaggacg aaggattgga     840
agttcagagt tcacacaaa  atttcccgaa aaagatcttc gacgccgaat atttcggtga     900 acattgaag  gagcttggtc tggtgcctag cgccagtctt attgtgaaat aatctaattg     960
ctctaactga tgacggcatg actatctgcg tgttttgatt catcgggaag agcgtagtat    1020
cgaatctaac gtggacgacg acatgataat caatttctac acctgaatta ttcgcgcttt    1080
tcgatttgaa attactacat aagcaatgtc tcgctagatc actccaaaag aaagcagtat    1140
tagagactgt atagtcaatt tggggaaggg atggaagagc caaatagtc  gtcatgagaa    1200 gcgtttctta tcttaagcta tttatcttaa gctatttaga gctctcttga ataaacatcg    1260
caaaagagat cttttagaat gcatgtgttg tcgtatacat gtactccgta gagcaagtgt    1320
ttccaattcg atcacgtgaa caggcgcccc gtcgtgttga tgacataagc agcatccgtc    1380
```

```
gcgtcgacac gtcggtgcct gtggagggcc gtgatagcgg gcaatcgcgt tgttaagagt    1440
tagatcagcc agcatcctct tgttgttgat gtccgccatt gtgctcttgg tccttacaaa    1500
atgcctgcgt aagtctgaat ttcatctgtt ctgatgagtt agttttact aacttgtacc     1560 ttaacagtgt cggtgaccag caccgtgtag gaccgggtac tgtgatatca accatggctg    1620
gtaccgtctc tgcgaatcct ttcgaggaac caccccgtcg aattagcgaa tatactgctc    1680
aggaaattgc cactcttcaa tctcgccttg ataagcagct gggaccagag tacatctcct    1740
caagagccgg cccctctggg cagaaggtgc actacctagc ggcagagaaa tgtataaacc    1800
ttgcgaacga ggtctttgga ttcaatggct ggtccagttc gatccaaagt atacagatcg    1860
actttgtgag tgcaacaggt tggacgattg ttgagcaatg ggctgattgt cgggtactag    1920
gttgatgaga gtccaagcac gggtaagata agtctggggt tatccgtgat tgtgagagtc    1980
acattgaagg atggcacata tcatgaggta cgggagcgat atgtcacgtt atcatcggct    2040
ctgtggagga gactgactgt ggtggcttct aggatatcgg ctatggccat attgagaatt    2100
gcaaaggcaa agcggcagct tttgagaaag caaagaagga gggaacaaca gatgctctta    2160
aacgagctct gaggacattt ggcaatgttc tgggcaactg catctacgac aaagagtatc    2220
ttgccagagt cactagagtc aaagtggctc ctgtaagttc cattcccttc atgtctcttg    2280
atcagtctac taattaggag tagaccaagt gggatgtgga taaccttcat cgtcaccctg    2340
attacgcccc ggtcaaaaag gagcctgtcg aagacaagaa ggtctctgaa gataatgatc    2400
ttcctccccg tccaactgaa gcttccacga caacgcgaa tccttcttct cccgcattcg      2460
acggagacgg cgaatttggc agtaagtctc tcctgatttg tggaattggc ctgatgctca    2520
aatattggca ggtgatcttt tcgacgaggc agacttcgcg gtgtgcaacc ctgatgaggt    2580
ggttttagac ccagaacctc cacaacagca gcagcagcag cagcaacagc agtcgcatcc    2640
acaagctcag gtgccccagc aagggcctca agggaacaac tcacgacccg ctcgacctcc    2700
tcctgagatg gttactccct caaaaccaga aaggtcttgg aatgccggcc ctactcctgc    2760
tgcacgacag ccagcacaga cgccgcagaa caagacagct tcaggagctc aacataatat    2820
gtctatgaac cgtcctcagg gcatgatgca aaggcagccg accccctggtc cgcgaccaca    2880 gcaaccagag cgcaactcag cggctgcccc tcaggcttat tcaagatcta gccaagaaat    2940
gtcatcaaat gctcaaggcg gttcaggaat caaatcagag cgtctgctca gctccgcgga    3000
ctctaagcct cagcaagcca ataataataa tcagggacaa tcttcgggaa gcgattcgga    3060
gaacagggtc cagccggatc cagcagctgg ctttttctct gcaaaagcag ttgacatact    3120
acgagaaaac cctcaggcac ctccatcaat ggcaccgaag tttaacccgc atgccgagag    3180
tccttcaatc cgcaaaacag caggtatcga ccatagcaag agccttccta tttctaaacc    3240
gatgcttgca ggagtttctc cttcccaaaa tagtacacgg gattttataa atccttctgc    3300
agatatgcat cgcagaatag gcgctcctgg cggtagtgga atcgccagcc cagtgggcag    3360
gccgcagagc acatcctctt atcgcccatt aacccgaccg aacattgacc caagaaatgc    3420
tggaagcaat actgggttta atcgagaaaa ccctgcacag cagaatgcaa gcctgaagag    3480
accgccgctc aacgacgtga caaattcttc cctctcatcg ggcacgtctg ggcccggtga    3540
tcccaaaaga cccaaagtca cgccgaaga acagactgcg ccacagcaac aaaagtgttg    3600 acatgttgc caatcagtaa agttctcctg tgttattcat ctgtcgtgaa cattagcgct     3660
ttgttatttg acatgactcg gtgagtatat ggcgtttagg aggccaagga atagtatatg    3720
acgcactcgt ctgtgcaatt gtcctgaact ggttattttg ctgtggggat tcggtacctg    3780
```

-continued

```
ttaacatata ttatttacgt tgcatatcca tcaactctat cataacttac ttcattttt     3840
tattcttggt gtttgggaag aggaatgaac ggcaatggtt tctttcgtgt ggcttgctgg     3900
tgttaaaatg gatggatgtt atactctgtg tattaattag ttgatcaagg atggaaaagg     3960
atcgatctat caatcagctg gcgttggtat tgatatagtc aatattgaaa tttctgatat     4020
tgatattctg acatggtcag agcttctcac cattacattg cgcgcgttct aaaaaagtat     4080
cagagtggaa cgaaaaaaaa atgaatacac cgtagctggc tagttatgac tgacacttgc     4140
attaacttca ctaatcctac atacgtacat acatgacaca tgaaaaactg ttgttggatt     4200
tttttttcgg aatgagtttt tgttttcgaa aacagcaaac aaacaactaa agaaaagaaa     4260
agaaagaagg gcttttttga gggatgatag taatgataca ggtcaaacgg aagaaagaag     4320
aagcaaagaa aggaggaaaa aaaaactacc accacacaac ttttcgcttt catctcaggt     4380
aagtagttat gacaccgcta atcgatcgaa actggatatc atcaatcaat cgaaaatggg     4440
gaaaatgaat attcgttatc atcatcctcg tgagaatcat aaccggacgt atcactcttt     4500
agggcttttt ttttctaacc cccgcaccgc gattcgtcat cttcgcttgg agcaagtacg     4560
tcatctgagc ttagcggaga ggtttcttct tgtcgtcgtc gggtaggatc gcatatctag     4620
atgcgtagag actgcgggtt tgcggaagag gagggctctg tggactttgt gctgcggctg     4680
ctacaggagg ctgctgctgg tattggctcg gttgcattgg ttgattggaa gaagaagaag     4740
acactcctgc tgcagacgca gcggaccagg gatgtgggaa tcctcgttgc tgaaagctag     4800
gagcagcctg attctgacgt gcaaacggct ggttggtgtg ttgctctgct tgttggtgac     4860
taaaccgtgg ggaaggagaa gccgcaggac ttgaagaagc cgtaggcgca tgtctcgagg     4920
cgtaaaggct gcgcgtagga ggggcagggc taggctgttg ctcagtctgc actggagcct     4980
ggtattgcgc tggttgcgac ggttgaccga accctcctgg gagagacgca ctcgctgtcg     5040
gcgcgtgcct ggaagcacac aaactgtggg aagcgtggtg cgcaggagat tggttctctc     5100
c                                                                     5101
```

<210> SEQ ID NO 32
<211> LENGTH: 1821
<212> TYPE: DNA
<213> ORGANISM: Rasamsonia emersonii

<400> SEQUENCE: 32

```
atgcctgctg tcggtgacca gcaccgtgta ggaccgggta ctgtgatatc aaccatggct      60
ggtaccgtct ctgcgaatcc tttcgaggaa ccaccccgtc gaattagcga atatactgct     120
caggaaattg ccactcttca atctcgcctt gataagcagc tgggaccaga gtacatctcc     180
tcaagagccg gcccctctgg gcagaaggtg cactacctag cggcagagaa atgtataaac     240
cttgcgaacg aggtctttgg attcaatggc tggtccagtt cgatccaaag tatacagatc     300
gactttgttg atgagagtcc aagcacgggt aagataagtc tggggttatc cgtgattgtg     360
agagtcacat tgaaggatgg cacatatcat gaggatatcg gctatggcca tattgagaat     420
tgcaaaggca agcggcagc ttttgagaaa gcaagaagg agggaacaac agatgctctt     480
aaacgagctc tgaggacatt tggcaatgtt ctgggcaact gcatctacga caaagagtat     540
cttgccagag tcactagagt caaagtggct cctaccaagt gggatgtgga taaccttcat     600
cgtcaccctg attacgcccc ggtcaaaaag gagcctgtcg aagacaagaa ggtctctgaa     660
gataatgatc ttcctccccg tccaactgaa gcttccacga caacgcgaa tccttcttct     720
```

```
cccgcattcg acggagacgg cgaatttggc agtgatcttt tcgacgaggc agacttcgcg    780
gtgtgcaacc ctgatgaggt ggttttagac ccagaacctc cacaacagca gcagcagcag    840
cagcaacagc agtcgcatcc acaagctcag gtgccccagc aagggcctca agggaacaac    900
tcacgacccg ctcgacctcc tcctgagatg gttactccct caaaaccaga aggtcttgg     960
aatgccggcc ctactcctgc tgcacgacag ccagcacaga cgccgcagaa caagacagct   1020
tcaggagctc aacataatat gtctatgaac cgtcctcagg gcatgatgca aaggcagccg   1080
accctggtc cgcgaccaca gcaaccagag cgcaactcag cggctgcccc tcaggcttat    1140
tcaagatcta gccaagaaat gtcatcaaat gctcaaggcg gttcaggaat caaatcagag   1200
gcgtctgcta gctccgcgga ctctaagcct cagcaagcca ataataataa tcagggacaa   1260
tcttcgggaa gcgattcgga gaacagggtc cagccggatc cagcagctgg ctttttctct   1320
gcaaaagcag ttgacatact acgagaaaac cctcaggcac ctccatcaat ggcaccgaag   1380
tttaacccgc atgccgagag tccttcaatc cgcaaaacag caggtatcga ccatagcaag   1440
agccttccta tttctaaacc gatgcttgca ggagtttctc cttcccaaaa tagtacacgg   1500
gattttataa atccttctgc agatatgcat cgcagaatag gcgctcctgg cggtagtgga   1560
atcgccagcc cagtgggcag gccgcagagc acatcctctt atcgcccatt aacccgaccg   1620
aacattgacc caagaaatgc tggaagcaat actgggttta atcgagaaaa ccctgcacag   1680
cagaatgcaa gcctgaagag accgccgctc aacgacgtga caattcttc cctctcatcg    1740
ggcacgtctg ggcccggtga tcccaaaaga cccaaagtca acgccgaaga acagactgcg   1800
ccacagcaac aaaagtgttg a                                              1821
```

<210> SEQ ID NO 33
<211> LENGTH: 606
<212> TYPE: PRT
<213> ORGANISM: Rasamsonia emersonii

<400> SEQUENCE: 33

Met Pro Ala Val Gly Asp Gln His Arg Val Gly Pro Gly Thr Val Ile
1               5                   10                  15

Ser Thr Met Ala Gly Thr Val Ser Ala Asn Pro Phe Glu Glu Pro Pro
            20                  25                  30

Arg Arg Ile Ser Glu Tyr Thr Ala Gln Glu Ile Ala Thr Leu Gln Ser
        35                  40                  45

Arg Leu Asp Lys Gln Leu Gly Pro Glu Tyr Ile Ser Ser Arg Ala Gly
    50                  55                  60

Pro Ser Gly Gln Lys Val His Tyr Leu Ala Ala Glu Lys Cys Ile Asn
65                  70                  75                  80

Leu Ala Asn Glu Val Phe Gly Phe Asn Gly Trp Ser Ser Ser Ile Gln
                85                  90                  95

Ser Ile Gln Ile Asp Phe Val Asp Glu Ser Pro Ser Thr Gly Lys Ile
            100                 105                 110

Ser Leu Gly Leu Ser Val Ile Val Arg Val Thr Leu Lys Asp Gly Thr
        115                 120                 125

Tyr His Glu Asp Ile Gly Tyr Gly His Ile Glu Asn Cys Lys Gly Lys
    130                 135                 140

Ala Ala Ala Phe Glu Lys Ala Lys Lys Glu Gly Thr Thr Asp Ala Leu
145                 150                 155                 160

Lys Arg Ala Leu Arg Thr Phe Gly Asn Val Leu Gly Asn Cys Ile Tyr
                165                 170                 175

-continued

```
Asp Lys Glu Tyr Leu Ala Arg Val Thr Arg Val Lys Val Ala Pro Thr
            180                 185                 190

Lys Trp Asp Val Asp Asn Leu His Arg His Pro Asp Tyr Ala Pro Val
        195                 200                 205

Lys Lys Glu Pro Val Glu Asp Lys Lys Val Ser Glu Asp Asn Asp Leu
    210                 215                 220

Pro Pro Arg Pro Thr Glu Ala Ser Thr Asn Asn Ala Asn Pro Ser Ser
225                 230                 235                 240

Pro Ala Phe Asp Gly Asp Gly Glu Phe Gly Ser Asp Leu Phe Asp Glu
            245                 250                 255

Ala Asp Phe Ala Val Cys Asn Pro Asp Glu Val Val Leu Asp Pro Glu
        260                 265                 270

Pro Pro Gln Gln Gln Gln Gln Gln Gln Gln Gln Ser His Pro Gln
    275                 280                 285

Ala Gln Val Pro Gln Gln Gly Pro Gln Gly Asn Asn Ser Arg Pro Ala
            290                 295                 300

Arg Pro Pro Pro Glu Met Val Thr Pro Ser Lys Pro Glu Arg Ser Trp
305                 310                 315                 320

Asn Ala Gly Pro Thr Pro Ala Ala Arg Gln Pro Ala Gln Thr Pro Gln
            325                 330                 335

Asn Lys Thr Ala Ser Gly Ala Gln His Asn Met Ser Met Asn Arg Pro
        340                 345                 350

Gln Gly Met Met Gln Arg Gln Pro Thr Pro Gly Pro Arg Pro Gln Gln
    355                 360                 365

Pro Glu Arg Asn Ser Ala Ala Ala Pro Gln Ala Tyr Ser Arg Ser Ser
370                 375                 380

Gln Glu Met Ser Ser Asn Ala Gln Gly Gly Ser Gly Ile Lys Ser Glu
385                 390                 395                 400

Ala Ser Ala Ser Ser Ala Asp Ser Lys Pro Gln Gln Ala Asn Asn Asn
            405                 410                 415

Asn Gln Gly Gln Ser Ser Gly Ser Asp Ser Glu Asn Arg Val Gln Pro
        420                 425                 430

Asp Pro Ala Ala Gly Phe Phe Ser Ala Lys Ala Val Asp Ile Leu Arg
    435                 440                 445

Glu Asn Pro Gln Ala Pro Pro Ser Met Ala Pro Lys Phe Asn Pro His
450                 455                 460

Ala Glu Ser Pro Ser Ile Arg Lys Thr Ala Gly Ile Asp His Ser Lys
465                 470                 475                 480

Ser Leu Pro Ile Ser Lys Pro Met Leu Ala Gly Val Ser Pro Ser Gln
            485                 490                 495

Asn Ser Thr Arg Asp Phe Ile Asn Pro Ser Ala Asp Met His Arg Arg
        500                 505                 510

Ile Gly Ala Pro Gly Gly Ser Gly Ile Ala Ser Pro Val Gly Arg Pro
    515                 520                 525

Gln Ser Thr Ser Ser Tyr Arg Pro Leu Thr Arg Pro Asn Ile Asp Pro
530                 535                 540

Arg Asn Ala Gly Ser Asn Thr Gly Phe Asn Arg Glu Asn Pro Ala Gln
545                 550                 555                 560

Gln Asn Ala Ser Leu Lys Arg Pro Pro Leu Asn Asp Val Thr Asn Ser
            565                 570                 575

Ser Leu Ser Ser Gly Thr Ser Gly Pro Gly Asp Pro Lys Arg Pro Lys
        580                 585                 590

Val Asn Ala Glu Glu Gln Thr Ala Pro Gln Gln Gln Lys Cys
```

<210> SEQ ID NO 34
<211> LENGTH: 6043
<212> TYPE: DNA
<213> ORGANISM: Rasamsonia emersonii

<400> SEQUENCE: 34

```
acctcacgtg ctacatttat ccccagaaga acggacatca cccctgtgag caatattctc      60
aatctgctaa gcccaacaag atctgcgggc ttgaaggaga ggaactgcca acgacaattg     120
cgatacccat tttctatctg aattccatga agcgaaggaa attttacgaa tgcgacgctc     180
gactcactag gctaattctt ggatccagag ttccagacga gtgagttgtt cgaagttccg     240
attttcgcca tcaaattttc cgcaatagcc ggtccgaggt agtcagagtt ccgattcacg     300
gcagaaaccg ctccttcgga acagcactgg ccatagcagg tatcacggcc cgccggatta     360
tctccctcaa ttaggtagct tttcatgtgc cgaggtatta ttatttttta cgccactgta     420
ctctttttc tctattactg ttcttcttgt ggattcctgt cattatcata tacccacttg     480
agctgggtct aaagatccgc ttaatacttt catgagccat tcgtatgtcg cccactttgt     540
attagataat cgaatgagta agcaatcgcc gccatctttg tgcagtttac ctgggataat     600
aatggaacaa catacctgaa cggcatttac tataaatgct ctaatgctac aaattcccag     660
gccgcgataq aatacttgga aaccctctgt gcgataagct tgctgagcga ctccaatga     720
ccccattatt cgttccgtag gcattgtcgg ccgaagaagt gatcgtgtct caggagatat     780
gtctctcgaa ggctccagaa acgattgggc ttgcagcctt gtctttatga cgtcgagtgg     840
gaaaacagag gcccatgtca ctatcccagc aattccgccg cagatgagaa ccttcaatgc     900
agcctgatga gcagtttcgt ccgcagaagt catacttcgc ttacatagct cataggacca     960
gaaactgtag caactgacgt caatatcctg cttgggccga tggcgggtat ctctggagtc    1020
aaggggatga ttcgtactaa aatccgtaac ccacggaatc tctgatactt gttattgctc    1080
ccccgaaata gagtcccttc catcctgctt ttcggatgat atcactggca actgtccacg    1140
atgagatttg cggatttcta ctcagctgcg cccggcattt aatgagctct gttggtgacg    1200
aaaccaccca actggcaatg ccgcccgcgg cgccagctag ccagattttg tttaacgaga    1260
cgccgtctgg tttggttgga tcagtcacgg aagaatccag tgctttcagg cttcggttgt    1320
aggcaacgta aagcagggca tttagagcac catagccaag aatagggggca gcagcgccta    1380
attcaacgtc aatagaggat gaataatgtc cacacagtta cacgcacctc gcaccaagga    1440
ggtggcggtc tcaaattgac ctcgagataa ccgcggggtt ggttctggag agctcccagt    1500
atggtatgcc tgcaggcgga ctttgactag gtcgagtgga ttgccaatga ttataccaat    1560
ggctccgctt atgtagcctg cccaaaagtc ggaggacatt ggttttaaaa atcacaaatg    1620
taagttttca ttactcagtt ggtaaatgcc atgattgttc tgacaatcat cggcacagcg    1680
gagccccgcg atgacggcgg attgatatca cgtgagttcg cgacactttg gcgaaacagg    1740
ggaaatccga acgcgcttac gaacgacgcg tacttgattg ccagcaaacg gagcagtcat    1800
tattccgact tgaaccagct cggtgaccat accaacggtg ggactgtgag aagagttgat    1860
ccgacctagg ggcttcattt tttacttttct cttccaatgt atggaggtct ttgaatgttc    1920
attatccaga aaccaatgct aacctttttgt taggcatcgt ccacggccca ccacggtaga    1980
aggtggtcaa acattagtat cagcacagaa gccagttcga ctctacgccc catcacaaca    2040
gtcgatcgat cgcctctcga agccattcaa atgtccaggc caggcaacag cttctgtagc    2100
```

```
atccgataga ccggccagaa agaggcgcaa agtggattat agcggtgctg acggaagcgc    2160
tgaggatgga agcaaaccat ggaccaacga ggagcgtctt gctcttgcaa accgcgacgc    2220
taacaaattc ccggtctata aagtgaaaga caaagaagta gcacttaaac aacgattctc    2280 tgtacccttta atcgataaga catccagcaa ttatgatccc tccagacctg caccgactct    2340
tggaatgagg cgaggcgcct catttgtcgt gaaacctttg cacgatccga gtggagagtt    2400
cgcaattgtc ttgtatgacc ctacagttga tgacaaaccg gagccaaaga aggaggagga    2460
cggggagaaa accgaagaaa agccaaagct ggatgcaccc attgtgcata gagtttggc     2520 cgatattctt ggtctaaaga aacgcgtcga gtctcgtcct aaggtccctg tggtcattga    2580
cccaagactt gccaaggtct tgcggccaca tcaagtagag ggagtaaagg tgaggcacta    2640
ctcaatcatc tggcatgttt ggttttttaat ataataattg ttttcttcc acagtttctt    2700 tatcgttgca caactggcat gattgatgag aatgcgaatg gctgcatcat ggcagacgaa    2760
atgggcttgg gcaagacggt aatctccagc cctcaattct gtcggattga tgctgatggc    2820
gacagctcca atgtatcact ctgatgtgga cactccttaa gcaatcgcct gaagcgggaa    2880
agccaactat ccagaagtgt gtcattgctt gcccatcaag cttagttaaa aactgggcca    2940
atgaactagg tatgtgatat gtaggccttc ttctacgttg ctactgacag ttatagtgaa    3000
atggcttgga aatgacgcca ttacaccgtt tgcagttgac ggtaaagcct caaaggctga    3060
gctttcctcg cagcttaaac agtgggcaat tgcctcgggt cgctcaatcg tccggccggt    3120
cctcatagtg tcatacgaga cattaaggct atacgttgaa gacctaaagg acacacagat    3180
aggtttgcta ctatgtgacg aaggacacag actcaaaaat aaagagagct tgacctggac    3240
agcgttgaac agcctcaacg tcagccgccg ggtcatcctt tctgggacac ctatacagaa    3300
cgatttgtct gaatatttcg ccctttttgca ttttgcaaac ccaaacttgc tcgggactca    3360
ggctgaattc agaaaaagat ttgaaattcc gattttgaaa ggaagggatg ctgcagggac    3420
ggatgaggat cgaaggaaag gtgatgagcg cttggcagag ctctccagca tcgtcaacaa    3480
attcattata cggcgcacca acgacattct ttcaaagtac ttgccgatca agtacgaaca    3540
tgttgtgttc tgcaatctta gcaagtttca ggttgaccta tataaccatt tcttacagag    3600
cccagacatc aaaagtctgc tcaaaggcaa gggaagccag ccattgaaag cgattggaat    3660
tttgaagaaa ctctgcaatc atccggacct gctggatctg tcaacggaat tgcctggatg    3720
tgaacaattt ttccctgatg actatgttcc accggaagcc agaggccgcg acagagacgt    3780
caaatcctgg tattccggga aaatgatggt tcttgagcgc atgctggcgc gaatacgcca    3840
ggacactaat gataagatcg ttctgatcag taactataca caaacacttg accttttcga    3900
gagactttgc cgctctcgag ggtatgggtg tttgcgactg gacggcacca tgaatgtcaa    3960
taagcgacaa aaactggtgg acaaaattcaa tgaccccgat ggtgaagaat ttatatttttt  4020 gttaagcagc aaggcaggcg gctgtggttt gaacctgatt ggagcgaatc gtttggtttt    4080
atttgatcca gactggaatc ctgctgccga ccagcaagca ctggctcggg tctggcgtga    4140
cggccaaaag aaggactgtt tgtttatcg gttcattgca accggatcga tcgaagaaaa    4200
gatcttccag aggcagtccc acaagcagtc actctcttcc tgcgttgtcg attctgcgga    4260
agacgttgaa cgtcactttt ctctcgactc ccttcgagaa cttttccagt tcaagccaaa    4320
cacgcggagc gacacacatg acacgttcaa atgcaagagg tgcaggccag atgggaccca    4380
gtttatcaag gctccagcca tgttatatgg cgatacgagt acatggaatc attttgtcaa    4440
```

```
cgacggtgag aacggaccat tgaacaaaat acaggacttg ctcttaagac aagaaacctc    4500
cgagaaggat gtttccgctg tttttcaata tatcagtcat tgatacgttg gtggccgctg    4560
ttggcttggt cgatgcaatc gacgatctgt attgaaaccg acatgcatac ttggacagga    4620
tagctttcaa cgtaaatgga tatgtttctt taatttagga atataatgat tgcatagaga    4680
ttattaaatg tttgtttctt tgttgtgaag tactccagcc atcggttctc agttgatgta    4740
ggctccgcgg ataccgtacg atacacggct tgtgacaata catcactacc actgaagccg    4800
catctgcatt gacgctccgc gctgttgaca acacatgcat gctccccgca tacctggcat    4860
caggaagctg aaatgattgt tccgcatgtg cctgcatcca ctacagtttg agacgcagtg    4920
tctgacaatt catgttaccg cccagagcag cttcccggca gtgcagttta taatcccagc    4980
agcatcagcc caccttgctc ccacgcattc cattcgcaac cacgatgagt gttgcctaac    5040
acgaatacgg agtctgtgac ttgtagaaag tcaaccgcca tttcacaatg gaccaatcag    5100
ttcagcgtct gctgaacgac aagctctacg acaagagaaa acagggtgcc ttagagtacg    5160
ttgcagcttc tgtagacaag tgtcccgaaa gctgcagtgc tgaccacaat aatgttctta    5220
ggcttgaaaa gatcgtccgc gatgccatat tcagaggaga gcacgataaa atccagaaga    5280
tcgtcgatca gctctgccac gactatgcct acgctgttca ccaaccacac gcgcgaaatg    5340
gaggtctgat cggtctggcc gccgcctcga tagcattggg atctgtgagt tgagacaata    5400
ttataggatg gtttgtggat ttcagggctg atcaagcgca ggaggggggtc gctccttacc    5460 tccaagagat cgttcctcct gttctcgctt gcttctctga tcaggatgcg cgtgttaggt    5520
attatgcatg cgagagcatg tacaacattg cgaaggtggc taaggagag atactggttt    5580 tcttcaatga tatatttgat gcattatgca aggtctgtgt gctcggtgta cgtccacgg    5640 atgtatatct ctcctactga cacacaccag ctagcatccg actcggagct ctccgtaaag    5700
aacggagctg agctacttga ccgacttgtg aaagacattg tcgctgaatc ggcagcttcc    5760
tatgtctccg tcttacagta tccggagaag aacgtgcaag acctagatgc tactcgagaa    5820
gcagaagaaa tctcaaatga tctgccaaca gcattctcac tggccaagtt cataccgctg    5880
ttgcaggagc gaatacatgt cctgaatcct tttacccgaa cattcctcgt atcatggttg    5940
actttgttag acacaattcc ggacctggag ctcgtgtgtt acttaccagc ttttctcggc    6000
ggattgataa agttcctagg agatccaaac aaggatgttc atg                      6043
```

<210> SEQ ID NO 35
<211> LENGTH: 2568
<212> TYPE: DNA
<213> ORGANISM: Rasamsonia emersonii

<400> SEQUENCE: 35

```
atgcctgccc aaaagtcgga ggacattggt tttaaaaatc acaaatcgga gccccgcgat      60
gacggcggat tgatatcacg tgagttcgcg acactttggc gaaacagggg aaatccgaac     120
gcgcttacga acgacgcgca tcgtccacga cccaccacgg tagaaggtgg tcaaacatta     180
gtatcagcac agaagccagt tcgactctac ggcccatcac aacagtcgat cgatcgcctc     240
tcgaagccat tcaaatgtcc aggccaggca acagcttctg tagcatccga tagaccggcc     300
agaaagaggc gcaaagtgga ttatagcggt gctgacggaa gcgctgagga tggaagcaaa     360
ccatggacca acgaggagcg tcttgctctt gcaaaccgcg acgctaacaa attcccggtc     420
tataaagtga aagacaaaga agtagcactt aaacaacgat tctctgtacc tttaatcgat     480
aagacatcca gcaattatga tccctccaga cctgcaccga ctcttggaat gaggcgaggc     540
```

```
gcctcatttg tcgtgaaacc tttgcacgat ccgagtggag agttcgcaat tgtcttgtat     600
gaccctacag ttgatgacaa accggagcca agaaggagg aggacgggga gaaaaccgaa     660
gaaaagccaa agctggatgc acccattgtg cataagagtt tggccgatat tcttggtcta     720
aagaaacgcg tcgagtctcg tcctaaggtc cctgtggtca ttgacccaag acttgccaag     780
gtcttgcggc cacatcaagt agagggagta agtttctttt atcgttgcac aactggcatg     840
attgatgaga atgcgaatgg ctgcatcatg gcagacgaaa tgggcttggg caagacgctc     900
caatgtatca ctctgatgtg gacactcctt aagcaatcgc ctgaagcggg aaagccaact     960
atccagaagt gtgtcattgc ttgcccatca agcttagtta aaaactgggc caatgaacta    1020
gtgaaatggc ttggaaatga cgccattaca ccgtttgcag ttgacggtaa agcctcaaag    1080
gctgagcttt cctcgcagct taaacagtgg gcaattgcct cgggtcgctc aatcgtccgg    1140
ccggtcctca tagtgtcata cgagacatta aggctatacg ttgaagacct aaaggacaca    1200
cagataggtt tgctactatg tgacgaagga cacagactca aaaataaaga gagcttgacc    1260
tggacagcgt tgaacagcct caacgtcagc cgccgggtca tcctttctgg gacacctata    1320
cagaacgatt tgtctgaata tttcgcccctt ttgcattttg caaacccaaa cttgctcggg    1380
actcaggctg aattcagaaa aagatttgaa attccgattt tgaaaggaag ggatgctgca    1440
gggacggatg aggatcgaag gaaaggtgat gagcgcttgg cagagctctc cagcatcgtc    1500
aacaaattca ttatacggcg caccaacgac attctttcaa agtacttgcc gatcaagtac    1560
gaacatgttg tgttctgcaa tcttagcaag tttcaggttg acctatataa ccatttctta    1620
cagagcccag acatcaaaag tctgctcaaa ggcaagggaa gccagccatt gaaagcgatt    1680
ggaattttga agaaactctg caatcatccg gacctgctgg atctgtcaac ggaattgcct    1740
ggatgtgaac aatttttccc tgatgactat gttccaccgg aagccagagg ccgcgacaga    1800
gacgtcaaat cctggtattc cgggaaaatg atggttcttg agcgcatgct ggcgcgaata    1860
cgccaggaca ctaatgataa gatcgttctg atcagtaact atacacaaac acttgacctt    1920
ttcgagagac tttgccgctc tcgagggtat gggtgtttgc gactggacgg caccatgaat    1980
gtcaataagc gacaaaaact ggtggacaaa ttcaatgacc ccgatggtga agaatttata    2040
tttttgttaa gcagcaaggc aggcggctgt ggtttgaacc tgattggagc gaatcgtttg    2100
gttttatttg atccagactg gaatcctgct gccgaccagc aagcactggc tcgggtctgg    2160
cgtgacggcc aaaagaagga ctgttttgtt tatcggttca ttgcaaccgg atcgatcgaa    2220
gaaaagatct tccagaggca gtcccacaag cagtcactct cttcctgcgt tgtcgattct    2280
gcggaagacg ttgaacgtca cttttctctc gactcccttc gagaactttt ccagttcaag    2340
ccaaacacgc ggagcgacac acatgacacg ttcaaatgca agaggtgcag gccagatggg    2400
acccagttta tcaaggctcc agccatgtta tatggcgata cgagtacatg gaatcatttt    2460
gtcaacgacg tgagaacgg accattgaac aaaatacagg acttgctctt aagacaagaa    2520
acctccgaga aggatgtttc cgctgttttt caatatatca gtcattga                2568
```

<210> SEQ ID NO 36
<211> LENGTH: 855
<212> TYPE: PRT
<213> ORGANISM: Rasamsonia emersonii

<400> SEQUENCE: 36

Met Pro Ala Gln Lys Ser Glu Asp Ile Gly Phe Lys Asn His Lys Ser
1               5                   10                  15

```
Glu Pro Arg Asp Asp Gly Gly Leu Ile Ser Arg Glu Phe Ala Thr Leu
             20                  25                  30

Trp Arg Asn Arg Gly Asn Pro Asn Ala Leu Thr Asn Asp Ala His Arg
         35                  40                  45

Pro Arg Pro Thr Thr Val Glu Gly Gly Gln Thr Leu Val Ser Ala Gln
     50                  55                  60

Lys Pro Val Arg Leu Tyr Gly Pro Ser Gln Ser Ile Asp Arg Leu
 65                  70                  75                  80

Ser Lys Pro Phe Lys Cys Pro Gly Gln Ala Thr Ala Ser Val Ala Ser
                 85                  90                  95

Asp Arg Pro Ala Arg Lys Arg Lys Val Asp Tyr Ser Gly Ala Asp
             100                 105                 110

Gly Ser Ala Glu Asp Gly Ser Lys Pro Trp Thr Asn Glu Glu Arg Leu
         115                 120                 125

Ala Leu Ala Asn Arg Asp Ala Asn Lys Phe Pro Val Tyr Lys Val Lys
     130                 135                 140

Asp Lys Glu Val Ala Leu Lys Gln Arg Phe Ser Val Pro Leu Ile Asp
145                 150                 155                 160

Lys Thr Ser Ser Asn Tyr Asp Pro Ser Arg Pro Ala Pro Thr Leu Gly
                 165                 170                 175

Met Arg Arg Gly Ala Ser Phe Val Val Lys Pro Leu His Asp Pro Ser
             180                 185                 190

Gly Glu Phe Ala Ile Val Leu Tyr Asp Pro Thr Val Asp Asp Lys Pro
         195                 200                 205

Glu Pro Lys Lys Glu Glu Asp Gly Glu Lys Thr Glu Glu Lys Pro Lys
     210                 215                 220

Leu Asp Ala Pro Ile Val His Lys Ser Leu Ala Asp Ile Leu Gly Leu
225                 230                 235                 240

Lys Lys Arg Val Glu Ser Arg Pro Lys Val Pro Val Ile Asp Pro
                 245                 250                 255

Arg Leu Ala Lys Val Leu Arg Pro His Gln Val Glu Gly Val Lys Phe
             260                 265                 270

Leu Tyr Arg Cys Thr Thr Gly Met Ile Asp Glu Asn Ala Asn Gly Cys
         275                 280                 285

Ile Met Ala Asp Glu Met Gly Leu Gly Lys Thr Leu Gln Cys Ile Thr
     290                 295                 300

Leu Met Trp Thr Leu Leu Lys Gln Ser Pro Glu Ala Gly Lys Pro Thr
305                 310                 315                 320

Ile Gln Lys Cys Val Ile Ala Cys Pro Ser Ser Leu Val Lys Asn Trp
                 325                 330                 335

Ala Asn Glu Leu Val Lys Trp Leu Gly Asn Asp Ala Ile Thr Pro Phe
             340                 345                 350

Ala Val Asp Gly Lys Ala Ser Lys Ala Glu Leu Ser Ser Gln Leu Lys
         355                 360                 365

Gln Trp Ala Ile Ala Ser Gly Arg Ser Ile Val Arg Pro Val Leu Ile
     370                 375                 380

Val Ser Tyr Glu Thr Leu Arg Leu Tyr Val Glu Asp Leu Lys Asp Thr
385                 390                 395                 400

Gln Ile Gly Leu Leu Leu Cys Asp Glu Gly His Arg Leu Lys Asn Lys
                 405                 410                 415

Glu Ser Leu Thr Trp Thr Ala Leu Asn Ser Leu Asn Val Ser Arg Arg
             420                 425                 430
```

-continued

Val Ile Leu Ser Gly Thr Pro Ile Gln Asn Asp Leu Ser Glu Tyr Phe
            435                 440                 445

Ala Leu Leu His Phe Ala Asn Pro Asn Leu Leu Gly Thr Gln Ala Glu
450                 455                 460

Phe Arg Lys Arg Phe Glu Ile Pro Ile Leu Lys Gly Arg Asp Ala Ala
465                 470                 475                 480

Gly Thr Asp Glu Asp Arg Arg Lys Gly Asp Glu Arg Leu Ala Glu Leu
                485                 490                 495

Ser Ser Ile Val Asn Lys Phe Ile Ile Arg Arg Thr Asn Asp Ile Leu
            500                 505                 510

Ser Lys Tyr Leu Pro Ile Lys Tyr Glu His Val Val Phe Cys Asn Leu
            515                 520                 525

Ser Lys Phe Gln Val Asp Leu Tyr Asn His Phe Leu Gln Ser Pro Asp
            530                 535                 540

Ile Lys Ser Leu Leu Lys Gly Lys Gly Ser Gln Pro Leu Lys Ala Ile
545                 550                 555                 560

Gly Ile Leu Lys Lys Leu Cys Asn His Pro Asp Leu Leu Asp Leu Ser
                565                 570                 575

Thr Glu Leu Pro Gly Cys Glu Gln Phe Phe Pro Asp Asp Tyr Val Pro
            580                 585                 590

Pro Glu Ala Arg Gly Arg Asp Arg Asp Val Lys Ser Trp Tyr Ser Gly
            595                 600                 605

Lys Met Met Val Leu Glu Arg Met Leu Ala Arg Ile Arg Gln Asp Thr
            610                 615                 620

Asn Asp Lys Ile Val Leu Ile Ser Asn Tyr Thr Gln Thr Leu Asp Leu
625                 630                 635                 640

Phe Glu Arg Leu Cys Arg Ser Arg Gly Tyr Gly Cys Leu Arg Leu Asp
                645                 650                 655

Gly Thr Met Asn Val Asn Lys Arg Gln Lys Leu Val Asp Lys Phe Asn
                660                 665                 670

Asp Pro Asp Gly Glu Glu Phe Ile Phe Leu Leu Ser Ser Lys Ala Gly
            675                 680                 685

Gly Cys Gly Leu Asn Leu Ile Gly Ala Asn Arg Leu Val Leu Phe Asp
690                 695                 700

Pro Asp Trp Asn Pro Ala Ala Asp Gln Gln Ala Leu Ala Arg Val Trp
705                 710                 715                 720

Arg Asp Gly Gln Lys Lys Asp Cys Phe Val Tyr Arg Phe Ile Ala Thr
                725                 730                 735

Gly Ser Ile Glu Glu Lys Ile Phe Gln Arg Gln Ser Lys Gln Ser
            740                 745                 750

Leu Ser Ser Cys Val Val Asp Ser Ala Glu Asp Val Glu Arg His Phe
            755                 760                 765

Ser Leu Asp Ser Leu Arg Glu Leu Phe Gln Phe Lys Pro Asn Thr Arg
770                 775                 780

Ser Asp Thr His Asp Thr Phe Lys Cys Lys Arg Cys Arg Pro Asp Gly
785                 790                 795                 800

Thr Gln Phe Ile Lys Ala Pro Ala Met Leu Tyr Gly Asp Thr Ser Thr
                805                 810                 815

Trp Asn His Phe Val Asn Asp Gly Glu Asn Gly Pro Leu Asn Lys Ile
                820                 825                 830

Gln Asp Leu Leu Leu Arg Gln Glu Thr Ser Glu Lys Asp Val Ser Ala
            835                 840                 845

Val Phe Gln Tyr Ile Ser His

<210> SEQ ID NO 37
<211> LENGTH: 6139
<212> TYPE: DNA
<213> ORGANISM: Rasamsonia emersonii

<400> SEQUENCE: 37

```
acagcaagat gcacaatccg ttcaatgcaa cgctggtctg cggcctgctc atcacggtcc      60
ttgcatgcat ctatgtcggc tcgaccactg cttctcaacgc cttcgttggc tcctatgtcc    120
aactctcgac cctctcttac tttgcggcca tcttccctca cgtcctgaac cgtcgttcgc    180
tcatcacacc gggatacttc tggatgaagg gtccaatcgg ctacatcgtt aacattctga    240
gttgcatcta catcttagct ttcattgtca ttttctgctt ccctgcttcc cttcctacca    300
atgcgcaatc catgaactac gcgagtttga tcactggcgg tttcaccatt ttcatcgccg    360
cctggtggtt cgtccggcag cgccactacc aaggaccgca agtcatccca ctgaccgatc    420
ggaaaatcgc tgaagacgca aagtgaatct cgttgtaaat ccaacattgg ttttggcgac    480
cactgtgact ggaaatgaca atcgttatgt caatatttta ccacctttgt gtatccccca    540
cattgtaaat tcgcggacaa ttttgcttac taataatttc tgcacgtgtg attggttgaa    600
ttcgcggata atgttgctta ctaagacatt tccggctgca tgattggtta aaaccgctta    660
aaaatcacgt gcctgaaact tttacgtaag catctgtctg cttacagttg gctacggccc    720
tgggactccc tataggccta tgggcttcat attggcaccc ttagaggcct cacgctggca    780
cccctagagg ctttatatag gcttgcatta aaggtatgcg gagggccgaa ggtccggagc    840
atttaggtat aagcacttaa gtatactagg cttcatatta gcttatatgg gcttcataat    900
ggctctctta tgggcttcct cagaggtttt ataaaggctt acatatatta taggctggcg    960
gagggccgaa ggtcccgagc attataggca ttagtaagcc tagatagtct tccccttcaa   1020
gcctagacga gcggagcgag tcgttaaagg cttgtgaggt ctataaagag actggagttc   1080
cccatgtttt cgtcatgttc aaatatgttt catttcttgg atatatatgc acatgtagta   1140
tatctgttgt caacatgggg taacagcctc gatacatgat cctaattgta atgggatttt   1200
aatgcgccac aatctcagct gactgatctg gaaacacact ctgtttacat tctttcgtag   1260
atacaacact cattcttgct gttcaattca attgtatgta caatgcaata aaaatcacag   1320
aaacaccaga tgttcgttcg aagtcggtaa taatcaagcg tgatcacgtg ggttcgcgtt   1380
tccctcgcgt cgcggatggc cttggcaaag agcacgtgtc agcttatctc aacaggatgg   1440
aacagtcgaa gtgtctccgg tccataacga ggcattattg aaaatcatcg gctggccgcc   1500
atggttttca agccttttcg tcctccgctg ataagaaagc ccctcctcc agcggaatct    1560
tcaacaccga taactggaga tagtggaaac cctcacccgt cgaaacgacc gcggttgagt   1620
gaggacgacg atcagtccgc aaaagatgag aagacatcca cttctgtggt cgagagcaag   1680
agcactaagg ataagccgaa gccacagctt gcgtaccgca agccgttgat ccaggtgaag   1740
aacttgactg gaaaggcggc tccgtccgta gacgatgcca gcaactctgc gaacacggaa   1800
aataataatg gctctactca ggaagtggag gcttattata atgttctctg gttagttgcc   1860
ttttctattc gatgccttta ctcagacatt aaccattccc cttctaccgt atcttaggcg   1920
aaaattcacg actaagaaac acaaaacctg ggatggcgat ggcattctct ccatccgtgg   1980
aggatacggc tatcttcagg atgtatcagg ccgagacatg gggcgcataa tgatcaactc   2040
gactctggaa cctggagcaa ctttgacgat tgggggaaaa gatgtcgagg tgcaatccgc   2100
```

```
catgtcgaaa gaagagtact tgtctggtcg atcttttctg ggaggggcaa agaaaaccct    2160
gacgtctcct ctcgcgtctc gtgagaagac acaagcctct gttgtcccta ctcaagcatc    2220
aaagctgccg aaagtctccg cgacgctaac tgaaggcgca agaagccat tgagtcggac     2280 aagctctcgg aatgacagtg aaaaagatgc cttcgtgaaa aatctcaatg ttgccgctcc    2340
aagaagcgca gcattgggca acgctttcaa gaacccggtg aaagagagca cagtttcttc    2400
cgcaaaaccg gcagcacagc ctattccccg tcatgatcca aatgcgccgg cgccttggt    2460 catgaaacgg ccggatgtcg ttccaaaggg aaagacgatt gttgatgtcg tcgtggaccc    2520
catccttacc aaacacctcc gcaacacca acgggagggt gtcaaatttc tttacgagtg     2580
tgtcatgggg ttaagggatt acaatggtga aggagcaatc ctagcggacg agatgggtct    2640
ggggaagacc ctgcaaacaa tcacactctt gtggacattg ctcaaacaaa atccgatcta    2700
cgaagagccc ccagtcgtca agaaggcgtt gattgtttgc ccagtaaccc tcatcaacaa    2760
ctggagaaaa gaattccgca aatggctggg aaatgaacgg ataggcgtgt tcgtcttcga    2820
tgacaagagg aaacgactga cggactttac tatgggcaaa gcctataatg ttatgatcgt    2880
cgggtacgaa aagctgcgaa ccgtccagga agggctcatc aaaggtgccg gggtcgatat    2940
cgtcattgca gatgaaggcc acagactaaa gacactacag aacaagagcg gccaggccat    3000
tcaagcgctc aacaccacga agaggatcat cctctctggc actccgattc agaatgatct    3060
gagtgaattc ttcgcggcgg tcgacctggt caatcctggg attctgggta catacaagaa    3120
cttcatgaaa gaattcgagg ggcctattat gaggagtagg cagcccgagg caacaaaaag    3180
agagattgag aaaggagagg cgaggagtga ggagctcaga aatctcacgt ccatgttcat    3240
gctacgcagg acggcggata tcctgtccaa atacctgccg ccaaaaacgg agtatgtgct    3300
cctgtgcgaa cctacggcga tacaagcaag catctaccgt cacgtcctcg cgtcgcccat    3360 cttttcaaagc gctcttggta acaccgaggg tgcattccat ctcattacta ttctcaagaa    3420
attatgtaac agcccatcgt tgctcactgc gaagacggaa gacgaaacac cgaatgctac    3480
ggtttccgcg ctgctgtcta cgctgccacc gaatcttctg cgtcatttct ccccttcctc    3540
gagcgggaaa ttgagggtac tcgaccaact cctccataat ctgcgcacaa ccacgtcgga    3600
aaagatcgtg ctggtctcca actatacctc gacattgaac cttctcgcca cgctgctcac    3660
gtcgctttcg ctcccgttcc tgcgtctgga cggcaccacg ccgtcctcga aacggcagtc    3720
gctcgttgac gacttcaatc gcagtcccgc gagtacctgc tttgcgtttc tactctccgc    3780
aaaggccgga ggcacaggcc tgaatctgat tggggccagc cgcctcgtcc ttttcgacgt    3840
cgattggaat ccggcgacgg acatgcaggc catggcgcgg atccatcgag acggacaaac    3900
acgccactgc tggatatatc gcatcatgct gaaaggcggg ctgaggagga agatctggca    3960
gagacaagtg accaaaatcg ggctggcgga cagcgtcatg gaacagaaag gcggcatggc    4020
acagttctcg cggaggagc tcaaggacct atttcgactg tatgagggcg aaggatgcca    4080
gacacatgat cttctgtgct gtaactgcgg cgggcggggg acaccatcca ccgacggagg    4140
tgatcgtcca gtctccacag attccgacga taaatccagc agcagctgtt cttcagcaga    4200
agacgaggag gagactgatg atgaagacga tgaagaagac atcgatctac cagacctccc    4260
aactctcatc aaagtatcac aactagacat cgacgcgcaa gaggcccaaa tccgacgagg    4320
ctcccatcct ctccagcgac gtcagagcaa caagaccaag gacaagaaca agaaaaaaga    4380
cacaaagaac ccgcgtggga ggaagaagaa gaacagcgac caagccagga tgcagcaatt    4440
```

```
cctctccgaa tactcgcaca tcgacccttc cgcctttggt gcagacgacc atggggagga      4500
gggcacggat ctagccagcc agatccgcga tccggtgctc ctttctctct tgagggagga      4560
ggatcatggc gtggggttca tctttgagaa gacggcgttt cctgctgctg atgctgatgc      4620
tcctgctgag aagaaataag aaatctctac ccgccttcct acttacgcaa ggtagtagga      4680
acagactaga tcctcaccat cctttttttt tgcatttatg tgtatacact ataatcatga      4740
taataaccac tgcatatatc catatgatac tatcgatctc gtacggttat agcatagcca      4800
tgatcagggt cagggtcagg gtcagggaca gggacagggt tcgtcaggaa gtaattgcat      4860
ggatggattc atttaacatt tctctacggc tactcgatag acagatagat aggtatacag      4920
caatgaatac aatgagcatt aacgaacgac tgactaactg actgactgac tgactagtca      4980
atcagttgaa ctgattaatt cctgaaacac tccagtacta tctatttatt ctttaccacc      5040
ttctttctta cccttacata tacatatatt taatatttag acataaatac gaacgaactg      5100
caccagctag ctagctagct aactacacaa gctagacaag tcgtgaccat ggatgacgat      5160
gacggataga tagatagata cgatgagaga gggatggatg gaaatgaact ggaaaatgga      5220
aaaatggaaa atgcaactca actcaacaat gcaatcttct tctacctacc tcctccatct      5280
atcaacacgt aaattggtat aaaattggta taaagcttga agtatgaagg gtgaaggggga      5340 gacttgagcg gccaaaacta catacatacg tacgtcaaat gtcgtagaca gggcatgaga      5400
catgacataa agacatgaca tgagacataa catgaggaca tgaagacatg aaggcatgaa      5460
ggcatgaggg gatagttggg gggggggggga aatagttcca aaaaatgaac aaaaaaaggc      5520
aaatagagaa gtctccacaa tcatcgaaaa tgtagactag atatattgca aaacaccacc      5580
aatgcagtgg attacattcc aacatgatag gcaagttaat accgcagctt tcctaccagt      5640
gaaaacgtat aagctgcctc ggcctcgctc ttcatctgga tcatatatac tcggaacgag      5700
ccgccggtga caccgccctc cttgctgact gcaccgcctt cattctcttc ccagaccgag      5760
actgcaatgc ccgttctggc cacgcgctca aatgagctct cgcccagagt agcatcgagc      5820
aagacctctc cccgcgtctt tccccggatc agaatccgtt tttcctgtgg tatagcgaca      5880
cgacgtggtg atgcagcggc cggagtagcg cggcctctg ccactggtgc atcaccctcc       5940
cctgtttcac ctgctgcggc attggcattg gcatcagcag gagcagcaac gctccccgct      6000
gtgccagggc gagaggatct tggcgtcgca ggcatgatgg tcaatcgagc tgctcccaga      6060
tcacgccatt tcgacacact ttcacggaca taaagccgga tcttcgcatt ggacaagcca      6120
atcccgtccg caccccttga                                                 6139
```

<210> SEQ ID NO 38
<211> LENGTH: 3072
<212> TYPE: DNA
<213> ORGANISM: Rasamsonia emersonii

<400> SEQUENCE: 38

```
atggttttca agccttttcg tcctccgctg ataagaaagc cccctcctcc agcggaatct        60
tcaacaccga taactggaga tagtggaaac cctcacccgt cgaaacgacc gcggttgagt       120
gaggacgacg atcagtccgc aaaagatgag aagacatcca cttctgtggt cgagagcaag       180
agcactaagg ataagccgaa gccacagctt gcgtaccgca agccgttgat ccaggtgaag       240
aacttgactg gaaaggcggc tccgtccgta gacgatgcca gcaactctgc gaacacggaa       300
aataataatg gctctactca ggaagtggag gcttattata atgttctctg gcgaaaattc       360
acgactaaga aacacaaaac ctgggatggc gatggcattc tctccatccg tggaggatac       420
```

-continued

```
ggctatcttc aggatgtatc aggccgagac atggggcgca taatgatcaa ctcgactctg      480
gaacctggag caactttgac gattggggga aaagatgtcg aggtgcaatc cgccatgtcg      540
aaagaagagt acttgtctgg tcgatctttt ctgggagggg caaagaaaac cctgacgtct      600
cctctcgcgt ctcgtgagaa gacacaagcc tctgttgtcc ctactcaagc atcaaagctg      660
ccgaaagtct ccgcgacgct aactgaaggc gcaagaagc cattgagtcg acaagctct       720 cggaatgaca gtgaaaaaga tgccttcgtg aaaaatctca atgttgccgc tccaagaagc     780
gcagcattgg gcaacgcttt caagaacccg tgaaagaga gcacagtttc ttccgcaaaa      840
ccggcagcac agcctattcc ccgtcatgat ccaaatgcgc cgggcgcctt ggtcatgaaa     900
cggccggatg tcgttccaaa gggaagacg attgttgatg tcgtcgtgga ccccatcctt     960
accaaacacc tccgcgaaca ccaacgggag ggtgtcaaat ttctttacga gtgtgtcatg    1020
gggttaaggg attacaatgg tgaaggagca atcctagcgg acgagatggg tctggggaag   1080
accctgcaaa caatcacact cttgtggaca ttgctcaaac aaaatccgat ctacgaagag    1140
cccccagtcg tcaagaaggc gttgattgtt tgcccagtaa ccctcatcaa caactggaga    1200
aaagaattcc gcaaatggct gggaaatgaa cggataggcg tgttcgtctt cgatgacaag    1260
aggaaacgac tgacggactt tactatgggc aaagcctata atgttatgat cgtcgggtac   1320
gaaaagctgc gaaccgtcca ggaagggctc atcaaaggtg ccggggtcga tatcgtcatt    1380
gcagatgaag gccacagact aaagacacta cagaacaaga gcggccaggc cattcaagcg    1440
ctcaacacca cgaagaggat catcctctct ggcactccga ttcagaatga tctgagtgaa    1500
ttcttcgcgg cggtcgacct ggtcaatcct gggattctgg gtacatacaa gaacttcatg    1560
aaagaattcg aggggcctat tatgaggagt aggcagcccg aggcaacaaa agagagatt    1620 gagaaggag aggcgaggag tgaggagctc agaaatctca cgtccatgtt catgctacgc    1680
aggacggcgg atatcctgtc caaatacctg ccgccaaaaa cggagtatgt gctcctgtgc    1740
gaacctacgg cgatacaagc aagcatctac cgtcacgtcc tcgcgtcgcc catctttcaa    1800
agcgctcttg gtaacaccga gggtgcattc catctcatta ctattctcaa gaaattatgt    1860
aacagcccat cgttgctcac tgcgaagacg gaagacgaaa caccgaatgc tacggtttcc    1920
gcgctgctgt ctacgctgcc accgaatctt ctgcgtcatt tctccccttc ctcgagcggg    1980
aaattgaggg tactcgacca actcctccat aatctgcgca caaccacgtc ggaaaagatc    2040
gtgctggtct ccaactatac ctcgacattg aaccttctcg ccacgctgct cacgtcgctt    2100
tcgctcccgt tcctgcgtct ggacggcacc acgccgtcct cgaaacggca gtcgctcgtt    2160
gacgacttca atcgcagtcc cgcgagtacc tgctttgcgt ttctactctc cgcaaaggcc    2220
ggaggcacag gcctgaatct gattgggcc agccgcctcg tccttttcga cgtcgattgg   2280
aatccggcga cggacatgca ggccatggcg cggatccatc gagacggaca aacacgccac   2340
tgctggatat atcgcatcat gctgaaaggc gggctggagg agaagatctg gcagagacaa    2400
gtgaccaaaa tcgggctggc ggacagcgtc atggaacaga aaggcggcat ggcacagttc    2460
tcgcgggagg agctcaagga cctatttcga ctgtatgagg gcgaaggatg ccagacacat    2520
gatcttctgt gctgtaactg cggcgggcgg gggacaccat ccaccgacgg aggtgatcgt   2580
ccagtctcca cagattccga cgataaatcc agcagcagct gttcttcagc agaagacgag    2640
gaggagactg atgatgaaga cgatgaagaa gacatcgatc taccagacct cccaactctc    2700
atcaaagtat cacaactaga catcgacgcg caagaggccc aaatccgacg aggctcccat    2760
```

-continued

```
cctctccagc gacgtcagag caacaagacc aaggacaaga caagaaaaa agacacaaag    2820 aacccgcgtg ggaggaagaa gaagaacagc gaccaagcca ggatgcagca attcctctcc    2880
gaatactcgc acatcgaccc ttccgccttt ggtgcagacg accatgggga ggagggcacg    2940
gatctagcca gccagatccg cgatccggtg ctcctttctc tcttgaggga ggaggatcat    3000
ggcgtggggt tcatctttga aagacggcg tttcctgctg ctgatgctga tgctcctgct    3060
gagaagaaat aa                                                        3072
```

<210> SEQ ID NO 39
<211> LENGTH: 1023
<212> TYPE: PRT
<213> ORGANISM: Rasamsonia emersonii

<400> SEQUENCE: 39

```
Met Val Phe Lys Pro Phe Arg Pro Pro Leu Ile Arg Lys Pro Pro
1               5                   10                  15

Pro Ala Glu Ser Ser Thr Pro Ile Thr Gly Asp Ser Gly Asn Pro His
                20                  25                  30

Pro Ser Lys Arg Pro Arg Leu Ser Glu Asp Asp Gln Ser Ala Lys
            35                  40                  45

Asp Glu Lys Thr Ser Thr Ser Val Val Glu Ser Lys Ser Thr Lys Asp
    50                  55                  60

Lys Pro Lys Pro Gln Leu Ala Tyr Arg Lys Pro Leu Ile Gln Val Lys
65                  70                  75                  80

Asn Leu Thr Gly Lys Ala Ala Pro Ser Val Asp Asp Ala Ser Asn Ser
                85                  90                  95

Ala Asn Thr Glu Asn Asn Gly Ser Thr Gln Glu Val Glu Ala Tyr
            100                 105                 110

Tyr Asn Val Leu Trp Arg Lys Phe Thr Thr Lys His Lys Thr Trp
        115                 120                 125

Asp Gly Asp Gly Ile Leu Ser Ile Arg Gly Tyr Gly Tyr Leu Gln
        130                 135                 140

Asp Val Ser Gly Arg Asp Met Gly Arg Ile Met Ile Asn Ser Thr Leu
145                 150                 155                 160

Glu Pro Gly Ala Thr Leu Thr Ile Gly Gly Lys Asp Val Glu Val Gln
                165                 170                 175

Ser Ala Met Ser Lys Glu Glu Tyr Leu Ser Gly Arg Ser Phe Leu Gly
            180                 185                 190

Gly Ala Lys Lys Thr Leu Thr Ser Pro Leu Ala Ser Arg Glu Lys Thr
        195                 200                 205

Gln Ala Ser Val Val Pro Thr Gln Ala Ser Lys Leu Pro Lys Val Ser
    210                 215                 220

Ala Thr Leu Thr Glu Gly Ala Lys Lys Pro Leu Ser Arg Thr Ser Ser
225                 230                 235                 240

Arg Asn Asp Ser Glu Lys Asp Ala Phe Val Lys Asn Leu Asn Val Ala
                245                 250                 255

Ala Pro Arg Ser Ala Ala Leu Gly Asn Ala Phe Lys Asn Pro Val Lys
            260                 265                 270

Glu Ser Thr Val Ser Ser Ala Lys Pro Ala Ala Gln Pro Ile Pro Arg
        275                 280                 285

His Asp Pro Asn Ala Pro Gly Ala Leu Val Met Lys Arg Pro Asp Val
    290                 295                 300

Val Pro Lys Gly Lys Thr Ile Val Asp Val Val Asp Pro Ile Leu
305                 310                 315                 320
```

```
Thr Lys His Leu Arg Glu His Gln Arg Glu Gly Val Lys Phe Leu Tyr
            325                 330                 335
Glu Cys Val Met Gly Leu Arg Asp Tyr Asn Gly Glu Gly Ala Ile Leu
            340                 345                 350
Ala Asp Glu Met Gly Leu Gly Lys Thr Leu Gln Thr Ile Thr Leu Leu
            355                 360                 365
Trp Thr Leu Leu Lys Gln Asn Pro Ile Tyr Glu Glu Pro Pro Val Val
370                 375                 380
Lys Lys Ala Leu Ile Val Cys Pro Val Thr Leu Ile Asn Asn Trp Arg
385                 390                 395                 400
Lys Glu Phe Arg Lys Trp Leu Gly Asn Glu Arg Ile Gly Val Phe Val
            405                 410                 415
Phe Asp Asp Lys Arg Lys Arg Leu Thr Asp Phe Thr Met Gly Lys Ala
            420                 425                 430
Tyr Asn Val Met Ile Val Gly Tyr Glu Lys Leu Arg Thr Val Gln Glu
            435                 440                 445
Gly Leu Ile Lys Gly Ala Gly Val Asp Ile Val Ile Ala Asp Glu Gly
            450                 455                 460
His Arg Leu Lys Thr Leu Gln Asn Lys Ser Gly Gln Ala Ile Gln Ala
465                 470                 475                 480
Leu Asn Thr Thr Lys Arg Ile Ile Leu Ser Gly Thr Pro Ile Gln Asn
            485                 490                 495
Asp Leu Ser Glu Phe Phe Ala Ala Val Asp Leu Val Asn Pro Gly Ile
            500                 505                 510
Leu Gly Thr Tyr Lys Asn Phe Met Lys Glu Phe Glu Gly Pro Ile Met
            515                 520                 525
Arg Ser Arg Gln Pro Glu Ala Thr Lys Arg Glu Ile Glu Lys Gly Glu
            530                 535                 540
Ala Arg Ser Glu Glu Leu Arg Asn Leu Thr Ser Met Phe Met Leu Arg
545                 550                 555                 560
Arg Thr Ala Asp Ile Leu Ser Lys Tyr Leu Pro Pro Lys Thr Glu Tyr
            565                 570                 575
Val Leu Leu Cys Glu Pro Thr Ala Ile Gln Ala Ser Ile Tyr Arg His
            580                 585                 590
Val Leu Ala Ser Pro Ile Phe Gln Ser Ala Leu Gly Asn Thr Glu Gly
            595                 600                 605
Ala Phe His Leu Ile Thr Ile Leu Lys Lys Leu Cys Asn Ser Pro Ser
            610                 615                 620
Leu Leu Thr Ala Lys Thr Glu Asp Glu Thr Pro Asn Ala Thr Val Ser
625                 630                 635                 640
Ala Leu Leu Ser Thr Leu Pro Pro Asn Leu Leu Arg His Phe Ser Pro
            645                 650                 655
Ser Ser Ser Gly Lys Leu Arg Val Leu Asp Gln Leu Leu His Asn Leu
            660                 665                 670
Arg Thr Thr Thr Ser Glu Lys Ile Val Leu Val Ser Asn Tyr Thr Ser
            675                 680                 685
Thr Leu Asn Leu Leu Ala Thr Leu Leu Thr Ser Leu Ser Leu Pro Phe
            690                 695                 700
Leu Arg Leu Asp Gly Thr Thr Pro Ser Ser Lys Arg Gln Ser Leu Val
705                 710                 715                 720
Asp Asp Phe Asn Arg Ser Pro Ala Ser Thr Cys Phe Ala Phe Leu Leu
            725                 730                 735
```

Ser Ala Lys Ala Gly Gly Thr Gly Leu Asn Leu Ile Gly Ala Ser Arg
            740                 745                 750

Leu Val Leu Phe Asp Val Asp Trp Asn Pro Ala Thr Asp Met Gln Ala
            755                 760                 765

Met Ala Arg Ile His Arg Asp Gly Gln Thr Arg His Cys Trp Ile Tyr
    770                 775                 780

Arg Ile Met Leu Lys Gly Gly Leu Glu Glu Lys Ile Trp Gln Arg Gln
785                 790                 795                 800

Val Thr Lys Ile Gly Leu Ala Asp Ser Val Met Glu Gln Lys Gly Gly
                805                 810                 815

Met Ala Gln Phe Ser Arg Glu Glu Leu Lys Asp Leu Phe Arg Leu Tyr
            820                 825                 830

Glu Gly Glu Gly Cys Gln Thr His Asp Leu Leu Cys Cys Asn Cys Gly
            835                 840                 845

Gly Arg Gly Thr Pro Ser Thr Asp Gly Gly Asp Arg Pro Val Ser Thr
    850                 855                 860

Asp Ser Asp Asp Lys Ser Ser Ser Cys Ser Ser Ala Glu Asp Glu
865                 870                 875                 880

Glu Glu Thr Asp Asp Glu Asp Glu Glu Asp Ile Asp Leu Pro Asp
                885                 890                 895

Leu Pro Thr Leu Ile Lys Val Ser Gln Leu Asp Ile Asp Ala Gln Glu
            900                 905                 910

Ala Gln Ile Arg Arg Gly Ser His Pro Leu Gln Arg Gln Ser Asn
            915                 920                 925

Lys Thr Lys Asp Lys Asn Lys Lys Asp Thr Lys Asn Pro Arg Gly
930                 935                 940

Arg Lys Lys Lys Asn Ser Asp Gln Ala Arg Met Gln Gln Phe Leu Ser
945                 950                 955                 960

Glu Tyr Ser His Ile Asp Pro Ser Ala Phe Gly Ala Asp His Gly
                965                 970                 975

Glu Glu Gly Thr Asp Leu Ala Ser Gln Ile Arg Asp Pro Val Leu Leu
            980                 985                 990

Ser Leu Leu Arg Glu Glu Asp His Gly Val Gly Phe Ile Phe Glu Lys
            995                 1000                1005

Thr Ala Phe Pro Ala Ala Asp Ala Asp Ala Pro Ala Glu Lys Lys
    1010                1015                1020

<210> SEQ ID NO 40
<211> LENGTH: 4591
<212> TYPE: DNA
<213> ORGANISM: Rasamsonia emersonii

<400> SEQUENCE: 40
accctagctc tgatgaacgt ctctgatgtg tttcggcatc aagcgcaatt gcccgaatcc      60
taatgtgcaa ggagccggcc gtggtggagt cgctgctcgt ggaggtttca acggacctta     120
tcgcggtggc tatggcggat accccagagc tgcgacttgc tacaagtgcg gtggtcccaa     180
ccacttcgct cgggactgcc aagctcaggc catgaaatgc tatgcctgtg caagctggt     240 gagtcaggtt tcttgatgaa atcacatgga tataccatct aatgcgctcc cagggccata     300
tctcgcgcga ttgcactgct cccaacggtg ggcccctgag ctctgcaggc aaggtctgct     360
ataagtgctc gcaggctggc cacatctccc gagactgccc caacaacgaa tccaacaaca     420
cacagtcggc tgctgagact actacctccg cccctctgc cccggccgcc actgcctctg      480
ccagtgcccc tgtcgttgag agcactgctg aggttgctgc ccctgttgct caggctgctc     540

```
cggctgccgc agtcgcttag agtgggtttt tgaaacgaaa cccatcctac taccattctt    600 cttttttgtat taggttcgcc gactcggtct atctttcaat cctttttttt ttcctctcga    660
cctttcttct gttacatata ttatgccctt gtttcaggtt ttcggcaacg gcacttgtta    720
tgtatacgac gaacaaaaag tttcacgaag tcccaggatt cttccatgac ttggatcctc    780
tgcatggctc aagcctcatg attggcgtct tattttttcta tcgaatgtgt ctcaggaatt    840
tgaggaaaga aaaagggtg caaccggagg agacgaggca agactgaggg ttaattgagc    900
agtggagagt tgtcggtgga tcgaaacaag cgagttgctg tgtggacctg acttcaaggt    960
gtatggatga agtggttgat gtccaagaag tatatcacaa aaatatcaaa aaatgcgag    1020 gcatgaggta cctacctcta tcagtctaca aaatctctat catatatact cgttagactg    1080
agtattaaaa caaatattga caaaaaaaag cacttattgc atcatctatg gtcttgcaag    1140
gcagcgtttc aactttgcgc gttcgagata actggtgttg agaataccctc acgttccatc    1200 aaggatctat ctcaggcact gcattttatg ctcagctgta aaagcttcta ttttgtcata    1260
tcgtatccag ttcattcccg ccgatcaaac agattgcttc gtagagattc agcttgctgg    1320
tcagccaccc tttccagaca gacccgtga catccatttc cccaacactt cccctcgat    1380 cttctgatgg tccgccttc gtctcgctca ctgtccctac gagctgaaac aagcaacgtg    1440
gccatctctc tctctctgtt taatctctct gcattgcgtc cctgactacg aagttccaag    1500
atgcctggct ccactgcaag cgatgaattc gacgatgatg tacgatgtct ctcccttgga    1560
ccataggctt cagaatcagg atctaacaag ccatcgtccg ttattcttga tagggtttta    1620
ttgtggacat tgacactatt caagctcatg gtatgatctt tcaaaccccgt aaatgacatc    1680 tcctttgtct cttctttctt tccatgtctg ttatgactac cggacattac tgagggagac    1740
ataggcattg gcgtagcgga tatcacgaaa ctcaaggcca atggattcta tacagttgcc    1800
gtatctactt ctcacctgca gtctgttgtc cttctttgcc ttttgtgctg atctatggcc    1860
ccgactccac agtctgtcca cggagccacc cgcagaacgc tgttgaagat caaaggattc    1920
agcgaagtca aggtcgagaa gatcaaggaa gctattcaga aatgtttggt atggagatgg    1980
agatatccag cctattctcc ctcacagaag cgggtcttgg tcactgacat acatcgtaca    2040
gccatctgca agtggtttca ttaccgcaat ggaactgaac catcagcgta aaagggtgtt    2100
caagatttcc actggcagca agcaatttga cgctattcta gggggtcag ttggctctat    2160 cctcgtctga tttacgcttc taatcagttg ccatccagtg gcttccaaag catgagtatc    2220
agcgaggtgt acggcgagtt tcgctgtggc aaaacccagc tgtcccatac catgtccgtc    2280
atcgcgcagc ttcccaaaga aatgggggc ggagagggca agtcgcata cattgacaca    2340 gaaggaacat tcagaccgga acgtatcgcc cagatagcgg aacgttttgg tgttgaccct    2400
gagtctgctc aagagaacat tgcttacgct cgcgcactca acagcgaaca tcagctagaa    2460
ttgctcaaca cgctttcgaa ggaattcgct ggtggtgatt acaggctcct tatcatcgac    2520
agcatcatga attgcttccg cgtggattat tgcggccgtg gagaactcgc cgaacgccag    2580
cagaagttga accaatttct gataaaactg gcgcatatgg ccgaaggtag ttttccaat    2640 cttttttta tctctgcaaa tcgcagataa gctagcataa actgacagtc catcttccag    2700
aattcaacgt ctgtgtgctg atggtatggc ccctggacac ccgttatctg agttatctat    2760
catctatctt accttttttcc ccaaaagacc aatcaagtgc aaagcgatcc tggagccagc    2820
gctctctttg caggcgccga tggtcgtaag cccgtgggcg gtcatgtcct cgctcatgcc    2880
```

```
tcgacgactc gggtccttct tcgcaagggt agaggtgaag agcgcgttgc taagattcag    2940
gactctccag gtctgccttc tgcttttttct tgagtaatgg gaatttgtaa ggatattcct   3000
cactgacgca tttcgcttca cagactgccc cgagcgcgag gcaacgtacg tcatcactaa    3060
cggtggcatt aatgatcccg ataaggtcta ggtaggagag tccgtaggac attaagaaaa    3120
aaatacctgg gggagaagaa ccgatgtgag agacattttc tattgaacga atcttcgacg    3180
ggatttcagt tttcatgatc actaaaacat gcagaaggga tcgtctagtg aagttgatgt    3240
gtctgtatat tttagacgct gagaattacg gaatgcagtt agtttgaccg gttgaggagt    3300
agctccctag ataaactatc ccgagaccag caggtcgcca gatacccttt ccgttctagg    3360
gttggaggca cgccgccttt gaatacccc ctcgcgctgt agtagggtga ggcaggctgc      3420
ggccaggtga ggcagtgctg agggccaaga tcgagaacat tatatgagtg aatggcatga    3480
tcacccatgt ccaattaaac acggctaaag ttgccgcacg ttatggaact taatctgaca    3540
ggtttattat tggcctgttc tatagtgtac gactactaaa tcgtattaag agtcatactt    3600
gtcaatcgtt aataaaacca gcatgaacta ttattatatc agaaagcaag caatgtcact    3660
actatatata taactactgc cgcagatatc gatcagcata gacaggaagg ccatagatta    3720
ataatctact cattaactca tataggaaat ggtctgttag tccttgcttc gaaccgaata    3780
ttaactagac ttgctgctct cctcctaatg ccttttccat cctataggta accagtttcg    3840
atattaaatc tattttttaa atctaaattt ttcaacttta tttgaaattc caggataggc    3900
tttttttatat atctctataa ctggccagta tagtctatat tatggcattt gatttatcct   3960
ttctaggggc tgctatatct attcttcccc ctgctagata ctaaagagtt ggcaggggct    4020
tctcaggaag ttctacataa tataagctgg cagtaatttt aagattttta atgtcttacc    4080
agtcttctgt gataccataa agcttctaaa agttatatta ctatctatgc tgctataacg    4140
cgaactgcta atagtaggca taagtgccaa aacttattat atctaaaaca ccattagaaa    4200
gaaatgttat atacttcctc acaatattag cattatagag cagagtatgg aagcatacca    4260
taataaagct aatatctacc ttatttgggg aaaatacctg cttattgcca catgtttggc    4320
tattagtccc tataaggaat atattaatct tgagtactat ctaactagca atcttaagta    4380
atatatcaat caatagtaac cacataagta ttatagaggc agacctgaag cattaggcct    4440
attaaacatt taaagtatt acatatatct atttaaaggg tgttaggtat tctaatatca     4500
ggcttaatta ggagctggta gctataagct taaatgccta gctcagcaac tttaacacat    4560
ccagatttaa ctgttatgag ccaacaggaa t                                   4591
```

<210> SEQ ID NO 41
<211> LENGTH: 840
<212> TYPE: DNA
<213> ORGANISM: Rasamsonia emersonii

<400> SEQUENCE: 41

```
atgcctggct ccactgcaag cgatgaattc gacgatgatt ctgtccacgg agccacccgc     60
agaacgctgt tgaagatcaa aggattcagc gaagtcaagg tcgagaagat caaggaagct    120
attcagaaat gtttgttgcc atccagtggc ttccaaagca tgagtatcag cgaggtgtac    180
ggcgagtttc gctgtggcaa aacccagctg tcccatacca tgtccgtcat cgcgcagctt    240
cccaaagaaa tggggggcgg agagggcaaa gtcgcataca ttgacacaga aggaacattc    300
agaccggaac gtatcgccca gatagcggaa cgttttggtg ttgaccctga gtctgctcaa    360
gagaacattg cttacgctcg cgcactcaac agcgaacatc agctagaatt gctcaacacg    420
```

```
ctttcgaagg aattcgctgg tggtgattac aggctcctta tcatcgacag catcatgaat      480
tgcttccgcg tggattattg cggccgtgga gaactcgccg aacgccagca gaagttgaac      540
caatttctga taaaactggc gcatatggcc gaagtccatc ttccagaatt caacgtctgt      600
gtgctgatga ccaatcaagt gcaaagcgat cctggagcca gcgctctctt tgcaggcgcc      660
gatggtcgta agcccgtggg cggtcatgtc ctcgctcatg cctcgacgac tcgggtcctt      720
cttcgcaagg gtagaggtga agagcgcgtt gctaagattc aggactctcc agactgcccc      780
gagcgcgagg caacgtacgt catcactaac ggtggcatta atgatcccga taaggtctag      840
```

<210> SEQ ID NO 42
<211> LENGTH: 279
<212> TYPE: PRT
<213> ORGANISM: Rasamsonia emersonii
<400> SEQUENCE: 42

Met Pro Gly Ser Thr Ala Ser Asp Glu Phe Asp Asp Ser Val His
 1               5                  10                  15

Gly Ala Thr Arg Arg Thr Leu Leu Lys Ile Lys Gly Phe Ser Glu Val
                20                  25                  30

Lys Val Glu Lys Ile Lys Glu Ala Ile Gln Lys Cys Leu Leu Pro Ser
            35                  40                  45

Ser Gly Phe Gln Ser Met Ser Ile Ser Glu Val Tyr Gly Glu Phe Arg
        50                  55                  60

Cys Gly Lys Thr Gln Leu Ser His Thr Met Ser Val Ile Ala Gln Leu
65                  70                  75                  80

Pro Lys Glu Met Gly Gly Glu Gly Lys Val Ala Tyr Ile Asp Thr
                85                  90                  95

Glu Gly Thr Phe Arg Pro Glu Arg Ile Ala Gln Ile Ala Glu Arg Phe
            100                 105                 110

Gly Val Asp Pro Glu Ser Ala Gln Glu Asn Ile Ala Tyr Ala Arg Ala
        115                 120                 125

Leu Asn Ser Glu His Gln Leu Glu Leu Leu Asn Thr Leu Ser Lys Glu
    130                 135                 140

Phe Ala Gly Gly Asp Tyr Arg Leu Leu Ile Ile Asp Ser Ile Met Asn
145                 150                 155                 160

Cys Phe Arg Val Asp Tyr Cys Gly Arg Gly Glu Leu Ala Glu Arg Gln
                165                 170                 175

Gln Lys Leu Asn Gln Phe Leu Ile Lys Leu Ala His Met Ala Glu Val
            180                 185                 190

His Leu Pro Glu Phe Asn Val Cys Val Leu Met Thr Asn Gln Val Gln
        195                 200                 205

Ser Asp Pro Gly Ala Ser Ala Leu Phe Ala Gly Ala Asp Gly Arg Lys
    210                 215                 220

Pro Val Gly Gly His Val Leu Ala His Ala Ser Thr Thr Arg Val Leu
225                 230                 235                 240

Leu Arg Lys Gly Arg Gly Glu Glu Arg Val Ala Lys Ile Gln Asp Ser
                245                 250                 255

Pro Asp Cys Pro Glu Arg Glu Ala Thr Tyr Val Ile Thr Asn Gly Gly
            260                 265                 270

Ile Asn Asp Pro Asp Lys Val
        275

<210> SEQ ID NO 43

<211> LENGTH: 4626
<212> TYPE: DNA
<213> ORGANISM: Rasamsonia emersonii

<400> SEQUENCE: 43

```
atctttttcct ttttttttct actctcgtcc ccttgcagat gacatctctc atgcatgtgc      60
atgcacggta cttccctaat ctgataaaac tccgaaaggc aaaaaaaaaa gactcaagct     120
cggagacaat agtctaagtc taacgaaatg atccaccaga tgataagcac ctccaaggga     180
tggtgtggtg tggtgtggag aggacggagt aatagtaata gtcgtcctca tgacccgaac     240
gccctcgtgc tgcctgtcac cacttccagt ctgtcgggtg gatgacttc ataggaataa      300
ttactgatca tatgcaaatg aagtatggag tattctgggt gggacaaatc ggcatttgtg     360
aatgacttat ctagtgcctt tttttttttgg ttcttcggca attttggaaa tgtattctat    420
cgagtcagtt cagcgattgc tctgctgtct ttccgtccag agtgtgattt cgttttgagt     480
ttgatatcat tcgtccatat ccattgcttt actgttcagg tgaggaaact cccgtccgta     540
gaaggttgac tcgtttggga tattattatt ccttgcgttt ttgagcttca aaactagtag     600
aataataaac gaaagagaaa aaaaaagtg cagcttcgcg aaataggaaa cgtactgtgc      660
gattttctgg agaatgcttt tctcgtcaga cgaaatgctt aacagttatg ctatagaatt     720
ttcaaaatac tggttagtgc atcgggctct tgtgtcgagg atatgggatt gttattggta     780
gttattcttc ctttgacaat aactgggcag tgtaatggta tatttggtgg ttaatcatca     840
tatatctatt ctaatagctc tgagcctgtg tttagatcct aagagtcact ggtgcagctt     900
tttttatatc aaccacgcat aggtgtgata gtgtcattct gttttatata ttaactctac     960
tgtattaagg ggcatcggaa cgaaaaaaaa atcaaattat tatgatagta ttctaagttt    1020
gtccggagtt cttcatgtct ctttgctgtc gatacagtca gataccccttc agtttctaca    1080
ggtttcagta aatcaaaata aatatagctt attatgatga gttgacgctg caaagcatac    1140
cttattgcga gtctgtgtgt ggcttctga tattagtgac taatggtctg gatctatgta     1200
atgggttcag tgtaaccgta aactggaaat atatatattt caacaaatac atgctcaacg    1260
tattgcaatc tctgatcatc ttagttctag taaatcacaa cagaaattct ttcgatgctt    1320
ctcaattatg aattaataaa ttcattgaaa cctacatgaa aaaagtaggt tgaacatgga    1380
tgttgaaact agataattgt ttccagtgtt ctggtaccgc ggaaaggaag cggaagcaac    1440
tctgactgcg aacgtacgcg tgcacagtag aaagaacatc actcaacgcc tctcacttgc    1500
atggatctcc tatcaatcct gcccagattg tcgacaaaac aatacaccca tatcctcccg    1560
tccctcgaga ggaagcacat cagcactgtc gacttgatca ccctcgacac gcttgagatc    1620
gcgaaacgcg cgcacgttcc ccccgccgat gtccgtcgcc tgtgcgccga tgtcctcgag    1680
gcattacacc gcgacctggg attcgagcgc gaacagccca agaccaaggt gcaggatgag    1740
gaagaaacaa gcccaagcac cctggatgag ccccgtctca tccctgggcc gtcaaccaag    1800
ctagatcttt cgcattggag cacgatcagc actcttgacc ccgcgctgga cgcgctcttg    1860
gatggtggaa taccaacggg atatctcacg gaagtgactg gagagaggtt cgttgcactt    1920
cgttttctgac actttctta cacgagcagg tctgaccgcg gttgcagcgg gagtggtaag    1980
acgcaattcc tgctcaatct tctcctcaca gcccagcttc cccgacctcg aggcctcggc    2040
aagagagcga tctacatatc gacggaggca ccgttgtcaa cgacgaggct gtcccagctg    2100
ttggagaccc atccgtatct atctactcta cctcccgata ctgcgccgtc tctcgccaat    2160
atcctttcta tcaacgctat cgacttggaa acccaggacc acatcctcaa ttaccagctc    2220
```

```
ccggttgcca tatcgcgtta cgatgtcggc cttgtggtta ttgattcgat cgctgcgaat    2280
taccgtgccg aacacgaatc gcacaatgtg tccgggatat ccacgcgctc gggagaactg    2340
gcaagactgg gtcagatgtt gcgaaatctc gctgtcaagg aagacattgc tgtcgtagtc    2400
gcaaaccagg tctctgaccg gttcgattcc ttcgacgacc aaccgcgatt gaggtccagc    2460
caaaccttga cgcctgcgat gcgagagcgt gagtctggtg ccagatcccc cctgccgaga    2520
aatcgagtcg aaggttggaa cgcggagaca acccctccct catcaccagg cccgtcttcg    2580
ccgtacgtcg aggatgaatc tttcgatggc gcgtacatcg ttggccatcc ggtgagaaac    2640
gagactctca gtctagccca tcaacagcgc ttttcaccg gttggggtga cgcaccggag     2700
ctcgagtttt cagagtctca aaagacgccg gctttgggct tgtctggtc aaaccagata     2760 gcttgtcgca tatcactgaa gaaggaggac gaaattcaac ctctaccggt tcctgtcgac    2820
acggttcctg cggcgacccc ctcttcacag acacggccac cggaagcaac tccagtccca    2880
gacgattcga agacagcttc tcaagagaca gattccaccg acgtaaagcc aacagcaagc    2940
caaggggacg agagggtct gtccgcgaga gtacccacgt caacaccatc cctagttgca     3000
gacaagatta ccaagagacg gctcaaactg gtatttgcgc cgtggacagc cggaagggcg    3060
gacaatgcca gcgatgaggt agaattcgag atatggaagg cggaattag aagtataaag     3120 caataaaatg aacttgttat cttgaacgga gtgtttcaca acagaggcac acttctatgc    3180
tgctagtccg cagcatgttc ttgcggatat gctttctata atatgatgta ctagacccctt   3240 gaatatgagc aggcattcga agtatagga atgcgacaac tatgcccctg catttcctca     3300
ggaatcaagc agtgcttgct acagctacag gatccatcgt gcataggcga cgtaagctca    3360
gtccaagctc ctgagcgctg tagctctcat taccgaacaa tatcgaactg cctcttatta    3420
tcattacaaa tccagtgtca gatcaatgtc atactccagc ttcatttcag ctcaatctca    3480
gattgttatt ttattagaga gattctaagg ccagagcttg cctggcgcg gtgtgcggaa     3540 gcttaggaag caccttcccc gcactttaga cagtaaatag taaacacacc ctcttgatga    3600
tttcattctg ttgtcttcga ttatccttca tttctgtcac cattaatctt gcctttcctc    3660
cttccatact ctgactactc tcatgcaagc tactacactg actcctgttt actcttgtcg    3720
acattctcat ccactttact acccaaacag gtctagattc ttctcgtcta tgatctctat    3780
tctcattgca ctcatccttt catccatact atggatggct cctccactct cgatgcatct    3840
gtcgcaacat aacatccacg gtggatggaa gtgaagccga aagggaacaa caagctcgaa    3900
tacatatgcg atcatggctg gcacaaacat ccaagaaaca aaaaaatcta tctggcagaa    3960
cactaacaga ttaacaaagt gtaatatagc aatgagaaga gatcactcct gatgccttga    4020
acgcagagtc cacgatatct acagtgaagc gctcaatcgt ggccgctcga tccggcgaga    4080
gtaccacaaa aagcactcaa gtgtcatcga ctcgcagttg atcgctcgct tcaagaagaa    4140
ggcgggggga tcttggccgg gggaacacca agtccgttcc tgttgcggta aacaggaca    4200 cctttgcttt caccctcggc accctccgtg ggctcaaccc actggcatac acggcagctg    4260
gtccagagcg ccttgaagaa acccagaggg ccggtgtgcg cttcgctgcg gtagtgcttg    4320
cccatcacct tcttgatggc ctcgctcgcc tcatcagcat ggtagaatgg gatggtgctc    4380
acataatggt gcagaacatg ggtttcgatg atgccgtgga aaggtgacg gccaacccag     4440 ccaaagtcgc ggtcgatggt ggcagctgca ccacgagtga agttccagac ctcgggttca    4500
tagtgaggga gagtcgggtc ggtgtgctgc aggtaggtga tggcgactgc aaacctatca    4560
```

-continued

```
gaagaaaccc ttaaaaaaat ctgctgatgg agtaagactt accaagccag tggttcaccc    4620
agagat                                                               4626
```

<210> SEQ ID NO 44
<211> LENGTH: 1584
<212> TYPE: DNA
<213> ORGANISM: Rasamsonia emersonii

<400> SEQUENCE: 44

```
atggatctcc tatcaatcct gcccagattg tcgacaaaac aatacaccca tatcctcccg      60
tccctcgaga ggaagcacat cagcactgtc gacttgatca ccctcgacac gcttgagatc    120
gcgaaacgcg cgcacgttcc ccccgccgat gtccgtcgcc tgtgcgccga tgtcctcgag    180
gcattacacc gcgacctggg attcgagcgc aacagccca agaccaaggt gcaggatgag    240
gaagaaacaa gcccaagcac cctggatgag ccccgtctca tccctgggcc gtcaaccaag    300
ctagatcttt cgcattggag cacgatcagc actcttgacc ccgcgctgga cgcgctcttg    360
gatggtggaa taccaacggg atatctcacg gaagtgactg agagaggtc tgaccgcggt    420 tgcagcggga gtggtaagac gcaattcctg ctcaatcttc tcctcacagc ccagcttccc    480
cgacctcgag gcctcggcaa gagagcgatc tacatatcga cggaggcacc gttgtcaacg    540
acgaggctgt cccagctgtt ggagacccat ccgtatctat ctactctacc tcccgatact    600
gcgccgtctc tcgccaatat cctttctatc aacgctatcg acttggaaac ccaggaccac    660
atcctcaatt accagctccc ggttgccata tcgcgttacg atgtcggcct tgtggttatt    720
gattcgatcg ctgcgaatta ccgtgccgaa cacgaatcgc acaatgtgtc cgggatatcc    780
acgcgctcgg agaactggc aagactgggt cagatgttgc gaaatctcgc tgtcaaggaa    840
gacattgctg tcgtagtcgc aaaccaggtc tctgaccggt tcgattcctt cgacgaccaa    900
ccgcgattga ggtccagcca aaccttgacg cctgcgatgc gagagcgtga gtctggtgcc    960
agatcccccc tgccgagaaa tcgagtcgaa ggttggaacg cggagacaac cccttcctca   1020
tcaccaggcc cgtcttcgcc gtacgtcgag gatgaatctt tcgatggcgc gtacatcgtt   1080
ggccatccgg tgagaaacga gactctcagt ctagcccatc aacagcgctt tttcaccggt   1140
tggggtgacg caccggagct cgagttttca gagtctcaaa agacgccggc tttgggcttt   1200
gtctggtcaa accagatagc ttgtcgcata tcactgaaga aggaggacga aattcaacct   1260
ctaccggttc ctgtcgacac ggttcctgcg gcgaccccct cttcacagac acggccaccg   1320
gaagcaactc cagtcccaga cgattcgaag acagcttctc aagagacaga ttccaccgac   1380
gtaaagccaa cagcaagcca aggggacgag aggggtctgt ccgcgagagt acccacgtca   1440
acaccatccc tagttgcaga caagattacc aagagacggc tcaaactggt atttgcgccg   1500
tggacagccg aagggcgga caatgccagc gatgaggtag aattcgagat atggaagggc   1560
ggaattagaa gtataaagca ataa                                         1584
```

<210> SEQ ID NO 45
<211> LENGTH: 527
<212> TYPE: PRT
<213> ORGANISM: Rasamsonia emersonii

<400> SEQUENCE: 45

```
Met Asp Leu Leu Ser Ile Leu Pro Arg Leu Ser Thr Lys Gln Tyr Thr
1               5                   10                  15

His Ile Leu Pro Ser Leu Glu Arg Lys His Ile Ser Thr Val Asp Leu
            20                  25                  30
```

```
Ile Thr Leu Asp Thr Leu Glu Ile Ala Lys Arg Ala His Val Pro Pro
         35                  40                  45

Ala Asp Val Arg Arg Leu Cys Ala Asp Val Leu Glu Ala Leu His Arg
 50                  55                  60

Asp Leu Gly Phe Glu Arg Glu Gln Pro Lys Thr Lys Val Gln Asp Glu
 65                  70                  75                  80

Glu Glu Thr Ser Pro Ser Thr Leu Asp Glu Pro Arg Leu Ile Pro Gly
                 85                  90                  95

Pro Ser Thr Lys Leu Asp Leu Ser His Trp Ser Thr Ile Ser Thr Leu
                100                 105                 110

Asp Pro Ala Leu Asp Ala Leu Leu Asp Gly Ile Pro Thr Gly Tyr
                115                 120                 125

Leu Thr Glu Val Thr Gly Glu Arg Ser Asp Arg Gly Cys Ser Gly Ser
        130                 135                 140

Gly Lys Thr Gln Phe Leu Leu Asn Leu Leu Leu Thr Ala Gln Leu Pro
145                 150                 155                 160

Arg Pro Arg Gly Leu Gly Lys Arg Ala Ile Tyr Ile Ser Thr Glu Ala
                        165                 170                 175

Pro Leu Ser Thr Thr Arg Leu Ser Gln Leu Leu Glu Thr His Pro Tyr
                180                 185                 190

Leu Ser Thr Leu Pro Pro Asp Thr Ala Pro Ser Leu Ala Asn Ile Leu
        195                 200                 205

Ser Ile Asn Ala Ile Asp Leu Glu Thr Gln Asp His Ile Leu Asn Tyr
        210                 215                 220

Gln Leu Pro Val Ala Ile Ser Arg Tyr Asp Val Gly Leu Val Val Ile
225                 230                 235                 240

Asp Ser Ile Ala Ala Asn Tyr Arg Ala Glu His Glu Ser His Asn Val
                245                 250                 255

Ser Gly Ile Ser Thr Arg Ser Gly Glu Leu Ala Arg Leu Gly Gln Met
            260                 265                 270

Leu Arg Asn Leu Ala Val Lys Glu Asp Ile Ala Val Val Ala Asn
        275                 280                 285

Gln Val Ser Asp Arg Phe Asp Ser Phe Asp Asp Gln Pro Arg Leu Arg
290                 295                 300

Ser Ser Gln Thr Leu Thr Pro Ala Met Arg Glu Arg Glu Ser Gly Ala
305                 310                 315                 320

Arg Ser Pro Leu Pro Arg Asn Arg Val Glu Gly Trp Asn Ala Glu Thr
                    325                 330                 335

Thr Pro Ser Ser Ser Pro Gly Pro Ser Ser Pro Tyr Val Glu Asp Glu
                340                 345                 350

Ser Phe Asp Gly Ala Tyr Ile Val Gly His Pro Val Arg Asn Glu Thr
            355                 360                 365

Leu Ser Leu Ala His Gln Gln Arg Phe Phe Thr Gly Trp Gly Asp Ala
370                 375                 380

Pro Glu Leu Glu Phe Ser Glu Ser Gln Lys Thr Pro Ala Leu Gly Phe
385                 390                 395                 400

Val Trp Ser Asn Gln Ile Ala Cys Arg Ile Ser Leu Lys Lys Glu Asp
                405                 410                 415

Glu Ile Gln Pro Leu Pro Val Pro Val Asp Thr Val Pro Ala Ala Thr
            420                 425                 430

Pro Ser Ser Gln Thr Arg Pro Pro Glu Ala Thr Pro Val Pro Asp Asp
        435                 440                 445
```

```
Ser Lys Thr Ala Ser Gln Glu Thr Asp Ser Thr Asp Val Lys Pro Thr
    450                 455                 460
Ala Ser Gln Gly Asp Glu Arg Gly Leu Ser Ala Arg Val Pro Thr Ser
465                 470                 475                 480
Thr Pro Ser Leu Val Ala Asp Lys Ile Thr Lys Arg Arg Leu Lys Leu
                485                 490                 495
Val Phe Ala Pro Trp Thr Ala Gly Arg Ala Asp Asn Ala Ser Asp Glu
            500                 505                 510
Val Glu Phe Glu Ile Trp Lys Gly Gly Ile Arg Ser Ile Lys Gln
        515                 520                 525
```

<210> SEQ ID NO 46
<211> LENGTH: 8136
<212> TYPE: DNA
<213> ORGANISM: Rasamsonia emersonii

<400> SEQUENCE: 46

| | | | | | |
|---|---|---|---|---|---|
| ccccattgga | agttagacca | ccagcttccc | cacaccgacg | tgtggttatt | gatgagcacg | 60 |
| tcctctgcat | acttcgactt | ggccgctctc | tttggcgctc | ccttaatggc | tcctgtttcg | 120 |
| tcgtattcga | catatcgctc | attctcgata | cagcagcgt  | catgtgacgg | agccgccttc | 180 |
| aaatgttctt | cgccaccata | tttctcaagg | agctgtttcc | gttgagcctc | acgtttggct | 240 |
| tcatttccg  | ccttctcctt | ctttctcaag | atttcgccag | aagttggatt | ggcttgcaga | 300 |
| tgataagatt | tgtctccccg | ttcctgcgcc | tcccatgcga | ggcgttgcgc | ttttcgaat  | 360 |
| tctgcagcat | caccagatgc | ccgtacgaag | ttctcctcgg | ctacaagtgc | tgctgcttga | 420 |
| tctgcttgcg | cgcccatatc | aaccattttt | cttgtcttcg | gatcatactt | ggctgaatca | 480 |
| aggtcaaggt | taaggagata | tttcgccgta | tcttcgcgaa | ttcgcagatt | ccgggtggct | 540 |
| gtactctgct | ttcttcccat | gtccgattcc | tcggcgtatc | gggcctcttc | ctgttcatcg | 600 |
| tcactctcgt | cctcgccatc | ctgagatttg | ttctttttct | cagcttcctg | cttcgccttg | 660 |
| cgcttcaagt | tctccagctc | ttcgtattcc | tcaacgacct | tccgatattc | tgcggggtca | 720 |
| tatccgttcc | aacggtcccg | cttcgcatcc | caaccaagct | cgaccttctg | aatcacttcg | 780 |
| tctggttgta | tatccttccc | tgtccatcga | gctccgagtt | tccgcggccg | actcaagcat | 840 |
| tccttcgttt | tgtgtgtcat | tgcgccgcag | ttctcgcaag | cgccctttcg | gtatttcgta | 900 |
| gcagccggac | ctagccgttt | gcctctttca | taccatttcg | actgatccga | tgtcgacttc | 960 |
| tgtagacgct | gatgctctag | gtagtcattt | gctgaggagt | catcgtcgac | gtagaagggc | 1020 |
| ttcttcgaaa | tgaacgaagg | aatgtattcg | ttgcgctcct | tcgacgccac | atcggtaggc | 1080 |
| cttcgcgaca | tcgtggcaat | atttgaggag | ccgatctcaa | aactctcaga | gatagctcac | 1140 |
| ttgacactca | caactaggag | tgtctctagt | ccaggcgaat | agaaaagatg | cggtttggag | 1200 |
| agcagaggtc | gatggagagg | cggtggtttg | gaatcgccga | cgtccgagat | aggtagtttt | 1260 |
| atatcacgtg | accaggagtc | tgtcgtgtgg | cgcggcaact | cggcggggcg | cgcctaacta | 1320 |
| atgcacgtca | tgttcgcctt | gttgatagcg | gtatgcgacg | cgaatatcga | gtagattaaa | 1380 |
| ggcaaaacga | tgccagaaac | gcttttttcta | cacagtctca | agtcgttata | taacatttgc | 1440 |
| gtgcattagc | cgttacgcaa | tgttttttcag | atttttatct | ttaccatcct | gagagccggg | 1500 |
| atggatatct | ttcgagttcg | tttgaattgt | atcgatcatt | atcaggcaac | tccaacggaa | 1560 |
| ttcgacccct | ccgtgccata | tggcgtcggt | atatcgcaaa | gaaatgaaag | gccaaaggta | 1620 |
| cctgtcattc | gcgcctttgg | ggcgactgaa | acaggccaga | aggtctgtgc | ccatatccat | 1680 |

```
ggtgccttc  cttacctcta  tattgagtac  aagggaagcc  tagaaccaga  tgaaggtcgg    1740
tacgatttct  ctagtatgca  aatcagtttt  gcttaaagct  atattgtttt  agtgaacacc    1800
gccattcgta  atctacatct  ctcaatcgac  catgctttgg  ctgttagcta  ccgtcggaac    1860
gcatacgagg  ggaagacggc  ttacgtcgcc  cacatatccc  tggtcaaagg  gatacccttc    1920
tatggttatc  atgtgggata  tcagttttat  ttcaaaatat  acctgttgaa  cccactgaat    1980
ataaccaggc  tcgctgatct  cctacgtcaa  ggggctgtgt  tgaaacgtcc  tatgcagccg    2040
tatgaaagtc  accttcaata  cataccgcag  tggatgtgtg  atttcaacct  gtatggctgt    2100
gcgtacatgg  agtgtgcgaa  ggtcaagttc  cgctcgccgg  ttccaagcta  tctcgaactt    2160
tccaatctgg  atcatcgttg  gcatgatcgc  tcaataccta  gcgaactcat  ttcgaacgaa    2220
tccgaattac  cgaagcagag  tcattgctcc  ttggaagtgg  atgtctgtgt  ccaggatatc    2280
attaaccggc  acgctataaa  agagaggccg  ttacatcatg  actttgttga  gcgaatacat    2340
cctctatccc  ccgaagagaa  actcgttcac  agtatggccg  gtttgtggca  ggatgagacg    2400
cgaaggcgta  aaagagact  tggaattaag  gatcctggaa  gcagcccttt  cggcccggag    2460
gagctagtct  cgatgtctgc  tagccccaga  gaccagaaca  caggtggctg  gatccacgaa    2520
gacgagttct  gggagaaatt  gcgtgaaatt  gttgaggagg  aaaagcggaa  gagtgatggc    2580
acaagcgtct  ctttcgaaac  atacgtgaag  aaggatcctc  tcgaacatac  ggtcaagact    2640
gcacttgaga  gtgtcgagga  tttgtttcca  cagaagctgg  agcctctgaa  tcatgagagc    2700
aatcacctgc  aggatggagc  tatggatact  ggtatcgagg  ttgatgaaaa  tacagcgctc    2760
tcatttgaat  cggatgatcg  atatgactat  tcagatgacg  aggtctctgt  ccagccagat    2820
ttcggatttg  tgcaagatga  tcctgctctc  gaggagcttg  gtgttaattc  agactcaaat    2880
aatgacggac  ccaaacaatg  cgatggaaac  ggtctaccca  aacctgacgg  tttagctcgt    2940
cgcagaagta  ccacagcccg  tatcagagaa  acagatggga  tgcataatgc  agaatttgat    3000
cccggcgcca  tttcacgacc  gcagaaacga  tcagatggcg  aagaaataaa  cgtaggacat    3060
gtggcaaaac  gatcgaaaca  acttaatggc  gaatatattc  acaatcgaga  aacttattca    3120
actgccacta  cggacacagg  aatttccccg  tttgacactc  ccgcagcttt  gggggatgtt    3180
gctgctcaaa  ctaatcatca  aagtagtgca  gacggcatgg  tcaagccact  tccccaacca    3240
aagccgtctt  cctcgcagag  gatgctcccg  ggtagagcct  cgagtcaaaa  tcagcggctt    3300
tcgtttccgg  ttgtcaagga  ccctaatgat  cctttaacac  tgttgcgctt  tagtcaaagt    3360
cagaaaagca  tttcttcgaa  accgacttct  caactctccc  aggagacgga  gaaggtttcc    3420
gcacaaggac  atcgtgaaga  ctctcaagct  aggtcgtctt  cgcagttgca  ttcaacaaat    3480
agcgatcaaa  ccctgcaaga  tttcaataca  gatgaccttc  tgacggcctc  taaaattcat    3540
gatgcgtttc  acatccctag  gaatcgcaaa  atcctgtgtt  actgccaccc  ttgtccccgg    3600
cctagtgaaa  taatgtcaac  gatcaatgac  gaaggacgcc  cgacagtcgt  ttatcagaag    3660
gcctactata  gtgacgagag  tgatgttcct  gagcggcagc  gggagtatgc  gggacgtgaa    3720
tttcgtctgg  ggagtgatac  cttacaatac  ctacctgagt  ttgatagaac  aggcaggtcg    3780
ccttcactgc  ttggagaaca  gattcctcca  tccgctacca  acctcgaaaa  tcagagaaaa    3840
caggatcaga  aattgcgcga  gctgtcttca  tgtcgtatat  gggaatttgc  tcaggtgcca    3900
ccacgtcgct  cagaagtcgt  agaatggttc  gaaagggaaa  tagcgcatcc  aaaacaggac    3960
tcatcaaatg  gctcccgccg  tctgcctgaa  acgaagccaa  acgtattatg  gcagattgag    4020
ggcgcgacac  agaaggatcc  acacgggttc  aaatactccc  agaagcaggg  gtccacgagt    4080
```

```
gtggaacacc agactcaata catgagcgta atgagccttg aagtgcatgt caatactaga    4140
gactctttgg ctccaaatcc ggaagaggat gagatagcct gtgtttttg gtgtctccag    4200
tccgacgacg aagatctcga tgttaacagt gccctggacg gcgttcatgt tggaatcctt    4260
gcccagtcgg gatctgatgc cctgggaaaa gtagcgcggt ctataactgt cgattttgaa    4320
cgggagccaa cggaattgga tttgatcact cgcctggttg atatcgtgcg atactatgac    4380
ccggatattc ttacgggcta tgaggtgcat aatagctctt ggggatattt gattgagcgg    4440
gcgcggtaca agtacgactt ggatttatgc gacgagctct ctcgagtcaa agcacaatcc    4500
catggtagat ttggtaaaga aaacgaccgc tggggtttca accacacctc tagcattcgg    4560
gtgactgggc gacatatgat caacatctgg cgtgcaatga aagcgagct caatctcttg    4620
caatatacga tggagaatgt tgtctttcat ctgctacaca ggcgaatccc acactacccg    4680
ttcaaagagc taacggcgtg gtacaagagc agcaagccgc gggacgtgat gaaagtcatt    4740
gaatattttg tctccagaac cctgatggat ctggaaattc tcgaagcgaa cgagctaatc    4800
cccagaacta gcgaacaagc tcgtctgctg ggcatcgact tttactctgt tttctctcgt    4860
ggctcgcagt tcaaggtgga gtccctgatg tttcgaatcg ccaagcccga aaatttcata    4920
ttgatctctc caagcaagaa gcaagtcggt caacagaacg ctcttgaatg tcttcctctg    4980
gtgatggaac ctcaaagtga ttttacacc agtccgcttg tggtcttaga ttttcaatct    5040
ctgtatccga gtgtcatgat agcatacaat tattgctatt caaccttcct cggccgactt    5100
gtcagctggc gtgggcggaa caaaatgggg ttcactgact acgagaggcc acctcgtctg    5160
ctggagctcc ttggggacaa tattaatatt gctcctaacg gaatgatgta taccaagcct    5220
gagatacgga agtcacttct cgcccgaatg ctaagcgaaa tcttggagac tcgtgtcatg    5280
gtcaaaagtg gtatgaaagt cgacaaggat gacaggattt gcagcgctt gctcaataac    5340
cggcaattgg cgctcaagct gattgccaac gtcacatatg gctacgtc tgcctcgttc    5400
tcgggacgaa tgccatgctc tgaaattgcg gatagtattg tccagacagg acgagagacc    5460
ctagaaaagg cgattgcctt aatacactct gtcgaacgct ggggcgctga ggtggtgtat    5520
ggcgatacgg acagtctctt cgtctatctc aaaggacgtt cacgggacga agcattcact    5580
attggggagg agattgccca ggccgtcact aagatgaatc ctcgtccggt taaactcaaa    5640
tttgagaagg tttatcatcc atgcgttctc ctggcgaaga agcgatatgt tggcttcaag    5700
tacgaacgta gagaacagac agaacccgag ttcgatgcga aggggatcga gactgttcgt    5760
cgagatggca caccggctga gcagaagatt aagagaagg ccctcaagat tcttttcagg    5820
acggcagatt tgagtcaggt caagaggtac ttccagagtc aatgttcgaa aatcatgcag    5880
ggcaaggtgt ccatccagga tttctgtttt gcgagagaag tgaggctggg aacgtacagc    5940
gagaagggct tgcttcctcc tggagctttg atcagtgcca agaggatgct catggaccct    6000
cgtttggagc cccaatacgg cgagcgcgtg ccatacgtgg tggtcactgg tgctcccggg    6060
tcgagactgg ttgatcgctg tgtcgccccc gaagtacttc ttgacaaccc gcatcttgag    6120
ctcgatgccg agtattatat aaccaagaac atcattccgc cattggaacg tatattcaac    6180
ctggttgggg cgaacgtccg ccagtggtac gacgaaatgc cgaagttcca acgaattcga    6240
cgcatcgagg gcgtggctac tgctgctggg gaggccggat cctccaaaaa gacccttgag    6300
tcgtacatga atcgtccgc ttgtatcctc tgcaaggata aactcgacga tgctgaactc    6360
cccatttgca gctcttgtgc caatcaacct cacatttccc ttttcaccct aacgtctcgc    6420
```

| | |
|---|---|
| ctcaagcagg ccgagaggag agtcaacgat cttctcaaga tctgtcggtc atgcatgggc | 6480 |
| gttccatttg gcgatgatgt caagtgcgac agtaaggact gtccagtatt ctactcgagg | 6540 |
| acaagggata tggccaattg gaagcattcg aatgccgtcc tcgaacccgt catcaggatg | 6600 |
| ctggaagaac ggagcgagag cgtcttggaa tggtagcaaa cgacagaaga cacggaggga | 6660 |
| aattataata tgatcaggag ataggtttct tttagataac cgctggcatg tgtatttggc | 6720 |
| tgttgcatgt tggaagggac ggtaggcagt gatacccccgg cgtctatttc ggagttgttt | 6780 |
| ggttacctga gttagtcgtg cttcctctct gggacgagct tggtctgcta atctgatatg | 6840 |
| gttgttcctt cctcattggt atgtccgtat gataaagtat acagtaaata aaatttatca | 6900 |
| cgtggctcta gcctcgtgta ctgtctccgg agcactcttg tccggaccaa tgtgagacat | 6960 |
| gtccgtactt cttaatcatc tcgtggttct ccatagacct gcagtctggc accaggacaa | 7020 |
| tgggccggga acagaccatc ccacggggtg gctagactcg gaacagggcc gccggcgcta | 7080 |
| agtcctccgg tacgccgtcc tccgtgttga gcacaattaa ttgcagaatc cctgcactcc | 7140 |
| accccttaca accggcctta ttccttctga tcccaatctc atgatggcgt gcgtatcaag | 7200 |
| attgactaaa caactgggta agttcctttt ttctggacag gctttgacag aatcgttggc | 7260 |
| taaagacatc caactccgca gcctgagtcc agttccgatg ggtctcgagt cggtcacaca | 7320 |
| cgagccttat tcggcaaagg atcgccgatg gaaacttcca tcccccgcag gaggaaaaaa | 7380 |
| ctggggaagc ctcggggttt cccccgcact cttcagctac catcccgaga accgaccaat | 7440 |
| cccggtctca taacaggccg gagtacagta ctccgctgtc atcctagatt agcttgggcc | 7500 |
| taatcttaaa acaaagaaaa gctccaattc gggaaggacg gggagctgtg tagcccgggt | 7560 |
| aattggctcg tgcggatgaa gtataaaatg gaggccgttg gcacttgcag ggatcctgca | 7620 |
| tattccgtct ttacatgggt gttgaaaagt gcccgcgaca gacagttgca tggcagtttg | 7680 |
| actgtgacgg ttagttgagg gagacctgac catcggcttt gggaatccat gatggcgtcc | 7740 |
| gtatcggacc tggagggcca ggcctccaag gctggcggct ttcagcttgt atacaggaat | 7800 |
| ccatatctct ttggagtcgc gttggtaagc atctgggcaa tttatggacg atctaacggc | 7860 |
| tgtacctcgc taacttgatt ctgcacagtt ttcgaccttg ggtggtctgt tgtttggcta | 7920 |
| tgaccagggt gtcgtgtccg gtatcctgac gatggaatcg tttggagctc gattccctcg | 7980 |
| gatctactct gacagcagct tcaagggatg gtttgtctcg acgcttctac taagtacgtc | 8040 |
| cggccgatat ccaatgatta tacgttctgt tttccatatc tacccatctt catccgacta | 8100 |
| acagagctag atagctgcgt ggttcggatc tcttgt | 8136 |

<210> SEQ ID NO 47
<211> LENGTH: 5079
<212> TYPE: DNA
<213> ORGANISM: Rasamsonia emersonii

<400> SEQUENCE: 47

| | |
|---|---|
| atggatatct ttcgagttcg tttgaattgt atcgatcatt atcaggcaac tccaacggaa | 60 |
| ttcgacccct ccgtgccata tggcgtcggt atatcgcaaa gaaatgaaag gccaaaggta | 120 |
| cctgtcattc gcgcctttgg ggcgactgaa acaggccaga aggtctgtgc ccatatccat | 180 |
| ggtgcctttc cttacctcta tattgagtac aagggaagcc tagaaccaga tgaagtgaac | 240 |
| accgccattc gtaatctaca tctctcaatc gaccatgctt tggctgttag ctaccgtcgg | 300 |
| aacgcatacg aggggaagac ggcttacgtc gcccacatat ccctggtcaa agggataccc | 360 |
| ttctatggtt atcatgtggg atatcagttt tatttcaaaa tatacctgtt gaacccactg | 420 |

```
aatataacca ggctcgctga tctcctacgt caaggggctg tgttgaaacg tcctatgcag    480
ccgtatgaaa gtcaccttca atacataccg cagtggatgt gtgatttcaa cctgtatggc    540
tgtgcgtaca tggagtgtgc gaaggtcaag ttccgctcgc cggttccaag ctatctcgaa    600 cttttccaatc tggatcatcg ttggcatgat cgctcaatac ctagcgaact catttcgaac    660
gaatccgaat taccgaagca gagtcattgc tccttggaag tggatgtctg tgtccaggat    720
atcattaacc ggcacgctat aaaagagagg ccgttacatc atgactttgt tgagcgaata    780
catcctctat cccccgaaga gaaactcgtt cacagtatgg ccggtttgtg gcaggatgag    840
acgcgaaggc gtaaaaagag acttggaatt aaggatcctg gaagcagccc tttcggcccg    900
gaggagctag tctcgatgtc tgctagcccc agagaccaga acacaggtgg ctggatccac    960
gaagacgagt tctgggagaa attgcgtgaa attgttgagg aggaaaagcg gaagagtgat   1020
ggcacaagcg tctctttcga acatacgtg aagaaggatc ctctcgaaca tacggtcaag   1080
actgcacttg agagtgtcga ggatttgttt ccacagaagc tggagcctct gaatcatgag   1140
agcaatcacc tgcaggatgg agctatggat actggtatcg aggttgatga aaatacagcg   1200
ctctcatttg aatcggatga tcgatatgac tattcagatg acgaggtctc tgtccagcca   1260
gatttcggat ttgtgcaaga tgatcctgct ctcgaggagc ttggtgttaa ttcagactca   1320
aataatgacg gacccaaaca atgcgatgga aacggtctac ccaaacctga cggtttagct   1380
cgtcgcagaa gtaccacagc ccgtatcaga gaaacagatg ggatgcataa tgcagaattt   1440
gatcccggcg ccatttcacg accgcagaaa cgatcagatg cgaagaaat aaacgtagga   1500 catgtggcaa acgatcgaa acaacttaat ggcgaatata ttcacaatcg agaaacttat   1560
tcaactgcca ctacgacac aggaatttcc ccgtttgaca ctcccgcagc tttgggggat   1620
gttgctgctc aaactaatca tcaaagtagt gcagacggca tggtcaagcc acttccccaa   1680
ccaaagccgt cttcctcgca gaggatgctc ccgggtagag cctcgagtca aaatcagcgg   1740
cttttcgttc cggttgtcaa ggaccctaat gatcctttaa cactgttgcg ctttagtcaa   1800
agtcagaaaa gcatttcttc gaaaccgact tctcaactct cccaggagac ggagaaggtt   1860
tccgcacaag gacatcgtga agactctcaa gctaggtcgt cttcgcagtt gcattcaaca   1920
aatagcgatc aaaccctgca agatttcaat acagatgacc ttctgacggc ctctaaaatt   1980
catgatgcgt ttcacatccc taggaatcgc aaaatcctgt gttactgcca cccttgtccc   2040
cggcctagtg aaataatgtc aacgatcaat gacgaaggac gcccgacagt cgtttatcag   2100
aaggcctact atagtgacga gagtgatgtt cctgagcggc agcgggagta tgcgggacgt   2160
gaatttcgtc tggggagtga taccttacaa tacctacctg agtttgatag aacaggcagg   2220
tcgccttcac tgcttggaga acagattcct ccatccgcta ccaacctcga aaatcagaga   2280
aaacaggatc agaaattgcg cgagctgtct tcatgtcgta tatgggaatt tgctcaggtg   2340
ccaccacgtc gctcagaagt cgtagaatgg ttcgaaaggg aaatagcgca tccaaaacag   2400
gactcatcaa atggctcccg ccgtctgcct gaaacgaagc caaacgtatt atggcagatt   2460
gagggcgcga cacagaagga tccacacggg ttcaaatact cccagaagca ggggtccacg   2520
agtgtggaac accagactca atacatgagc gtaatgagcc ttgaagtgca tgtcaatact   2580
agagactctt tggctccaaa tccggaagag gatgagatag cctgtgtttt tggtgtctc   2640 cagtccgacg acgaagatct cgatgttaac agtgccctgg acggcgttca tgttggaatc   2700
cttgcccagt cgggatctga tgccctggga aaagtagcgc ggtctataac tgtcgatttt   2760
```

```
gaacgggagc caacggaatt ggatttgatc actcgcctgg ttgatatcgt gcgatactat    2820
gacccgata ttcttacggg ctatgaggtg cataatagct cttggggata tttgattgag    2880
cgggcgcggt acaagtacga cttggattta tgcgacgagc tctctcgagt caaagcacaa    2940
tcccatggta gatttggtaa agaaaacgac cgctgggggtt tcaaccacac ctctagcatt   3000
cgggtgactg ggcgacatat gatcaacatc tggcgtgcaa tgagaagcga gctcaatctc    3060
ttgcaatata cgatggagaa tgttgtcttt catctgctac acaggcgaat cccacactac    3120
ccgttcaaag agctaacggc gtggtacaag agcagcaagc cgcgggacgt gatgaaagtc    3180
attgaatatt ttgtctccag aaccctgatg gatctggaaa ttctcgaagc gaacgagcta    3240
atccccagaa ctagcgaaca agctcgtctg ctgggcatcg acttttactc tgttttctct    3300
cgtggctcgc agttcaaggt ggagtccctg atgtttcgaa tcgccaagcc cgaaaatttc    3360
atattgatct ctccaagcaa gaagcaagtc ggtcaacaga acgctcttga atgtcttcct    3420
ctggtgatgg aacctcaaag tgatttttac accagtccgc ttgtggtctt agattttcaa    3480
tctctgtatc cgagtgtcat gatagcatac aattattgct attcaacctt cctcggccga    3540
cttgtcagct ggcgtgggcg gaacaaaatg gggttcactg actacgagag gccacctcgt    3600
ctgctggagc tccttgggga caatattaat attgctccta acggaatgat gtataccaag    3660
cctgagatac ggaagtcact tctcgcccga atgctaagcg aaatcttgga gactcgtgtc    3720
atggtcaaaa gtggtatgaa agtcgacaag gatgacagga ttttgcagcg cttgctcaat    3780
aaccggcaat tggcgctcaa gctgattgcc aacgtcacat atggctacac gtctgcctcg    3840
ttctcgggac gaatgccatg ctctgaaatt gcggatagta ttgtccagac aggacgagag    3900
accctagaaa aggcgattgc cttaatacac tctgtcgaac gctggggcgc tgaggtggtg    3960
tatggcgata cggacagtct cttcgtctat ctcaaaggac gttcacggga cgaagcattc    4020
actattgggg aggagattgc ccaggccgtc actaagatga atcctcgtcc ggttaaactc    4080
aaatttgaga aggtttatca tccatgcgtt ctccctggcga agaagcgata tgttggcttc    4140
aagtacgaac gtagagaaca gacagaaccc gagttcgatg cgaaggggat cgagactgtt    4200
cgtcgagatg gcacaccggc tgagcagaag attgaagaga aggccctcaa gattcttttc    4260
aggacggcag atttgagtca ggtcaagagg tacttccaga gtcaatgttc gaaaatcatg    4320
cagggcaagg tgtccatcca ggatttctgt tttgcgagag aagtgaggct gggaacgtac    4380
agcgagaagg gcttgcttcc tcctggagct ttgatcagtg ccaagaggat gctcatggac    4440
cctcgtttgg agccccaata cggcgagcgc gtgccatacg tggtggtcac tggtgctccc    4500
gggtcgagac tggttgatcg ctgtgtcgcc cccgaagtac ttcttgacaa cccgcatctt    4560
gagctcgatg ccgagtatta tataaccaag aacatcattc cgccattgga acgtatattc    4620
aacctggttg gggcgaacgt ccgccagtgg tacgacgaaa tgccgaagtt ccaacgaatt    4680
cgacgcatcg agggcgtggc tactgctgct ggggaggccg gatcctccaa aaagacccttt    4740
gagtcgtaca tgaaatcgtc cgcttgtatc ctctgcaagg ataaactcga cgatgctgaa    4800
ctccccattt gcagctcttg tgccaatcaa cctcacattt cccttttcac cctaacgtct    4860
cgcctcaagc aggccgagag gagagtcaac gatcttctca agatctgtcg gtcatgcatg    4920
ggcgttccat ttggcgatga tgtcaagtgc gacagtaagg actgtccagt attctactcg    4980
aggacaaggg atatggccaa ttggaagcat tcgaatgccg tcctcgaacc cgtcatcagg    5040
atgctggaag aacggagcga gagcgtcttg gaatggtag                          5079
```

```
<210> SEQ ID NO 48
<211> LENGTH: 1692
<212> TYPE: PRT
<213> ORGANISM: Rasamsonia emersonii

<400> SEQUENCE: 48

Met Asp Ile Phe Arg Val Arg Leu Asn Cys Ile Asp His Tyr Gln Ala
1               5                   10                  15

Thr Pro Thr Glu Phe Asp Pro Val Pro Tyr Gly Val Gly Ile Ser
            20                  25                  30

Gln Arg Asn Glu Arg Pro Lys Val Pro Val Ile Arg Ala Phe Gly Ala
        35                  40                  45

Thr Glu Thr Gly Gln Lys Val Cys Ala His Ile His Gly Ala Phe Pro
    50                  55                  60

Tyr Leu Tyr Ile Glu Tyr Lys Gly Ser Leu Glu Pro Asp Glu Val Asn
65                  70                  75                  80

Thr Ala Ile Arg Asn Leu His Leu Ser Ile Asp His Ala Leu Ala Val
                85                  90                  95

Ser Tyr Arg Arg Asn Ala Tyr Glu Gly Lys Thr Ala Tyr Val Ala His
            100                 105                 110

Ile Ser Leu Val Lys Gly Ile Pro Phe Tyr Gly Tyr His Val Gly Tyr
        115                 120                 125

Gln Phe Tyr Phe Lys Ile Tyr Leu Leu Asn Pro Leu Asn Ile Thr Arg
    130                 135                 140

Leu Ala Asp Leu Leu Arg Gln Gly Ala Val Leu Lys Arg Pro Met Gln
145                 150                 155                 160

Pro Tyr Glu Ser His Leu Gln Tyr Ile Pro Gln Trp Met Cys Asp Phe
                165                 170                 175

Asn Leu Tyr Gly Cys Ala Tyr Met Glu Cys Ala Lys Val Lys Phe Arg
            180                 185                 190

Ser Pro Val Pro Ser Tyr Leu Glu Leu Ser Asn Leu Asp His Arg Trp
        195                 200                 205

His Asp Arg Ser Ile Pro Ser Glu Leu Ile Ser Asn Glu Ser Glu Leu
    210                 215                 220

Pro Lys Gln Ser His Cys Ser Leu Glu Val Asp Val Cys Val Gln Asp
225                 230                 235                 240

Ile Ile Asn Arg His Ala Ile Lys Glu Arg Pro Leu His His Asp Phe
                245                 250                 255

Val Glu Arg Ile His Pro Leu Ser Pro Glu Glu Lys Leu Val His Ser
            260                 265                 270

Met Ala Gly Leu Trp Gln Asp Glu Thr Arg Arg Lys Lys Arg Leu
        275                 280                 285

Gly Ile Lys Asp Pro Gly Ser Ser Pro Phe Gly Pro Glu Glu Leu Val
    290                 295                 300

Ser Met Ser Ala Ser Pro Arg Asp Gln Asn Thr Gly Gly Trp Ile His
305                 310                 315                 320

Glu Asp Glu Phe Trp Glu Lys Leu Arg Glu Ile Val Glu Glu Glu Lys
                325                 330                 335

Arg Lys Ser Asp Gly Thr Ser Val Ser Phe Glu Thr Tyr Val Lys Lys
            340                 345                 350

Asp Pro Leu Glu His Thr Val Lys Thr Ala Leu Glu Ser Val Glu Asp
        355                 360                 365

Leu Phe Pro Gln Lys Leu Glu Pro Leu Asn His Glu Ser Asn His Leu
    370                 375                 380
```

```
Gln Asp Gly Ala Met Asp Thr Gly Ile Glu Val Asp Glu Asn Thr Ala
385                 390                 395                 400

Leu Ser Phe Glu Ser Asp Asp Arg Tyr Asp Tyr Ser Asp Asp Glu Val
            405                 410                 415

Ser Val Gln Pro Asp Phe Gly Phe Val Gln Asp Asp Pro Ala Leu Glu
        420                 425                 430

Glu Leu Gly Val Asn Ser Asp Ser Asn Asn Asp Gly Pro Lys Gln Cys
            435                 440                 445

Asp Gly Asn Gly Leu Pro Lys Pro Asp Gly Leu Ala Arg Arg Arg Ser
    450                 455                 460

Thr Thr Ala Arg Ile Arg Glu Thr Asp Gly Met His Asn Ala Glu Phe
465                 470                 475                 480

Asp Pro Gly Ala Ile Ser Arg Pro Gln Lys Arg Ser Asp Gly Glu Glu
                485                 490                 495

Ile Asn Val Gly His Val Ala Lys Arg Ser Lys Gln Leu Asn Gly Glu
            500                 505                 510

Tyr Ile His Asn Arg Glu Thr Tyr Ser Thr Ala Thr Asp Thr Gly
        515                 520                 525

Ile Ser Pro Phe Asp Thr Pro Ala Ala Leu Gly Asp Val Ala Ala Gln
530                 535                 540

Thr Asn His Gln Ser Ser Ala Asp Gly Met Val Lys Pro Leu Pro Gln
545                 550                 555                 560

Pro Lys Pro Ser Ser Ser Gln Arg Met Leu Pro Gly Arg Ala Ser Ser
            565                 570                 575

Gln Asn Gln Arg Leu Ser Phe Pro Val Val Lys Asp Pro Asn Asp Pro
        580                 585                 590

Leu Thr Leu Leu Arg Phe Ser Gln Ser Gln Lys Ser Ile Ser Ser Lys
            595                 600                 605

Pro Thr Ser Gln Leu Ser Gln Glu Thr Glu Lys Val Ser Ala Gln Gly
    610                 615                 620

His Arg Glu Asp Ser Gln Ala Arg Ser Ser Ser Gln Leu His Ser Thr
625                 630                 635                 640

Asn Ser Asp Gln Thr Leu Gln Asp Phe Asn Thr Asp Asp Leu Leu Thr
                645                 650                 655

Ala Ser Lys Ile His Asp Ala Phe His Ile Pro Arg Asn Arg Lys Ile
            660                 665                 670

Leu Cys Tyr Cys His Pro Cys Pro Arg Pro Ser Glu Ile Met Ser Thr
        675                 680                 685

Ile Asn Asp Glu Gly Arg Pro Thr Val Val Tyr Gln Lys Ala Tyr Tyr
    690                 695                 700

Ser Asp Glu Ser Asp Val Pro Glu Arg Gln Arg Glu Tyr Ala Gly Arg
705                 710                 715                 720

Glu Phe Arg Leu Gly Ser Asp Thr Leu Gln Tyr Leu Pro Glu Phe Asp
            725                 730                 735

Arg Thr Gly Arg Ser Pro Ser Leu Leu Gly Glu Gln Ile Pro Pro Ser
        740                 745                 750

Ala Thr Asn Leu Glu Asn Gln Arg Lys Gln Asp Gln Lys Leu Arg Glu
    755                 760                 765

Leu Ser Ser Cys Arg Ile Trp Glu Phe Ala Gln Val Pro Pro Arg Arg
        770                 775                 780

Ser Glu Val Val Glu Trp Phe Glu Arg Glu Ile Ala His Pro Lys Gln
785                 790                 795                 800

Asp Ser Ser Asn Gly Ser Arg Arg Leu Pro Glu Thr Lys Pro Asn Val
```

-continued

```
            805                 810                 815
Leu Trp Gln Ile Glu Gly Ala Thr Gln Lys Asp Pro His Gly Phe Lys
        820                 825                 830

Tyr Ser Gln Lys Gln Gly Ser Thr Ser Val Glu His Gln Thr Gln Tyr
        835                 840                 845

Met Ser Val Met Ser Leu Glu Val His Val Asn Thr Arg Asp Ser Leu
    850                 855                 860

Ala Pro Asn Pro Glu Glu Asp Glu Ile Ala Cys Val Phe Trp Cys Leu
865                 870                 875                 880

Gln Ser Asp Asp Glu Asp Leu Asp Val Asn Ser Ala Leu Asp Gly Val
                885                 890                 895

His Val Gly Ile Leu Ala Gln Ser Gly Ser Asp Ala Leu Gly Lys Val
            900                 905                 910

Ala Arg Ser Ile Thr Val Asp Phe Glu Arg Glu Pro Thr Glu Leu Asp
        915                 920                 925

Leu Ile Thr Arg Leu Val Asp Ile Val Arg Tyr Tyr Asp Pro Asp Ile
    930                 935                 940

Leu Thr Gly Tyr Glu Val His Asn Ser Ser Trp Gly Tyr Leu Ile Glu
945                 950                 955                 960

Arg Ala Arg Tyr Lys Tyr Asp Leu Asp Leu Cys Asp Glu Leu Ser Arg
                965                 970                 975

Val Lys Ala Gln Ser His Gly Arg Phe Gly Lys Glu Asn Asp Arg Trp
            980                 985                 990

Gly Phe Asn His Thr Ser Ser Ile Arg Val Thr Gly Arg His Met Ile
        995                 1000                1005

Asn Ile Trp Arg Ala Met Arg Ser Glu Leu Asn Leu Leu Gln Tyr
    1010                1015                1020

Thr Met Glu Asn Val Val Phe His Leu Leu His Arg Arg Ile Pro
    1025                1030                1035

His Tyr Pro Phe Lys Glu Leu Thr Ala Trp Tyr Lys Ser Ser Lys
    1040                1045                1050

Pro Arg Asp Val Met Lys Val Ile Glu Tyr Phe Val Ser Arg Thr
    1055                1060                1065

Leu Met Asp Leu Glu Ile Leu Glu Ala Asn Glu Leu Ile Pro Arg
    1070                1075                1080

Thr Ser Glu Gln Ala Arg Leu Leu Gly Ile Asp Phe Tyr Ser Val
    1085                1090                1095

Phe Ser Arg Gly Ser Gln Phe Lys Val Glu Ser Leu Met Phe Arg
    1100                1105                1110

Ile Ala Lys Pro Glu Asn Phe Ile Leu Ile Ser Pro Ser Lys Lys
    1115                1120                1125

Gln Val Gly Gln Gln Asn Ala Leu Glu Cys Leu Pro Leu Val Met
    1130                1135                1140

Glu Pro Gln Ser Asp Phe Tyr Thr Ser Pro Leu Val Val Leu Asp
    1145                1150                1155

Phe Gln Ser Leu Tyr Pro Ser Val Met Ile Ala Tyr Asn Tyr Cys
    1160                1165                1170

Tyr Ser Thr Phe Leu Gly Arg Leu Val Ser Trp Arg Gly Arg Asn
    1175                1180                1185

Lys Met Gly Phe Thr Asp Tyr Glu Arg Pro Pro Arg Leu Leu Glu
    1190                1195                1200

Leu Leu Gly Asp Asn Ile Asn Ile Ala Pro Asn Gly Met Met Tyr
    1205                1210                1215
```

-continued

Thr Lys Pro Glu Ile Arg Lys Ser Leu Leu Ala Arg Met Leu Ser
1220                1225                1230

Glu Ile Leu Glu Thr Arg Val Met Val Lys Ser Gly Met Lys Val
1235                1240                1245

Asp Lys Asp Asp Arg Ile Leu Gln Arg Leu Leu Asn Asn Arg Gln
1250                1255                1260

Leu Ala Leu Lys Leu Ile Ala Asn Val Thr Tyr Gly Tyr Thr Ser
1265                1270                1275

Ala Ser Phe Ser Gly Arg Met Pro Cys Ser Glu Ile Ala Asp Ser
1280                1285                1290

Ile Val Gln Thr Gly Arg Glu Thr Leu Glu Lys Ala Ile Ala Leu
1295                1300                1305

Ile His Ser Val Glu Arg Trp Gly Ala Glu Val Val Tyr Gly Asp
1310                1315                1320

Thr Asp Ser Leu Phe Val Tyr Leu Lys Gly Arg Ser Arg Asp Glu
1325                1330                1335

Ala Phe Thr Ile Gly Glu Glu Ile Ala Gln Ala Val Thr Lys Met
1340                1345                1350

Asn Pro Arg Pro Val Lys Leu Lys Phe Glu Lys Val Tyr His Pro
1355                1360                1365

Cys Val Leu Leu Ala Lys Lys Arg Tyr Val Gly Phe Lys Tyr Glu
1370                1375                1380

Arg Arg Glu Gln Thr Glu Pro Glu Phe Asp Ala Lys Gly Ile Glu
1385                1390                1395

Thr Val Arg Arg Asp Gly Thr Pro Ala Glu Gln Lys Ile Glu Glu
1400                1405                1410

Lys Ala Leu Lys Ile Leu Phe Arg Thr Ala Asp Leu Ser Gln Val
1415                1420                1425

Lys Arg Tyr Phe Gln Ser Gln Cys Ser Lys Ile Met Gln Gly Lys
1430                1435                1440

Val Ser Ile Gln Asp Phe Cys Phe Ala Arg Glu Val Arg Leu Gly
1445                1450                1455

Thr Tyr Ser Glu Lys Gly Leu Leu Pro Pro Gly Ala Leu Ile Ser
1460                1465                1470

Ala Lys Arg Met Leu Met Asp Pro Arg Leu Glu Pro Gln Tyr Gly
1475                1480                1485

Glu Arg Val Pro Tyr Val Val Thr Gly Ala Pro Gly Ser Arg
1490                1495                1500

Leu Val Asp Arg Cys Val Ala Pro Glu Val Leu Leu Asp Asn Pro
1505                1510                1515

His Leu Glu Leu Asp Ala Glu Tyr Tyr Ile Thr Lys Asn Ile Ile
1520                1525                1530

Pro Pro Leu Glu Arg Ile Phe Asn Leu Val Gly Ala Asn Val Arg
1535                1540                1545

Gln Trp Tyr Asp Glu Met Pro Lys Phe Gln Arg Ile Arg Arg Ile
1550                1555                1560

Glu Gly Val Ala Thr Ala Ala Gly Glu Ala Gly Ser Ser Lys Lys
1565                1570                1575

Thr Leu Glu Ser Tyr Met Lys Ser Ser Ala Cys Ile Leu Cys Lys
1580                1585                1590

Asp Lys Leu Asp Asp Ala Glu Leu Pro Ile Cys Ser Ser Cys Ala
1595                1600                1605

```
Asn Gln Pro His Ile Ser Leu Phe Thr Leu Thr Ser Arg Leu Lys
    1610                1615                1620

Gln Ala Glu Arg Arg Val Asn Asp Leu Leu Lys Ile Cys Arg Ser
    1625                1630                1635

Cys Met Gly Val Pro Phe Gly Asp Asp Val Lys Cys Asp Ser Lys
    1640                1645                1650

Asp Cys Pro Val Phe Tyr Ser Arg Thr Arg Asp Met Ala Asn Trp
    1655                1660                1665

Lys His Ser Asn Ala Val Leu Glu Pro Val Ile Arg Met Leu Glu
    1670                1675                1680

Glu Arg Ser Glu Ser Val Leu Glu Trp
    1685                1690

<210> SEQ ID NO 49
<211> LENGTH: 7127
<212> TYPE: DNA
<213> ORGANISM: Rasamsonia emersonii
<400> SEQUENCE: 49
ccgaacccgc cagcgtctct tcgaagccgt caagcccgtc tcgcaccttt cctcgattag     60
gatcgacgtt caagtcgaat ctcaccgctt cattgcgagc catcaagtca gctgcacaga    120
cggtgtcgaa ctttgcgacg ccatcggttc aaccggatga ttttctcacg cgttctctgt    180
tctcgatcac ccccgaatta accgatgacc ggcgccccct tccgatgagc gaaccccctt    240
caccggctct tcgacgctat ctcaatccga tccaccttgtc gcctgccgag atgcatgttt    300
atcatgaatc tcccgcaggg tcggaccagt tcgctcacag ctgcccggtg tcgatccaga    360
tgcaaacgta caaccgatct gggtcttcaa ccggccgcag acggagccgt ttcagcacgg    420
gcaacgccag tggatacgaa caacagctgt gctcgttcga tccagagatc caatgaccc     480
gtcaacgcga ccgcgcgag aacagtgatt tcctgcgcgt ggtcgtccta gagatgaata    540
tgcggcgcag cggcaaatta cgcgatgaca tcccgagccg gccaaggtc tggctgcctc    600
cacgcaagcc agcacggttg gtctcgagcg cctacggtga tgaggaggag actgccattc    660
cccaacgatg ggttgggggtt tcaatcgagt gcgcttgaac gacctggccg agctctttac    720
cgatctactt tccgatcttc ttcatgattg tacatatgca tcacttcaac gtgtctttta    780
atttgttttt tacccctttt cggcgtcttt tcagaatttg gttcggatct acaatgacat    840
ggcatgagat agcgaggcgt ttgaggagga aatgggcacg gcaatagcat catgggcatt    900
tctttgcatg cttcggagca agggcaggtc gttagttcat tagccatgta ttattctctt    960
ggttttcccg agtgctcgac gatagtgaaa tgaattttgt atccagcgca tttcatgact   1020
atttctcccg tcctcacgtc attagatatt taccatttct ccagggttat tatcagacat   1080
ttgtgagaaa aggttcaagc atcacagtag gcattaaggc cgtgtgtaca ctccagccat   1140
tgtccattcc attctatcat attccgacgc gtcagtcaac ttacggact catttactga   1200
ccaacgcatt atggagagcg ccacgtgtct gaggaggact ctgcataagt tgccttttca   1260
attacgacga atatgatatg acagtactcc ggagtacgcc agttgattaa тактggcctg   1320
tagatcaata gcgcgcacgg tactctttct gttctggagg tccatgcgca tttgcatgac   1380
catctcctct tccatctttg tttttctttc ctttgaaaaa gaatcctcac ctgtttcctc   1440
tccttcccgc gaatcccgca atgccatacc tgctaatcta gctagctgta ccgtatagac   1500
atgtactgta cagtaggaag tagaaaagat gaggggtaag tgattggaac caggccggca   1560
tagtatggta tagcaacata gcattgatga tatatgcgtc aatggtaagc gataaaagcg   1620
```

```
cgctgtgcgg ggtttattag tattattctt ttattcgtgc actccagtcg agtcgagttg    1680
agagtgaggc aacaagagaa ttagtgcctc aggcactaaa ttcaaatgtc gtacagacta    1740
ccgatgacgt cgagtcacat gttctgcgtc tcctctggcg ctgcagcctg acagaccgc    1800 gtccggaccg tgtattaggt agaaaattaa tataaaattt ggcaattaaa aaaaagaaca    1860
ggaaggttat cgcttccgtt cttttgatgg tgtgatatcc cctggatcac aatattacaa    1920
tgaactggat ctgacagccg atcgctggtc gaaaatggat ccgcatgatg atgaggagca    1980
gctttccgat gctggccccg tggagactga aaaggacctt gatgagaagt aagccagcgg    2040
tgtagaaaga aaaagtatt gtcttactgg ctgacttgtt atgtgtgaag gtatccaaat     2100
cgacctcata accactcccc tacattgccc ttccacgagc tcttcttgtc cctgttcaac    2160
ccgttaaacg agaataagaa gaagcctacc ggtcctgctg ctgttgcggc tgcaaggagg    2220
aaagtcggcc caaatggcac gagtgcagcg aatctcaccc cccaggaacg tcggcgcgat    2280
atcatccagc ggttcatctc gcgatggaga aaagaagtcg gagacgatat ctacccggcc    2340
ttccgcctca tcgtcccgga caaggaccgc gatcgggcca tgtacgggct gaaagagaaa    2400
gttattggca agctactcgt caaaatcatg aagatcgaca agcactcgga ggatggattt    2460
agtctgctga actggaaact gcccggccag agcgcagcca gccggatggc gggcgacttt    2520
gccggacgat gctacgaagt catctccaaa cggccgatga ggactgaggt cggcgatatg    2580
ctcatcgagg aagtcaacga gaagctggac cagctctctg cggcctccaa ggaagagcag    2640 cagctccccca ttctggcgga gttctaccgg cggatgaacc cggaggagct gatgtggctc    2700
atcaggatca tcctccgaca gatgaagatc ggtgtttcgg agcggacgtt tttcgatgtg    2760
tggcatccgg acgcggagag gctgttcagc atctccagca gccttcgtcg cgtgtgctgg    2820
gagctccacg atccgaatat ccggttggag gccgatgaac ggggcgtttc gcttatgcag    2880
tgctttcagc ctcaactggc ccagttccag atgcattctt tcgaacggat ggtggagcga    2940
atgaggccca cggaggatga tcccgttttc tggatcgaag agaagctcga tggcgagcgc    3000
atgcagcttc acatggtatc agatgactcg atagaaggtg ggaagaggtt tgggttctgg    3060
tcacggaaag ccaaggatta tacgtatctt tacggcaatg ggctgaacga ccccaacggt    3120
gctctcacgc gccatctgaa agacgcgttt gctgagggtg tggacaacat cattctggat    3180
ggcgagatga tcacctggga ccccgagcaa gatgctccgg tcccctttgg gaccctcaaa    3240
accgccgcac tgtcagaaca acgtgacccg ttttctaaag gcccgcggcc actgtttcga    3300
gtcttcgata ttttgtatct taatgatcgg gacctgacca ggtatacact ccgtgaccgg    3360
cgaaatgcgt tggagaagag catcaaaccg gttcatcgaa gatttgagat acacccatac    3420
caagaggcca ccaaagcttc cgacatcgag ccgatcctta ggaaggttgt tgcagaagca    3480
tcagaaggac tggtcctgaa gaatccaagg tcgccttacc gtctgaatga acggcacgat    3540
gactggatga aggtcaagcc ggaatacatg tctgagtttg cgaatcgct ggacgtcatc     3600 gtgattgggg gttattatgg ttctggacgt cgcggtggca atctctccag cttcctatgc    3660
ggactccggg tcgaccaggc tcaggtccag aaaggagcaa atccgatgaa atgctattcc    3720
ttctgcaagg ttggaggcgg cttcaccgcg gccgattatg caaatatccg tcaccacacg    3780
gacgggaaat ggaagccgtg ggaccccaat aaacctccca ctgagtacat tgaattggca    3840
gggggagacg cccagtatga gcggcctgat atgtggatca gccggatga ctcggtagtc     3900 ctctgtgtca aggccgcttc tgtctccgtc agcgaccagt ttcggcttgg tttgacgcta    3960
```

```
cgattccctc gattcaagag gctgcgcatg gacaaggact ggaaaacagc attgtcagtg      4020
caagagtttc tggatctcaa atcgaacgtg gagcaggagc agaaagaaaa gcagtttact      4080
gtcgacaatt cccgcaagaa acggataaag agaaccacca agaagcctct caccgtcgct      4140
ggttacgacg ctgatgcaca agttcaatat cagggccctt cgggacacat tttcgacggg      4200
ttgaatttct gtatgcacga ttccattcac ctttcagtcc aggctaggac gtttgctgat      4260
cattgaatgt cgtagttatc atgacggaat ccagtgcacc ggtaaagaaa tccaagctcg      4320
agttggagca actggtcaaa tcgaacgggg gaaagattta ccagacgaac acggctgctc      4380
cggacaccgt gtgtatcgct gaccgaagta cgttacacct gacgataaat cagttgggag      4440
ggatggtaga gctaaatctt gcctcaatga acaggaacgg tcaaggtagc atccttgcag      4500
aaaagcgcca aagagaacat catccggccg ctgtggcttt tcgactgcat caagcagaat      4560
gaggctgatg cagggttgcc aaactttctc cttccattgg aaccacggta tgtgacgaaa      4620 gtacacctt gagaacctgc tgactgacac tgagacttct gcagacacat gttctttacc      4680
aaggaggatc agcgagatga gatcgaaggg aacgtggaca agttccatga tagttacgcg      4740
agggacacca ctgtggagga gctcaaggtg gtgagtgctg tctctctccc cctccctctc      4800
tgtttcttac taacaacaaa caatcggaca agctcctcga taacatgaag gtacccggca      4860
agatgaacca cgcccaagtc tcccagatca cagaacgact gtttgcgcgg gctcaacaag      4920
aagggcaaga ccgcggacaa gggatatctc caggctggct cttcaagggt ctcacgatct      4980
acttccacca cgacccgtcg tcggccacca attcgcaccg cctccgtcta gcatccaatc      5040
tggctcgatt tggcggggcc agcattgcca gcacgtacga cacgtcgaac aagaacaaag      5100
acaaaggcgt aacccacgtc atcatcgatc ccttatcgac agaggctccc gagcaacaac      5160
tctcctccct caggaaaact ttatcgtctc acgctgcttc gggcatgcga atcccccatc      5220
tggtcactgt ggaatggatc gaagagtgct ggaaggagcg gacgttgttg gatgaagaga      5280
gtatgtcctc tccctgttac cttcaaaacc gaagatgaca gtcagggttt gtgaaatatt      5340
gaaaagtgag agaagaaact gacgtgttac gtttactttc tgtctaggat tccaaccgcc      5400
gcggtgagat gagacgagat aacgacctat gatacaatga tggagttcct atgttgtgct      5460
taattaattg catttacatg tatgtactgt atgtattgta cattaccttg gatagataga      5520
tagctagcta ggtagtttag gaaacatcca aagctatgct agctatgttc tacgctgtac      5580
ttgtgtactt gtatgtactg tacaatacta ctaccatggt gagatgagta atgaccagga      5640
agaaaaaaat agaaagcgaa gagataataa gtatgtactg tatacacatg gagagaaact      5700
gcatctgcag acttccaagt tcttattgac atttttttcca ccttatctcg gtaggaatga      5760
gcgtcaatat aatacagaca tatatatata tatattcatg ctatttacgg tacgcttcac      5820
gactccatca atcggacgca gcagatgctg atacagatgc tgatgacgca ggagacgaga      5880
cctgctcgcc caagcgggtt agaatgccga tgtactcatg cgcgatcccc caagacgaca      5940
tcagccccga cagcgtgcgg atgccttcct tcaggatcct cgccggccct gatggtccgc      6000
agatgtcgcc taccccggtc acgttgcccc gcatcgtgtg gccctcgcgc acgaaaagct      6060
gcacgagctc gtcgtcgcag ggccggtcga gatggatgaa tgttggaccg ggggctggct      6120
cggatacgtc aggctgaggt cgcagctcat ccgagtcttc aacattgttg ctgttgttgc      6180
tgttgctgct attgttgttc tggccggagg ctgctgctgt tgctttgtgg tggcatgatc      6240
catatgccca gagggtgagg gtggctagga agacggccac aggctcatgg aaggcattcg      6300
tggaatagcg acggacgtac cacaagacgg aaccggcgtg gatcagtgcc agccgggctt      6360
```

| | |
|---|---|
| tatactggtc atgcttgacc cagcgccaga tgtggtgcca ctcgatggct tgctcgtgct | 6420 |
| cactccaatg tagggtccct cttgctaaag aagtcgccag tgctcggatc tcccggaacg | 6480 |
| ggaccaggag gacaatccgc gcagcgtgta gatgaaggac ggtagggtgc tccaatccgg | 6540 |
| ccgctttggc aatcgtgccg ttggctgtcc aatggaggat gtccaagcag tcacaggcgc | 6600 |
| tgtttcgcca tttcgagtac acgggtatcc caggaagcca aacagaccca gacgggatcg | 6660 |
| cggagtctcg ggattgcttc ttagccgtag gattccaaca agacagcggt cgccggaagt | 6720 |
| aatcgctcac ttcccacatt ctctggtaga gagcatggac aagcaggaca tgactgaatt | 6780 |
| ccccgatccc agggactagt ctcttttcga tgtatagaat ctgcgttgcg gagtagagcg | 6840 |
| attcattttc ttgagtttta ttagcagtgt gcagtcctgt actcggaagt gattgcttac | 6900 |
| cacctgaaga ccgttcgtgc agttgccgcc agctttcctc agactttgcc tgccacggat | 6960 |
| cctcatgcga cggtaatggg gcttgtgcat cgtcgagcga taagtgcggt cgggtatcaa | 7020 |
| aagcatacgc caatgtgcaa tcaaggagct gcaggaatcc atcagcacgc ttctgtatct | 7080 |
| gtcgatgata ttatccaagg ctgacgtacc catatacaat agcctgt | 7127 |

<210> SEQ ID NO 50
<211> LENGTH: 3246
<212> TYPE: DNA
<213> ORGANISM: Rasamsonia emersonii

<400> SEQUENCE: 50

| | |
|---|---|
| atgtactgta cagtaggaag tagaaaagat gagggcaaca tagcattgat gatatatgcg | 60 |
| tcaatggaag gttatcgctt ccgttctttt gatggtgtga tatccctgg atcacaatat | 120 |
| tacaatgaac tggatctgac agccgatcgc tggtcgaaaa tggatccgca tgatgatgag | 180 |
| gagcagcttt ccgatgctgg ccccgtggag actgaaaagg accttgatga aagtatcca | 240 |
| aatcgacctc ataaccactc ccctacattg cccttccacg agctcttctt gtccctgttc | 300 |
| aacccgttaa acgagaataa gaagaagcct accggtcctg ctgctgttgc ggctgcaagg | 360 |
| aggaaagtcg gcccaaatgg cacgagtgca gcgaatctca cccccagga acgtcggcgc | 420 |
| gatatcatcc agcggttcat ctcgcgatgg agaaaagaag tcggagacga tatctacccg | 480 |
| gccttccgcc tcatcgtccc ggacaaggac cgcgatcggg ccatgtacgg gctgaaagag | 540 |
| aaagttattg gcaagctact cgtcaaaatc atgaagatcg acaagcactc ggaggatgga | 600 |
| tttagtctgc tgaactggaa actgcccggc cagagcgcag ccagccggat ggcgggcgac | 660 |
| tttgccggac gatgctacga agtcatctcc aaacggccga tgaggactga ggtcggcgat | 720 |
| atgctcatcg aggaagtcaa cgagaagctg gaccagctct ctgcggcctc caaggaagag | 780 |
| cagcagctcc ccattctggc ggagttctac cggcggatga acccggagga gctgatgtgg | 840 |
| ctcatcagga tcatcctccg acagatgaag atcggtgttt cggagcggac gttttcgat | 900 |
| gtgtggcatc cggacgcgga gaggctgttc agcatctcca gcagccttcg tcgcgtgtgc | 960 |
| tgggagctcc acgatccgaa tatccggttg gaggccgatg aacgggcgt ttcgcttatg | 1020 |
| cagtgctttc agcctcaact ggcccagttc cagatgcatt ctttcgaacg gatggtggag | 1080 |
| cgaatgaggc ccacggagga tgatcccgtt ttctggatcg aagagaagct cgatggcgag | 1140 |
| cgcatgcagc ttcacatggt atcagatgac tcgatagaag gtgggaagag gtttggttc | 1200 |
| tggtcacgga aagccaagga ttatacgtat ctttacggca atgggctgaa cgaccccaac | 1260 |
| ggtgctctca cgcgccatct gaaagacgcg tttgctgagg gtgtggacaa catcattctg | 1320 |

```
gatggcgaga tgatcacctg gaccccgag caagatgctc cggtcccctt tgggaccctc    1380
aaaaccgccg cactgtcaga acaacgtgac ccgttttcta aaggcccgcg gccactgttt    1440
cgagtcttcg atattttgta tcttaatgat cgggacctga ccaggtatac actccgtgac    1500
cggcgaaatg cgttggagaa gagcatcaaa ccggttcatc gaagatttga gatacaccca    1560
taccaagagg ccaccaaagc ttccgacatc gagccgatcc ttaggaaggt tgttgcagaa    1620
gcatcagaag gactggtcct gaagaatcca aggtcgcctt accgtctgaa tgaacggcac    1680
gatgactgga tgaaggtcaa gccggaatac atgtctgagt ttggcgaatc gctggacgtc    1740
atcgtgattg ggggttatta tggttctgga cgtcgcggtg gcaatctctc cagcttccta    1800
tgcggactcc gggtcgacca ggctcaggtc cagaaaggag caaatccgat gaaatgctat    1860
tccttctgca aggttggagg cggcttcacc gcggccgatt atgcaaatat ccgtcaccac    1920
acggacggga atggaagcc gtgggacccc aataaacctc ccactgagta cattgaattg    1980 gcaggggag acgcccagta tgagcggcct gatatgtgga tcaagccgga tgactcggta    2040
gtcctctgtg tcaaggccgc ttctgtctcc gtcagcgacc agtttcggct tggtttgacg    2100
ctacgattcc ctcgattcaa gaggctgcgc atggacaagg actggaaaac agcattgtca    2160
gtgcaagagt ttctggatct caaatcgaac gtggagcagg agcagaaaga aaagcagttt    2220
actgtcgaca attcccgcaa gaaacggata aagagaacca ccaagaagcc tctcaccgtc    2280
gctggttacg acgctgatgc acaagttcaa tatcagggcc cttcgggaca cttttcgac    2340 gggttgaatt tctttatcat gacggaatcc agtgcaccgg taaagaaatc caagctcgag    2400
ttggagcaac tggtcaaatc gaacggggga agatttacc agacgaacac ggctgctccg    2460
gacaccgtgt gtatcgctga ccgaagaacg gtcaaggtag catccttgca gaaaagcgcc    2520
aaagagaaca tcatccggcc gctgtggctt ttcgactgca tcaagcagaa tgaggctgat    2580
gcagggttgc caaactttct ccttccattg gaaccacgac acatgttctt taccaaggag    2640
gatcagcgag atgagatcga agggaacgtg acaagttcc atgatagtta cgcgagggac    2700
accactgtgg aggagctcaa ggtgctcctc gataacatga aggtacccgg caagatgaac    2760
cacgcccaag tctcccagat cacagaacga ctgtttgcgc gggctcaaca agaagggcaa    2820
gaccgcggac aagggatatc tccaggctgg ctcttcaagg gtctcacgat ctacttccac    2880
cacgacccgt cgtcggccac caattcgcac cgcctccgtc tagcatccaa tctggctcga    2940
tttggcgggg ccagcattgc cagcacgtac gacacgtcga acaagaacaa agacaaaggc    3000
gtaacccacg tcatcatcga tcccttatcg acagaggctc ccgagcaaca actctcctcc    3060
ctcaggaaaa ctttatcgtc tcacgctgct tcgggcatgc gaatcccca tctggtcact    3120 gtggaatgga tcgaagagtg ctggaaggag cggacgttgt tggatgaaga gactatgcta    3180
gctatgttct acgctgtact tgtgtacttg tatgtactgt acaatactac taccatggtg    3240
agatga                                                              3246
```

<210> SEQ ID NO 51
<211> LENGTH: 1081
<212> TYPE: PRT
<213> ORGANISM: Rasamsonia emersonii

<400> SEQUENCE: 51

Met Tyr Cys Thr Val Gly Ser Arg Lys Asp Glu Gly Asn Ile Ala Leu
1               5                   10                  15

Met Ile Tyr Ala Ser Met Glu Gly Tyr Arg Phe Arg Ser Phe Asp Gly
            20                  25                  30

```
Val Ile Ser Pro Gly Ser Gln Tyr Tyr Asn Glu Leu Asp Leu Thr Ala
        35                  40                  45

Asp Arg Trp Ser Lys Met Asp Pro His Asp Asp Glu Glu Gln Leu Ser
 50                  55                  60

Asp Ala Gly Pro Val Glu Thr Glu Lys Asp Leu Asp Gly Lys Tyr Pro
 65                  70                  75                  80

Asn Arg Pro His Asn His Ser Pro Thr Leu Pro Phe His Glu Leu Phe
                 85                  90                  95

Leu Ser Leu Phe Asn Pro Leu Asn Glu Asn Lys Lys Pro Thr Gly
                100                 105                 110

Pro Ala Ala Val Ala Ala Arg Arg Lys Val Gly Pro Asn Gly Thr
             115                 120                 125

Ser Ala Ala Asn Leu Thr Pro Gln Glu Arg Arg Asp Ile Ile Gln
 130                 135                 140

Arg Phe Ile Ser Arg Trp Arg Lys Glu Val Gly Asp Asp Ile Tyr Pro
 145                 150                 155                 160

Ala Phe Arg Leu Ile Val Pro Asp Lys Asp Arg Asp Arg Ala Met Tyr
                 165                 170                 175

Gly Leu Lys Glu Lys Val Ile Gly Lys Leu Leu Val Lys Ile Met Lys
             180                 185                 190

Ile Asp Lys His Ser Glu Asp Gly Phe Ser Leu Leu Asn Trp Lys Leu
                 195                 200                 205

Pro Gly Gln Ser Ala Ala Ser Arg Met Ala Gly Asp Phe Ala Gly Arg
             210                 215                 220

Cys Tyr Glu Val Ile Ser Lys Arg Pro Met Arg Thr Glu Val Gly Asp
225                 230                 235                 240

Met Leu Ile Glu Glu Val Asn Glu Lys Leu Asp Gln Leu Ser Ala Ala
                 245                 250                 255

Ser Lys Glu Glu Gln Gln Leu Pro Ile Leu Ala Glu Phe Tyr Arg Arg
             260                 265                 270

Met Asn Pro Glu Glu Leu Met Trp Leu Ile Arg Ile Ile Leu Arg Gln
             275                 280                 285

Met Lys Ile Gly Val Ser Glu Arg Thr Phe Phe Asp Val Trp His Pro
 290                 295                 300

Asp Ala Glu Arg Leu Phe Ser Ile Ser Ser Ser Leu Arg Arg Val Cys
305                 310                 315                 320

Trp Glu Leu His Asp Pro Asn Ile Arg Leu Glu Ala Asp Glu Arg Gly
                 325                 330                 335

Val Ser Leu Met Gln Cys Phe Gln Pro Gln Leu Ala Gln Phe Gln Met
             340                 345                 350

His Ser Phe Glu Arg Met Val Glu Arg Met Arg Pro Thr Glu Asp Asp
             355                 360                 365

Pro Val Phe Trp Ile Glu Glu Lys Leu Asp Gly Glu Arg Met Gln Leu
 370                 375                 380

His Met Val Ser Asp Asp Ser Ile Glu Gly Lys Arg Phe Gly Phe
385                 390                 395                 400

Trp Ser Arg Lys Ala Lys Asp Tyr Thr Tyr Leu Tyr Gly Asn Gly Leu
                 405                 410                 415

Asn Asp Pro Asn Gly Ala Leu Thr Arg His Leu Lys Asp Ala Phe Ala
             420                 425                 430

Glu Gly Val Asp Asn Ile Ile Leu Asp Gly Glu Met Ile Thr Trp Asp
             435                 440                 445
```

-continued

```
Pro Glu Gln Asp Ala Pro Val Pro Phe Gly Thr Leu Lys Thr Ala Ala
    450                 455                 460

Leu Ser Glu Gln Arg Asp Pro Phe Ser Lys Gly Pro Arg Pro Leu Phe
465                 470                 475                 480

Arg Val Phe Asp Ile Leu Tyr Leu Asn Asp Arg Asp Leu Thr Arg Tyr
                485                 490                 495

Thr Leu Arg Asp Arg Arg Asn Ala Leu Glu Lys Ser Ile Lys Pro Val
            500                 505                 510

His Arg Arg Phe Glu Ile His Pro Tyr Gln Ala Thr Lys Ala Ser
        515                 520                 525

Asp Ile Glu Pro Ile Leu Arg Lys Val Val Ala Glu Ala Ser Glu Gly
530                 535                 540

Leu Val Leu Lys Asn Pro Arg Ser Pro Tyr Arg Leu Asn Glu Arg His
545                 550                 555                 560

Asp Asp Trp Met Lys Val Lys Pro Glu Tyr Met Ser Glu Phe Gly Glu
                565                 570                 575

Ser Leu Asp Val Ile Val Ile Gly Gly Tyr Tyr Gly Ser Gly Arg Arg
            580                 585                 590

Gly Gly Asn Leu Ser Ser Phe Leu Cys Gly Leu Arg Val Asp Gln Ala
        595                 600                 605

Gln Val Gln Lys Gly Ala Asn Pro Met Lys Cys Tyr Ser Phe Cys Lys
610                 615                 620

Val Gly Gly Gly Phe Thr Ala Ala Asp Tyr Ala Asn Ile Arg His His
625                 630                 635                 640

Thr Asp Gly Lys Trp Lys Pro Trp Asp Pro Asn Lys Pro Pro Thr Glu
                645                 650                 655

Tyr Ile Glu Leu Ala Gly Gly Asp Ala Gln Tyr Glu Arg Pro Asp Met
            660                 665                 670

Trp Ile Lys Pro Asp Asp Ser Val Val Leu Cys Val Lys Ala Ala Ser
        675                 680                 685

Val Ser Val Ser Asp Gln Phe Arg Leu Gly Leu Thr Leu Arg Phe Pro
690                 695                 700

Arg Phe Lys Arg Leu Arg Met Asp Lys Asp Trp Lys Thr Ala Leu Ser
705                 710                 715                 720

Val Gln Glu Phe Leu Asp Leu Lys Ser Asn Val Glu Gln Glu Gln Lys
                725                 730                 735

Glu Lys Gln Phe Thr Val Asp Asn Ser Arg Lys Lys Arg Ile Lys Arg
            740                 745                 750

Thr Thr Lys Lys Pro Leu Thr Val Ala Gly Tyr Asp Ala Asp Ala Gln
        755                 760                 765

Val Gln Tyr Gln Gly Pro Ser Gly His Ile Phe Asp Gly Leu Asn Phe
770                 775                 780

Phe Ile Met Thr Glu Ser Ser Ala Pro Val Lys Lys Ser Lys Leu Glu
785                 790                 795                 800

Leu Glu Gln Leu Val Lys Ser Asn Gly Gly Lys Ile Tyr Gln Thr Asn
                805                 810                 815

Thr Ala Ala Pro Asp Thr Val Cys Ile Ala Asp Arg Arg Thr Val Lys
            820                 825                 830

Val Ala Ser Leu Gln Lys Ser Ala Lys Glu Asn Ile Ile Arg Pro Leu
        835                 840                 845

Trp Leu Phe Asp Cys Ile Lys Gln Asn Glu Ala Asp Ala Gly Leu Pro
850                 855                 860

Asn Phe Leu Leu Pro Leu Glu Pro Arg His Met Phe Phe Thr Lys Glu
```

```
                865           870           875           880
Asp Gln Arg Asp Glu Ile Glu Gly Asn Val Asp Lys Phe His Asp Ser
                    885               890               895
Tyr Ala Arg Asp Thr Thr Val Glu Glu Leu Lys Val Leu Leu Asp Asn
                900               905               910
Met Lys Val Pro Gly Lys Met Asn His Ala Gln Val Ser Gln Ile Thr
            915               920               925
Glu Arg Leu Phe Ala Arg Ala Gln Gln Glu Gly Gln Asp Arg Gly Gln
        930               935               940
Gly Ile Ser Pro Gly Trp Leu Phe Lys Gly Leu Thr Ile Tyr Phe His
945               950               955               960
His Asp Pro Ser Ser Ala Thr Asn Ser His Arg Leu Arg Leu Ala Ser
                965               970               975
Asn Leu Ala Arg Phe Gly Gly Ala Ser Ile Ala Ser Thr Tyr Asp Thr
                980               985               990
Ser Asn Lys Asn Lys Asp Lys Gly  Val Thr His Val Ile  Ile Asp Pro
                995               1000              1005
Leu Ser  Thr Glu Ala Pro Glu  Gln Gln Leu Ser Ser  Leu Arg Lys
    1010              1015              1020
Thr Leu  Ser Ser His Ala Ala  Ser Gly Met Arg Ile  Pro His Leu
    1025              1030              1035
Val Thr  Val Glu Trp Ile Glu  Glu Cys Trp Lys Glu  Arg Thr Leu
    1040              1045              1050
Leu Asp  Glu Glu Thr Met Leu  Ala Met Phe Tyr Ala  Val Leu Val
    1055              1060              1065
Tyr Leu  Tyr Val Leu Tyr Asn  Thr Thr Thr Met Val  Arg
    1070              1075              1080

<210> SEQ ID NO 52
<211> LENGTH: 5720
<212> TYPE: DNA
<213> ORGANISM: Rasamonia emersonii

<400> SEQUENCE: 52
gcctcgtcag gtcaagctga gctccctcgg gcgggctgct gctactgctg cgatggactg    60
atggcgatga cgcagaaagt gcgttatcgg tcgtgctcag tcgtcgcaac agcgagccgt   120
catcctcggc cgggacgcga gagggggatg catcagggtc gacgatgtcg acggatgccc   180
cgtggccttc ggcatctcca ctagggagca tgccgaagac cgattcatca cgacaaaggt   240
catttccatg ctggaagagg ttggaaggaa ctgcggggtt ggcgtctacg ggagtacttt   300
gggagacggc agtattaggc tctgatggca taaaatgtgg tgacgcggga gtgagggaaa   360 gcggagcga ctgatccagg ctagactggg tcagtcgaaa gcaatgataa cgagcaatgc    420
gcggggagga gcgacgtgag agaccggctg tgacgtgcga cgatgggaga acaagagagg   480
agggacggag gaaggaggaa cgcgaagatg caacgaaaac gacacgggcg agtcccgatg   540
ctgactaagc cgtttcttgc agcacgttcg ccttcgaaga tatgcaatag gacagacgat   600
tcagatgcag tcaggagagc tttaacgttc aattttctag tattttctct gataagaatg   660
ccctcatctg aatttcattg tgagtctgct tttccagata gaatcacgat caacaatacc   720
gtactcgaag gggtgtcaat tcctcgagac accgtaacgg gataaattag ttaagcgtat   780
cgacactcaa catatgtggc aattcatttc ctgtagtctc ttgtttgctc tcttttcccc   840
ttcatttcct tcctttttc ttccttacat ttactttga ttctcttctt cttttttgtt     900
```

-continued

```
tttatttttcc tgatcagtgt cccatattgc agtattattg gcaaattacg gtactgaaaa    960
ttaattgcac gtaattttc atgtctgcgg gaacgcgtca cgtggcgagg acgcgccaga     1020
aacacgactg accaggaaga gacgaaatca acaaaagaac aagaggggaa agaaaaggga    1080
aggggatctt aggccgacga gcaacacaaa gggtcgttag gtcgatgcgt gtaataaggc    1140
ctgtgctgtt ttccccggt gggttttgat cctgggcggc ttctaggcaa catcccgcag     1200
cctcacccctt ttacaaactg acgggggtgg tactttcttt gagggcaatc ttcctttctt   1260
tcctctacta gatagaaagg ataggttttt atcactgagg atgccctcac tcaccggtaa    1320
ggctaactac gccctcgcag tctgtcctcc cgactaaccc gtatagccgc ggatacgatc    1380
cgcatcctcg tctcaaccga caaccatgtc ggctacaatg agcgagatcc tatccgggt    1440
gacgacagtt ggaaaagctt ccacgagatt atgtgtctgg cgaaggagcg cgatgtcgac    1500
atggtcctcc tcgctggcga tctcttccac gagaacaagc cgtctcgcaa gtccatgtac    1560
caggtgatgc ggtcactgcg catgaactgc ttgggcgata agccctgcga gttggagatg    1620
ctcagtgacg ccagtgagaa cttccagggc gctttcaacc acgtcaacta cgaggacctc    1680
gacatcaatg tcgccatccc cgtcttttcc attcatggta accatgacga tccatccggg    1740
gaaggtcatc tggctgccct ggacatactc caagtgtccg gactgatcaa ctacttcggt    1800
cggacgccag agtcggacaa tattcaggtc aaacctgtcc ttctacagaa aggccgcacc    1860
aaattggcgc tctacggcat cagcaacgtt cgtgatgaac ggctgtttcg tacatttcgc    1920
gatgggaaag tcaagttctt ccggccctcg atccagaagg aggactggtt caacctgatc    1980
tgtgtccatc agaaccacca cgcccacacg gagacgggct acctcccga atccttcctg     2040
ccagactttc tcgacctggt catctggggc cacgaacacg agtgtctgat aaaccccaga    2100
cgcaaccctg aaatgaattt ccacgtcatg cagcctggct cctctgtggc cacgtcactg    2160
gtccagggag aagcagcacc caagcatgta gcgattctca gcatcaaggg ccgggagttc    2220
cactgtgaac ctatccgctt gaaaacagtg cgtccatttg tcgtgcgaga atcgtcctc    2280
tctgaggaga aggggccca gaaactggcc cgaaaggaga ataatcggac agaagtcacc    2340
cggttcttaa tgtctatagt ggaggagctg attgaacaag ccaaagcaga gtggctggag    2400
gcacaccaag acgacgatgt cgatgagcag gatattcctc tccccttgt acgtcttaga    2460
gtggaggtt ctacaccaga aggtggcagc ttcgactgcg agaaccctca gcggttctcc     2520
aatcggttcg tgggcaaagt cgcgaacgtc aacgacgtgg ttcaattcta ccgtaaaaag    2580
aagtcaacaa cgacttcccg caaggcagat aatctcgatg aggcggtggt gtcgcatctt    2640
tccgagctcg atacggtgaa ggtcgagaag ctagtacggg agattctcac tgcacagtct    2700
ctcaccatcc ttcctcagaa ctcgttcagc gatgcagtct cccagttcgt ggacaaggat    2760
gacaagcacg ccatggaaat gttcgtgaac gagtcgctag agaaccaggt caagtatctg    2820
atgtccctgg aacgggaggc cgacatggac gatgaggagg agagtcatca atctttgcgg    2880
aacgccatgg aaaaatatccg cagtcagatg gaggagatgt tgcgaaggg cgccatgaga    2940
cgtacgcgag ggaagaagcg cttcaaaccg aagcccgatg gctgggatac cgatctcgac    3000
ggcgtatggg aagaccagcc gggcgcattg atcctctctg acaatgagga tgccgacccg    3060
aacgaagagg aggccgcaga ggatggtacg gagagacaga ccacgtccac tcgaggcaga    3120
ggtcgaggtc gtggaggccg ggctgcaacc accaccactt ccacgcgcaa acgactgct    3180
agcaagactc cagcagccag ctcacgaggc cggagacgcc aggctgtttc tgaagacgaa    3240
gacgaagacg agggcgatga tgtggtggtg ctggatgacg atcaggagga gccggaagaa    3300
```

```
atggtctcgg atgacgattc tcaggcactc tttgtcaaac aaacacctcc acccaaaacg   3360
ggtcgaacgc gccagacaac actcacttcg accacaacag gcacccagcg gcgatctgga   3420
cgaactgcac cttcgccagc gccctcctct gccactgcag cagcttcgac ggcccgaagt   3480
gggacgcgag gtgccgctgc tagcaaacgg acccagcaga cgacactcaa ctttgcgccg   3540
tcgcagacca gttccgtggg cactggacag gttacaggta ctgttacggg tacgaacacg   3600
agaccgtcac ggacaacacg aggcgttagc gtggtgagtg aggaagatat cgaggatgac   3660
gacgatgatg cgtttgagcc ggcaccagcg acgactcgga ggcggcgata aaaacagtcg   3720
ctcttgaaga gtaataattg ccgtaatgca gcgccatgag catgaaaata cgtgcagtct   3780
tttttttgtt gttattgtat ggattactgt ctaaaatctc aaggattcaa aaagcgtgta   3840
gtaaggagta aggtatctaa tctacaaatg gaactggaa aaattaaatt agatgaatgc   3900
agggatatat gcccccaaat tgaggactac aaatttagta tctatttgcc taatcatcgg   3960
gatgataggt atatacttct cctgggtttc aattttgtag aatcaatttt ttttacgatg   4020
aaatcatgac cttctagcag ttatatgtag aagcaagtaa tactaatact gaagacagtc   4080
actgggctcc gctgttaacc atgcatgcat tagtaggggc ctttcttggt cgacattcct   4140
cattcgttgc taatccatcc aacaggtctg aagagctcca ggcggggttc tatgctaaaa   4200
ggcaaaagga ggggcaatag caactttgtt ctataggggg aaaaaaatct ccatatgacc   4260
gatacgataa atatcttggg agtgtcataa ttcggcgtgt acagactcgg aactggaggg   4320
gaatacgggaa aaaatccata acaaatgtcg atgacagacc gcaactcgtt tacagaatta   4380
gatcgatgga gctgtgatcc ttgatctggt tggctcgtcc cctgagcctg gtccgggga   4440
atgacctgat cagcggctgg cgcgctgcgg ggtacgaagg ccgaaccccc tccgtcttcc   4500
gtctccccgg acacgccgtc tgttgcggag atttccgggg tgcgcaatcc caaataataa   4560
tatctgtccc gtgcctggcc gcagtgcgtg ccagcgttgg tgatagatat ttagggttgg   4620
tctggcttcg gtcagatggc agttcccttc atgagattag cagtgaatcc tgtatgcata   4680
ttgcgtcatc tgtcgccttc ccgtagatcg accatctttg cttgtcagat atcgatacac   4740
tagcaggctc gaaactccag gattggaatt gttccagcaa cggtcactac tgatgctgat   4800
ccccgccgcg tcgtagatt gtggagcaaa ctccgtgcgt ttaacccatg tctcttacgt   4860
gtcatctgaa acgcgtttga gagcaatcag cttccagcag gcaaaaatgc aggcctagaa   4920
ttggaatgtt ttcttagcac gtcgagtgcg ctcaacagct attggatgac agggcgatca   4980
ggaagcgcct cggacgaacg gcgaggagag aaggacgaga ggaagcttct cctgcatgat   5040
agaagtcaaa tcagcaatgc agcaccaagg gaatcgattc aggtagaact cactgttatt   5100
gattgcaaat actcctgctg gaaggtattc agccctctca ttcagtcgta tccctgccat   5160
gtcgagggtc tcgggactgg tagaacggca tcggaggtgc tccgatgcta tcctacatcc   5220
atcccgccaa ggcttcctgc gtcacacaag agatcctcag gcggatgcaa ccaggcatgc   5280
ttgaagaact cacgcagaga aacagaatgc acgattcagc agcacgagtg ggatggaacg   5340
acgtgtgaac gaacctccgg aaatccccgc ataacgcagg cagcccactc ccgaaatccc   5400
cggagtggac ccgctgcatg aaccttctgc gggggcgac gacagcgatg gacaaactgc   5460
atcaactcag cgagtccaga ctgaatctga ttccgcggcg cgcaggccgt actgtacggt   5520
aagctcgctg ccccgtccgt gggaggcagc tccttcgcag ctggcttccc ttggtgcggg   5580
cgggcctatc acgtcgtcgg atttgcggcc ttcttacctc acgtcccctc tgcgagtcac   5640
```

-continued

| | |
|---|---|
| tattacggcc aaccatgagg aaaggcacgg gtggcggcag aaaccccgca tcggcgatac | 5700 |
| agtctgcccg gggaactcga | 5720 |

<210> SEQ ID NO 53
<211> LENGTH: 2376
<212> TYPE: DNA
<213> ORGANISM: Rasamsonia emersonii

<400> SEQUENCE: 53

| | |
|---|---|
| atggtcctcc tcgctggcga tctcttccac gagaacaagc cgtctcgcaa gtccatgtac | 60 |
| caggtgatgc ggtcactgcg catgaactgc ttgggcgata agccctgcga gttggagatg | 120 |
| ctcagtgacg ccagtgagaa cttccagggc gctttcaacc acgtcaacta cgaggacctc | 180 |
| gacatcaatg tcgccatccc cgtctttttcc attcatggta accatgacga tccatccggg | 240 |
| gaaggtcatc tggctgccct ggacatactc caagtgtccg gactgatcaa ctacttcggt | 300 |
| cggacgccag agtcggacaa tattcaggtc aaacctgtcc ttctacagaa aggccgcacc | 360 |
| aaattggcgc tctacggcat cagcaacgtt cgtgatgaac ggctgtttcg tacatttcgc | 420 |
| gatgggaaag tcaagttctt ccggccctcg atccagaagg aggactggtt caacctgatc | 480 |
| tgtgtccatc agaaccacca cgcccacacg gagacgggct acctccccga atccttcctg | 540 |
| ccagactttc tcgacctggt catctggggc acgaacacg agtgtctgat aaacccaga | 600 |
| cgcaaccctg aaatgaattt ccacgtcatg cagcctggct cctctgtggc cacgtcactg | 660 |
| gtccagggag aagcagcacc caagcatgta gcgattctca gcatcaaggg ccgggagttc | 720 |
| cactgtgaac ctatccgctt gaaaacagtg cgtccatttg tcgtgcgaga atcgtcctc | 780 |
| tctgaggaga aggggccca gaaactggcc cgaaaggaga ataatcggac agaagtcacc | 840 |
| cggttcttaa tgtctatagt ggaggagctg attgaacaag ccaaagcaga gtggctggag | 900 |
| gcacaccaag acgacgatgt cgatgagcag gatattcctc tcccccttgt acgtcttaga | 960 |
| gtggaggttt ctacaccaga aggtggcagc ttcgactgcg agaaccctca gcggttctcc | 1020 |
| aatcggttcg tgggcaaagt cgcgaacgtc aacgacgtgg ttcaattcta ccgtaaaaag | 1080 |
| aagtcaacaa cgacttcccg caaggcagat aatctcgatg aggcggtggt gtcgcatctt | 1140 |
| tccgagctcg atacggtgaa ggtcgagaag ctagtacggg agattctcac tgcacagtct | 1200 |
| ctcaccatcc ttcctcagaa ctcgttcagc gatgcagtct cccagttcgt ggacaaggat | 1260 |
| gacaagcacg ccatggaaat gttcgtgaac gagtcgctag agaaccaggt caagtatctg | 1320 |
| atgtccctgg aacgggaggc cgacatggac gatgaggagg agagtcatca atctttgcgg | 1380 |
| aacgccatgg aaaaataccg cagtcagatg gaggagatgt ttgcgaaggg cgccatgaga | 1440 |
| cgtacgcgag ggaagaagcg cttcaaaccg aagcccgatg gctgggatac cgatctcgac | 1500 |
| ggcgtatggg aagaccagcc gggcgcattg atcctctctg acaatgagga tgccgacccg | 1560 |
| aacgaagagg aggccgcaga ggatggtacg gagagacaga ccacgtccac tcgaggcaga | 1620 |
| ggtcgaggtc gtggaggccg ggctgcaacc accaccactt ccacgcgcaa gacgactgct | 1680 |
| agcaagactc cagcagccag ctcacgaggc cggagacgcc aggctgtttc tgaagacgaa | 1740 |
| gacgaagacg agggcgatga tgtggtggtg ctggatgacg atcaggagga gccggaagaa | 1800 |
| atggtctcgg atgacgattc tcaggcactc tttgtcaaac aaacacctcc acccaaaacg | 1860 |
| ggtcgaacgc gccagacaac actcactccg accacaacag gcaccagcg gcgatctgga | 1920 |
| cgaactgcac cttcgccagc gccctcctct gccactgcag cagcttcgac ggcccgaagt | 1980 |
| gggacgcgag gtgccgctgc tagcaaacgg acccagcaga cgacactcaa ctttgcgccg | 2040 |

-continued

```
tcgcagacca gttccgtggg cactggacag gttacaggta ctgttacggg attcaaaaag   2100
cgtgtagtaa ggagtaaggt atctaatcta caaatgggaa ctggaaaaat taaattagat   2160
gaatgcaggg atatatgccc ccaaattgag gactacaaat ttagtatcta tttgcctaat   2220
catcgggatg atagtcactg ggctccgctg ttaaccatgc atgcattagt agggccttt    2280 cttggtcgac attcctcatt cgttgctaat ccatccaaca ggtctgaaga gctccaggcg   2340
gggttctatg ctaaaaggca aaggaggggg caatag                             2376
```

<210> SEQ ID NO 54
<211> LENGTH: 791
<212> TYPE: PRT
<213> ORGANISM: Rasamsonia emersonii

<400> SEQUENCE: 54

```
Met Val Leu Leu Ala Gly Asp Leu Phe His Glu Asn Lys Pro Ser Arg
1               5                   10                  15

Lys Ser Met Tyr Gln Val Met Arg Ser Leu Arg Met Asn Cys Leu Gly
                20                  25                  30

Asp Lys Pro Cys Glu Leu Glu Met Leu Ser Asp Ala Ser Glu Asn Phe
            35                  40                  45

Gln Gly Ala Phe Asn His Val Asn Tyr Glu Asp Leu Asp Ile Asn Val
        50                  55                  60

Ala Ile Pro Val Phe Ser Ile His Gly Asn His Asp Asp Pro Ser Gly
65                  70                  75                  80

Glu Gly His Leu Ala Ala Leu Asp Ile Leu Gln Val Ser Gly Leu Ile
                85                  90                  95

Asn Tyr Phe Gly Arg Thr Pro Glu Ser Asp Asn Ile Gln Val Lys Pro
            100                 105                 110

Val Leu Leu Gln Lys Gly Arg Thr Lys Leu Ala Leu Tyr Gly Ile Ser
        115                 120                 125

Asn Val Arg Asp Glu Arg Leu Phe Arg Thr Phe Arg Asp Gly Lys Val
    130                 135                 140

Lys Phe Phe Arg Pro Ser Ile Gln Lys Glu Asp Trp Phe Asn Leu Ile
145                 150                 155                 160

Cys Val His Gln Asn His His Ala His Thr Glu Thr Gly Tyr Leu Pro
                165                 170                 175

Glu Ser Phe Leu Pro Asp Phe Leu Asp Leu Val Ile Trp Gly His Glu
            180                 185                 190

His Glu Cys Leu Ile Asn Pro Arg Arg Asn Pro Glu Met Asn Phe His
        195                 200                 205

Val Met Gln Pro Gly Ser Ser Val Ala Thr Ser Leu Val Gln Gly Glu
    210                 215                 220

Ala Ala Pro Lys His Val Ala Ile Leu Ser Ile Lys Gly Arg Glu Phe
225                 230                 235                 240

His Cys Glu Pro Ile Arg Leu Lys Thr Val Arg Pro Phe Val Val Arg
                245                 250                 255

Glu Ile Val Leu Ser Glu Glu Lys Gly Ala Gln Lys Leu Ala Arg Lys
            260                 265                 270

Glu Asn Asn Arg Thr Glu Val Thr Arg Phe Leu Met Ser Ile Val Glu
        275                 280                 285

Glu Leu Ile Glu Gln Ala Lys Ala Glu Trp Leu Glu Ala His Gln Asp
    290                 295                 300

Asp Asp Val Asp Glu Gln Asp Ile Pro Leu Pro Leu Val Arg Leu Arg
```

-continued

```
305                 310                 315                 320
Val Glu Val Ser Thr Pro Glu Gly Ser Phe Asp Cys Glu Asn Pro
                325                 330                 335
Gln Arg Phe Ser Asn Arg Phe Val Gly Lys Val Ala Asn Val Asn Asp
                340                 345                 350
Val Val Gln Phe Tyr Arg Lys Lys Ser Thr Thr Ser Arg Lys
                355                 360                 365
Ala Asp Asn Leu Asp Glu Ala Val Val Ser His Leu Ser Glu Leu Asp
                370                 375                 380
Thr Val Lys Val Glu Lys Leu Val Arg Glu Ile Leu Thr Ala Gln Ser
385                 390                 395                 400
Leu Thr Ile Leu Pro Gln Asn Ser Phe Ser Asp Ala Val Ser Gln Phe
                405                 410                 415
Val Asp Lys Asp Asp Lys His Ala Met Glu Met Phe Val Asn Glu Ser
                420                 425                 430
Leu Glu Asn Gln Val Lys Tyr Leu Met Ser Leu Glu Arg Glu Ala Asp
                435                 440                 445
Met Asp Asp Glu Glu Glu Ser His Gln Ser Leu Arg Asn Ala Met Glu
        450                 455                 460
Lys Tyr Arg Ser Gln Met Glu Glu Met Phe Ala Lys Gly Ala Met Arg
465                 470                 475                 480
Arg Thr Arg Gly Lys Lys Arg Phe Lys Pro Lys Pro Asp Gly Trp Asp
                485                 490                 495
Thr Asp Leu Asp Gly Val Trp Glu Asp Gln Pro Gly Ala Leu Ile Leu
                500                 505                 510
Ser Asp Asn Glu Asp Ala Asp Pro Asn Glu Glu Ala Ala Glu Asp
                515                 520                 525
Gly Thr Glu Arg Gln Thr Thr Ser Thr Arg Gly Arg Gly Arg Gly Arg
                530                 535                 540
Gly Gly Arg Ala Ala Thr Thr Thr Ser Thr Arg Lys Thr Thr Ala
545                 550                 555                 560
Ser Lys Thr Pro Ala Ala Ser Ser Arg Gly Arg Arg Gln Ala Val
                565                 570                 575
Ser Glu Asp Glu Asp Glu Asp Glu Gly Asp Asp Val Val Leu Asp
                580                 585                 590
Asp Asp Gln Glu Glu Pro Glu Glu Met Val Ser Asp Asp Ser Gln
                595                 600                 605
Ala Leu Phe Val Lys Gln Thr Pro Pro Lys Thr Gly Arg Thr Arg
                610                 615                 620
Gln Thr Thr Leu Thr Ser Thr Thr Gly Thr Gln Arg Arg Ser Gly
625                 630                 635                 640
Arg Thr Ala Pro Ser Pro Ala Pro Ser Ser Ala Thr Ala Ala Ser
                645                 650                 655
Thr Ala Arg Ser Gly Thr Arg Gly Ala Ala Ser Lys Arg Thr Gln
                660                 665                 670
Gln Thr Thr Leu Asn Phe Ala Pro Ser Gln Thr Ser Ser Val Gly Thr
        675                 680                 685
Gly Gln Val Thr Gly Thr Val Thr Gly Phe Lys Lys Arg Val Val Arg
        690                 695                 700
Ser Lys Val Ser Asn Leu Gln Met Gly Thr Gly Lys Ile Lys Leu Asp
705                 710                 715                 720
Glu Cys Arg Asp Ile Cys Pro Gln Ile Glu Asp Tyr Lys Phe Ser Ile
                725                 730                 735
```

```
Tyr Leu Pro Asn His Arg Asp Asp Ser His Trp Ala Pro Leu Leu Thr
            740                 745                 750

Met His Ala Leu Val Gly Ala Phe Leu Gly Arg His Ser Ser Phe Val
            755                 760                 765

Ala Asn Pro Ser Asn Arg Ser Glu Glu Leu Gln Ala Gly Phe Tyr Ala
            770                 775                 780

Lys Arg Gln Lys Glu Gly Gln
785                 790

<210> SEQ ID NO 55
<211> LENGTH: 24
<212> TYPE: DNA
<213> ORGANISM: Artificial Sequence
<220> FEATURE:
<223> OTHER INFORMATION: Ku80-For primer

<400> SEQUENCE: 55
agggtatatg tggtctagta acgc                                            24

<210> SEQ ID NO 56
<211> LENGTH: 24
<212> TYPE: DNA
<213> ORGANISM: Artificial Sequence
<220> FEATURE:
<223> OTHER INFORMATION: Ku80-Rev primer

<400> SEQUENCE: 56
tcacaagtcc atcacggaac cggg                                            24

<210> SEQ ID NO 57
<211> LENGTH: 6429
<212> TYPE: DNA
<213> ORGANISM: Rasamsonia emersonii

<400> SEQUENCE: 57
agacaggtat tctgctgata gcatggattt atattatcaa taagcagagg cctaaagaca      60
ttcaaccaga agaaacgtcc ttcatgcaac agcaagctag aacatataca tatgagaaca    120
agcatagtgc aatcaagca gacctatact gtactctatt acaacaaact actatcacgg     180
tagtcgtaca ctggtcaatg aaataatgtg agtaaaaatg atcatgattc tatgacagaa    240
cagctagtac gcttgattta ttggggtata aattttactt tatttaggtg gttaagagcc    300
agcagactag atatatagct cagatataat ataattaata gtcacagaaa aaaataaata    360 aaataaaaa tagcaagatc catgatatgg tatacacaaa aaaataataa tcataaatca     420
cacaattcca tcctctccaa aaccacctag ccagctccta ccaaacgata catactcagt    480
ccaagcaaat ccccgttcc gtcctcccgt ccgtccgatc agtcccgaat ccgaccaaa      540 aaaaaaaga gacaaaatcc aaatcacggg ttcattcaca tccccacagg atacccatgg    600
atcagtcgtc ctactactg tggtacagat tagaacagaa aattaggttt ttacacaact     660
cagggtggtt gcattgcatt gcattgtgct gtggagttag ttaacttagt tgtactccat    720
ccagttcata cgcagtacat tattgggcat ttgaccccat cagacaagat atctaaggat    780
aagagtagaa attaggtaat aatagtcaaa agagaagaag agataccaag ggaactagat    840
actaacaacc aatcaggata tgccacagtg tggaacagaa tggaagcaga caggatcaac    900
ataactggaa ataaccttt ctttctttct tcgtacagca tcttggcagg aagtaacttg     960
atattgttaa ttaatgtcca tgtccatgtc catgtctttg ttatgtcttg tcttgtcttt   1020
```

```
cttgtgtgct acaagtacag tgtaacagat tcatatccgc tgaaacagac ataacattcg    1080
acacatggaa tacggagata aagaaataaa ttatactata tacggaatga tatcaataaa    1140
tatccgtgtt gtactcctta ttaagaaaga gtggcgcttg gcgcgtctac gtgcatggac    1200
tggtactaca tatttgatta cttcgatttt taataacaac aacctagtag acgtatgtat    1260
gtcatgtgaa actttcgatt gcgtgctttc ttgtctactt gtcgacttgt tacaatcttg    1320
tcgaatatta ataataataa tccatcgcac tgacatcttg gcaagtactc cgtacatcag    1380
gttacataca tactgattct ctaaagctag ataacgaata ggattctcgc acagacagta    1440
tgtgtctctt gtctgtcaga tgataagcag atgaacaaag aaagtataac tgcttactac    1500
ctacatgccg acatttagtc gattcctttc ggagaattta ttatggatta ttaatagcat    1560
accccgggat tggcagaagg ggtaaaaggt ccgactagac aaggatatcc atacagtaca    1620
taccgttgat acagatcgaa tcacatgcat actgctgatg gtgtgatgaa tccttgaatt    1680
agacaatcat ccagacctgt ctggacagag atcctggcac tgaacaatcc actcattgct    1740
atctatcggt actctgtacc tgtttcagct gaagcttgcc aatcgcagac tgccatctgc    1800
aactgatcag cgccaggatg caggtcatga taccccagcg ttgttcccga ggtgtcattg    1860
cttaaacgcg ttaaccagtg tgctaaacgt gctaaacgtg ctaaatgcta aactgctgat    1920
gctatgcagc tgcatcgccg aatctggaga atgcagatca cctgccgacg gcgggctccg    1980
ggcacgtgca cggggaccc cgtaggacag aaacgtccat cgagagtacg gagtacggag    2040
tattacaaga ccctgtccat cagaccctgt ccatcgtcat tgccaagatc tctcattgtt    2100
tgctgtttca tgctcggatc accagtggac agcaatgccc cgtgaacagc aagccgcatg    2160
ctggtccgtg tcttgtccgt gtgccgatgt agtattgcta acgagaccca gaatggcatc    2220
aatgacgttg cggatgacag aatgaggggg atcatcagta cgtctgctat caggatgatt    2280
atcctacgga gtatttactc agctgaagac aggaacaaga tcgtctgatg gatgaggccc    2340
acggccagcc agcacagact ccgtactctt cagtcttctg gatttgaccg ttcgacggcg    2400
cctccgacgt agcatctcgc tagcctgatc cttggctgcg cctatcgtcg gctcatgccc    2460
ctgttgatga cggggaagtg gagcggcgcc gcgataaggt tgccttgcta atttagcgcc    2520
tgcacgctcc agccaaaaag accaatattg aggtcgatcg tctcccctgg ctccgtgctg    2580
ctggcctgcg atcgccggcg cgatcatacc ctgcaatcac gccgccagcc tatcacagac    2640
catgcggtcc ttgcaccatc tgggagctcg agctctcctg actgccgtcg gggcgtcaat    2700
gcgtccggag cctccgacga gggcctctgc tcctcgtctg tcctactgga gcttgtccgt    2760
cagacgtcgc atcctgagcc gtgtgctgat atcgccatgg ctctgacgtg atcgactgcg    2820
agcggccggc gaggctataa gaagccgcaa cttgctgctc gaagtaccgt ctcccatcca    2880
tcgatcagac agtcagcagt cctcactcag tcagtcctca gtcgtccttc accaccatgg    2940
gtctgtccaa agccttcgtg tctgcactct cgctgtgctc cgccgtcgcc gtggccgccc    3000
cgaccgggcc agctcccaac gtgcagttct ccctgaagca ggtcgcggtg ccccggacca    3060
agcctcgtgc gcccccagct gccgactacg cgcgcgctct ggccaagtat ggcgctccaa    3120
ttccgtcgtc tgtgcggacg gccgcgtccg gcacgcagag cggctctgcg gccaacacgc    3180
ccgtcgccgg cgacagcttg tatctcacgc ccgttaccat cggccagagc acgctgaacc    3240
tggactttga cacgggctct gcggatctgt aagtgtccca actctcgcaa gaacaagaac    3300
ggagcagctg actcgtccag ctgggtcttc tccaacgaga cgcctccag cgagcgcggc    3360 aaccacgcca tctacaagcc cagctcgacg gccaagaagc tgaacggcta cacctggagc    3420
```

| | |
|---|---|
| atctcgtacg gcgacggcag ctcggccggc ggcgacgtct accaggacag cgtctcggtg | 3480 |
| ggcggcgtca acgcctccaa ccaggcggtc gaggccgcca ccaaggtcag ctccgagttc | 3540 |
| acgcaggagc cgggcgacgg cttgctgggc ctggccttca gcagcatcaa caccgtcaag | 3600 |
| cccaagccgc agacgacctt cttcgacacg gtcaagtcct cgctcgccaa gccgctgttc | 3660 |
| gccgtcaccc tcaagcacaa cgagcccggc agctacgact tggctacat cgacagctcc | 3720 |
| aagtacaagg gcagcatcca gtacacccag gtcgacaact cgcagggctt ctggcagttc | 3780 |
| acggccgacg gctactcgat tggcggcagc agcggcagcg gtggctccat ttctggcatt | 3840 |
| gctggtaaga actcccccta catcagagtt atctagatgc tgatttcgca gacaccggca | 3900 |
| ccaccctcct cctgctcgac gaccagatcg tcaacgagta ctaccagcag gtccagggcg | 3960 |
| cgcagaacga ccgaaacgcc ggcggctaca ccttcccgtg cgacgcgcag ctgcccgagc | 4020 |
| tgagcttcac catcggccag tacaccgcca ccgtgccggc cgagtacctc aacttccagc | 4080 |
| ccgtgtcgca gggcagccag acctgcttcg gcggtctgca gtccaaccag gcattggct | 4140 |
| tctccatctt cggcgacgtc ttcctcaaga gccagtacgt cgtctttgac tcggacggtc | 4200 |
| ctcagctggg ctttgctgct caggcgtaga ccagtcgtcc tccagcccag gttggttggt | 4260 |
| aggagatgat ttttcgatcg atcgattatc atggtgattg ataggatatg tgcatgagca | 4320 |
| gttgcctgta catacataca taatgattta ttgaatcaat tagttatgat caatctcgaa | 4380 |
| tatattttca gtgaaatacg tacatggtca tagcataacg atatactccg ttttcttcag | 4440 |
| gtagctagta aatatacaca aattcatcgt tctcccggtc cgtcaggtcc aggaaggctt | 4500 |
| tgtctccgat cgtcccgtcg ggatcactct cgctggtatc gtgatagcgc tccctcatcg | 4560 |
| agtaatcaac caccttggcc ggcttttccat tccgcacgcg ccgccgctcc tgcatccggt | 4620 |
| tcagcacgac caaattcgcc cactgcgcca gcacgacggc caccagcgcc acgaagatgg | 4680 |
| ccagacaagc ccgcacgccc ggccgatacg ccggcgcgtc cttcttgctg aagagcagcg | 4740 |
| ggccgacgat gttgcccgcc gagctggccg cgttgtacag gctcatcagc gccgatttct | 4800 |
| tcgttgtgcc gccgtgttg cccacgatcc acgtcacgat cagtgggttg ccgccgaaga | 4860 |
| gaaacgcgag caggtagtag cctaccagga gggagggttc gactgagttt tgcttcgtgc | 4920 |
| tgttattact gcgtggcacg gcgtacagaa ttgccaggcc cgcgactacc ggcagcatga | 4980 |
| agccggccag cacgacgccc ttcatccgcg cccgctgcgc cagatagctc cccgccagga | 5040 |
| tgaccagcag ctgcagcgcg ccaaacggca tgttgagcag actcgtcgtg tacgcgtcgt | 5100 |
| accccaggcc gttgaggatc agcgggccga acgtgttgct cacgctggcg ccgacgttca | 5160 |
| gcagcatcgc catgccgatc cagaggtagg ttttgggctc gagcgctgcc tcgacgacgt | 5220 |
| gccggatctt gaactcgcgg ctccctgtgc ccgtctggtt cgcgcgcagc cgctcgatgg | 5280 |
| cctgcgcttt ttccgtctcc gtcaggaacc gcgctgaggg gatgtcgttg tctagtttcc | 5340 |
| agtagatgaa cggcactgag atgatggtca ggaggccgac ggtgaggaag atactgcgcc | 5400 |
| agtcgtcagc agtcagtcag tcagcgttcg gggtagaagg ggagtacatc tgccatggcc | 5460 |
| tcagaacagg cgactcgata tggcccaacc cgtacgacag ggccgccgcg atgacagtcg | 5520 |
| ccgcgccgtt ggtactgtac caggccgcaa tgcgcagcgg ctgctcggcg cggcggtacc | 5580 |
| actggctggt gatgacgctg aacagcggca gacaggcggc ctcgaacagg ccgaggaaga | 5640 |
| agcgcgcggc catcagggag gcgaaactgc gacaggcggc catggcggcc tgggcgacgc | 5700 |
| cccagcccag acacagcgcg ggcatcaggc ggcgatgcgg cacgcgcacg atcagccacg | 5760 |

| | |
|---|---|
| acgagaacgg ctgccagacg agctgggcga tgggcgcgat cgaccccagc agcgagtact | 5820 |
| ggttgcccgt caggtgcgtg tcggcctgca agccgaaggt ggccccgtac ccgagcaccg | 5880 |
| acttgtccag gatctgcagg aagtacaccc acacgaggat ggccaggatg acgcggtctg | 5940 |
| tcttgcgccg gatgcgcttg ctgtcggcgt ccgtgagtgg gattctctgc tggccgatca | 6000 |
| ggcggagcgc cgtgtcgccg tggacggcgg gttgctcttc ttcatgggtg acggtcggtt | 6060 |
| tggatgccat ggtagcgatt actagatgta atcaagttgt aatgggagac aaacgaccaa | 6120 |
| gttctctctc gacgttttat accggcttat atgtctgttc agcagcattg caagtcaagt | 6180 |
| aatgacatcg gaattcctcc ggttcccgc attgcgcggc gatcatcggc tggcactagc | 6240 |
| agtatagcta gctcagagtc cgtattactg gattctattg cattgcgctg attgcagacg | 6300 |
| ttgactgaca gcaggagctt tgactctatt accccacgc ttcggcaatt ccccgcgtgc | 6360 |
| tcgggcctct atgcaccccc acgtggggga acattccaga gtatgcaggc agtagtatgc | 6420 |
| agcatggat | 6429 |

<210> SEQ ID NO 58
<211> LENGTH: 1194
<212> TYPE: DNA
<213> ORGANISM: Rasamsonia emersonii

<400> SEQUENCE: 58

| | |
|---|---|
| atgggtctgt ccaaagcctt cgtgtctgca ctctcgctgt gctccgccgt cgccgtggcc | 60 |
| gccccgaccg ggccagctcc caacgtgcag ttctccctga gcaggtcgc ggtgccccgg | 120 |
| accaagcctc gtcgcccccc agctgccgac tacgcgcgcg ctctggccaa gtatggcgct | 180 |
| ccaattccgt cgtctgtgcg gacggccgcg tccggcacgc agagcggctc tgcggccaac | 240 |
| acgcccgtcg ccggcgacag cttgtatctc acgcccgtta ccatcggcca gagcacgctg | 300 |
| aacctggact ttgacacggg ctctgcggat ctctgggtct tctccaacga gacgccctcc | 360 |
| agcgagcgcg gcaaccacgc catctacaag cccagctcga cggccaagaa gctgaacggc | 420 |
| tacacctgga gcatctcgta cggcgacggc agctcggccg gcggcgacgt ctaccaggac | 480 |
| agcgtctcgg tgggcggcgt caacgcctcc aaccaggcgg tcgaggccgc caccaaggtc | 540 |
| agctccgagt tcacgcagga gccgggcgac ggcttgctgg gcctggcctt cagcagcatc | 600 |
| aacaccgtca gcccaagcc gcagacgacc ttcttcgaca cggtcaagtc ctcgctcgcc | 660 |
| aagccgctgt tcgccgtcac cctcaagcac aacgagcccg gcagctacga ctttggctac | 720 |
| atcgacagct ccaagtacaa gggcagcatc cagtacaccc aggtcgacaa ctcgcagggc | 780 |
| ttctggcagt tcacggccga cggctactcg attggcggca gcagcggcag cggtggctcc | 840 |
| atttctggca ttgctgacac cggcaccacc tcctcctgc tcgacgacca gatcgtcaac | 900 |
| gagtactacc agcaggtcca gggcgcgcag aacgaccaga cgccggcgg ctacaccttc | 960 |
| ccgtgcgacg cgcagctgcc cgagctgagc ttcaccatcg gccagtacac cgccaccgtg | 1020 |
| ccggccgagt acctcaactt ccagcccgtg tcgcagggca gccagacctg cttcggcggt | 1080 |
| ctgcagtcca accagggcat tggcttctcc atcttcggcg acgtcttcct caagagccag | 1140 |
| tacgtcgtct ttgactcgga cggtcctcag ctgggctttg ctgctcaggc gtag | 1194 |

<210> SEQ ID NO 59
<211> LENGTH: 397
<212> TYPE: PRT
<213> ORGANISM: Rasamsonia emersonii

<400> SEQUENCE: 59

```
Met Gly Leu Ser Lys Ala Phe Val Ala Leu Ser Leu Cys Ser Ala
1               5                   10                  15

Val Ala Val Ala Ala Pro Thr Gly Pro Ala Pro Asn Val Gln Phe Ser
            20                  25                  30

Leu Lys Gln Val Ala Val Pro Arg Thr Lys Pro Arg Ala Pro Pro Ala
        35                  40                  45

Ala Asp Tyr Ala Arg Ala Leu Ala Lys Tyr Gly Ala Pro Ile Pro Ser
    50                  55                  60

Ser Val Arg Thr Ala Ala Ser Gly Thr Gln Ser Gly Ser Ala Ala Asn
65                  70                  75                  80

Thr Pro Val Ala Gly Asp Ser Leu Tyr Leu Thr Pro Val Thr Ile Gly
                85                  90                  95

Gln Ser Thr Leu Asn Leu Asp Phe Asp Thr Gly Ser Ala Asp Leu Trp
            100                 105                 110

Val Phe Ser Asn Glu Thr Pro Ser Ser Glu Arg Gly Asn His Ala Ile
        115                 120                 125

Tyr Lys Pro Ser Ser Thr Ala Lys Lys Leu Asn Gly Tyr Thr Trp Ser
    130                 135                 140

Ile Ser Tyr Gly Asp Gly Ser Ala Gly Gly Asp Val Tyr Gln Asp
145                 150                 155                 160

Ser Val Ser Val Gly Gly Val Asn Ala Ser Asn Gln Ala Val Glu Ala
                165                 170                 175

Ala Thr Lys Val Ser Ser Glu Phe Thr Gln Glu Pro Gly Asp Gly Leu
            180                 185                 190

Leu Gly Leu Ala Phe Ser Ser Ile Asn Thr Val Lys Pro Lys Pro Gln
        195                 200                 205

Thr Thr Phe Phe Asp Thr Val Lys Ser Ser Leu Ala Lys Pro Leu Phe
    210                 215                 220

Ala Val Thr Leu Lys His Asn Glu Pro Gly Ser Tyr Asp Phe Gly Tyr
225                 230                 235                 240

Ile Asp Ser Ser Lys Tyr Lys Gly Ser Ile Gln Tyr Thr Gln Val Asp
                245                 250                 255

Asn Ser Gln Gly Phe Trp Gln Phe Thr Ala Asp Gly Tyr Ser Ile Gly
            260                 265                 270

Gly Ser Ser Gly Ser Gly Gly Ser Ile Ser Gly Ile Ala Asp Thr Gly
        275                 280                 285

Thr Thr Leu Leu Leu Leu Asp Asp Gln Ile Val Asn Glu Tyr Tyr Gln
    290                 295                 300

Gln Val Gln Gly Ala Gln Asn Asp Gln Asn Ala Gly Gly Tyr Thr Phe
305                 310                 315                 320

Pro Cys Asp Ala Gln Leu Pro Glu Leu Ser Phe Thr Ile Gly Gln Tyr
                325                 330                 335

Thr Ala Thr Val Pro Ala Glu Tyr Leu Asn Phe Gln Pro Val Ser Gln
            340                 345                 350

Gly Ser Gln Thr Cys Phe Gly Gly Leu Gln Ser Asn Gln Gly Ile Gly
        355                 360                 365

Phe Ser Ile Phe Gly Asp Val Phe Leu Lys Ser Gln Tyr Val Val Phe
    370                 375                 380

Asp Ser Asp Gly Pro Gln Leu Gly Phe Ala Ala Gln Ala
385                 390                 395
```

<210> SEQ ID NO 60
<211> LENGTH: 1066

<212> TYPE: DNA
<213> ORGANISM: Artificial Sequence
<220> FEATURE:
<223> OTHER INFORMATION: A.nidulans gpdA promoter and 5' part of the ble
      coding region

<400> SEQUENCE: 60

```
agacagctct ggcggctctg aggtgcagtg gatgattatt aatccgggac cggccgcccc      60
tccgccccga gtggaaagg ctggtgtgcc cctcgttgac caagaatcta ttgcatcatc      120
ggagaatatg gagcttcatc gaatcaccgg cagtaagcga aggagaatgt gaagccaggg     180
gtgtatagcc gtcggcgaaa tagcatgcca ttaacctagg tacagaagtc caattgcttc     240
cgatctggta aagattcac gagatagtac cttctccgaa gtaggtagag cgagtacccg      300
gcgcgtaagc tccctaattg gcccatccgg catctgtagg gcgtccaaat atcgtgcctc     360
tcctgctttg cccggtgtat gaaaccggaa aggccgctca ggagctggcc agcggcgcag    420
accgggaaca caagctggca gtcgacccat ccggtgctct gcactcgacc tgctgaggtc    480
cctcagtccc tggtaggcag ctttgccccg tctgtccgcc cggtgtgtcg gcggggttga    540
caaggtcgtt gcgtcagtcc aacatttgtt gccatatttt cctgctctcc ccaccagctg    600
ctcttttctt ttctctttct tttcccatct tcagtatatt catcttccca tccaagaacc    660
tttatttccc ctaagtaagt actttgctac atccatactc catccttccc atcccttatt    720
cctttgaacc tttcagttcg agctttccca cttcatcgca gcttgactaa cagctacccc    780
gcttgagcag acatcaccat ggccaagttg accagtgccg ttccggtgct caccgcgcgc    840
gacgtcgccg gagcggtcga gttctggacc gaccggctcg ggttctcccg ggacttcgtg    900
gaggacgact tcgccggtgt ggtccgggac gacgtgaccc tgttcatcag cgcggtccag    960
gaccaggtgg tgccggacaa caccctggcc tgggtgtggg tgcgcggcct ggacgagctg   1020
tacgccgagt ggtcggaggt cgtgtccacg aacttccggg acgcct                  1066
```

<210> SEQ ID NO 61
<211> LENGTH: 1065
<212> TYPE: DNA
<213> ORGANISM: Artificial Sequence
<220> FEATURE:
<223> OTHER INFORMATION: 3' part of the ble coding region and A.nidulans
      TrpC terminator
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (893)..(893)
<223> OTHER INFORMATION: n is a, c, g, or t
<220> FEATURE:
<221> NAME/KEY: misc_feature
<222> LOCATION: (984)..(984)
<223> OTHER INFORMATION: n is a, c, g, or t

<400> SEQUENCE: 61

```
accagtgccg ttccggtgct caccgcgcgc gacgtcgccg gagcggtcga gttctggacc      60
gaccggctcg ggttctcccg ggacttcgtg gaggacgact tcgccggtgt ggtccgggac    120
gacgtgaccc tgttcatcag cgcggtccag gaccaggtgg tgccggacaa caccctggcc    180
tgggtgtggg tgcgcggcct ggacgagctg tacgccgagt ggtcggaggt cgtgtccacg    240
aacttccggg acgcctccgg gccggccatg accgagatcg gcgagcagcc gtggggggcgg    300
gagttcgccc tgcgcgaccc ggccggcaac tgcgtgcact tcgtggccga ggagcaggac    360
```

```
tgaccgacgc cgaccaacac cgccggtccg acggcggccc acgggtccca ggagcttgag    420
atccacttaa cgttactgaa atcatcaaac agcttgacga atctggatat aagatcgttg    480
gtgtcgatgt cagctccgga gttgagacaa atggtgttca ggatctcgat aagatacgtt    540
catttgtcca agcagcaaag agtgccttct agtgatttaa tagctccatg tcaacaagaa    600
taaaacgcgt tttcgggttt acctcttcca gatacagctc atctgcaatg cattaatgca    660
ttgactgcaa cctagtaacg ccttncaggc tccggcgaag agaagaatag cttagcagag    720 ctatttcat tttcgggaga cgagatcaag cagatcaacg gtcgtcaaga gacctacgag    780
actgaggaat ccgctcttgg ctccacgcga ctatatattt gtctctaatt gtactttgac    840
atgctcctct tctttactct gatagcttga ctatgaaaat tccgtcacca gcncctgggt    900
tcgcaaagat aattgcatgt ttcttccttg aactctcaag cctacaggac acacattcat    960
cgtaggtata aacctcgaaa tcanttccta ctaagatggt atacaatagt aaccatgcat   1020
ggttgcctag tgaatgctcc gtaacaccca atacgccggc cggcc                   1065
```

<210> SEQ ID NO 62
<211> LENGTH: 1063
<212> TYPE: DNA
<213> ORGANISM: Artificial Sequence
<220> FEATURE:
<223> OTHER INFORMATION: Sequence of basic construct 1

<400> SEQUENCE: 62

```
tcgacctcga gtaccgttcg tataatgtat gctatacgaa gttatattta aatcagtata    60
gcgaccagca ttcacatacg attgacgcat gatattactt tctgcgcact taacttcgca   120
tctgggcaga tgatgtcgag gcgaaaaaaa atataaatca cgctaacatt tgattaaaat   180
agaacaacta caatataaaa aaactataca aatgacaagt tcttgaaaac aagaatcttt   240
ttattgtcag tactgattag aaaaactcat cgagcatcaa atgaaactgc aatttattca   300
tatcaggatt atcaatacca tatttttgaa aaagccgttt ctgtaatgaa ggagaaaact   360
caccgaggca gttccatagg atggcaagat cctggtatcg gtctgcgatt ccgactcgtc   420
caacatcaat acaacctatt aatttcccct cgtcaaaaat aaggttatca agtgagaaat   480
caccatgagt gacgactgaa tccggtgaga atggcaaaag cttatgcatt tctttccaga   540
cttgttcaac aggccagcca ttacgctcgt catcaaaatc actcgcatca accaaaccgt   600
tattcattcg tgattgcgcc tgagcgagac gaaatacgcg atcgctgtta aaaggacaat   660
tacaaacagg aatcgaatgc aaccggcgca ggaacactgc cagcgcatca acaatatttt   720
cacctgaatc aggatattct tctaatacct ggaatgctgt tttgccgggg atcgcagtgg   780
tgagtaacca tgcatcatca ggagtacgga taaaatgctt gatggtcgga agaggcataa   840
attccgtcag ccagtttagt ctgaccatct catctgtaac atcattggca acgctacctt   900
tgccatgttt cagaaacaac tctggcgcat cgggcttccc atacaatcga tagattgtcg   960
cacctgattg cccgacatta tcgcgagccc atttataccc atataaatca gcatccatgt  1020
tggaatttaa tcgcggcctc gaaacgtgag tcttttcctt acc                     1063
```

<210> SEQ ID NO 63
<211> LENGTH: 2634
<212> TYPE: DNA
<213> ORGANISM: Artificial Sequence
<220> FEATURE:
<223> OTHER INFORMATION: Sequence of basic construct 2

<400> SEQUENCE: 63

-continued

```
cagcatccat gttggaattt aatcgcggcc tcgaaacgtg agtcttttcc ttacccatgg    60
ttgtttatgt tcggatgtga tgtgagaact gtatcctagc aagattttaa aaggaagtat   120
atgaaagaag aacctcagtg gcaaatccta accttttata tttctctaca ggggcgcggc   180
gtggggacaa ttcaacgcgt ctgtgagggg agcgtttccc tgctcgcagg tctgcagcga   240
ggagccgtaa tttttgcttc gcgccgtgcg gccatcaaaa tgtatggatg caaatgatta   300
tacatgggga tgtatgggct aaatgtacgg gcgacagtca catcatgccc ctgagctgcg   360
cacgtcaaga ctgtcaagga gggtattctg ggcctccatg tcatttaaat ctagtacgga   420
ttagaagccg ccgagcgggt gacagccctc cgaaggaaga ctctcctccg tgcgtcctcg   480
tcttcaccgg tcgcgttcct gaaacgcaga tgtgcctcgc gccgcactgc tccgaacaat   540
aaagattcta caatactagc ttttatggtt atgaagagga aaaattggca gtaacctggc   600
cccacaaacc ttcaaatgaa cgaatcaaat taacaaccat aggatgataa tgcgattagt   660
tttttagcct tatttctggg gtaattaatc agcgaagcga tgattttga tctattaaca   720
gatatataaa tgcaaaaact gcataaccac tttaactaat actttcaaca ttttcggttt   780
gtattacttc ttattcaaat gtaataaaag tatcaacaaa aaattgttaa tatacctcta   840
tactttaacg tcaaggagaa aaaccccgg attctagaac tagtggatcc cccgggctgc   900
aggaattcga tatcaagctt atcgataccg tcgaggggca gagccgatcc tgtacacttt   960
acttaaaacc attatctgag tgttaaatgt ccaattact gaccgtacac caaaatttgc  1020
ctgcattacc ggtcgatgca acgagtgatg aggttcgcaa gaacctgatg gacatgttca  1080
gggatcgcca ggcgttttct gagcatacct ggaaaatgct tctgtccgtt tgccggtcgt  1140
gggcggcatg gtgcaagttg aataaccgga aatggtttcc cgcagaacct gaagatgttc  1200
gcgattatct tctatatctt caggcgcgcg gtctggcagt aaaaactatc cagcaacatt  1260
tgggccagct aaacatgctt catcgtcggt ccgggctgcc acgaccaagt gacagcaatg  1320
ctgtttcact ggttatgcgg cggatccgaa aagaaaacgt tgatgccggt gaacgtgcaa  1380
aacaggctct agcgttcgaa cgcactgatt tcgaccaggt tcgttcactc atggaaaata  1440
gcgatcgctg ccaggatata cgtaatctgg catttctggg gattgcttat aacaccctgt  1500
tacgtatagc cgaaattgcc aggatcaggg ttaaagatat ctcacgtact gacggtggga  1560
gaatgttaat ccatattggc agaacgaaaa cgctggttag caccgcaggt gtagagaagg  1620
cacttagcct gggggtaact aaactggtcg agcgatggat ttccgtctct ggtgtagctg  1680
atgatccgaa taactacctg ttttgccggg tcagaaaaaa tggtgttgcc gcgccatctg  1740
ccaccagcca gctatcaact cgcgccctgg aagggatttt tgaagcaact catcgattga  1800
tttacggcgc taaggatgac tctggtcaga gatacctggc ctggtctgga cacagtgccc  1860
gtgtcggagc cgcgcgagat atggcccgcg ctggagtttc aataccggag atcatgcaag  1920
ctggtggctg gaccaatgta aatattgtca tgaactatat ccgtaccctg atagtgaaa  1980
caggggcaat ggtgcgcctg ctggaagatg gcgattagcc attaacgcgt aaatgattgc  2040
tataattatt tgatatttat ggtgacatat gagaaaggat ttcaacatcg acggaaaata  2100
tgtagtgctg tctgtaagca ctaatattca gtcgccagcc gtcattgtca ctgtaaagct  2160
gagcgataga atgcctgata ttgactcaat atccgttgcg tttcctgtca aaagtatgcg  2220
tagtgctgaa catttcgtga tgaatgccac cgaggaagaa gcacggcgcg gttttgctta  2280
aagtgatgtc tgagtttggc gaactcttgg gtaaggttgg aattgtcgac ctcgagtcat  2340
```

```
gtaattagtt atgtcacgct acattcacg ccctccccc acatccgctc taaccgaaaa    2400
ggaaggagtt agacaacctg aagtctaggt ccctatttat tttttatag ttatgttagt    2460 attaagaacg ttatttatat ttcaaatttt tcttttttt ctgtacagac gcgtgtacgc    2520
atgtaacatt atactgaaaa ccttgcttga aaggttttg ggacgctcga aggctttaat    2580
ttgcggccgg tacataactt cgtataatgt atgctatacg aacggtagga tccg         2634
```

<210> SEQ ID NO 64
<211> LENGTH: 20
<212> TYPE: DNA
<213> ORGANISM: Artificial Sequence
<220> FEATURE:
<223> OTHER INFORMATION: Forward primer Left ADE1 KO flank

<400> SEQUENCE: 64

```
ccgaataatc atatgagtcg                                              20
```

<210> SEQ ID NO 65
<211> LENGTH: 27
<212> TYPE: DNA
<213> ORGANISM: Artificial Sequence
<220> FEATURE:
<223> OTHER INFORMATION: Reverse primer left ADE1 KO flank

<400> SEQUENCE: 65

```
tatcgttaat atttcgtatg tgtattc                                      27
```

<210> SEQ ID NO 66
<211> LENGTH: 70
<212> TYPE: DNA
<213> ORGANISM: Artificial Sequence
<220> FEATURE:
<223> OTHER INFORMATION: Forward primer basic construct 1 with 50 bp
    ADE1 KO flank

<400> SEQUENCE: 66

```
gaatcataag cattgcttac aaagaataca catacgaaat attaacgata tcgacctcga    60
gtaccgttcg                                                         70
```

<210> SEQ ID NO 67
<211> LENGTH: 24
<212> TYPE: DNA
<213> ORGANISM: Artificial Sequence
<220> FEATURE:
<223> OTHER INFORMATION: Reverse primer basic construct 1

<400> SEQUENCE: 67

```
ggtaaggaaa agactcacgt ttcg                                         24
```

<210> SEQ ID NO 68
<211> LENGTH: 26
<212> TYPE: DNA
<213> ORGANISM: Artificial Sequence
<220> FEATURE:
<223> OTHER INFORMATION: Forward primer basic construct 2 creating
    overlap towards basic construct 1

<400> SEQUENCE: 68

```
cagcatccat gttggaattt aatcgc                                       26
```

<210> SEQ ID NO 69
<211> LENGTH: 71
<212> TYPE: DNA
<213> ORGANISM: Artificial Sequence

```
<220> FEATURE:
<223> OTHER INFORMATION: Reverse primer basic construct 2 with 50 bp
      ADE1 KO flank

<400> SEQUENCE: 69
attcagtgag gagttacact ggcgacttgt agtatatgta aatcacgtta cggatcctac      60
cgttcgtata g                                                          71

<210> SEQ ID NO 70
<211> LENGTH: 27
<212> TYPE: DNA
<213> ORGANISM: Artificial Sequence
<220> FEATURE:
<223> OTHER INFORMATION: Forward primer for amplification of right ADE1
      KO flank

<400> SEQUENCE: 70
taacgtgatt tacatatact acaagtc                                         27

<210> SEQ ID NO 71
<211> LENGTH: 24
<212> TYPE: DNA
<213> ORGANISM: Artificial Sequence
<220> FEATURE:
<223> OTHER INFORMATION: Reverse primer for amplification of right ADE1
      KO flank

<400> SEQUENCE: 71
tattgactgc gctctataaa tgtc                                            24

<210> SEQ ID NO 72
<211> LENGTH: 984
<212> TYPE: DNA
<213> ORGANISM: Artificial Sequence
<220> FEATURE:
<223> OTHER INFORMATION: PCR fragment 1 left flank ADE1

<400> SEQUENCE: 72
ccgaataatc atatgagtcg ggcaattccg aagaattttc tttgtaatgt cgctgatccc      60
ttttactgtt gctatgcata tgttttttcca cgttctcctc ctctaactct ttgtcatcat    120
ctctatttcg cagaacatca tggcccttttt ctgccgcatt actcagtata ttaagtttcg   180
aattgaaggg cgaactctta ttcgaagtcg gagtcaccac aacacttccg cccatactct    240
ccgaatcctc gtttcctaaa gtaagtttac ttccacttgt aggcctatta ttaatgatat    300
ctgaataatc ctctattagg gttggatcat tcagtagcgc gtgcgattga aaggagtcca    360
tgcccgacgt cgacgtgatt agcgaaggcg cgtaaccatt gtcatgtcta gcagctatag    420
aactaacctc cttgacacca cttgcggaag tctcatcaac atgctcttcc ttattactca    480
ttctcttacc aagcagagaa tgttatctaa aaactacgtg tatttcacct ctttctcgac    540
ttgaacacgt ccaactcctt aagtactacc acagccagga aagaatggat ccagttctac    600
acgatagcaa agcagaaaac acaaccagcg taccgctgta gaagcttctt tgtttacagc    660
acttgatcca tgtagccata ctcgaaattt caactcatct gaaacttttc ctgaaggttg    720
aaaaagaatg cctaaagggt cacccgaagc ttattcacga gtcagtctga ctcttgcgag    780
agatgaggat gtaataatac taatctcgaa gatgccatct aatacatata gacatacata    840
tatatatata tacattctat atattcttac ccagattctt tgaggtaaga cggttgggtt    900
ttatcttttg cagttggtac tattaagaac aatcgaatca taagcattgc ttacaaagaa    960
tacacatacg aaatattaac gata                                           984
```

<210> SEQ ID NO 73
<211> LENGTH: 1113
<212> TYPE: DNA
<213> ORGANISM: Artificial Sequence
<220> FEATURE:
<223> OTHER INFORMATION: PCR fragment 2 Basic construct 1 with ADE1 KO
      flanks

<400> SEQUENCE: 73

```
gaatcataag cattgcttac aaagaataca catacgaaat attaacgata tcgacctcga     60
gtaccgttcg tataatgtat gctatacgaa gttatattta atcagtata gcgaccagca    120
ttcacatacg attgacgcat gatattactt tctgcgcact taacttcgca tctgggcaga   180
tgatgtcgag gcgaaaaaaa atataaatca cgctaacatt tgattaaaat agaacaacta   240
caatataaaa aaactataca atgacaagt tcttgaaaac aagaatcttt ttattgtcag    300
tactgattag aaaaactcat cgagcatcaa atgaaactgc aatttattca tatcaggatt   360
atcaatacca tattttgaa aaagccgttt ctgtaatgaa ggagaaaact caccgaggca    420
gttccatagg atggcaagat cctggtatcg gtctgcgatt ccgactcgtc caacatcaat   480
acaacctatt aatttcccct cgtcaaaaat aaggttatca gtgagaaat caccatgagt    540
gacgactgaa tccggtgaga atggcaaaag cttatgcatt tctttccaga cttgttcaac   600
aggccagcca ttacgctcgt catcaaaatc actcgcatca accaaccgt tattcattcg    660
tgattgcgcc tgagcgagac gaaatacgcg atcgctgtta aaaggacaat tacaaacagg   720
aatcgaatgc aaccggcgca ggaacactgc cagcgcatca acaatatttt cacctgaatc   780
aggatattct tctaatacct ggaatgctgt tttgccgggg atcgcagtgg tgagtaacca   840
tgcatcatca ggagtacgga taaaatgctt gatggtcgga agaggcataa attccgtcag   900
ccagtttagt ctgaccatct catctgtaac atcattggca acgctacctt tgccatgttt   960
cagaaacaac tctggcgcat cgggcttccc atacaatcga tagattgtcg cacctgattg  1020
cccgacatta tcgcgagccc atttatacc atataaatca gcatccatgt tggaatttaa   1080
tcgcggcctc gaaacgtgag tcttttcctt acc                              1113
```

<210> SEQ ID NO 74
<211> LENGTH: 2684
<212> TYPE: DNA
<213> ORGANISM: Artificial Sequence
<220> FEATURE:
<223> OTHER INFORMATION: PCR fragment 3 Basic construct 2 with ADE1 KO
      flanks

<400> SEQUENCE: 74

```
cagcatccat gttggaattt aatcgcggcc tcgaaacgtg agtcttttcc ttacccatgg    60
ttgtttatgt tcggatgtga tgtgagaact gtatcctagc aagattttaa aaggaagtat   120
atgaaagaag aacctcagtg gcaaatccta acctttata tttctctaca ggggcgcggc    180
gtggggacaa ttcaacgcgt ctgtgagggg agcgtttccc tgctcgcagg tctgcagcga   240
ggagccgtaa ttttttgctt cgcgccgtgcg gccatcaaaa tgtatggatg caaatgatta   300
tacatgggga tgtatgggct aaatgtacgg gcgacagtca catcatgccc ctgagctgcg   360
cacgtcaaga ctgtcaagga gggtattctg ggcctccatg tcatttaaat ctagtacgga   420
ttagaagccg ccgagcgggt gacagccctc cgaaggaaga ctctcctccg tgcgtcctcg   480
tcttcaccgg tcgcgttcct gaaacgcaga gtgtgcctcgc ccgcactgc tccgaacaat   540
```

```
aaagattcta caatactagc ttttatggtt atgaagagga aaaattggca gtaacctggc    600
cccacaaacc ttcaaatgaa cgaatcaaat taacaaccat aggatgataa tgcgattagt    660
tttttagcct tatttctggg gtaattaatc agcgaagcga tgatttttga tctattaaca    720
gatatataaa tgcaaaaact gcataaccac tttaactaat actttcaaca ttttcggttt    780
gtattacttc ttattcaaat gtaataaaag tatcaacaaa aaattgttaa tatacctcta    840
tactttaacg tcaaggagaa aaaccccgg attctagaac tagtggatcc cccgggctgc    900
aggaattcga tatcaagctt atcgataccg tcgaggggca gagccgatcc tgtacacttt    960
acttaaaacc attatctgag tgttaaatgt ccaatttact gaccgtacac caaaatttgc   1020
ctgcattacc ggtcgatgca acgagtgatg aggttcgcaa gaacctgatg gacatgttca   1080
gggatcgcca ggcgttttct gagcatacct ggaaaatgct tctgtccgtt tgccggtcgt   1140
gggcggcatg gtgcaagttg aataaccgga aatggtttcc cgcagaacct gaagatgttc   1200
gcgattatct tctatatctt caggcgcgcg gtctggcagt aaaaactatc cagcaacatt   1260
tgggccagct aaacatgctt catcgtcggt ccgggctgcc acgaccaagt gacagcaatg   1320
ctgtttcact ggttatgcgg cggatccgaa agaaaacgt tgatgccggt gaacgtgcaa   1380
aacaggctct agcgttcgaa cgcactgatt tcgaccaggt tcgttcactc atggaaaata   1440
gcgatcgctg ccaggatata cgtaatctgg catttctggg gattgcttat aacaccctgt   1500
tacgtatagc cgaaattgcc aggatcaggg ttaaagatat ctcacgtact gacggtggga   1560
gaatgttaat ccatattggc agaacgaaaa cgctggttag caccgcaggt gtagagaagg   1620
cacttagcct gggggtaact aaactggtcg agcgatggat ttccgtctct ggtgtagctg   1680
atgatccgaa taactacctg ttttgccggg tcagaaaaaa tggtgttgcc gcgccatctg   1740
ccaccagcca gctatcaact cgcgcccctgg aagggatttt tgaagcaact catcgattga   1800
tttacggcgc taaggatgac tctggtcaga gatacctggc ctggtctgga cacagtgccc   1860
gtgtcggagc cgcgcgagat atggcccgcg ctggagtttc aataccggag atcatgcaag   1920
ctggtggctg gaccaatgta aatattgtca tgaactatat ccgtaccctg gatagtgaaa   1980
caggggcaat ggtgcgcctg ctggaagatg gcgattagcc attaacgcgt aaatgattgc   2040
tataattatt tgatatttat ggtgacatat gagaaaggat ttcaacatcg acggaaaata   2100
tgtagtgctg tctgtaagca ctaatattca gtcgccagcc gtcattgtca ctgtaaagct   2160
gagcgataga atgcctgata ttgactcaat atccgttgcg tttcctgtca aaagtatgcg   2220
tagtgctgaa catttcgtga tgaatgccac cgaggaagaa gcacggcgcg gttttgctta   2280
aagtgatgtc tgagtttggc gaactcttgg gtaaggttgg aattgtcgac ctcgagtcat   2340
gtaattagtt atgtcacgct tacattcacg ccctccccccc acatccgctc taaccgaaaa   2400
ggaaggagtt agacaacctg aagtctaggt ccctatttat ttttttatag ttatgttagt   2460
attaagaacg ttatttatat ttcaaatttt tcttttttttt ctgtacagac gcgtgtacgc   2520
atgtaacatt atactgaaaa ccttgcttga gaaggttttg ggacgctcga aggctttaat   2580
ttgcggccgg tacataactt cgtataatgt atgctatacg aacggtagga tccgtaacgt   2640
gatttacata tactacaagt cgccagtgta actcctcact gaat                    2684
```

<210> SEQ ID NO 75
<211> LENGTH: 1002
<212> TYPE: DNA
<213> ORGANISM: Artificial Sequence
<220> FEATURE:
<223> OTHER INFORMATION: PCR fragment left flank ADE1

```
<400> SEQUENCE: 75
taacgtgatt tacatatact acaagtcgcc agtgtaactc ctcactgaat atgattcata        60
catacccgta tgtattaatg tataaatgtt ctcagagcaa attttatcga tatcttgttt       120
gccagtggta tgcaggtttg gcaaattttt taccataata tccgtttata gattctggaa       180
ccttaccaac tttcttaccg ctaattactt ccctggctcg ctcctccact gcctgggtaa       240
attgttcctt caactgactc agttctcttt cgtattcaat agcttgcttc tcgaggattt       300
tttcaatgtt tgtcagctca ttttcatagt ccagtaactt cctttcaaat ctctctaatt       360
gcaacgactt tcttgcagtt cgtatctgaa tatcttgcag taattcaaaa gtggaaggcc       420
tggttcttaa gttcacatct atcattgaat gtattatggc attaagccct ctagagtaat       480
actcagggac ggtgtcacat ttcccgtttt taatcttagt ttgtagctcg agataatttt       540
ttgcctgaaa tgggggggtgc aacgaacaca tctcaaaaat aacacaacct agtgaccaga       600
tgtcggatag tggggagtat ggttggtcca tcaacacttc aggcgacatg taatatggtg       660
taccgacgta tgttgtggca aattgaatac tagtttccag agatttggct aacccaaaat       720
cacctaactt taccacaact tgactatagt ccatagggct cccccttttc cctgaattca       780
ctctatggtc tctgtaataa ttactattca cttcctcgtg accgtctact tgttcattaa       840
tattgtaatc gctatcatca tagcttaaga atatatttcc tggtttcaga tcacgatgga       900
taacgatgtt tttgccttt accggtggtt tcatccggtc atatattgtg gtcaaagttg       960
gcaattcaac accataatga catttataga gcgcagtcaa ta                        1002
```